United States Patent
Ashrafi (12)

(10) Patent No.: US 11,707,546 B2
(45) Date of Patent: Jul. 25, 2023

(54) MINIATURIZED DEVICE TO STERILIZE SURFACES FROM COVID-19 AND OTHER VIRUSES AND BACTERIA

(71) Applicant: NXGEN PARTNERS IP, LLC, Dallas, TX (US)

(72) Inventor: Solyman Ashrafi, Plano, TX (US)

(73) Assignee: NXGEN PARTNERS IP, LLC, Dallas, TX (US)

( * ) Notice: Subject to any disclaimer, the term of this patent is extended or adjusted under 35 U.S.C. 154(b) by 303 days.

(21) Appl. No.: 17/039,502

(22) Filed: Sep. 30, 2020

(65) Prior Publication Data

US 2021/0085814 A1    Mar. 25, 2021

Related U.S. Application Data

(63) Continuation-in-part of application No. 16/925,107, filed on Jul. 9, 2020, now Pat. No. 11,083,807, which
(Continued)

(51) Int. Cl.
*A61L 2/12* (2006.01)
*A61L 2/025* (2006.01)
(Continued)

(52) U.S. Cl.
CPC .............. *A61L 2/12* (2013.01); *A61L 2/025* (2013.01); *A61L 2/24* (2013.01); *A61L 2/26* (2013.01);
(Continued)

(58) Field of Classification Search
CPC .... A61L 2/0058; A61L 2/0064; A61L 2/0085; A61L 2/12; A61L 2202/14; A61L 2202/16; A61L 2202/20
See application file for complete search history.

(56) References Cited

U.S. PATENT DOCUMENTS 2,215,635 A * 9/1940 Collins ................... F21V 21/26
362/404
4,952,369 A 8/1990 Belilos
(Continued)

OTHER PUBLICATIONS

Gao et al., "Optical manipulation from the microscale to the nanoscale: fundamentals, advances and prospects," Light: Science & Applications (2017) (Year: 2017).*
(Continued)

*Primary Examiner* — Timothy C Cleveland

(57) ABSTRACT

A system for sterilizing biological material comprising beam generation circuitry for generating a radiating wave having radiating energy therein at a predetermined frequency therein. A controller controls the radiating wave generation at the predetermined frequency. The predetermined frequency equals a resonance frequency of a particular biological material and is determined responsive to a plurality of parameters from an influenza virus. The predetermined frequency induces a mechanical resonance vibration at the resonance frequency of the particular biological material within the particular biological material for destroying a capsid of the particular biological material. Radiating circuitry projects the radiating wave on a predetermined location to destroy the particular biological material at the predetermined location.

14 Claims, 59 Drawing Sheets

Related U.S. Application Data is a continuation-in-part of application No. 16/653,213, filed on Oct. 15, 2019, now Pat. No. 11,002,677, and a continuation-in-part of application No. 16/127,729, filed on Sep. 11, 2018, now Pat. No. 10,921,753.

(60) Provisional application No. 63/074,298, filed on Sep. 3, 2020, provisional application No. 63/032,256, filed on May 29, 2020.

(51) Int. Cl.
*A61L 2/24* (2006.01)
*A61L 2/26* (2006.01)

(52) U.S. Cl.
CPC ....... *A61L 2202/14* (2013.01); *A61L 2202/16* (2013.01); *A61L 2202/21* (2013.01)

(56) References Cited

U.S. PATENT DOCUMENTS

| | | | |
|---|---|---|---|
| 6,268,200 B1 | 7/2001 | Tucker et al. | |
| 10,279,190 B2 * | 5/2019 | Botsford | A61N 2/02 |
| 2005/0019209 A1 | 1/2005 | Burger et al. | |
| 2009/0237067 A1 | 9/2009 | Sun et al. | |
| 2010/0113983 A1 | 5/2010 | Heckerman et al. | |
| 2011/0070624 A1 | 3/2011 | Sun et al. | |
| 2020/0345873 A1 | 11/2020 | Ashraf | |

OTHER PUBLICATIONS

Patent Cooperation Treaty: International Preliminary Report on Patentability of PCT/US2021/040881 (related application); Fiona Doherty; dated Jan. 19, 2023; 9 pages.

Liu et al., "Microwave resonant absorption of viruses through dipolar coupling with confined acoustic vibration" Applied Physics Letters; Jan. 27, 2009; Taiwan, 4pgs.

Robert K. Adair, "Vibrational Resonances in Biological Systems at Microwave Frequencies" Biophysical Journal; vol. 82; Mar. 2002; 1147-1152.

Patent Cooperation Treaty: International Search Report and Written Opinion of Related Application PCT/US21/40881; Kari Rodriguez; dated Oct. 21, 2021; 11 pages.

Patent Cooperation Treaty: International Preliminary Report on Patentability of PCT/US2021/048961 (related application); Miki Kobayashi; dated Mar. 16, 2023; 10 pages.

* cited by examiner

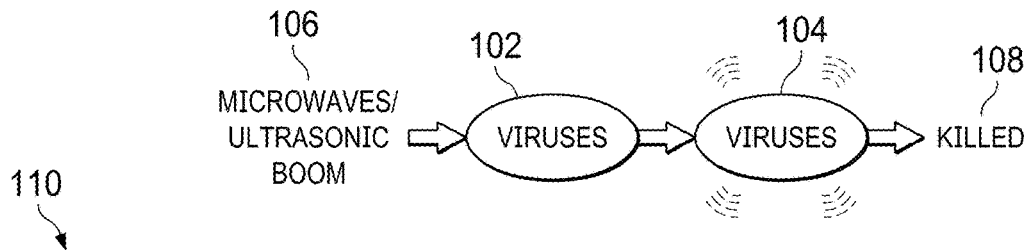
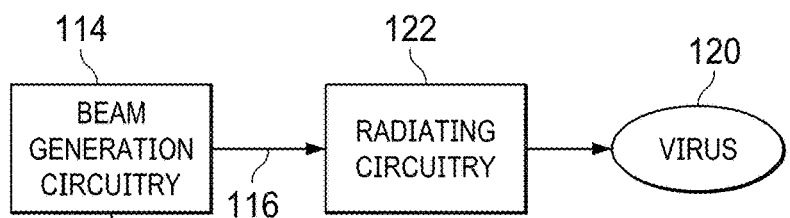
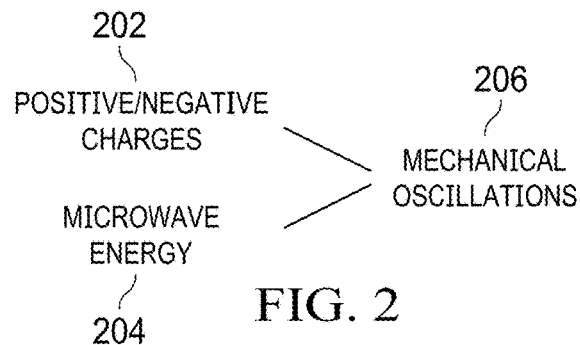
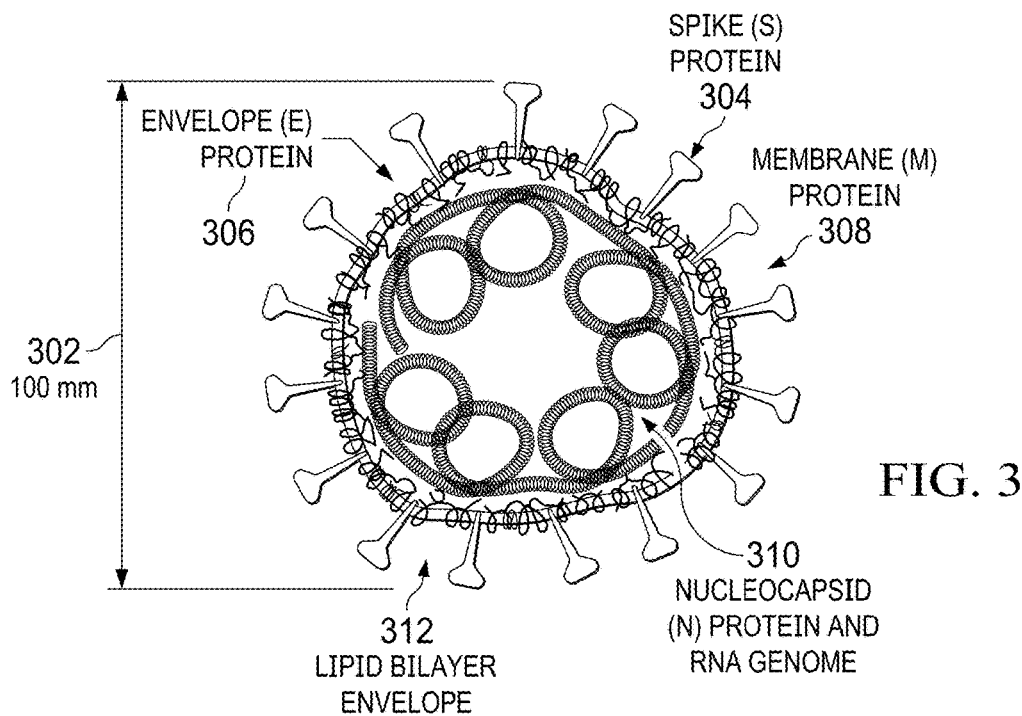

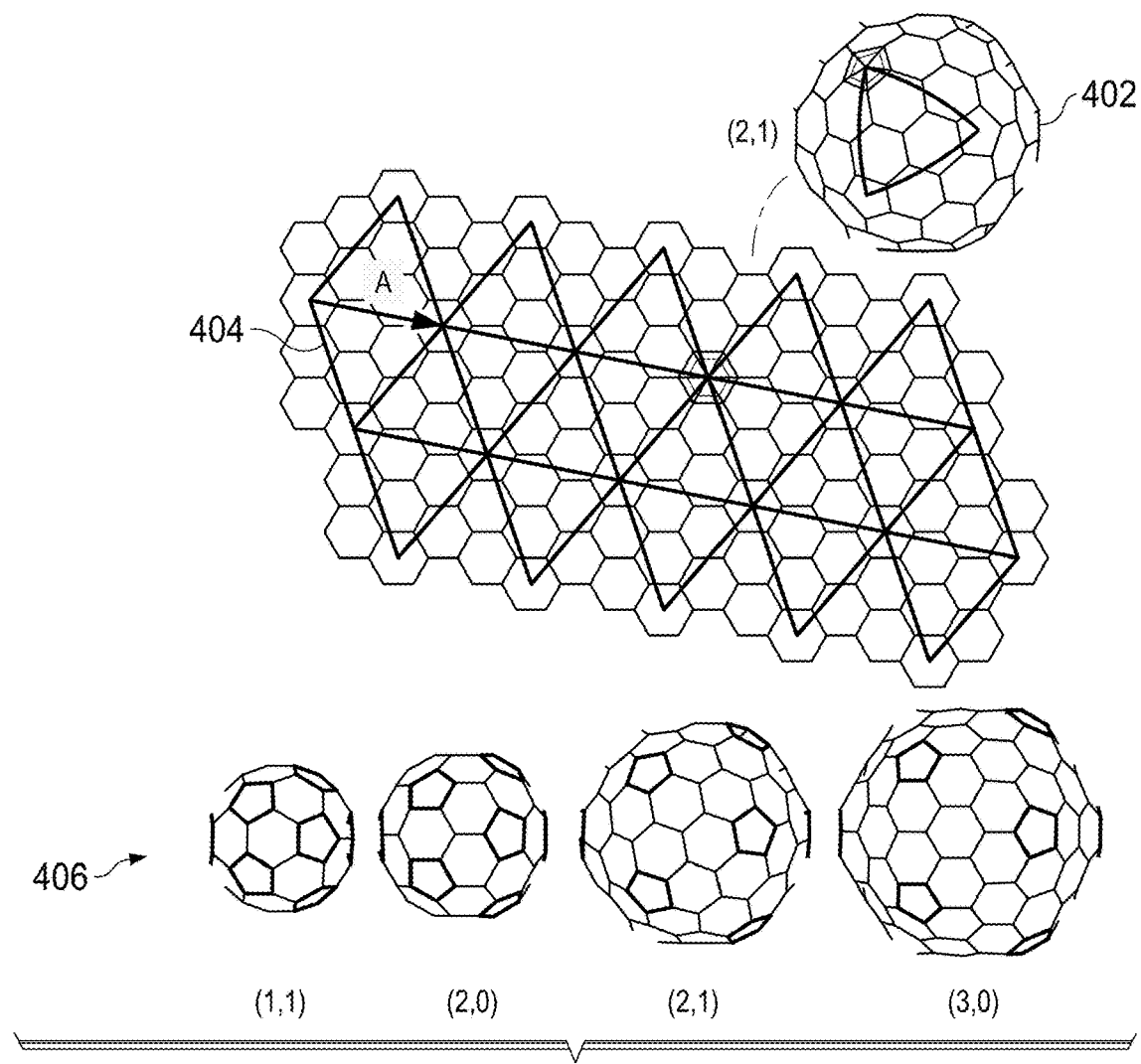
FIG. 4
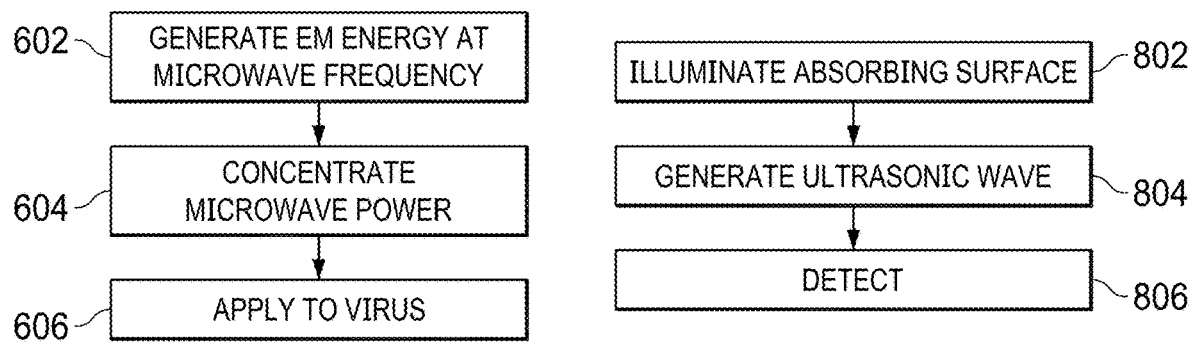
FIG. 6
FIG. 8

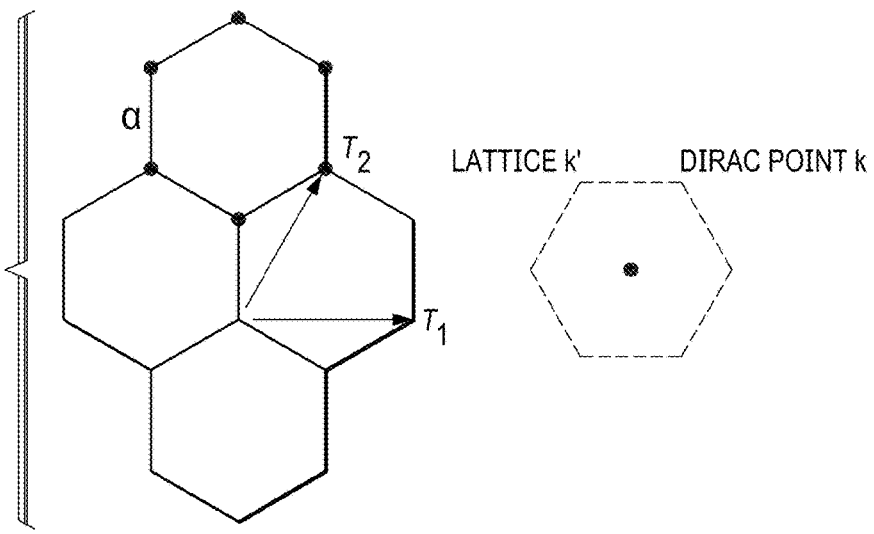
FIG. 24
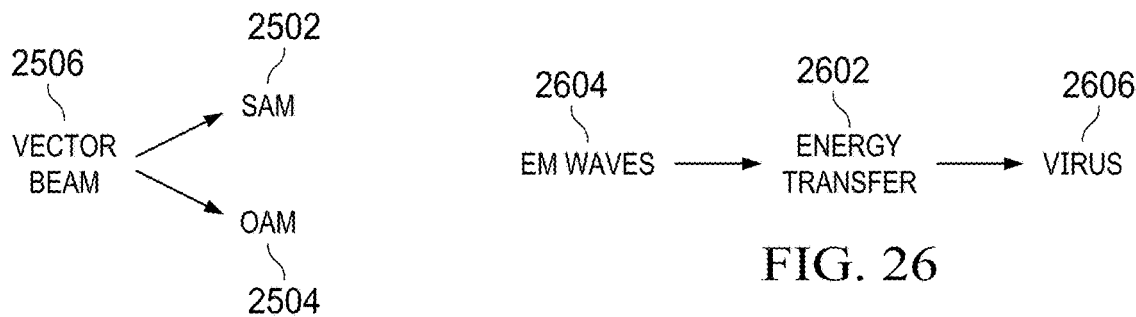
FIG. 25
FIG. 26
FIG. 27
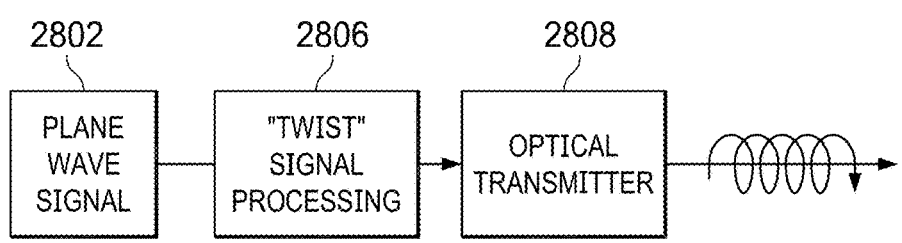
FIG. 28

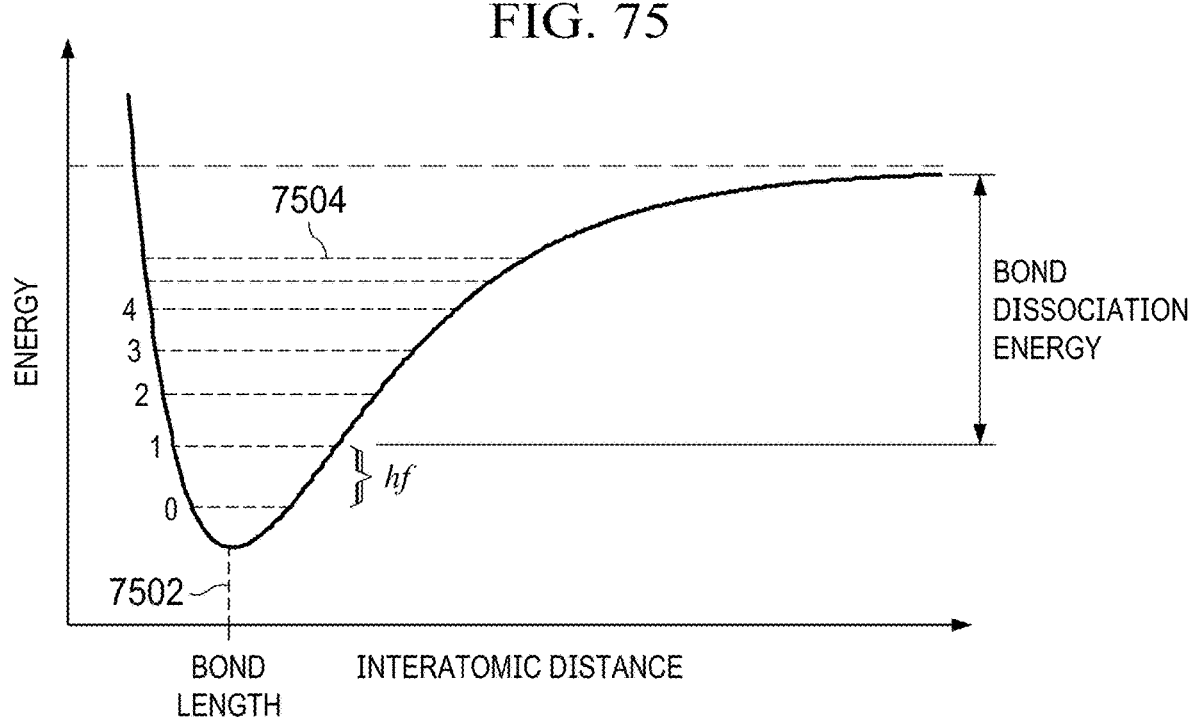

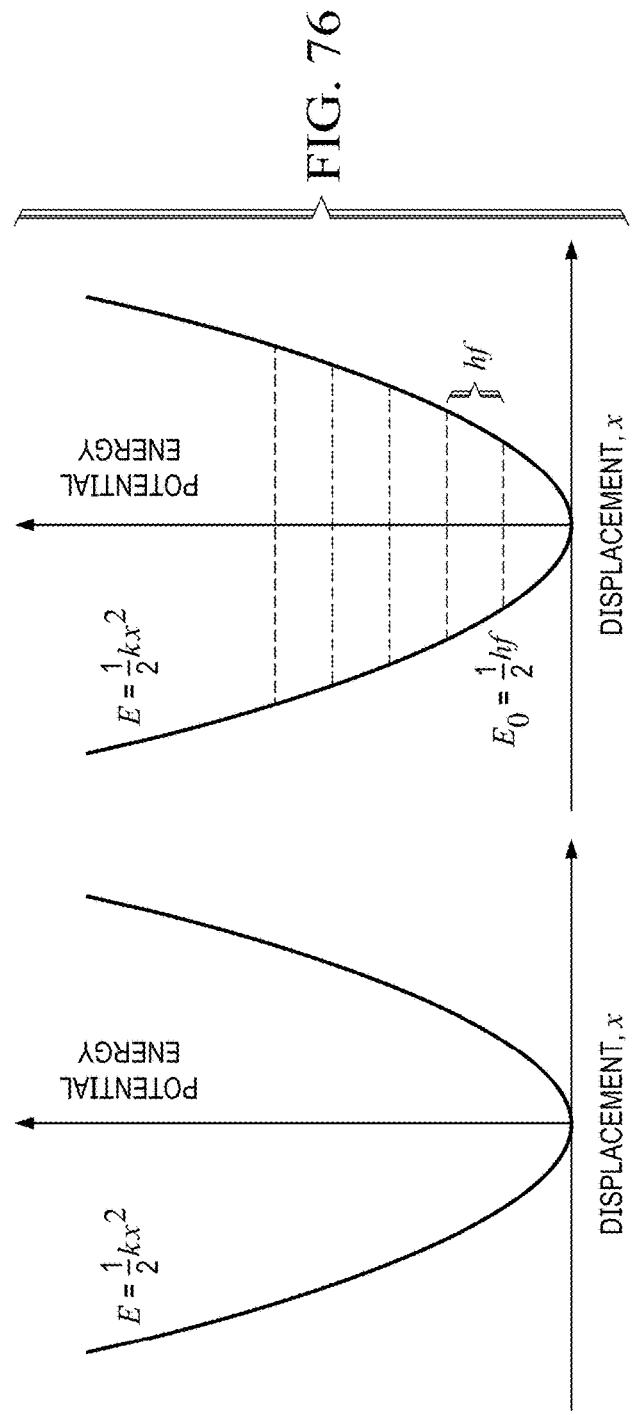
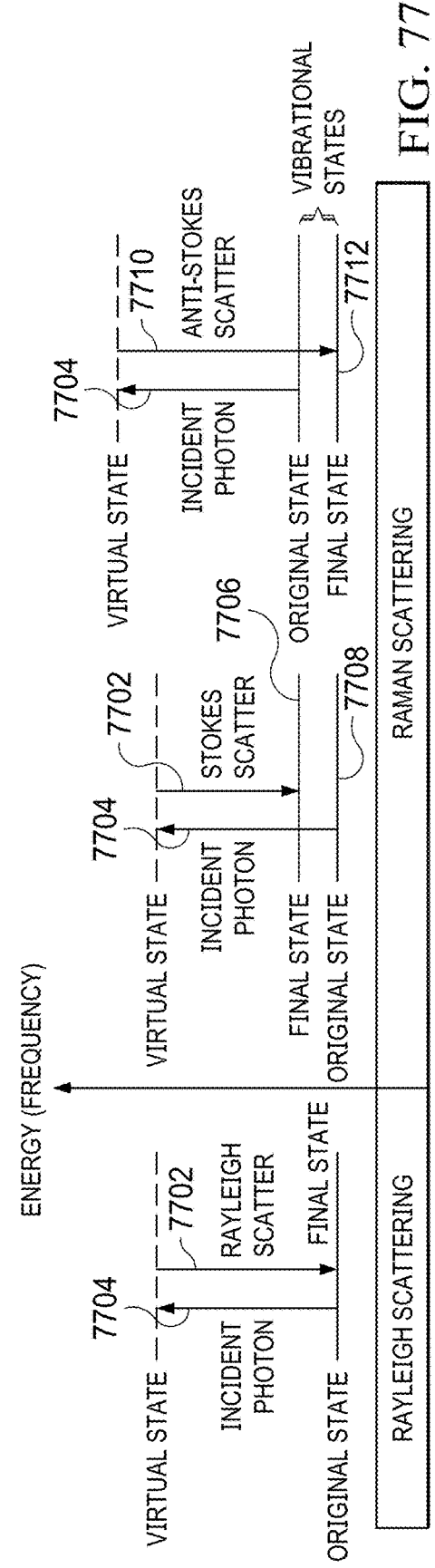

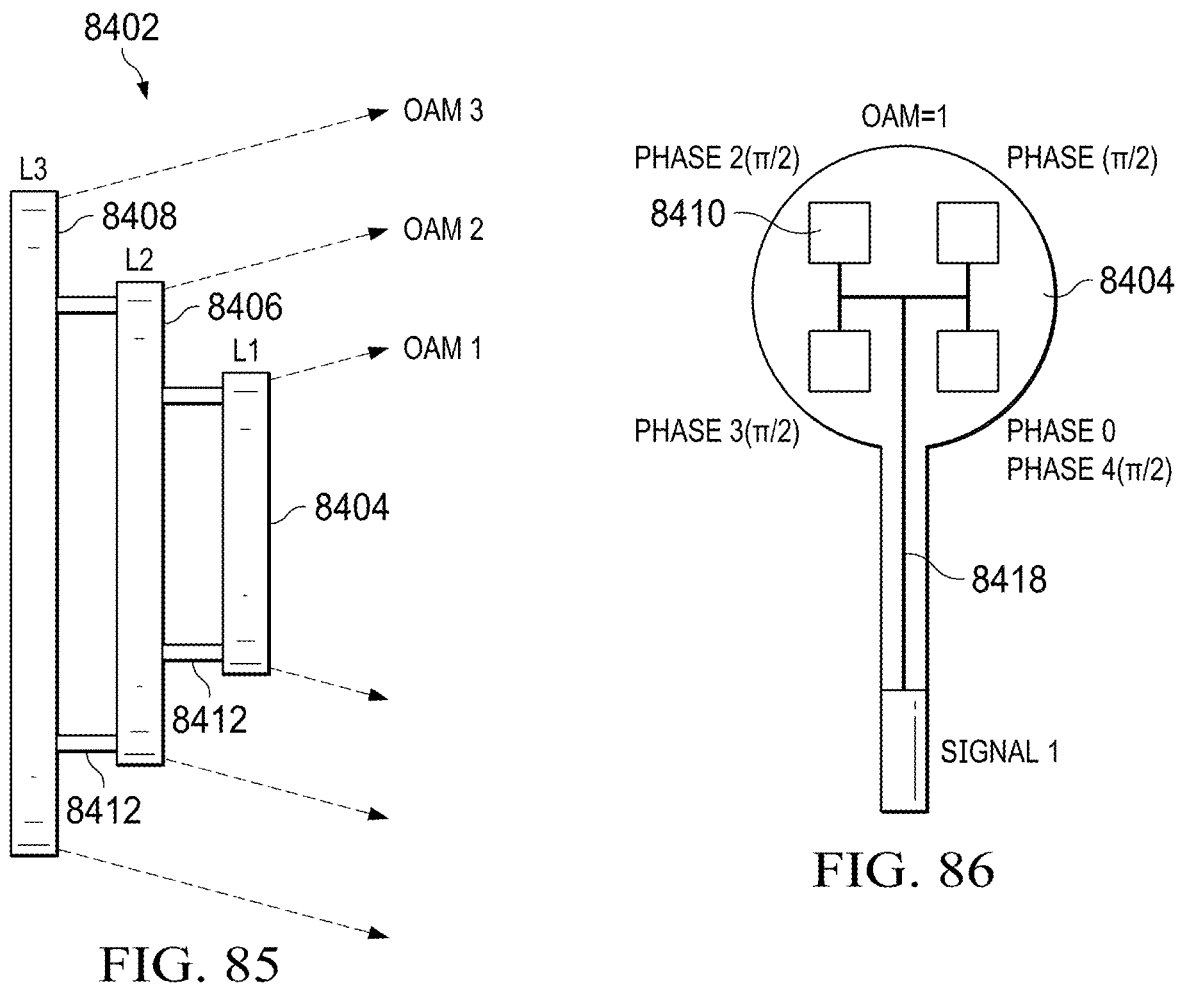
FIG. 85
FIG. 86
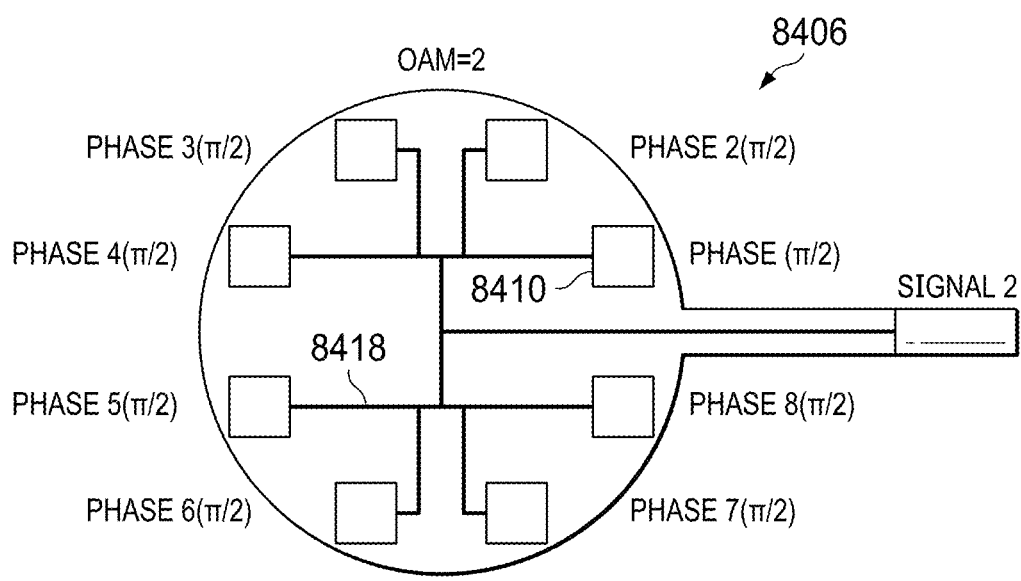
FIG. 87

MINIATURIZED DEVICE TO STERILIZE SURFACES FROM COVID-19 AND OTHER VIRUSES AND BACTERIA

CROSS-REFERENCE TO RELATED APPLICATIONS

This application is a continuation-in-part of U.S. patent application Ser. No. 16/925,107, entitled A MINIATURIZED DEVICE TO STERILIZE FROM COVID-19 AND OTHER VIRUSES, filed on Jul. 9, 2020. U.S. patent application Ser. No. 16/925,107 is a continuation-in-part of U.S. patent application Ser. No. 16/127,729, entitled SYSTEM AND METHOD FOR APPLYING ORTHOGONAL LIMITATIONS TO LIGHT BEAMS USING MICROELECTROMECHANICAL SYSTEMS, filed on Sep. 11, 2018, which is incorporated herein by reference. U.S. patent application Ser. No. 16/925,107 also a continuation-in-part of U.S. patent application Ser. No. 16/653,213, entitled SYSTEM AND METHOD FOR MULTI-PARAMETER SPECTROSCOPY, filed on Oct. 15, 2019, which is incorporated herein by reference. U.S. patent application Ser. No. 16/925,107 claims benefit of U.S. Provisional Patent Application No. 63/032,256, entitled A MINIATURIZED DEVICE TO STERILIZE SURFACES FROM COVID-19 AND OTHER VIRUSES, filed on May 29, 2020, which is incorporated herein by reference.

This application also claims priority to U.S. Provisional Patent Application No. 63/074,298, entitled A MINIATURIZED DEVICE TO STERILIZE SURFACES FROM COVID-19 AND OTHER VIRUSES AND BACTERIA, filed on Sep. 3, 2020, which is incorporated herein by reference.

TECHNICAL FIELD

The present invention relates to the detection and sterilization of viruses, and more particular to the detection and sterilization of virus using orbital angular momentum.

BACKGROUND

The spread of viruses presents a challenge to protecting individuals in a society where people live in close proximity to each other and commonly use areas in restaurants, offices, hotels and other public use facilities. The greatest challenge in these types of facilities is the sanitation of surfaces that people come in common contact with in these public and common use facilities. Current techniques involve the use of disinfectants to wipe down the commonly used surfaces and chemically kill the viruses or other biological materials on the surfaces. However, the use of disinfectants that must be wiped onto a surface can sometimes result in an incomplete disinfection since the entire surface must be touched in the physical cleaning of the surface. Additionally, areas other than surfaces must be sterilized from viruses. Thus, the ability to more completely cover the entirety of a surface or other area during the disinfection process could great help in limiting the spread of viruses or other contaminants that may be spread from contact with contaminated surfaces.

SUMMARY

The present invention, as disclosed and described herein in one aspect thereof, comprises a system for sterilizing biological material comprising beam generation circuitry for generating a radiating wave having radiating energy therein at a predetermined frequency therein. A controller controls the radiating wave generation at the predetermined frequency. The predetermined frequency equals a resonance frequency of a particular biological material and is determined responsive to a plurality of parameters from an influenza virus. The predetermined frequency induces a mechanical resonance vibration at the resonance frequency of the particular biological material within the particular biological material for destroying a capsid of the particular biological material. Radiating circuitry projects the radiating wave on a predetermined location to destroy the particular biological material at the predetermined location.

BRIEF DESCRIPTION OF THE DRAWINGS

For a more complete understanding, reference is now made to the following description taken in conjunction with the accompanying Drawings in which:

FIG. 1A illustrates the disabling of viruses using Eigen vibrations;

FIG. 1B illustrates a system for disabling viruses;

FIG. 2 illustrates the combination of charges and microwave energy to create mechanical oscillations and viruses;

FIG. 3 illustrates a Covid-19 virus;

FIG. 4 illustrates the geometry of Casper-Klug classification of viruses;

FIGS. 5A-C illustrates charge distribution on the capsid of a virus;

FIG. 6 illustrates a flow diagram of a process for providing energy to a virus;

FIGS. 7A-D illustrates different modes of Hermite-Gaussian for application to a virus;

FIG. 8 illustrates the optoacoustical generation of a helicoidal ultrasonic beam;

FIG. 9 illustrates various manners for generating a beam having orbital angular momentum applied thereto;

FIG. 10 illustrates the application of an OAM beam to a virus;

FIG. 11 illustrates the application of various OAM modes to a virus;

FIGS. 12A-B illustrates the application of different Hermite Gaussian mode signals to a virus;

FIG. 13 illustrates a patch antenna;

FIG. 14 illustrates patch antennas for providing different OAM modes;

FIG. 15 illustrates different intensity signatures provided from varying distances;

FIG. 16 is a block diagram of circuitry for applying signals to a virus to create mechanical resonance therein;

FIG. 17 illustrates a sterilization system implemented within a cell phone;

FIG. 18 illustrates a sterilization system implemented within a handheld flashlight;

FIG. 19 illustrates a sterilization system implemented within a portable light wand;

FIG. 20 illustrates a sterilization system implemented within a florescent light mounted on a ceiling;

FIG. 21 illustrates a sterilization system implemented within a florescent light mounted on a wall;

FIG. 22 illustrates a sterilization system implemented within an incandescent bulb.

FIG. 23 illustrates interaction between OAM light and graphene;

FIG. 24 illustrates a graphene lattice in a Honeycomb structure;

FIG. 25 illustrates the components of a vector beam;

FIG. 26 illustrates the use of electromagnetic waves for the transfer of energy to a virus;

FIG. 27 illustrates the use of orbital angular momentum for the transfer of energy to a virus;

FIG. 28 is a functional block diagram of a system for generating orbital angular momentum within a communication system;

FIG. 29 illustrates a single wavelength having two quanti-spin polarizations providing an infinite number of signals having various orbital angular momentums associated therewith;

FIG. 30A illustrates an object with only a spin angular momentum;

FIG. 30B illustrates an object with an orbital angular momentum;

FIG. 30C illustrates a circularly polarized beam carrying spin angular momentum;

FIG. 30D illustrates the phase structure of a light beam carrying an orbital angular momentum;

FIG. 31 illustrates a light beam having orbital angular momentum imparted thereto;

FIG. 32 illustrates a series of parallel wavefronts;

FIG. 33 illustrates a wavefront having a Poynting vector spiraling around a direction of propagation of the wavefront;

FIG. 34 illustrates a plane wavefront;

FIG. 35 illustrates a helical wavefront;

FIG. 36 illustrates a plane wave having only variations in the spin vector;

FIG. 37 illustrates the application of a unique orbital angular momentum to a wave;

FIGS. 38A-38C illustrate the differences between signals having different orbital angular momentum applied thereto;

FIG. 39A illustrates the propagation of Poynting vectors for various eigenmodes;

FIG. 39B illustrates a spiral phase plate;

FIG. 40 illustrates a block diagram of an apparatus for providing concentration measurements and presence detection of various materials using orbital angular momentum;

FIG. 41 illustrates an emitter of the system of FIG. 40;

FIG. 42 illustrates a fixed orbital angular momentum generator of the system of FIG. 40;

FIG. 43 illustrates one example of a hologram for use in applying an orbital angular momentum to a plane wave signal;

FIG. 44 illustrates the relationship between Hermite-Gaussian modes and Laguerre-Gaussian modes;

FIG. 45 illustrates super-imposed holograms for applying orbital angular momentum to a signal;

FIG. 46 illustrates a tunable orbital angular momentum generator for use in the system of FIG. 11;

FIG. 47 illustrates a block diagram of a tunable orbital angular momentum generator including multiple hologram images therein;

FIG. 48 illustrates the manner in which the output of the OAM generator may be varied by applying different orbital angular momentums thereto;

FIG. 49 illustrates an alternative manner in which the OAM generator may convert a Hermite-Gaussian beam to a Laguerre-Gaussian beam;

FIG. 50 illustrates the manner in which holograms within an OAM generator may twist a beam of light;

FIG. 51 illustrates the manner in which a sample receives an OAM twisted wave and provides an output wave having a particular OAM signature;

FIG. 52 illustrates the manner in which orbital angular momentum interacts with a molecule around its beam axis;

FIG. 53 illustrates a block diagram of the matching circuitry for amplifying a received orbital angular momentum signal;

FIG. 54 illustrates the manner in which the matching module may use non-linear crystals in order to generate a higher order orbital angular momentum light beam;

FIG. 55 illustrates a block diagram of an orbital angular momentum detector and user interface;

FIG. 56 illustrates the effect of sample concentrations upon the spin angular polarization and orbital angular polarization of a light beam passing through a sample;

FIG. 57 more particularly illustrates the process that alters the orbital angular momentum polarization of a light beam passing through a sample;

FIG. 58 provides a block diagram of a user interface of the system of FIG. 12;

FIG. 59 provides a block diagram of a more particular embodiment of an apparatus for measuring the concentration and presence of glucose using orbital angular momentum;

FIG. 60 is a flow diagram illustrating a process for analyzing intensity images;

FIG. 61 illustrates an ellipse fitting algorithm;

FIG. 62 illustrates the generation of fractional orthogonal states;

FIG. 63 illustrates the use of a spatial light modulator for the generation of fractional OAM beams;

FIG. 64 illustrates one manner for the generation of fractional OAM beam using superimposed Laguerre Gaussian beams;

FIG. 65 illustrates the decomposition of a fractional OAM beam into integer OAM states;

FIG. 66 illustrates the manner in which a spatial light modulator may generate a hologram for providing fractional OAM beams;

FIG. 67 illustrates the generation of a hologram to produce non-integer OAM beams;

FIG. 68 is a flow diagram illustrating the generation of a hologram for producing non-integer OAM beams;

FIG. 69 is a block diagram illustrating fractional OAM beams for OAM spectroscopy analysis;

FIG. 70 illustrates an example of an OAM state profile;

FIG. 71 illustrates the manner for combining multiple varied spectroscopy techniques to provide multiparameter spectroscopy analysis;

FIG. 72 illustrates a schematic drawing of a spec parameter for making relative measurements in an optical spectrum;

FIG. 73 illustrates the stretching and bending vibrational modes of water;

FIG. 74 illustrates the stretching and bending vibrational modes for $CO_2$;

FIG. 75 illustrates the energy of an anharmonic oscillator as a function of the interatomic distance;

FIG. 76 illustrates the energy curve for a vibrating spring and quantized energy level;

FIG. 77 illustrates Rayleigh scattering and Ramen scattering by Stokes and anti-Stokes resonance;

FIG. 78 illustrates circuits for carrying out polarized Rahman techniques;

FIG. 79 illustrates circuitry for combining polarized and non-polarized Rahman spectroscopy;

FIG. 80 illustrates a combination of polarized and non-polarized Rahman spectroscopy with optical vortices;

FIG. 81 illustrates the absorption and emission sequences associated with fluorescence spectroscopy;

FIG. 85 illustrates a side view of a multilayer patch antenna array;

FIG. 86 illustrates a first layer of a multilayer patch antenna array;

FIG. 87 illustrates a second layer of a multilayer patch antenna array;

Figure 100:
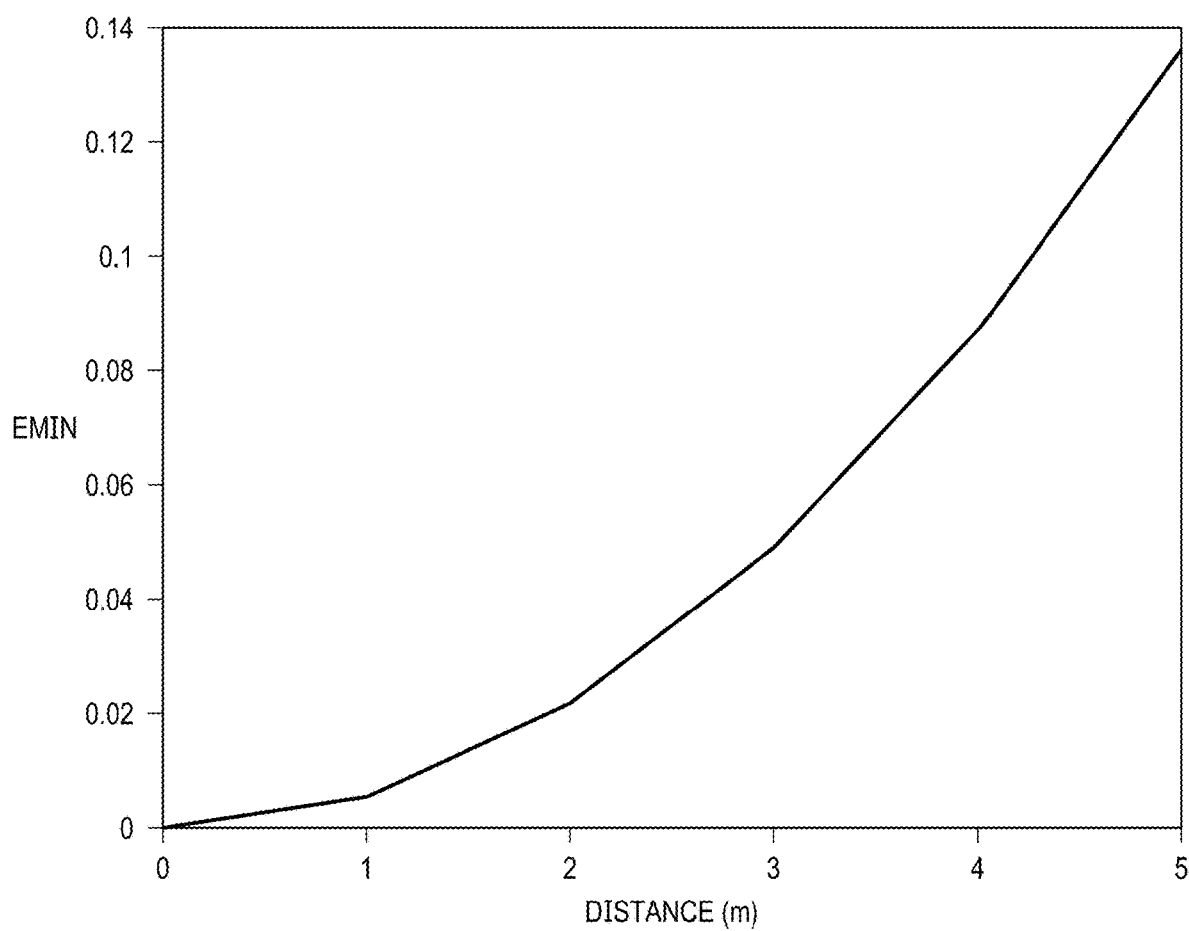
Figure 101:
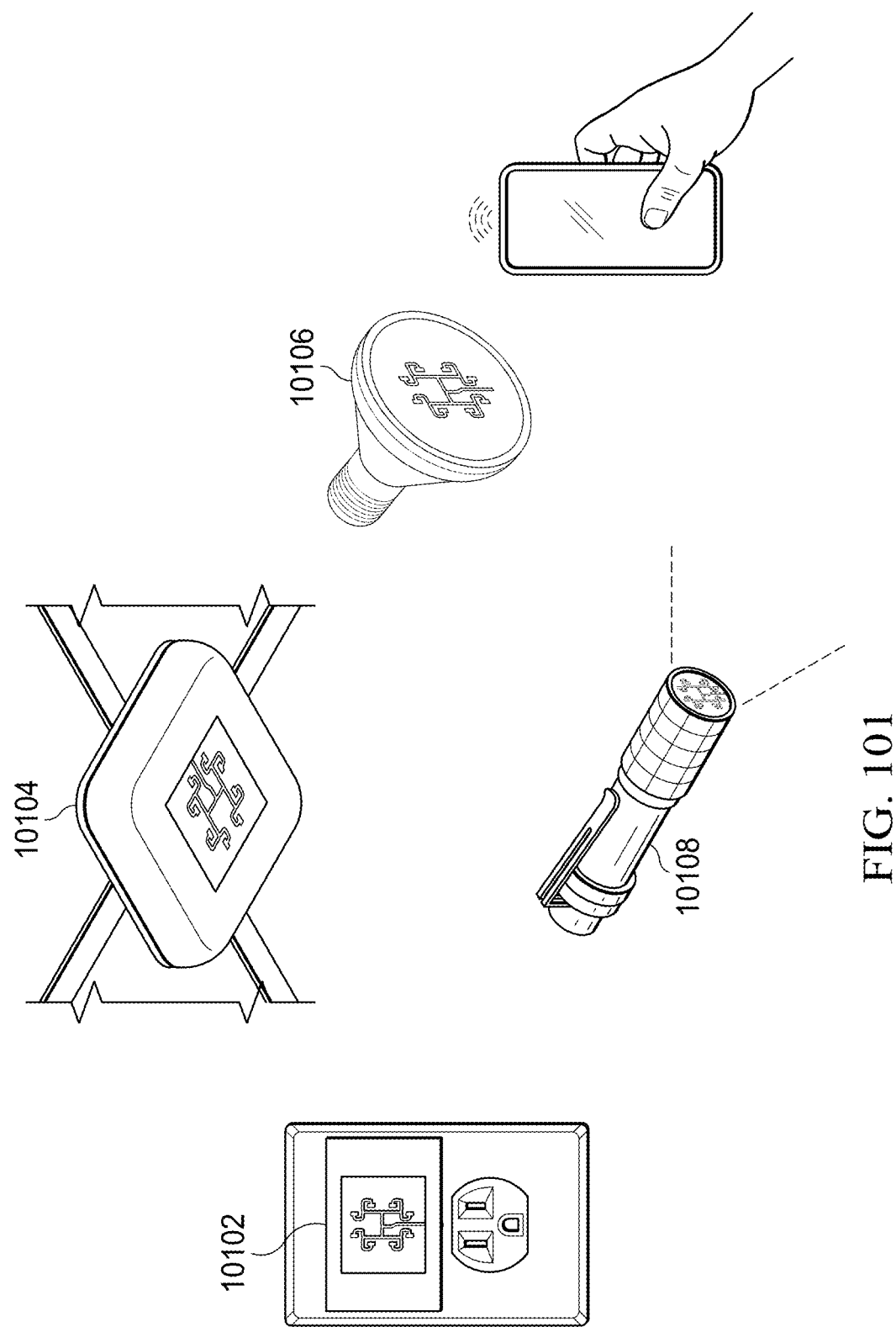

FIG. 99$a$ illustrates a plot of dE/dw versus distance;

FIG. 99$b$ illustrates a further plot of dE/dw versus distance;

FIG. 100 illustrates a plot of a minimum of electric field as a function of distance; and FIG. 101 illustrates various manners for implementing an antenna for transmitting signals to generate a residence within a virus or bacteria.

DETAILED DESCRIPTION

Referring now to the drawings, wherein like reference numbers are used herein to designate like elements throughout, the various views and embodiments of a miniaturized device to sterilize from COVID-19 and other viruses are illustrated and described, and other possible embodiments are described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

How quickly will our citizens revert to their old lifestyle patterns as our country begins to relax coronavirus related shelter-in-place guidelines? The economic wellbeing of our country turns on the answer to this question. A technology is proposed that can be embedded into different devices for the purpose of sterilizing Coronavirus (COVID-19) and other viruses and bacteria from surfaces as well as airborne spaces. If this technology is embedded into a handheld device (size of a small flashlight) or into a cell phone handset, then most of the population could use it to stop or minimize the propagation of the virus. The technology can also be embedded into fixed light fixtures to sanitize spaces without the use of harmful ionizing radiation (i.e. UVC). Though a lot of genetic information is already available about COVID-19, its physical properties are largely unknown. Identifying the physical virology information of this virus would allow us to develop safe and easy to use products that would sanitize many different environments. The required information includes: the frequency of a non-ionizing electromagnetic radiation (i.e. microwave region), the frequency of mechanical resonance, as well as stress levels needed to rupture the capsid of the virus.

The rational is that electromagnetic radiation can destroy the virus, but this radiation needs to be in a form that is entirely safe for direct human use and therefore non-ionizing. Microwave radiation can induce plasma oscillations on charge distribution of the virus, thereby creating mechanical (ultrasonic) longitudinal eigen-vibrations to rupture the capsid of the virus. In addition, this electromagnetic radiation can be a structured vector beam with Laguerre-Gaussian or Hermite Gaussian intensity so that transverse shear forces or torsion be can be imparted to the virus's icosahedral lattice structure where the frequencies are safe for humans and non-ionizing.

A theoretical model based on the size, geometry, and protein material of the virus enables identification of a range of electromagnetic frequencies needed to induce plasma oscillations on the charge distribution of the virus. The identification of the dominant frequency within the theoretical spectrum reduces trial and error experiments given the theoretical model. Aim 3 is to identify the theoretical and experimental mechanical stresses needed to rupture the capsid of the virus are identified and the frequency of the mechanical eigen-vibrations to achieve the required stresses are determined. Finally, the electromagnetic intensity required for the radiation is determined where the frequency of the radiation would match the eigen-vibrations and the intensity of the radiation would be slightly higher than the stresses needed to ensure the capsid will rupture The described technology will overcome the safety concerns regarding the use of ionizing radiations and provide an approach that will give our citizens the confidence to return to their normal routines with a simple method to sterilize surfaces and spaces from COVID-19. It also gives a greater insight into the physical virology of coronavirus, knowledge that is currently lacking and that promises to yield novel insights into virology and molecular biology. This new technology will provide a valuable resource even with respect to other viruses and bacteria with perhaps different frequencies, intensities, and modes of its structured vector beam.

A miniaturized device that can be embedded into a handheld unit (size of a small flashlight) or into a cell phone handset for sterilizing surfaces from Coronavirus (COVID-19) or other viruses/biological materials that radiates similar to flashlight on the cell phone but at a different frequency would provide a great benefit to heavy public use areas that require constant cleaning.

Inducement of Vibrations to COVID-19 and Other Viruses and Bacteria

The below described techniques for the generation Laguerre-Gaussian, Hermite-Gaussian, or Ince-Gaussian processed beams provide an improved manner for the sterilization from COVID-19 or other viruses and bacteria. The above described techniques may be used for generating a Laguerre-Gaussian, Hermite-Gaussian, or Ince-Gaussian beam that imparts resonance vibrations to the structures of COVID-19 or other viruses and bacteria in order to destroy on inactivate the virus. The circuitry for inducing the resonance may be provided in a handheld portable device similar to a flashlight or light wand or within a cell phone. Also, the circuitry can be implemented within a normal lighting fixture.

The following describes a miniaturized device that can be embedded into a handheld unit (size of a small flashlight) or into a cell phone handset for the purpose of sterilizing surfaces or areas from Coronavirus (COVID-19) or other viruses and bacteria. The objective of the device is to either kill or disable the virus. The product concept can easily extend to devices that can be plugged into the connectors of a regular lamp or fluorescent light for fixed applications. Surface areas can be illuminated for sterilizing objects as well as volumes that may contain airborne viruses.

This system also describes how energy configurations transmitted using antennas such as patch antenna arrays, horn and conical antennas can be used to sterilize surfaces or areas by transmitting signals at a given frequency. The system utilizes photonic and ultrasonic sources that could kill the viruses. As shown in FIG. 1A because viruses 102 can be disabled by inducing specific eigen vibrations 104 using safe microwaves and/or ultrasonic energy 106, this approach is quite different than using ionizing radiation (i.e. alpha, beta, gamma or even x-rays and ultraviolet). In this approach, the viruses 102 are killed by leveraging a natural sensitivity of the virus to certain resonant frequencies with a vector beam 106 specifically engineered to induce the frequency within the virus and kill the virus based on its size, structure, geometry, material (proteins) and boundary conditions. These vector beams 106 could take the form of Laguerre-Gaussian, Hermite-Gaussian, or Ince-Gaussian in both electromagnetic as well as ultrasonic waves to induce torsional, shear and longitudinal vibrations 104 to rupture the capsid of the virus 102. These beams can also be manually focused to increase the power density of the field for sterilizing keys, door handles or other objects.

Referring now to FIG. 1B, there is illustrated a general block diagram of a system for disabling a virus as discussed in FIG. 1A. The particular details of the system will be more fully described herein below. A system 110 for sterilizing viruses includes beam generation circuitry 114. The beam generation circuitry 114 for generates a radiating wave beam 116 having radiating energy therein at a predetermined frequency therein. A controller 118 controls the radiating wave beam to be generated at the predetermined frequency. The predetermined frequency equals a resonance frequency of a specific virus 120. The predetermined frequency induces a mechanical resonance vibration at the resonance frequency of the specific virus within the virus 120. The induced mechanical resonance vibration destroys a capsid of the particular virus 120 and destroys the virus. Radiating circuitry 122 projects the radiating wave on a predetermined location to destroy the particular virus 120 at the predetermined location.

Introduction

Three models have been developed for mechanical resonance of different geometries as described in S. Ashrafi, et al. "Spurious Resonances and Modeling of Composite Resonators," *IEEE Proceedings of the* 37*th Annual Symposium on Frequency Control,* 1983 which is incorporated herein by reference. The first model was a one-dimensional model that could predict the principal resonances of a given geometry but failed to account for spurious resonances which were observed experimentally. The two-dimensional model showed a refinement to predict the qualitative structure of the spectrum. However, a three-dimensional model not only predicted the dominant resonances, but it also predicted the spurious resonances of the geometry.

A model was also developed to predict the eigen-vibrations of an elastic body which could be traced to the excitation of circumferential waves in S. Ashrafi, et al. "Acoustically Induced Stresses in Elastic Cylinders and Their Visualization," *J. Acoust. Soc. Am.* 82 (4), October 1987 which is incorporated herein by reference. These waves propagate along the surface of the body, inside the body material, and partly also in ambient medium. In fact, an energy transfer from acoustic, ultrasonic, or mechanical waves to electromagnetic birefringence was shown. These birefringence patterns are different for different geometries (i.e. cylindrical, spherical, etc.)

A new property of photons related to electromagnetic (EM) vortices that carry orbital angular momentum (OAM) have been leveraged to detect certain molecules or tumors and also use such vectors beams to destroy or break up the molecules as described in A. Siber, et al. "Energies and pressures in viruses: contribution of nonspecific electrostatic interactions," *Phys. Chem. Chem. Phys.,* 2012, 14, 3746-3765; A. L. Bozic, et al. "How simple can a model of an empty viral capsid be? Charge distributions in viral capsids," *J Biol Phys.* 2012 September; 38(4): 657-671; S. Ashrafi, et al. "Recent advances in high-capacity free-space optical and radio-frequency communications using orbital angular momentum multiplexing," *Royal Society Publishing, Phil. Trans. R. Soc. A*375:20150439, Oct. 13, 2016; S. Ashrafi, et al. "Performance Metrics and Design Parameters for an FSO Communications Link Based on Multiplexing of Multiple Orbital-Angular-Momentum Beams," *Globecom*2014 *OWC Workshop,* 2014; S. Ashrafi, et al. "Optical Communications Using Orbital Angular Momentum Beams," Adv. Opt. Photon. 7, 66-106, *Advances in Optics and Photonic,* 2015; S. Ashrafi, et al. "Performance Enhancement of an Orbital-Angular-Momentum-Based Free-Space Optical Communication Link through Beam Divergence Controlling," *OSA,* 2015; S. Ashrafi, et al. "Link Analysis of Using Hermite-Gaussian Modes for Transmitting Multiple Channels in a Free-Space Optical Communication System," *The Optical Society, Vol.* 2, *No.* 4, April 2015; S. Ashrafi, et al. "Performance Metrics and Design Considerations for a Free-Space Optical Orbital-Angular-Momentum-Multiplexed Communication Link," *OSA, Vol.* 2, *No.* 4, April 2015; S. Ashrafi, et al. "Demonstration of Distance Emulation for an Orbital-Angular-Momentum Beam," *OSA,* 2015; S. Ashrafi, et al. "Free-Space Optical Communications Using Orbital-Angular-Momentum Multiplexing Combined with MIMO-Based Spatial Multiplexing," *Optics Letters,* 2015, each of which are incorporated herein by reference.

Vector beams have been used for advanced spectroscopy with specific interaction signatures with matter as described in S. Ashrafi, et al. "Orbital and Angular Momentum Multiplexed Free Space Optical Communication Link Using Transmitter Lenses," *Applied Optics, Vol.* 55, *No.* 8, March 2016; S. Ashrafi, et al. "Experimental Characterization of a 400 GBit/s Orbital Angular Momentum Multiplexed Free Space Optical Link Over 120 m," *Optics Letters,* 2016, which are incorporated herein by reference. We further studied OAM light-matter interactions using such vector beams as well as photon-phonon interaction with detailed interaction Hamiltonians have also been studied as described in S. Ashrafi, et al. "Orbital and Angular Momentum Multiplexed Free Space Optical Communication Link Using Transmitter Lenses," *Applied Optics, Vol.* 55, *No.* 8, March 2016; S. Ashrafi, et al. "Experimental Characterization of a 400 GBit/s Orbital Angular Momentum Multiplexed Free Space Optical Link Over 120 m," *Optics Letters,* 2016; S. Ashrafi, et al. "Demonstration of OAM-based MIMO FSO link using spatial diversity and MIMO equalization for turbulence mitigation," *Optical Fiber Conf; OSA* 2016, which are incorporated herein by reference.

Though earlier work has covered the transfer of energy from acoustic or ultrasonic waves to electromagnetic birefringence, the current system describes a reverse of the earlier work so that electromagnetic waves are incident on specific geometries (i.e. viruses) 102 and mechanical eigen-vibrations 104 are induced on the virus to destroy it 108. Our radiated vector beams 106 can also carry OAM to impart mechanical torque to the virus structure as well as possible UVC at powers that are safe for short periods of time.

Methodology

The methodology used in this system leverages previous published papers and patents and add new approaches and unique ingredients for sterilizing surfaces, volumes, and objects from COVID-19 or other viruses and bacteria. The uses the techniques described in the above mentioned S. Ashrafi, et al. "Spurious Resonances and Modeling of Composite Resonators," IEEE Proceedings of the 37$^{th}$ Annual Symposium on Frequency Control, 1983 and S. Ashrafi, et al. "Acoustically Induced Stresses in Elastic Cylinders and Their Visualization," *J. Acoust. Soc. Am.* 82 (4), October 1987. The methodology also uses techniques involving structured vector beams with Laguerre-Gaussian (LG), Hermite-Gaussian (HG), Ince-Gaussian (IG) as well as orthogonal Spheroidal structures for both electromagnetic and ultrasonic waves. On the electromagnetic beams the systems include frequencies from radio frequencies to higher millimeter waves to microwaves all the way to infrared (IR), visible light and ultraviolet (UV); techniques on vector beams with LG structure that carry Orbital Angular Momentum (OAM) or Fractional OAM with IR that uses absorption due to vibration (changes of dipole moment/Polarization); techniques on vector beams with LG structure that carry Orbital Angular Momentum (OAM) or Fractional OAM with Rayleigh and Raman spectroscopy; techniques on vector beams with LG structure that carry Orbital Angular Momentum (OAM) or Fractional OAM with IR spectroscopy that can have certain vibrational modes forbidden in IR with better signal/noise ratio; techniques on vector beams with LG structure that carry Orbital Angular Momentum (OAM) or Fractional OAM with Spontaneous, Stimulated, Resonance and Polarized Raman; techniques on vector beams with LG structure that carry Orbital Angular Momentum (OAM) or Fractional OAM with Tera Hertz (THz) Spectroscopy; techniques on vector beams with LG structure that carry Orbital Angular Momentum (OAM) or Fractional OAM with Fluorescence Spectroscopy; techniques on vector beams with LG structure that carry Orbital Angular Momentum (OAM) or Fractional OAM with pump & probe for Ultrafast Spectroscopy; techniques on vector beams with LG structure that carry Orbital Angular Momentum (OAM) or Fractional OAM with pump & probe for Ultrafast Spectroscopy; techniques on detection, tomography and destruction of tumors using structured beams; techniques on focusing structured vector beams; techniques on application of horn, conical and patch antennas for creation of structured beams; techniques on photon-phonon interactions; techniques on light-matter interaction; techniques on interaction Hamiltonians for quantum dots (This may allow finding of a method for making quantum dots of any size to either couple the virus to a quantum dot or encapsulating a fluorescent quantum dot inside a virus which will allow scientists a better understand physical virology and new ways to prevent viral infection.); techniques on Interaction Hamiltonian of LG beams with Graphene lattice. The honeycomb lattice of Graphene is a hexagonal lattice with primitive vectors that very much look like the Casper-Klug (CK) vectors for describing the hexamer structure for capsomers on the capsid of the virus. This enables building of a synthetic capsid lattice out of graphene for multiple purposes.

Approach

Mechanical properties of viruses have been studied experimentally using Atomic Force and Electron Microscopy (AFM). Also, mechanical, elastic, and electrostatic properties of viruses have been studied by several scientists. It was observed that under certain physiological conditions, virus capsid assembly requires the presence of genomic material that is oppositely charged to the core proteins. There is also some work on the possibility of inducing photon-phonon interactions in viruses.

Referring now to FIG. 2, the resonance phenomenon of the viruses is due to separation of positive-negative electric charges 102 on the body of the virus particles and the coupling of microwave energy 104 through the interaction with the three dimensional bipolar electric charges distributions, generating mechanical oscillations 106 at the same frequency. At specific microwave frequencies depending on the diameter and other properties of the virus, primarily the dipole acoustic mode, can be purposed as a mechanism to induce eigen-vibrations to viruses and kill them. The phenomenon here is of non-thermal nature related to non-ionizing radiation. Raman scattering phenomena should be able to show the existence of acoustic-mechanical resonance phenomena in viruses.

For the Covid-19 global pandemic, it is difficult to open the society from quarantine unless there is a way to sterilize spaces such as public venues, hospitals, clinics, commercial buildings, restaurants . . . etc. This can be done by large devices for big commercial use as well as small handheld unit (size of a small flashlight) or embedded into a cell phone handset for consumer use.

Current airborne virus epidemic prevention used in public space includes strong chemicals, UV irradiation, and microwave thermal heating. All these methods affect the open public. However, we know that ultrasonic energy can be absorbed by viruses. Viruses can be inactivated by generating the corresponding resonance ultrasound vibrations of viruses (in the GHz). Several groups started investigating the vibrational modes of viruses in this frequency range. The dipolar mode of the acoustic vibrations inside viruses can be resonantly excited by microwaves of the same frequency with a resonant microwave absorption effect. The resonance absorption is due to an energy transfer from electromagnetic waves to acoustic vibration of viruses. This is an efficient way to excite the vibrational mode of the whole virus structure because of a 100% energy conversion of a photon into a phonon of the same frequency, but the overall efficiency is also related to the mechanical properties of the surrounding environment. We would like the energy transfer from microwave to virus vibration be just enough to kill the virus while microwave power density be safe in open public places.

Induced stress (vibrations) on the virus can fracture its structure and the microwave energy needed is to achieve the virus inactivation threshold. These thresholds can be identified for different viruses at different microwave power densities.

Higher inactivation of viruses can be achieved at the dipolar resonant frequency. It is also important that at the resonant frequency, the microwave power density threshold for virus inactivation is below the IEEE safety standard. The main inactivation mechanism is through physically fracturing the viruses while the RNA genome is not degraded by the microwave illumination, supporting the fact that this approach is fundamentally different from the microwave thermal heating effect.

Framework

Referring now to FIG. 3, COVID-19 is a spherical shape virus with diameter of 100 nm. Since the protein and genome have similar mechanical properties, for the estimation of dipolar vibration frequencies, the virus can be treated as a homogenous sphere.

The virus has four structural proteins, known as the S (spike) 304, E (envelope) 306, M (membrane) 308, and N (nucleocapsid) proteins 310. The N protein 310 holds the RNA genome, and the S protein 304, E protein 306, and M protein 308 together create the viral envelope. The spike protein 304, which has been imaged at the atomic level using cryogenic electron microscopy, is the protein responsible for allowing the virus to attach to and fuse with the membrane of a host cell. The envelope, composed mainly of lipids 312, which can be destroyed with alcohol or soap There is quantization of certain physical parameters in both quantum mechanics as well as classical mechanics due to boundary conditions. Such quantization is seen in quantum dots and nanowires. In 1882, Lamb studied the torsional and spheroidal modes of a homogeneous sphere by considering thestress-free boundary condition on the surface. Among these modes, the SPH mode with $\ell=1$ allows dipolar coupling and the corresponding eigenvalue equation can be expressed as:

$$4\frac{j_2(\xi)}{j_1(\xi)}\xi - \eta^2 + 2\frac{j_2(\eta)}{j_1(\eta)}\eta = 0$$

where $$\xi = \frac{\omega_0 R}{V_L} \quad \eta = \frac{\omega_0 R}{V_T}$$

$j_\ell$=spherical Bessel function
$\omega_0$=angular frequency of vibrational mode
R=Radius of virus (i.e. 100 nm)
$V_L$=longitudinal mechanical velocity
$V_T$=Transverse mechanical velocity
$\ell=0$ breathing mode
$\ell=1$ dipolar mode
$\ell=2$ quadrupole mode When a resonantly oscillating electric field is applied to the nano-sphere, opposite displacement between core and shell can be generated and further excite the dipolar mode vibrations. Dipole mode is the only spherical mode to directly interact with the EM waves with wavelength much longer than the virus size. Due to the permanent charge separation nature of viruses, dipolar coupling is the mechanisms responsible for microwave resonant absorption in viruses by treating spherical viruses as homogeneous nanoparticles.

Electromagnetic-Mechanical Lorentz-Type Model

Let's describe the virus as a sphere with charge distribution and apply a damped mass-spring model.

$m_*\ddot{x}+m_*\gamma\dot{x}+kx=0$ $m_*$=effective mass

If damping=0
Then $x(t)=A_0 \sin(\omega_0 t)+B_0 \cos(\omega_0 t)$

Or $$x(t) = X_0 \cos(\omega t - \phi) \quad \omega_0 = \sqrt{\frac{k}{m}}$$

Now when we put this virus in an external $\vec{E}$ electric field of microwave frequency, we have $m_*\ddot{x}+m_*\gamma\dot{x}+kx=qE$ $E=E_0 \cos(\omega t)$ Using Laplace transform, the solution would be $x(t)=X_0 \cos(\omega t-\phi)$ Where $$X_0 = \frac{qE_0}{m_*\sqrt{(\omega_0^2-\omega^2)^2-\left(\frac{\omega_0\omega}{Q}\right)^2}} \quad \text{and} \quad \tan\phi = \frac{\omega_0\omega}{Q(\omega_0^2-\omega^2)}$$

Because of damping the decay rate of oscillation is equal to the imaginary part of the frequency $$\frac{\omega_0}{2Q} = \frac{m_*\gamma}{2m_*} \quad m_*\gamma = \frac{\omega_0 m_*}{Q}$$

If $x(t)=X_0 e^{i\omega t}$ $\dot{x}(t)=i\omega X_0 e^{i\omega t}$ $\ddot{x}(t)=(i\omega)^2 X_0 e^{i\omega t}=-\omega^2 x(t)$ Therefore $m_*\ddot{x} + m_*\gamma\dot{x} + kx = q\vec{E}$ $-m_*\omega^2 x(t) + m_*\gamma(i\omega)x(t) + kx(t) = q\vec{E}$ $-m_*\omega^2 x + im_*\omega\gamma x + kx = qE$ $x(t) = X_0 \cos(\omega t + \phi)$ $$\omega = \frac{im_*\gamma \pm \sqrt{-(m_*\gamma)^2 + 4km_*}}{2m_*}$$

The power absorption of this $P_{abs}=qEv-qE_0 \cos(\omega t)X_0\omega \sin(\omega t-\phi)$ Therefore, for one full cycle we have $$\langle P_{abs}\rangle = \frac{1}{2}\frac{Q(qE_0)^2\omega_0\omega^2}{Q^2 m_*(\omega_0^2-\omega^2)^2+(\omega_0\omega)^2 m_*} = \frac{\omega_0\omega^2 m_* X_0^2}{2Q}$$

The absorption cross-section of the virus $$\sigma_{abs} = \frac{\langle P_{abs}\rangle}{powerflux}$$

Let's try to breakup the outer layer (may be the lipid membrane of the envelope protein)

Estimate the Max Induced Stress $$stress_{max} = \frac{F_{max}^{induced}}{\text{Area of shell}}$$

Let's assume maximum induced stress=α average and the shell covers β% of equatorial plane $$stress_{max} = \frac{\alpha k X_0}{\beta \pi r^2} = \frac{\alpha}{\beta} \frac{m_* \omega_0^2 X_0}{\pi r^2} = \frac{\alpha}{\beta} \frac{m_* \omega_0^2}{\pi r^2} \frac{qE_0}{\sqrt{m_*^2(\omega_0 - \omega^2)^2 + \left(\frac{\omega_0 m_*}{Q}\right)^2 \omega^2}}$$

Therefore, if the stress is known experimentally from UTSW then the intensity of microwave can be found to be $$E_0 = (stress_{max}) \frac{\beta}{\alpha} \frac{\pi r^2 \sqrt{m_*^2(\omega_0^2 - \omega^2)^2 + \left(\frac{\omega_0 m_*}{Q}\right)^2 \omega^2}}{q m_* \omega_0^2}$$

$$m_* \ddot{x} + m_* \gamma \dot{x} + m_* \omega_0^2 x = q\vec{E}$$

$$\ddot{x} + \gamma \dot{x} + \omega_0^2 x = \frac{q}{m_*} E$$

$E \alpha e^{i\omega t}$ time variation $$-\omega^2 x + j\omega \gamma x + \omega_0^2 x = \frac{q}{m_*} E \quad x[-\omega^2 + j\omega \gamma + \omega_0^2] = \frac{q}{m_*} E$$

$$x = \frac{q}{m_*} \frac{1}{(\omega_0^2 - \omega^2) + j\omega \gamma} E$$

Since charge displacement $x(t) \alpha$ polarization $\vec{P}$ $$\vec{D} = \epsilon_0 \vec{E} + \vec{P} \quad P_x = Nqx$$

$$\left(\frac{d}{dt^2} + \gamma \frac{d}{dt} + \omega_0^2\right) P_x(t) = \frac{Nq^2}{m_*} E(t) = \epsilon_0 \omega_p^2 E(t)$$

$$\omega_p^2 = \frac{Nq^2}{\epsilon_0 m_*}$$

$$P_x = \frac{\omega_p^2}{(\omega_0^2 - \omega^2) + j\gamma\omega} \epsilon_0 E \quad D = \epsilon_0 E + P$$

$$\epsilon = \epsilon_0 \left[1 + \frac{\omega_p^2}{(\omega_0^2 - \omega^2) + j\gamma\omega}\right]$$

$$\epsilon = \epsilon_r - j\epsilon_i$$

Most viruses are composed of lipids, proteins, and genomes. Here are some things known about some of the viruses:
Most lipids, $V_L$=1520 m/s
Most proteins, $V_L$=1800 m/s
Most genomes, $V_L$=1700 m/s
Due to the fact that most viruses have highly compressed genomes and their capsid proteins have strong tension, the effective $V_L$ of a total virus should thus be on the order of 1500-2500 m/s if the virus does not have a soft envelope. Using the information above, the frequency of the [SPH, l=1, n=0] mode for a 100 nm spherical virus to be tens of GHz can be estimated.

Higher order modes (i.e. SPH, l=1, n=1) may also be observed in the microwave resonance absorption spectra at twice the frequency of dipole [SPH, l=1, n=0] mode, but at lower amplitude because dipole mode is a stronger coupling.
The torsional modes which are orthogonal to the spheroidal modes are purely transverse in nature and independent of the material property.
The torsional modes are defined for $\ell \geq 1$
The spheroidal modes are characterized by $\ell \geq 0$
$\ell = 0$ is the symmetric breathing mode (purely radial and produces polarized spectra)
$\ell = 1$ is the dipolar mode
$\ell = 2$ is the quadrupole mode (produces partially depolarized spectra)
Spheroidal modes for even l (i.e., $\ell = 0$ and $\ell = 2$) are Raman active
The lowest eigenfrequencies for n=0 for both spheroidal ($\ell \geq 0$) and torsional ($\ell \geq 0$) modes correspond to the surface modes
The lowest eigenfrequencies for n=1 for both spheroidal ($\ell \geq 0$) and torsional ($\ell \geq 0$) modes correspond to inner modes.

Lab Experiments

To identify the mechanical vibrations, Microwave Resonance spectral measurements on the viruses are performed. To do that the prepare viruses are prepared in a manner where they are cultured, isolated, purified, and then preserved in phosphate buffer saline liquids at PH of 7.4 at room temperature. In each measurement, one microliter viral solution is taken by a micropipette and uniformly dropped on a coplanar waveguide apparatus. The guided microwaves should be incident on the virus-containing solution. The reflection $S_{11}$ and transmission $S_{21}$ parameters are recorded simultaneously using a high bandwidth network analyzer (one that can measure from few tens of MHz to tens of GHz). The microwave attenuation spectra can be evaluated by $|S_{11}|^2 + |S_{21}|^2$. The attenuation spectrum of the buffer liquids is also measured with the same volume on the same device to compare the attenuation spectra of the buffer solutions with and without viruses, and deduce the microwave attenuation spectra of the viruses and identify the dominant resonance and spurious resonances of the specific virus.

Charge Distribution

There are electrostatic interactions in the virus due to the ionic atmospheres surrounding the viruses. Virus architecture, cell attachment, and other features are dependent on interactions between and within viruses and other structural components.

The charges of the amino acids on the surface of the capsomeres are known. However, to describe any charge distribution, the spatial region in which such a distribution resides must be identified and then quantify its geometry via multipolar moments. This minimal set of parameters includes the average size and thickness of the capsid, the surface charge density, and surface dipole density magnitude of the charge distribution.

There are two simple models most widely used: a single, infinitely thin charged shell of radius $R_M$ and surface charge density σ, and two thin shells of inner and outer radius $R_{in}$ and $R_{out}$ (giving a capsid thickness of $\delta_M = R_{out} - R_{in}$), carrying surface charges of $\sigma_{in}$ and $\sigma_{out}$. These are referred to as the single-shell and double-shell model, respectively. Besides the monopole (total) charge distribution, the dipole distribution on such model capsids can also be considered. Gaussian surfaces within and outside of the virus may be used to calculate the electric field inside and outside of the virus.

Electrostatic interactions are responsible for the assembly of spherical viral capsids. The charges on the protein subunits that make the viral capsid mutually interact and induce electrostatic repulsion acting against the assembly of capsids. Thus, attractive protein-protein interactions of non-electrostatic origin must act to enable the capsid formation. The interplay of repulsive electrostatic and attractive interactions between the protein subunits result in the formation of spherical viral capsids of a specific radius. Therefore, the attractive interactions must depend on the angle between the neighboring protein subunits (i.e. on the mean curvature of the viral capsid) so that specific angles are preferred imposed.

Viruses can be useful, and it is possible that there are no forms of life immune to the effect of viruses, which may be advantageous in the fight against diseases caused by microorganisms susceptible to viruses, such as bacteria. There are even viruses that initiate their "lifecycle" exclusively in combination with some other viruses and bacteria, often "stealing" the protein material of those viruses and diverting the cellular processes they initiated to their own advantage. The viruses are thus parasites even of their own kind. Although the exact nature (the shape and the genome) of only about a hundred viruses are known, it seems that they are almost as diverse as life itself. The viruses are then only a truncated, indexed, crippled representation of life and they can barely be classified as life. To a physicists or virologists, they are hetero-macromolecular complexes (complexes of viral proteins and the genome molecule DNA or RNA) that are reasonably stable in extra-cellular conditions and that initiate a complicated sequence of molecular interactions and transformations once they enter a cell. Therefore, a virus must somehow "encode" the crucial steps of its replication process based on its structure. For example, the proteins that make its protective shell (virus capsid) must have such geometric/chemical characteristics as to activate the appropriate receptors on the cell membrane so that they can attach to and penetrate its interior. The virus needs to be sufficiently stable in the extracellular conditions, yet sufficiently unstable once it enters the cell, so that it can disassemble and deliver its genome molecule to the cellular replication machinery. Once it fulfills walking this tightrope of emerging instability, the manufacturing of virus components in the cell proceeds, leading eventually to new viruses. In this view, virus has a structure in terms of the electrostatic and statistical mechanics of interactions. The major contribution to the energy of protein-genome packaging is of electrostatic nature.

As described above with respect to FIG. 3, all viruses are made of two essential parts: protein coating or a capsid and viral genome (of DNA or RNA type) situated in the capsid interior. There are also viruses that in addition to these two essential components need an additional "wrapper", i.e. a piece of cellular membrane, to function properly and fuse with the cellular membrane surface. These viruses are referred to as enveloped (in contrast to non-enveloped viruses which do not have a membrane coating). Because of restrictions on the length of their genome encoding the viral shell proteins, the virus capsids are made of many copies of one or at most a few types of proteins which are arranged in a highly symmetrical manner.

Spherical viruses, also called icosahedral viruses, show mostly icosahedral order and the proteins that make them can be arranged in the clusters of five (pentamers) or six (hexamers). This arrangement may be only conceptual but may also have a physical meaning that the interactions in clusters (capsomeres) are somewhat stronger than the interactions between the clusters (Caspar-Klug CK classification). Crick and Watson concluded that nearly all viruses can be classified either as nearly spherical, i.e. of icosahedral symmetry, or elongated of helical symmetry.

Referring now to FIG. 4, there is illustrated the geometry behind the Caspar-Klug (CK) classification of viruses. Icosahedral viruses that obey the CK principle can be "cut out" of the lattice of protein hexamers 402, as shown in FIG. 4. Upon folding of the cut-out piece, twelve of protein hexamers are transformed in pentamers. The CK viruses are described with two integers, h=2 and k=1 in the case shown, which parametrize the vector A 404. The T-number of the capsid is related to h and k as $T=h^2+hk+k^2$, and the number of protein subunits is 60T. The bottom row of images displays the CK structures with T=3, 4, 7, and 9 (from left to right).

Icosahedral viruses tend to look more polyhedral when larger. There are also non-icosahedral viruses that do not fit in the CK classification. For example, capsids of some bacteriophages (viruses that infect only bacteria) are "elongated" (prolate) icosahedra. Capsids of some plant viruses are open and hollow cylinders and their genome molecule is situated in the empty cylindrical space formed by proteins. HIV virus is also non-icosahedral but is not an elongated icosahedron. Its capsid looks conical, being elongated and narrower on one side. Furthermore, even when the viruses are spherical, it is sometimes difficult to classify them according to the CK scheme and the typical pentamer-hexamer ordering is not obvious. Non-icosahedral capsids can be observed in experiments as kinetically trapped structures, also second-order phase transitions on spherical surfaces allowed scientists to also classify those capsids that do not show a clear pentamer-hexamer pattern. A classification scheme based on the notion that the simplest capsid designs are also the fittest resulted in found in numerical simulations. Some viruses are multi-layered, i.e. they consist of several protein capsids each of which may be built from different proteins. Each of these capsid layers may individually conform to the CK principle. Alternatives to the CK classification have recently been proposed that apparently contain the CK shapes as the subset of all possible shapes. Application of the Landau theory of a "periodic table" of virus capsids that also uncovers strong evolutionary pressures. One of the consequences of icosahedral symmetry is that it puts restrictions on the number of proteins that can make up a spherical virus shell. It limits this number to 60 times the structural index T that almost always assumes certain "magic" integer values T=1, 3, 4, 7, . . . . There is a certain universality in the size of capsid proteins.

By analyzing more than 80 different viruses (with T numbers from 1 to 25), scientists have found that the area of a protein in a capsid is conserved and amounts to 25 nm². The thickness of the protein, i.e. the thickness of the virus capsid in question varies more but is typically in the interval 2 to 5 nm. The "typical" virus protein can thus be imagined as a disk/cylinder (or prism) of mean radius 3 nm and thickness/height 3 nm. In some viruses these "disks" have positively charged protein "tails" that protrude in the capsid interior and whose role is to bind to a negatively charged genome molecule (typically ssRNA). There is some universality in the distribution of charges along and within the virus capsid.

Figure 5C:
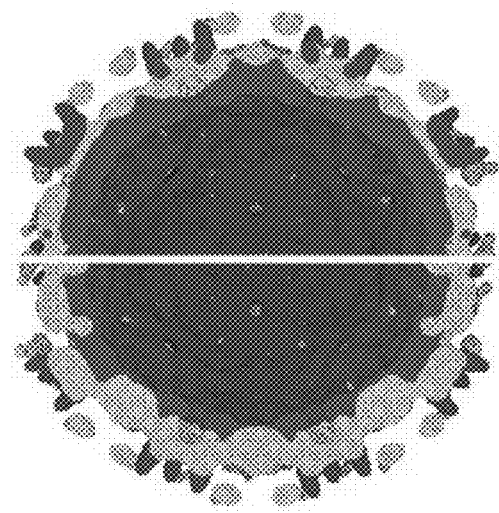
Figure 5B:
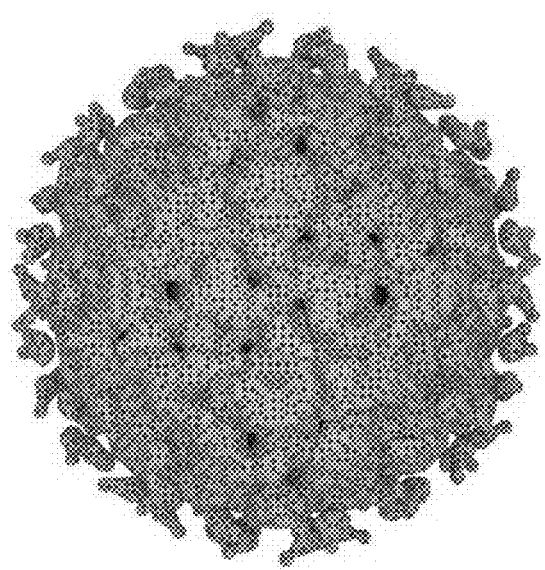
Figure 5A:
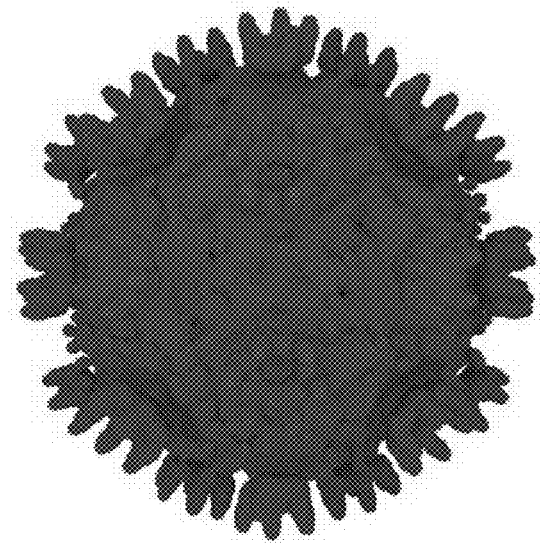

Referring now to FIG. 5, the calculated representation of the charge distribution on the capsid of a virus (ssRNA): (a) the isosurface of positive charge (single color pigment); (b) the isosurface of negative charge (dotted pattern) and (c) the combined isosurfaces of positive and negative charges shown in the capsid cut in half so that its interior is seen. On the left-hand side of the image in panel (c) (the left of the white vertical line), the (cut) isosurface of negative charge (dotted pattern) is translated infinitesimally closer to the viewer, while it is the opposite on the right-hand side of the image.

While Caspar-Klug dipoles corresponding to a bimodal distribution of positive charges on the inside and negative charges on the outside of the capsid can be observed, but this is certainly not a rule as mono-modal, distributions can also be observed. The in-plane angular distribution of charges along the capsid thickness also shows complicated variations within the constraints of the icosahedral symmetry group. Finally, the magnitude of the charges on the surface of the capsomeres is regulated by the dissociation equilibrium while for the buried charges it would have to be estimated from quantum chemical calculations. The virus genome molecule codes for the proteins of the capsid, but also for other proteins needed in the process of virus replication, depending on a virus in question. ssRNA viruses need to code for protein that replicates the virus ssRNA and some viruses also encode the regulatory proteins that are required for correct assembly and the proteins required for release of viruses from the infected cell. The amount of information that is required constrains the length of the genome molecule.

Besides their efficient assembly mechanism, viruses also present unique mechanical properties. During the different stages of infection, the viral capsid undergoes changes switching from highly stable states, protecting the genome, to unstable states facilitating genome release. Thus, capsids play a major role in the viral life cycle, and an understanding of their meta-stability and conformational plasticity is key to deciphering the mechanisms governing the successive steps in viral infection. In addition, viral mechanical properties, such as elasticity/deformability, brittleness/hardness, material fatigue, and resistance to osmotic stress, are of interest in many areas beyond virology; for instance, soft matter physics, (bio)nanotechnology, and nanomedicine.

In the simplest scenario of capsid formation, the functional capacity to self-assemble resides in the primary amino acid sequence of the capsid proteins (CPs) and, hence, the folded structure of the viral protein subunits. Thus, the assembly process is solely driven by protein-protein and, for co-assembly with viral nucleic acids, protein-genome interactions. The probability of formation of a highly complex structure from its elements is increased, or the number of possible ways of doing it diminished, if the structure in question can be broken down in a finite series of successively smaller substrates. One of the main challenges of this process is that all viral proteins must encounter and assemble in the crowded environment of cells, where ~200 mg/mL of irrelevant, cellular, proteins are present. An additional challenge to capsid formation is the fact that the packaging must be selective to encapsidate the viral genome, discriminating between cellular and viral genetic material, thus ensuring infectivity. Clearly, viruses have found strategies to overcome these challenges, and recent literature has reviewed different aspect of viral assembly.

Figure 7A:
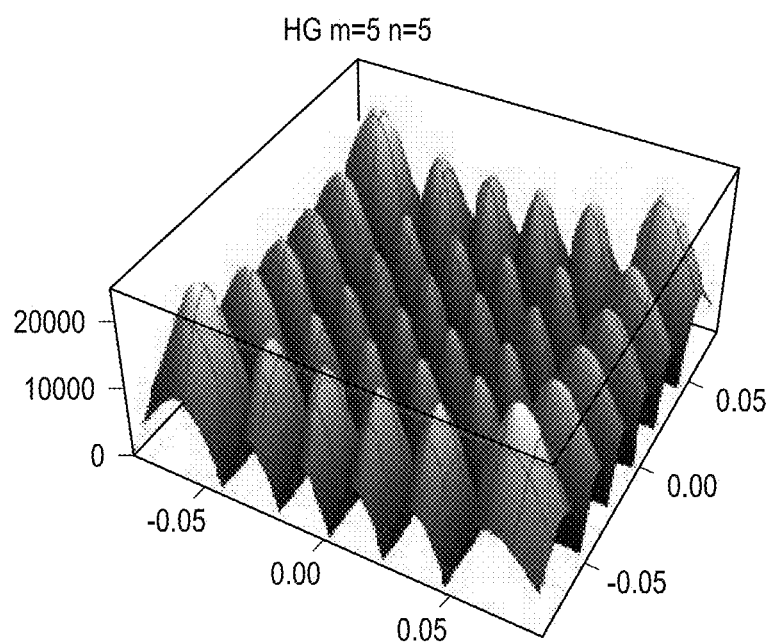
Figure 7B:
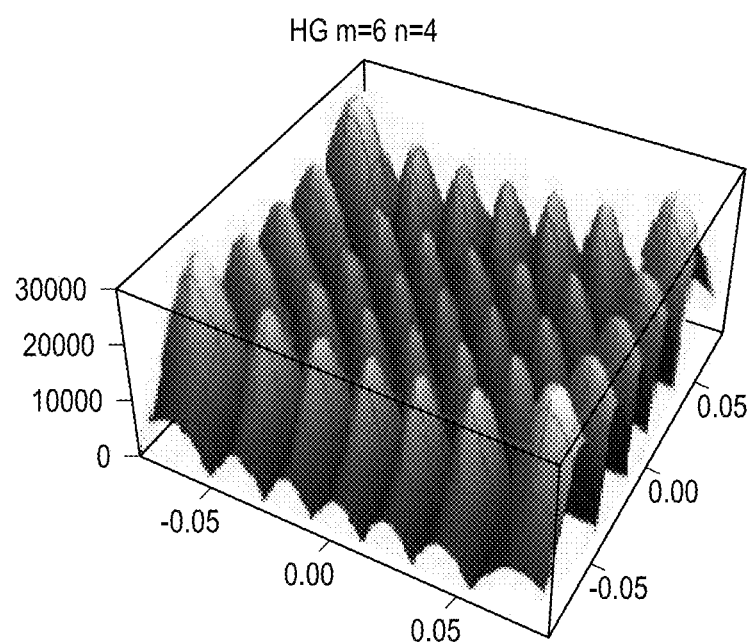
Figure 7C:
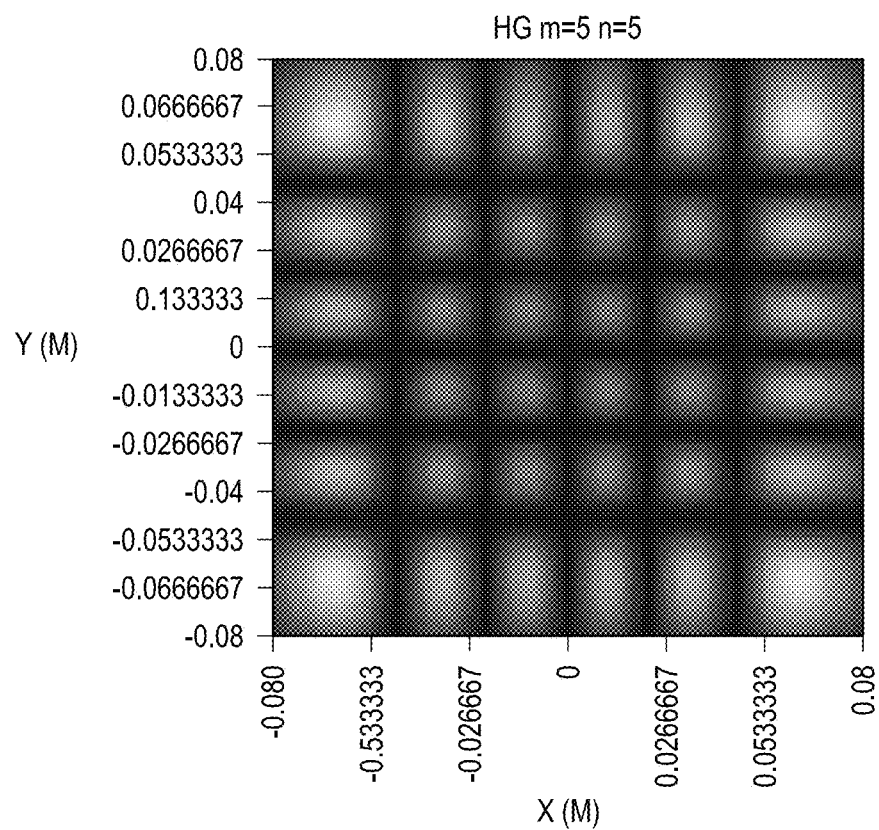
Figure 7D:
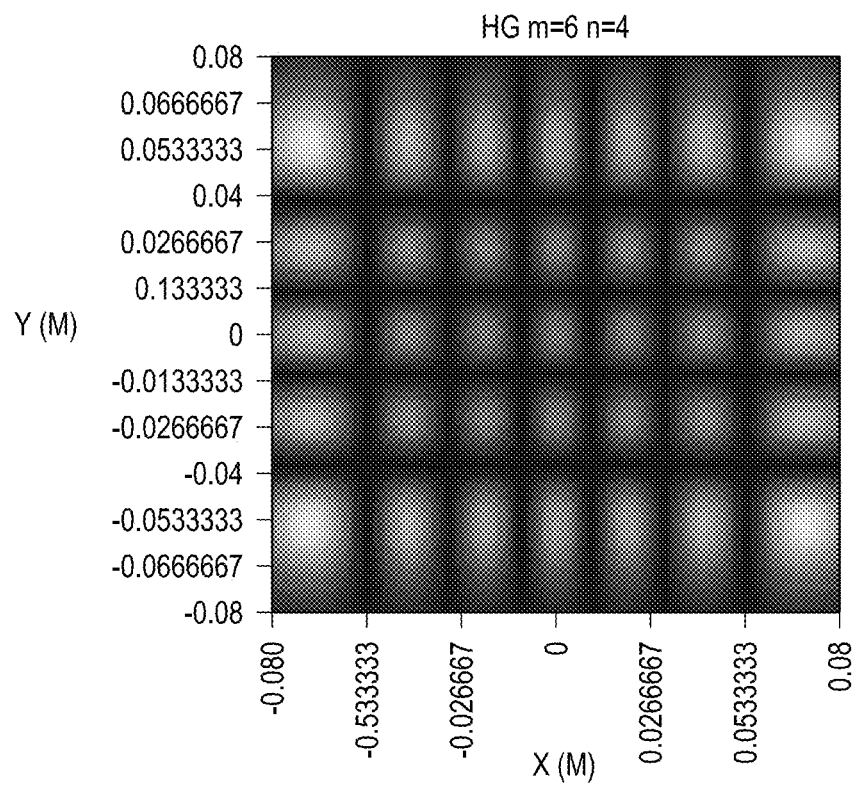

Referring now to FIG. 6, with microwave resonant absorption, electromagnetic energy at a specific microwave frequency is used at step 602, which is determined by the diameters of the virus (80 to 120 nm). The diameter of cells in human body is about 50 μm which is 500× larger than the size of the virus. Therefore, it would not have much effect on human cells. The diameter of each virus remains unchanged during virus mutation, which guarantees the feasibility of microwave resonant absorption. Since a certain level of power density is needed to destroy the virus, we need to concentrate microwave power at a specific distance using high-gain or focusing antennas at step 604. The concentrated power is then focused on the virus at step 606. Examples of manners for focusing the signal include designed high-gain antenna arrays with patch arrays, such as those described below, where the radiated fields are collimated for short distances. As for the focusing antennas, reflector antennas and lens antennas, including the microwave counterparts of the optical lens, are two major antenna types, and both are capable of concentrating microwave power onto a specific point or collimating the fields to a specific far-field direction. However, conventional reflector antennas and lens antennas are very bulky, heavy, and expensive to be used in a handheld device. To that end, array antennas are used that are designed to transmit Hermite-Gaussian beams to rupture the Cartesian grid structure of the capsid proteins. Conical and horn antennas with phase or amplitude masks may also be used to achieve the proper gain as well as the proper Hermite Gaussian or Laguerre Gaussian beams. Since the system is operating in high frequency GHz, 2×2, 4×4, 8×8 or even 16×16 arrays may be used. FIGS. 7a-7d illustrate the different modes of HG for illustration with respect to HG m=5, n=5 (FIGS. 7a, 7c) and HG m=6, n=4 (FIGS. 7b, 7d).

Referring now to FIG. 8, there is illustrated the optoacoustic generation of a helicoidal ultrasonic beam is demonstrated. Such an ultrasonic "doughnut" beam has a pressure amplitude minimum in the center along its entire longitudinal extension, and it carries orbital angular momentum. It is produced by illuminating at step 802 a specially structured absorbing surface in a water tank with pulsed laser light. The absorbing surface has a profile with a screw dislocation, like the transverse cross-sectional surface of a helix. Upon illumination with modulated light, a correspondingly prepared absorber generates at step 804 an ultrasonic wave with the desired phase discontinuity in its wave front, which propagates through the water tank and is detected at step 806 with spatial resolution using a scanning needle hydrophone. This situation can be viewed as the optoacoustic realization of a diffractive acoustical element. The method can be extended to tailor otoacoustically generated ultrasonic waves in a customized way.

Figure 9:
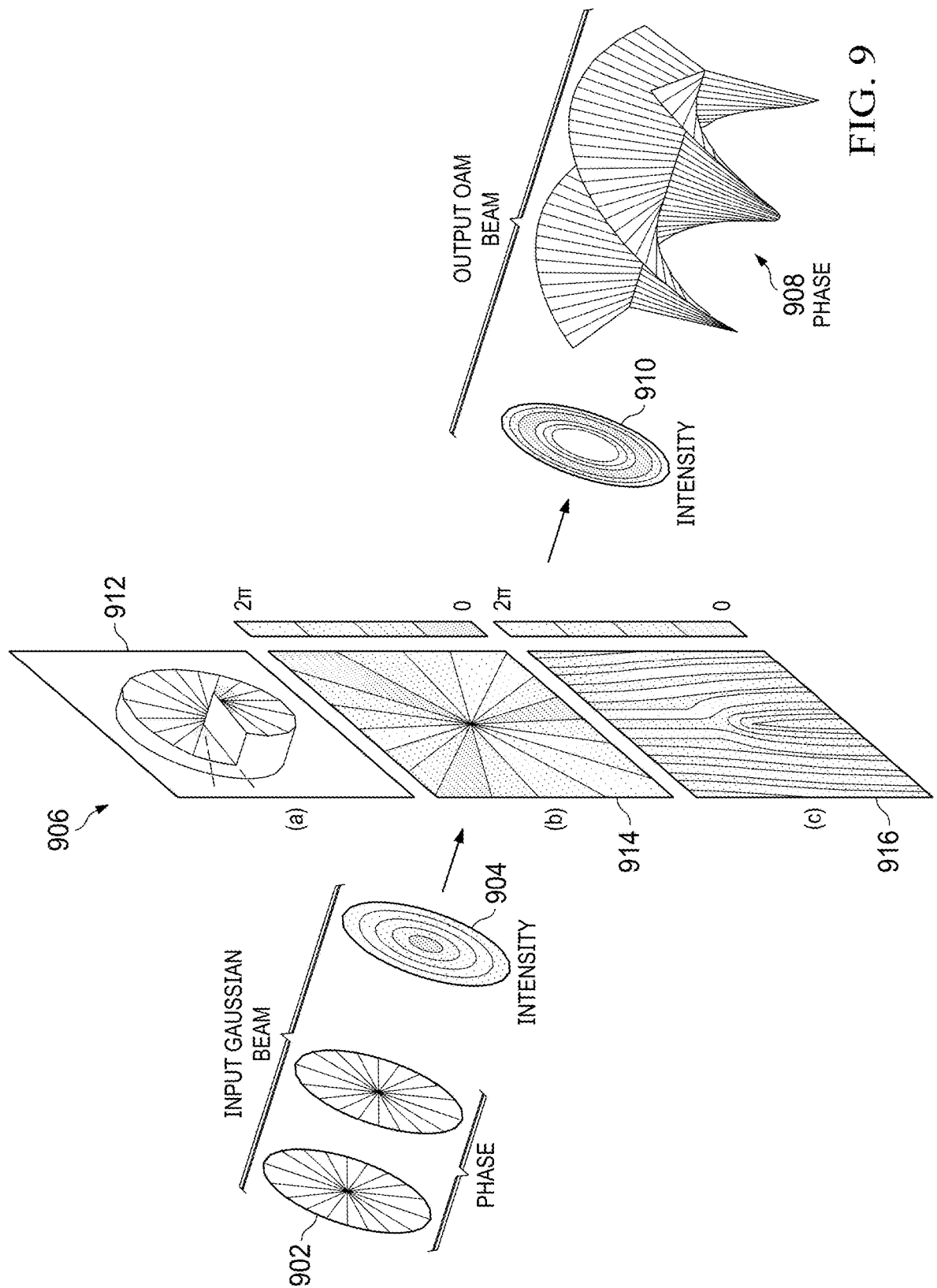
Figure 10:
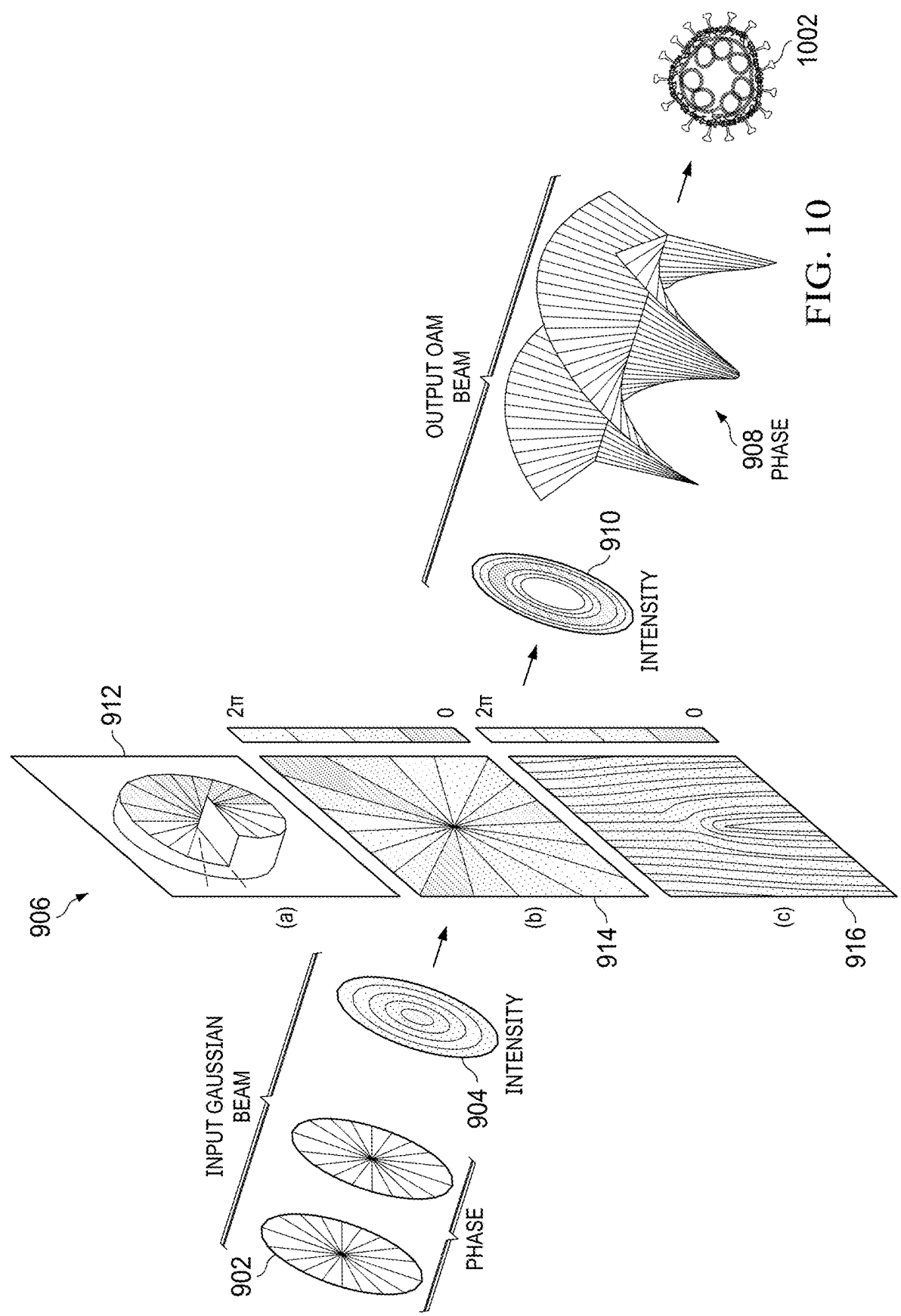

Referring now to FIG. 9, there is illustrated various manners for generating a beam having orbital angular momentum applied thereto. A series of plane waves 902 within a beam having an intensity 904 are processed using one of a variety of techniques 906 in order to generate the OAM infused beam 908 including an altered intensity profile 910. The variety of techniques 906 can include a spiral phase plate 912 that changes the phase, but for radio frequencies, a phase hologram 914 or a amplitude hologram 916 may be applied to photonic signals. Each of these techniques have been more fully described hereinabove. Referring now also to FIG. 10, using the techniques for applying the orbital angular momentum to create the OAM beam 908 as described in FIG. 9, the OAM beam 908 may be focused on to a Covid-19 virus 1002 to induce resonances therein as described herein.

Figure 11:
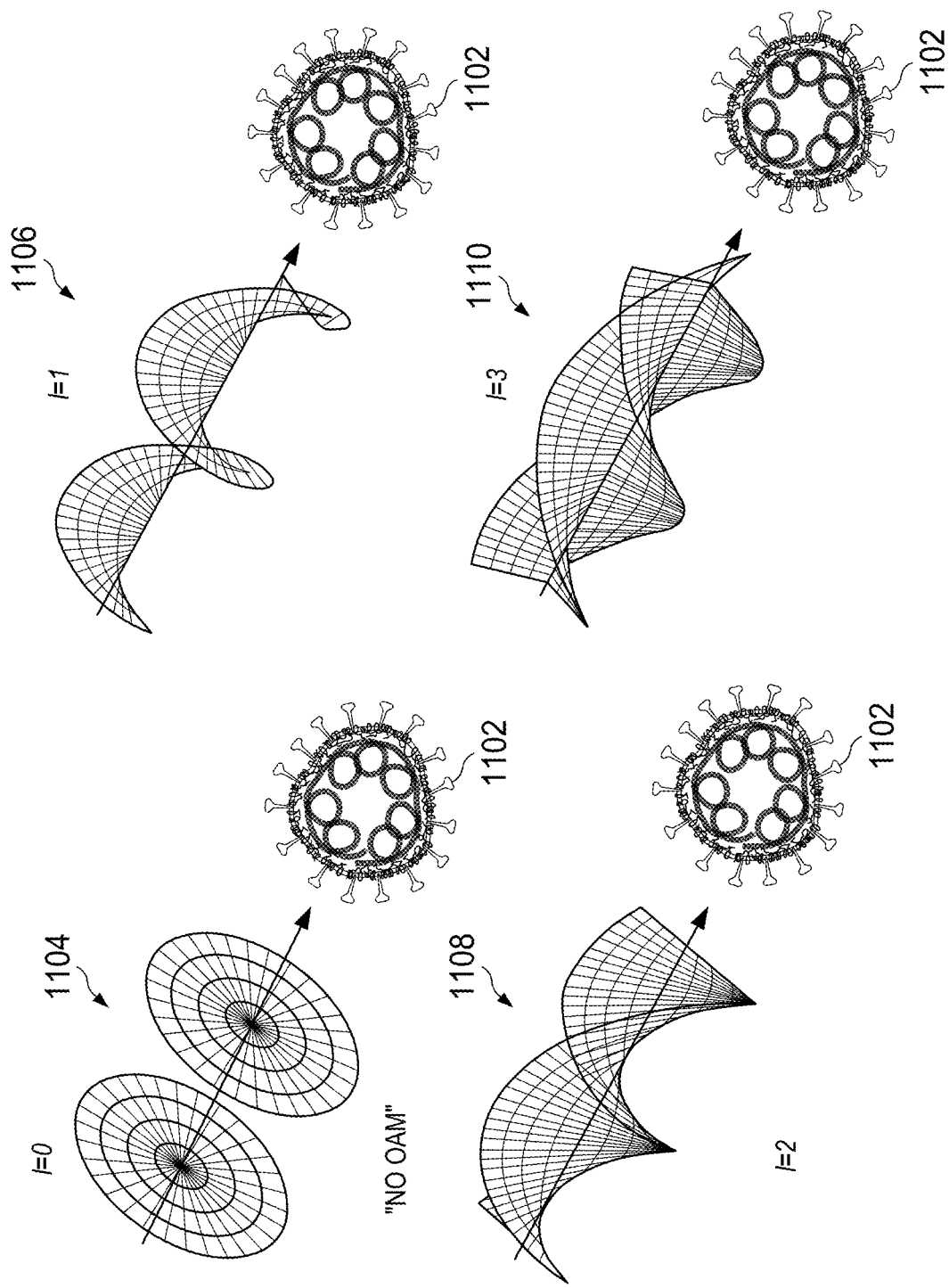

FIG. 11 illustrates the manner in which various beams having different OAM values may be applied to a Covid-19 virus 1102. In a first embodiment, plane waves 1104 having no OAM value applied thereto are focused on the virus 1102. As no OAM value is applied via the plane waves 1104 no resonance would be generated within the virus 1102. In order to apply a resonance to the virus 1102, differing values of OAM may be applied to a beam that is focused on the virus 1102. Beam 1106 has an OAM value of I=1 focused on the virus 1102 while beam 1108 applies an OAM value of I=2 to the virus, and beam 1110 applies and OAM value of I=3 to the virus 1102. Each of the OAM values will have a different effect on the generation of a resonance within the virus 1102 in order to inactivate the virus, and particular OAM values may prove more or less effective depending upon the situation.

Figure 12A:
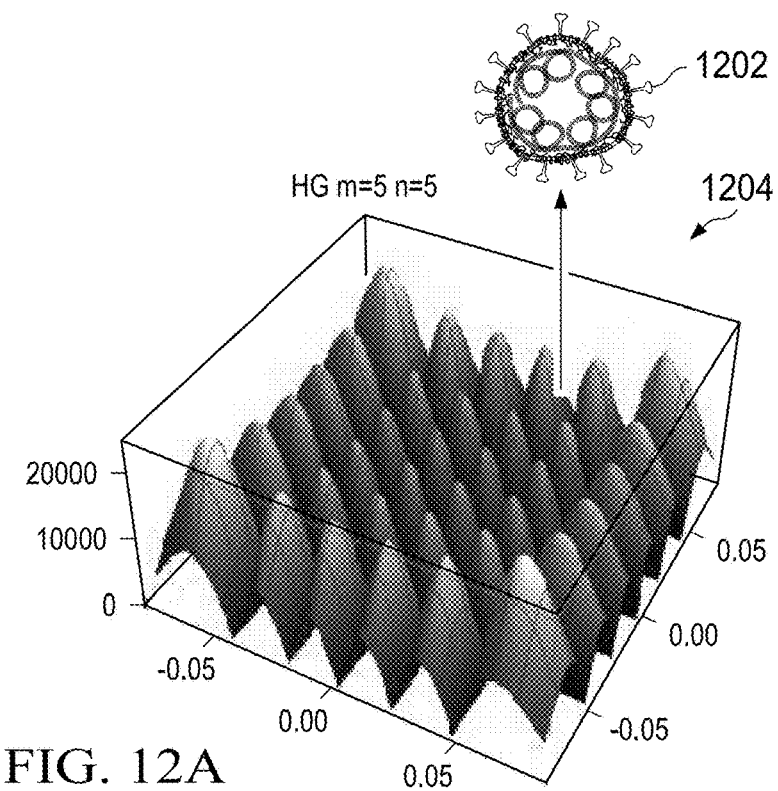
Figure 12B:
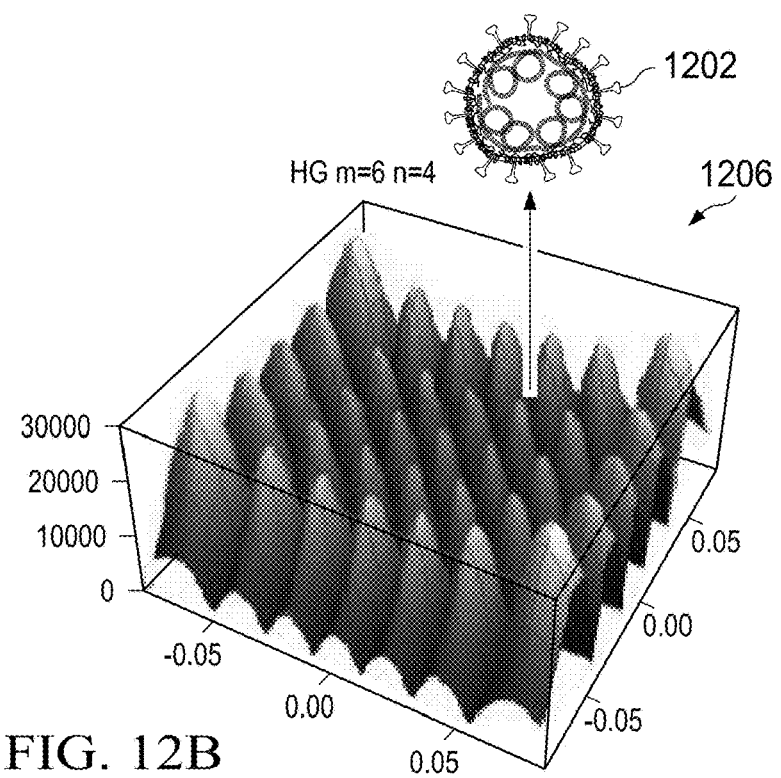

FIG. 12 illustrates the application of different Hermite Gaussian modes to a virus 1202 such as those described previously with respect to FIG. 7. A first Hermite Gaussian beam 1204 having characteristics m=5, n=5 and a second Hermite Gaussian beam 1206 having characteristics m=6, n=4 may be applied to viruses 1202 in order to induce resonances therein to inactivate or destroy the viruses.

Figure 13:
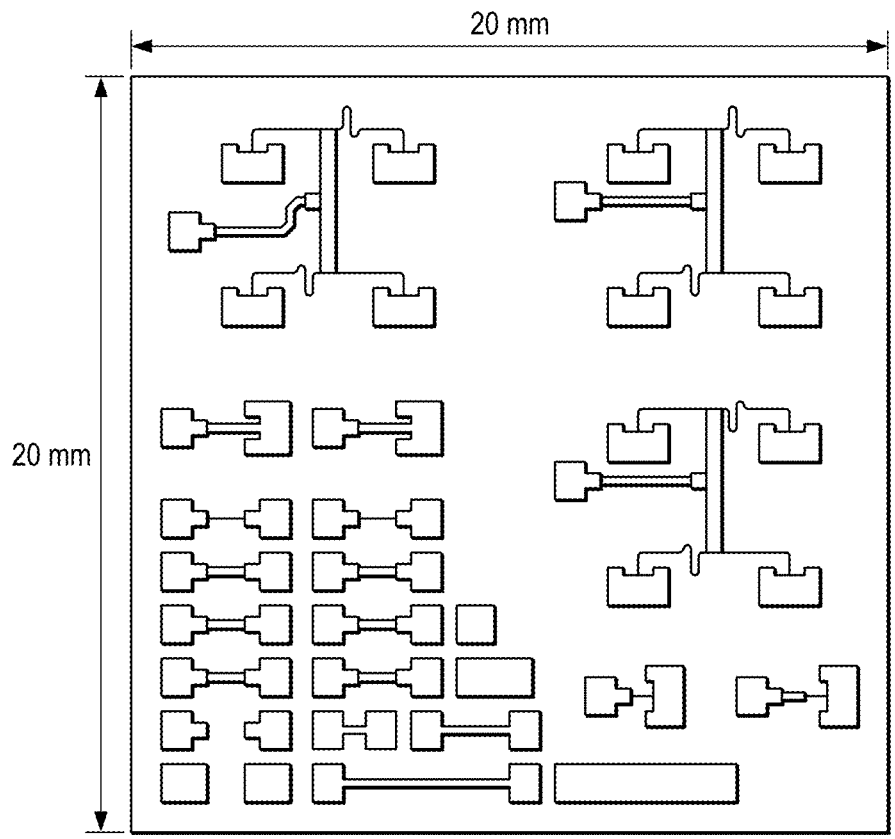
Figure 14:
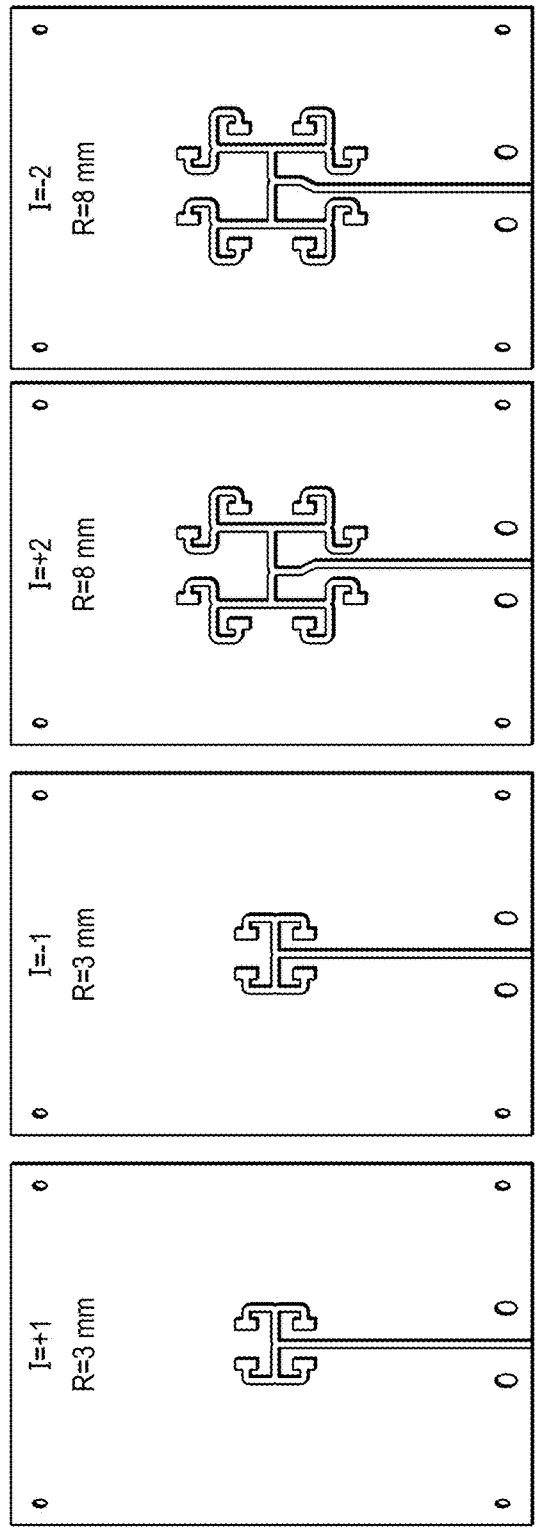
Figure 15:
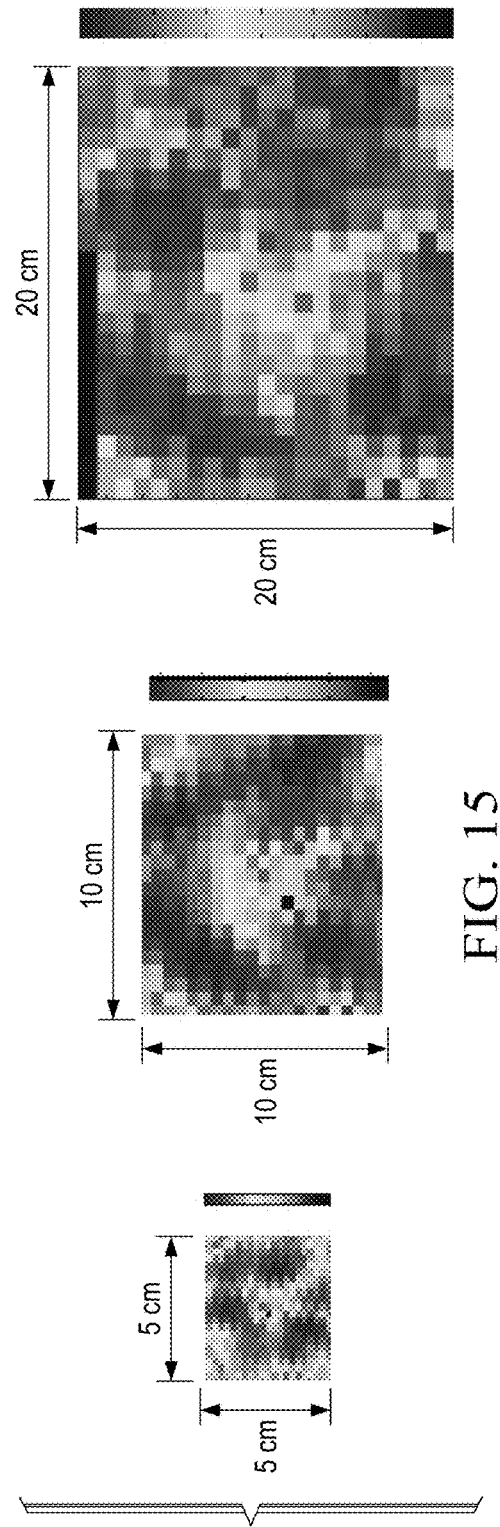

As discussed previously, one manner for applying the generated beams to a virus is by the use of patch antennas is generally illustrated in FIG. 13. FIG. 14 illustrates the manner in which various patch antennas of different sizes may be used to provide different OAM values for application to a virus. FIG. 14 illustrates the provision of a +1, −1, +2 and −2 OAM values from different sized patch antennas. FIG. 15 illustrates the different intensity signatures provided at distances of 5 cm, 12.5 cm and 25 cm. Patch antennas can be used for generating both Hermite Gaussian, Laguerre Gaussian and other types of beams in order to induce resonances with in viruses to which the beams are applied.

Figure 16:
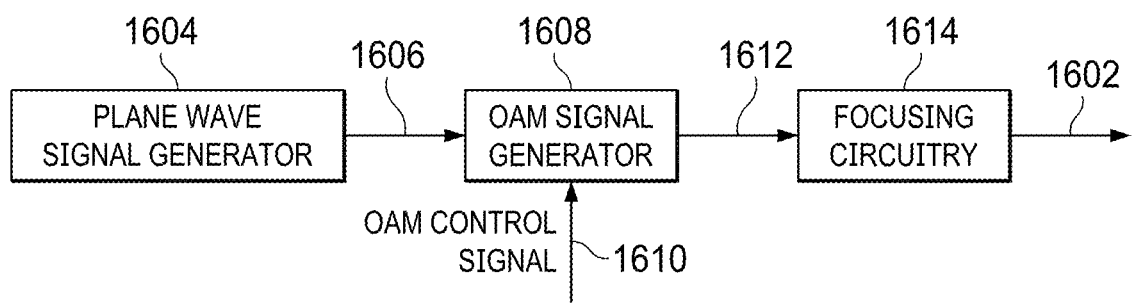

Referring now to FIG. 16, there is illustrated a general block diagram of the circuitry for generating an OAM beam 1602 for application to a virus such as Covid-19. Plane wave signal generator 1604 generates a plane wave signal 1606 that has no OAM values applied thereto. The signal may be optical or RF in nature depending upon the particular application. The plane wave signal 1606 is an applied to an OAM signal generator 1608 along with an OAM control signal 1610. Responsive to the OAM control signal 1610 and the plane wave signal 1606, the OAM signal generator 1608 generates an OAM beam 1612 in accordance with the OAM value or values indicated by the OAM control signal 1610. The control signals are established based on the OAM values needed to induce a resonance within a virus that will destroy the virus. The OAM beam 1612 is then provided to focusing circuitry 1614 which may be used for focusing a beam 1602 onto a particular location. The focusing circuitry 1614 may comprise components such as patch antennas, patch antenna arrays, conical antennas, or antennas or any of the other means for applying OAM beams that are described hereinabove.

Figure 17:
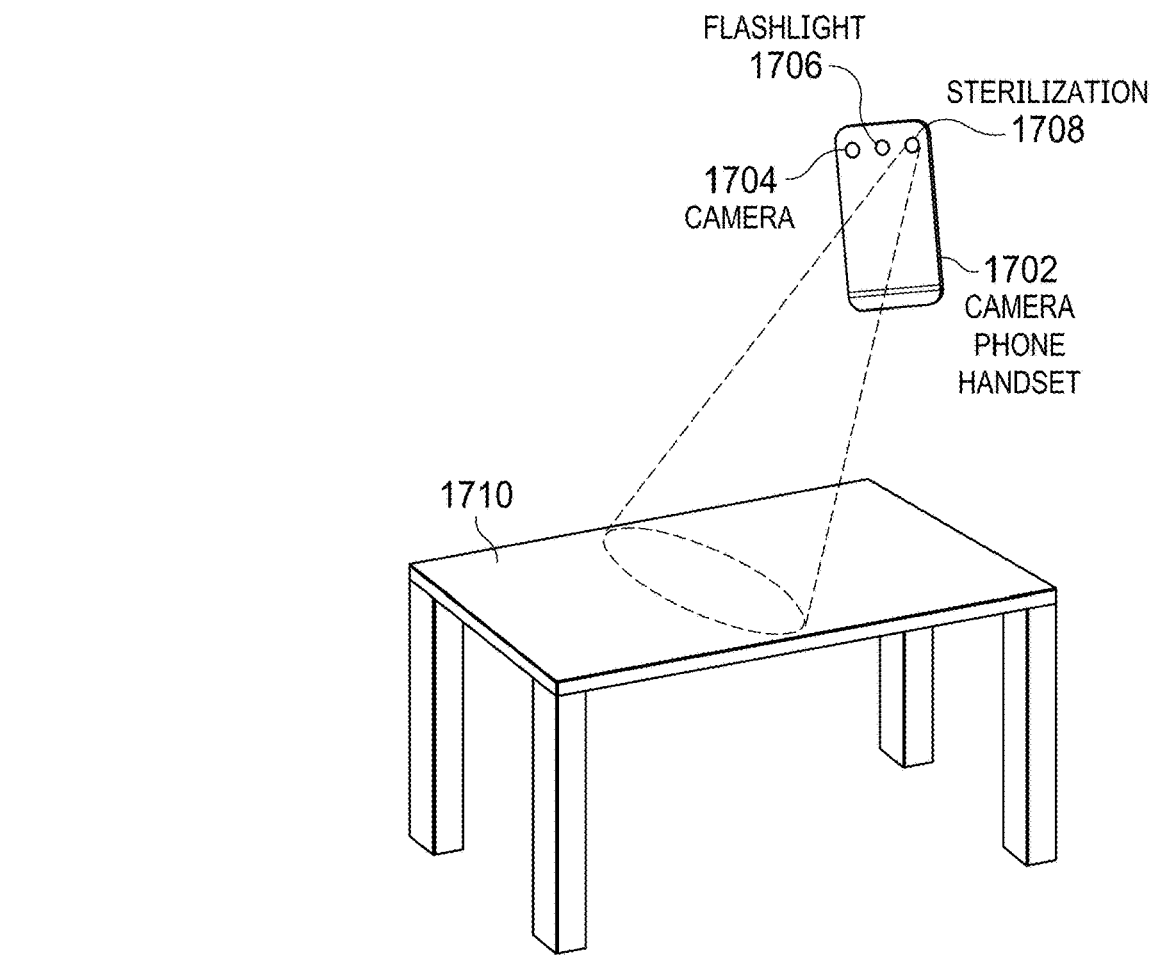

FIG. 17 illustrates one embodiment wherein the above circuitry is implemented within a cell phone handset 1702. In this embodiment, the cell phone includes a camera 1704, a flashlight 1706 and the sterilization beam 1708. The sterilization beam 1708 is generated in the manner discussed above and the cell phone handset 1702 may be manipulated to locate the beam on various surfaces, items and areas 1710 in order to sterilize them.

Figure 18:
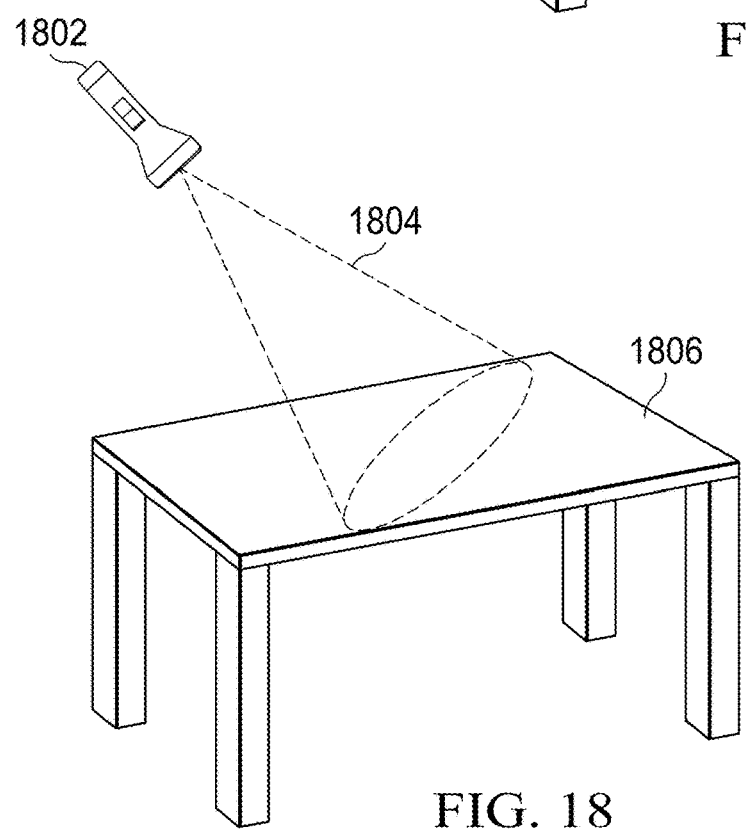

In an alternative embodiment illustrated in FIG. 18, a handheld flashlight 1702 includes the above described circuitry. The flashlight 1802 generates the sterilization beam 1804 which may then be played across surfaces, items and areas 1806 in order to sterilize them using the resonance techniques described herein.

Figure 19:
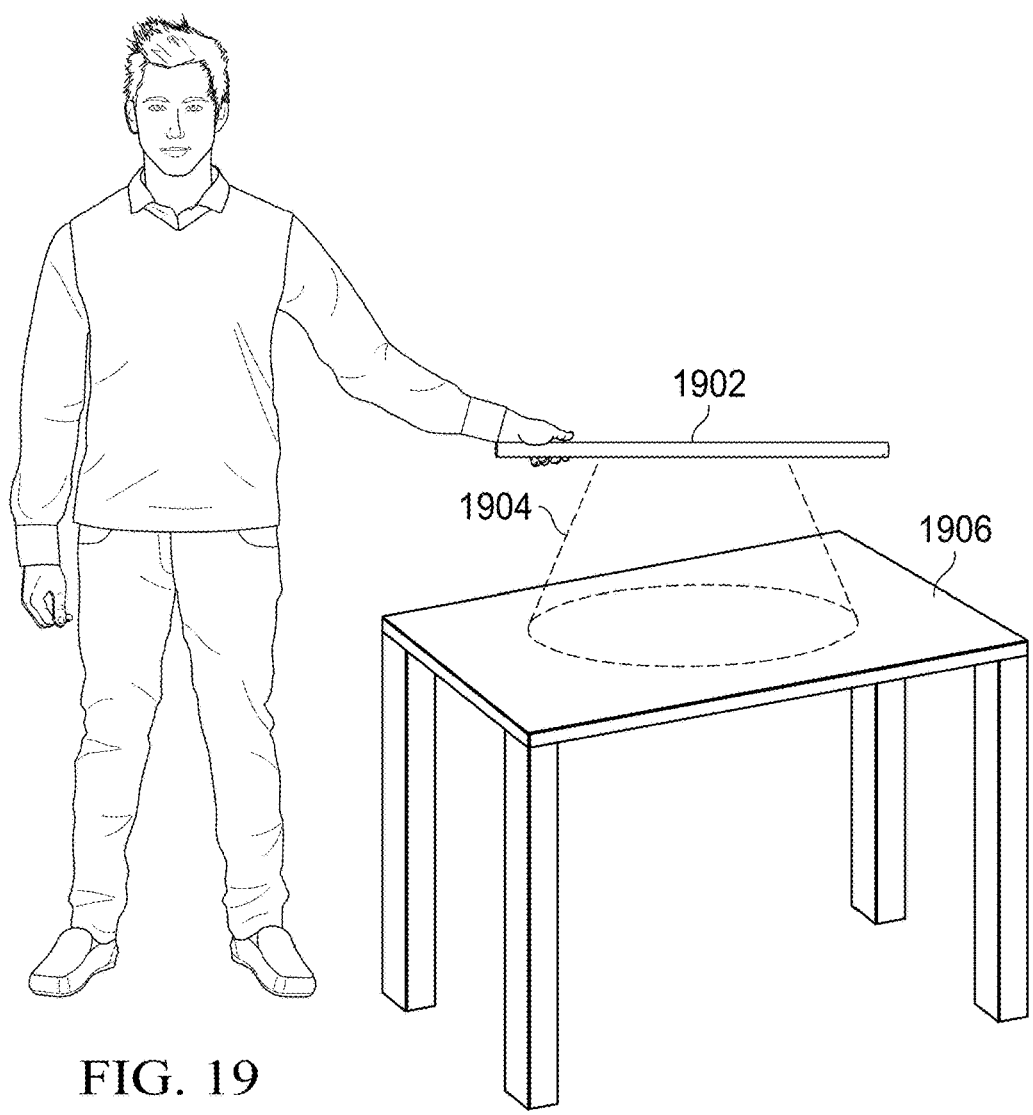

FIG. 19 illustrates a further embodiment wherein the circuitry of FIG. 16 is implemented within a handheld lightbar 1902. An individual may hold the lightbar and direct the sanitizing beam 1904 onto various surfaces 1906 in order to sanitize them from the Covid-19 virus through induced resonance by the sanitizing beam.

Figure 20:
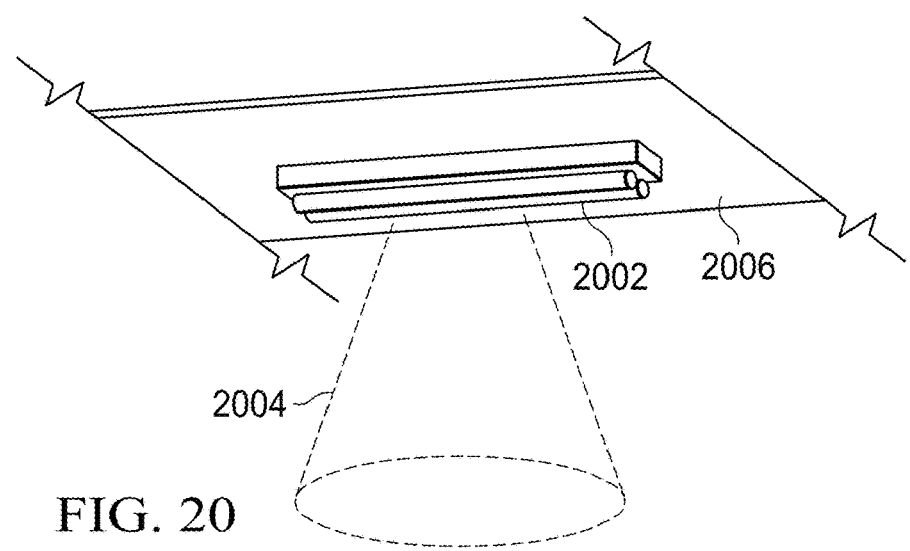
Figure 21:
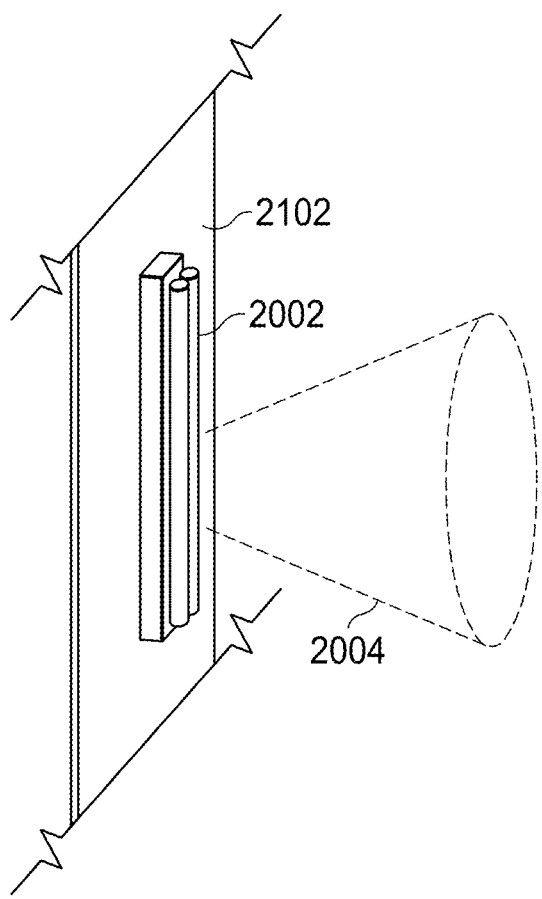

Alternatively, the circuitry of FIG. 16 may be implemented within a florescent ceiling light 2002 as shown in FIG. 20. Florescent ceiling light 2002 would generate the sanitizing beam 2004 that would be shined over the entire room in which the light fixtures were installed. This would enable the inducement of resonances within any viruses located within the room. The fluorescent light fixture 2002 could be mounted on a ceiling 2006 as illustrated in FIG. 20 or on a wall 2102 installed as a florescent light 2002 as illustrated in FIG. 21.

Figure 22:
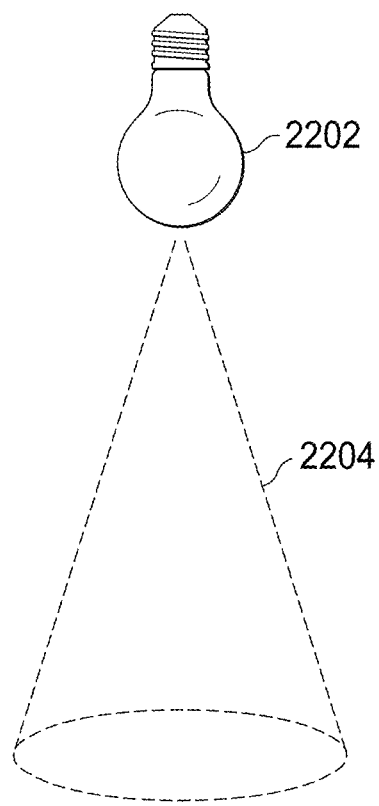

Finally, as illustrated in FIG. 22, the circuitry of FIG. 16 could be implemented with an incandescent light bulb 2202. The incandescent bulb 2202 would generate a sanitizing beam 10904 that would sanitize an entire room in which the incandescent bulb or bulbs were installed.

New OAM and Matter Interactions with Graphene Honeycomb Lattice

Due to crystalline structure, graphene behaves like a semi-metallic material, and its low-energy excitations behave as massless Dirac fermions. Because of this, graphene shows unusual transport properties, like an anomalous quantum hall effect and Klein tunneling. Its optical properties are strange: despite being one-atom thick, graphene absorbs a significant amount of white light, and its transparency is governed by the fine structure constant, usually associated with quantum electrodynamics rather than condensed matter physics.

Current efforts in study of structured light are directed, on the one hand, to the understanding and generation of twisted light beams, and, on the other hand, to the study of interaction with particles, atoms and molecules, and Bose-Einstein condensates.

Figure 23:
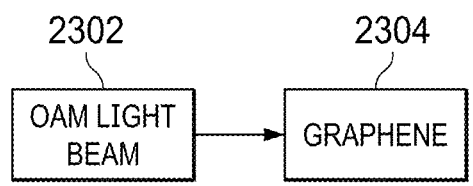

Thus, as shown in FIG. 23, an OAM light beam 2302 may be interacted with graphene 2304 to enable the OAM processed photons to alter the state of the particles in the graphene 2304. The interaction of graphene 2304 with light 2302 has been studied theoretically with different approaches, for instance by the calculation of optical conductivity, or control of photocurrents. The study of the interaction of graphene 2304 with light carrying OAM 2302 is interesting because the world is moving towards using properties of graphene for many diverse applications. Since the twisted light 2302 has orbital angular momentum, one may expect a transfer of OAM from the photons to the electrons in graphene 2304. However, the analysis is complicated by the fact that the low-lying excitations of graphene 2304 are Dirac fermions, whose OAM is not well-defined. Nevertheless, there is another angular momentum, known as pseudospin, associated with the honeycomb lattice of graphene 2304, and the total angular momentum (orbital plus pseudospin) is conserved. This will work in a similar manner when OAM beams interact with viruses.

The interaction Hamiltonian between OAM and matter described herein can be used to study the interaction of graphene with twisted light and calculate relevant physical observables such as the photo-induced electric currents and the transfer of angular momentum from light to electron particles of a material such as a virus.

The low-energy states of graphene are two-component spinors. These spinors are not the spin states of the electron, but they are related to the physical lattice. Each component is associated with the relative amplitude of the Bloch function in each sub-lattice of the honeycomb lattice. They have a SU(2) algebra. This degree of freedom is pseudospin. It plays a role in the Hamiltonian like the one played by the regular spin in the Dirac Hamiltonian. It has the same SU(2) algebra but, unlike the isospin symmetry that connects protons and neutrons, pseudospin is an angular momentum. This pseudospin would be pointing up in z (outside the plane containing the graphene disk) in a state where all the electrons would be found in A site, while it would be pointing down in z if the electrons were located in the B sub-lattice.

Interaction Hamiltonian OAM with Graphene lattice (Honeycomb)

Referring now to FIG. 24, there is illustrated a Graphene lattice in a Honeycomb structure. If $T_1$ and $T_2$ are the primitive vectors of the Bravais lattice and k and k' are the corners of the first Brillouin zone, then the Hamiltonian is:

$$H_0(k) = t \begin{bmatrix} 0 & 1 + e^{-ik \cdot T_2} + e^{-ik \cdot (T_2 - T_1)} \\ 1 + e^{ik \cdot T_2} + e^{ik \cdot (T_2 - T_1)} & 0 \end{bmatrix}$$

The carbon atom separation on the lattice is a=1.42 Å. If this matrix is diagonalized, the energy Eigen values representing energy bands of graphene is obtained.

$$E_\pm(k) = \pm t \sqrt{2 + 2\cos(\sqrt{3} k_y a) + 4 \cos\left(\frac{\sqrt{3}}{2} k_y a\right) \cos\left(\frac{3}{2} k_x \alpha\right)}$$

If $k = K + (q_x, q_y)$

Then $$H_0^K(q) = \frac{3ta}{2} \begin{pmatrix} 0 & q_x + iq_y \\ q_x - iq_y & 0 \end{pmatrix} \text{ for } q_x a \ll 1$$

$q_y a \ll 1$

So for 2D-Hamiltonian:

$$H_0^\alpha(q) = \hbar v_f \alpha(\sigma_x q_x - \sigma_y q_y) \quad \sigma = (\sigma_x, \sigma_y) \text{ Pauli matrices}$$

$\alpha = \pm 1$

Where Fermi velocity equals:

$$v_f = \frac{3at}{2\hbar} \sim 300 \text{ times slower than } c$$

The Eigen states of these Hamiltonians are spinors with 2-components which are 2 elements of lattice base.

For circular graphene of radius $r_0$, the low-energy states can be found in cylindrical coordinates with $$\Psi_{mv}(r, \theta) = \frac{N_{mv}}{2\pi} J_m(q_{mv} r) e^{im\theta} \quad q_{mv} = \frac{x_{mv}}{r_0}$$

where $x_{mv}$ has a zero of $J_m(X)$

To study the interaction of graphene with OAM beam, the z-component of OAM operator $$L_z = -i\hbar \frac{d}{d\theta} 1$$

is examined and then the commutation relationship between Hamiltonian and OAM is:

$[H_0^\alpha, L_z] = i\hbar v_f \alpha (\sigma_x P_x + \sigma_y P_y)$

To construct a conserved angular momentum, pseudospin is added to $L_z$ and the total angular momentum is:

$$J_z^\alpha = L_z - \alpha \frac{\hbar}{2} \sigma_z$$

This operator does commute with Hamiltonian and $J_z \Psi_{mv,k} = (m + \frac{1}{2}) \hbar \Psi_{mv,k}$ near k or k'

Interaction Hamiltonian

We know the vector potential for OAM beam in Coulomb gauge is:

$$A(r, t) = A_0 e^{i(q_z z - \omega t)} \left[ \epsilon_\sigma J_l(qr) e^{il\theta} - \sigma i \hat{z} \frac{q}{q_z} J_{l+\sigma}(q_r) e^{i(l+\sigma)\theta} \right] + \cdots$$

where $\epsilon_\sigma = \hat{x} + i\sigma \hat{y}$ polarization vectors $\sigma = \pm 1$ The radial part of the beam are Bessel functions $J_l(qr)$ and $J_{l+r}(qr)$. A Laguerre-Gaussian function could also be used instead of Bessel functions. Here $q_z$ and q are for structured light and $q_x$, $q_y$, $q_{mv}$ are for electrons.

To construct the interaction Hamiltonian:

$\vec{P} \rightarrow \vec{P} + e\vec{A}$

Then $$H^\alpha = \hbar v_f \alpha (\sigma_x q_x - \sigma_y q_y) + ev_f \alpha (\sigma_x A_x - \sigma_y A_y) = H_0^\alpha + H_{int}^\alpha$$

Since Graphene is 2D, there are only x, y values of the EM field.

At z=0 (Graphene disk), the vector potential is:

$A(r, 0, t) = A_0 (\hat{x} + i\sigma \hat{y}) e^{-i\omega t} J_l(qr) e^{il\theta} + \ldots$ Let's have $A_+ = A_0 e^{-i\omega t} J_l(qr) e^{il\theta}$ Absorption of 1 photon $A_- = A_0 e^{-i\omega t} J_l(qr) e^{-il\theta}$ emission of 1 photon Then the interaction Hamiltonian close to a Dirac point a is:

$$H_{int}^{\alpha,\sigma} = ev_f \begin{bmatrix} 0 & (\sigma - \alpha) A_+ + (\alpha + \sigma) A_- \\ (\alpha + \sigma) A_+ + (\alpha - \sigma) A_- & 0 \end{bmatrix}$$

For $\alpha = 1$ (near K) and $\sigma = +1$ $$H_{int}^{K+} = 2ev_f \begin{bmatrix} 0 & A_- \\ A_+ & 0 \end{bmatrix}$$

For $\alpha = -1$ (near K') and $\sigma = +1$ $$H_{int}^{K'+} = 2ev_f \begin{bmatrix} 0 & A_+ \\ A_- & 0 \end{bmatrix}$$

Then the transition matrix becomes:

$$M_{if} = \langle i|H_{int}|f\rangle =$$

$$\langle c, m', v', \alpha|H_{int}^{a\sigma}|v, m, v, \alpha\rangle = \int \Psi_{m'v'\alpha}^{c\dagger}(r,\theta) H_{int}^{a\sigma}(r,\theta) \Psi_{mv\alpha}^{v}(r,\theta) r\, dr\, d\theta$$

Where near K:

$$\Omega_{mvK}^{v} = \frac{1}{\sqrt{2}}\begin{pmatrix} \Psi_{m+1,v} \\ i\Psi_{mv} \end{pmatrix} \Psi_{mvK}^{c} = \frac{1}{\sqrt{2}}\begin{pmatrix} \Psi_{m+1,v} \\ -i\Psi_{mv} \end{pmatrix}$$

Where $$\Psi_{mv}(r,\theta) = \frac{N_{mv}}{2\pi} J_m(q_{mv} r) e^{im\theta}$$

as before $$W_{if} = \frac{2\pi}{\hbar}|M_{if}|^2 \rho(E) \text{ transition rate}$$

Ultraviolet Sterilizing

The above described techniques can also be combined with ultraviolet sterilization techniques to improve the virus destruction capabilities. Ultraviolet light is the low wavelength part of electromagnetic spectrum. X-rays and gamma rays are even shorter wavelength and visible light and radio are higher wavelength than ultraviolet. However, within ultraviolet, we have varying wavelengths decreasing from UVA, UVB, UVC and UVV.

UVC light has wavelengths between 200 to 280 nm and has been used extensively for more than 40 years in disinfecting drinking water, wastewater, air, pharmaceutical products, and surfaces against a whole suite of human pathogens. All bacteria and viruses tested to date (many hundreds over the years, including other coronaviruses) respond to UV disinfection. Some organisms are more susceptible to UVC disinfection than others, but all tested so far do respond at the appropriate doses.

COVID-19 infections can be caused by contact with contaminated surfaces and then touching facial areas. Minimizing this risk is key because COVID-19 virus can live on plastic and steel surfaces for up to 3 days. Normal cleaning and disinfection may leave behind some residual contamination, which UVC can treat suggesting that a multiple disinfectant approach is sensible.

In the cases where the UVC light cannot reach a particular pathogen, that pathogen will not be disinfected. However, in general, reducing the total number of pathogens reduces the risk of transmission. The total pathogenic load can be reduced substantially by applying UV to the many surfaces that are readily exposed, as a secondary barrier to cleaning, especially in hurried conditions. This would be a relatively straight-forward matter of illuminating the relevant surfaces with UVC light, for example the air and surfaces around/in rooms and personal protective equipment.

UVC light inactivates or kills at least two other coronaviruses that are near-relatives of the COVID-19 virus: 1) SARS-CoV-1 and 2) MERS-CoV. An important caveat is this inactivation has been demonstrated under controlled conditions in the laboratory. The effectiveness of UV light in practice depends on factors such the exposure time and the ability of the UV light to reach the viruses in water, air, and in the folds and crevices of materials and surfaces.

Like any disinfection system, UVC devices must be used properly to be safe. This UVC light is much "stronger" than normal sunlight and can cause a severe sunburn-like reaction to skin and could damage the retina of eye, if exposed. Some devices also produce ozone as part of their cycle, others produce light and heat like an arc welder, others move during their cycles. Hence, general machine-human safety needs to be considered with all disinfection devices, and these considerations should be addressed in the operations manual, in the user training, and appropriate safety compliance.

Electromagnetic (EM) waves carry spin angular momentum (SAM). Its analog in classical electrodynamics is polarization (linear or circular). However, a new property of photons was recently discovered that relate to electromagnetic (EM) vortices. Such a vortex beam has specific helicity and an associated angular momentum which is "orbital" in nature. This orbital angular momentum (OAM) of the beam is called a "twisted" or "helical" property of the beam. Current spectroscopy techniques involve circularly polarized light in which a plane polarized state is understood as a superposition of circular polarizations with opposite handedness. The right- and left-handedness of circularly polarized light indicates its SAM. However as shown in FIG. 25, in general an EM beam can be engineered to have both SAM 2502 and OAM 2504 and such beams are called vector beams 2506. The vector beams 2506 can be used for new spectroscopy techniques with specific interaction signatures with matter, but also for destroying, or diminishing the viability of viruses. Experiments support the existence of measurable OAM light-matter interactions using such vector beams 2506. By applying directed energy sources (using, for example, patch antenna arrays or photonic sources) a virus may be killed. A miniaturized device may be used to either kill or limit the capability of the virus to infect others. Specifically, the virus can be killed by exploiting a natural susceptibility of the virus to certain resonant frequencies as well as a specific helicity of the beam corresponding to virus structure that exhibit susceptibility.

Current airborne virus epidemic prevention efforts used in public space, includes strong chemicals, UV radiation, ultrasonic signals and microwaves. Viruses may be inactivated or destroyed in a number of fashions. Viruses, however, can also be inactivated by generating the corresponding resonance ultrasound vibrations of viruses (in the GHz). Therefore, there are vibrational modes of viruses in this frequency range. It is also known that dipolar mode of the confined acoustic vibrations inside viruses can be resonantly excited by microwaves of the same frequency with a resonant microwave absorption effect. Therefore, as shown in FIG. 26, a structure-resonant energy transfer effect 2602 from electromagnetic waves 2604 to vibrations of viruses 2606 can enable destruction of the viruses. This means that energy transfer process 2602 is an efficient way to excite the vibrational mode of the whole virus structure due to an energy conversion of a photon into a phonon of the same frequency. This would also include a transfer of the angular momentum using structured vector beams that carry OAM as shown in FIG. 27.

As more fully described herein below, a model of an interaction Hamiltonian which can be used to study light-matter interaction and explore the relation between the induced stress and the field magnitude of the microwave.

Since the viruses could be inactivated when the induced stress fractures the structure of viruses, the SRET efficiency from microwaves to COVID-19 may be explored through measuring the virus inactivation threshold. Based on the model, the inactivation ratio of the virus at dipolar-mode-resonance and off-resonance microwave frequencies as well as with different microwave powers may be determined. The resonant frequency, the microwave power density threshold for COVID-19 inactivation must be below the IEEE safety standard to enable use of the device. The main inactivation mechanism is through physically fracturing the viruses, while the RNA genome is not degraded by the microwave illumination, supporting the fact that this approach is fundamentally different from the microwave thermal heating effect. The COVID-19 virus is a 100 nm virus with different types of proteins (spike, envelope, membrane, nucleocapsid) as well as RNA.

Referring now more particularly to FIG. 28, there is illustrated a functional block diagram of a system for generating the orbital angular momentum "twist" that may be imparted to a virus. A plane wave signal 2802 is provided to the transmission processing circuitry 2800. The plane wave signal is provided to the orbital angular momentum (OAM) signal processing block 2806. The plane wave signal is provided a different orbital angular momentum by the orbital angular momentum electromagnetic block 2806 depending on the virus that is to be deactivated or destroyed. Each of the signals having an associated orbital angular momentum are provided to an optical transmitter 2808 that transmits each of the data streams having a unique orbital angular momentum on a same wavelength.

Figure 29:
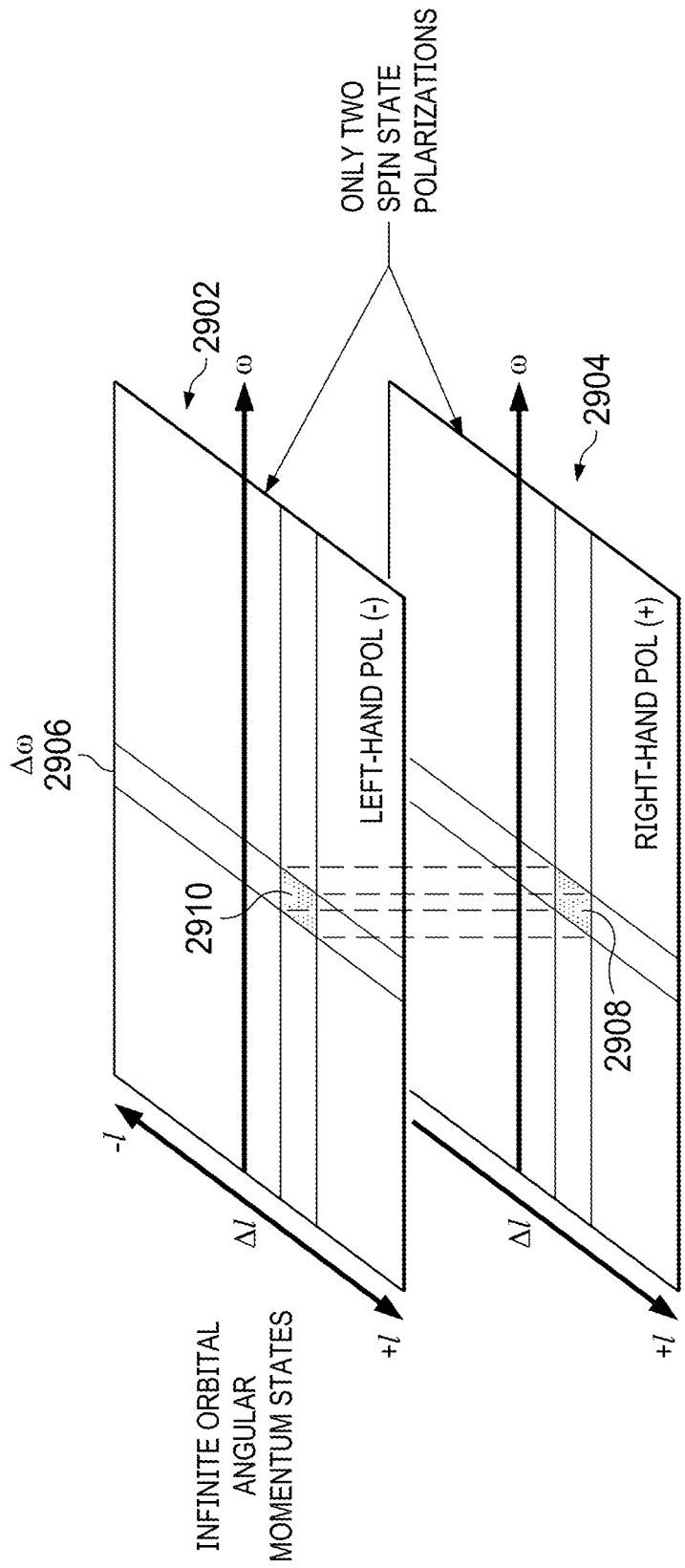

FIG. 29 illustrates in a manner in which a single wavelength or frequency, having two quanti-spin polarizations may provide an infinite number of twists having various orbital angular momentums associated therewith. The l axis represents the various quantized orbital angular momentum states which may be applied to a particular signal at a selected frequency or wavelength. The symbol omega ($\omega$) represents the various frequencies to which the signals of differing orbital angular momentum may be applied. The top grid 2902 represents the potentially available signals for a left-handed signal polarization, while the bottom grid 2904 is for potentially available signals having right handed polarization.

By applying different orbital angular momentum states to a signal at a particular frequency or wavelength, a potentially infinite number of states may be provided at the frequency or wavelength. Thus, the state at the frequency $\Delta\omega$ or wavelength 2906 in both the left-handed polarization plane 2902 and the right-handed polarization plane 2904 can provide an infinite number of signals at different orbital angular momentum states $\Delta l$. Blocks 2908 and 2910 represent a particular signal having an orbital angular momentum $\Delta l$ at a frequency $\Delta\omega$ or wavelength in both the right-handed polarization plane 2904 and left-handed polarization plane 2910, respectively. By changing to a different orbital angular momentum within the same frequency $\Delta\omega$ or wavelength 2906, different signals may also be transmitted. Each angular momentum state corresponds to a different determined current level for transmission from the optical transmitter. By estimating the equivalent current for generating a particular orbital angular momentum within the optical domain and applying this current for transmission of the signals, the transmission of the signal may be achieved at a desired orbital angular momentum state.

Thus, the illustration of FIG. 29, illustrates two possible angular momentums, the spin angular momentum, and the orbital angular momentum. The spin version is manifested within the polarizations of macroscopic electromagnetism and has only left and right-hand polarizations due to up and down spin directions. However, the orbital angular momentum indicates an infinite number of states that are quantized. The paths are more than two and can theoretically be infinite through the quantized orbital angular momentum levels.

Figure 30A:
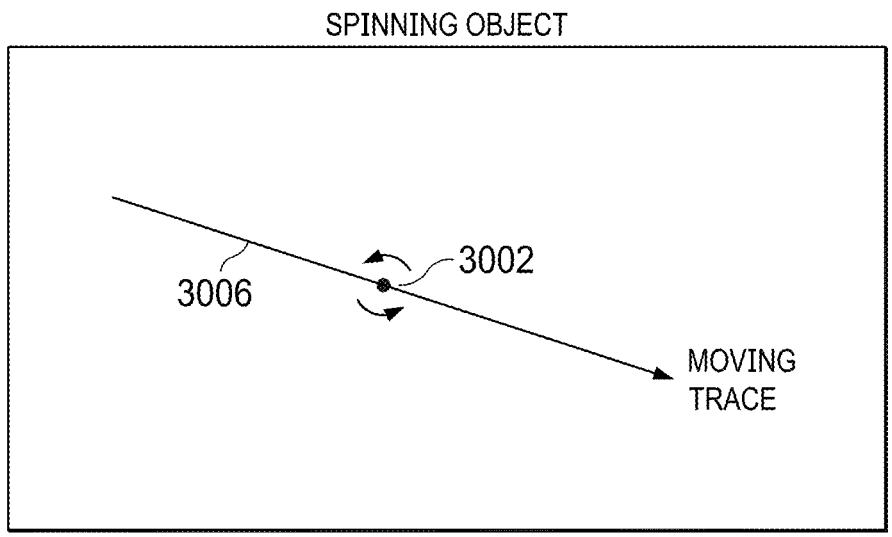
Figure 30B:
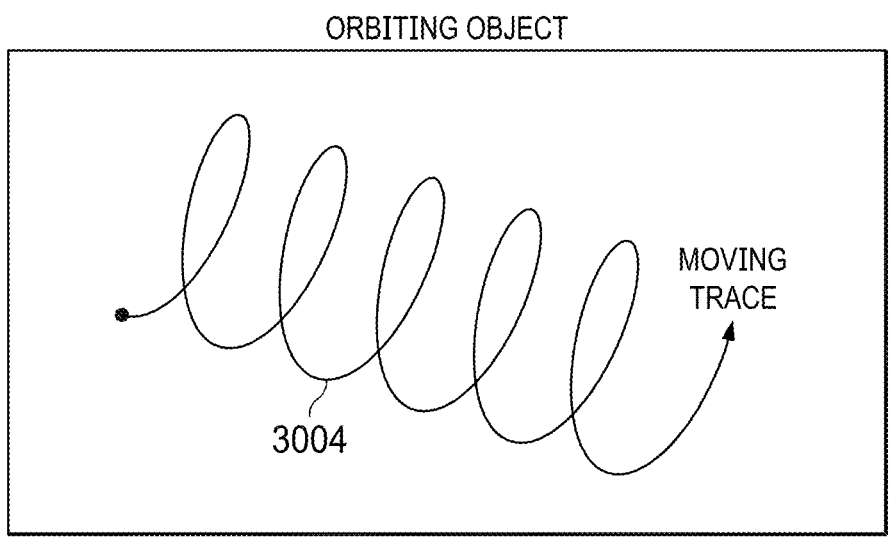
Figure 30C:
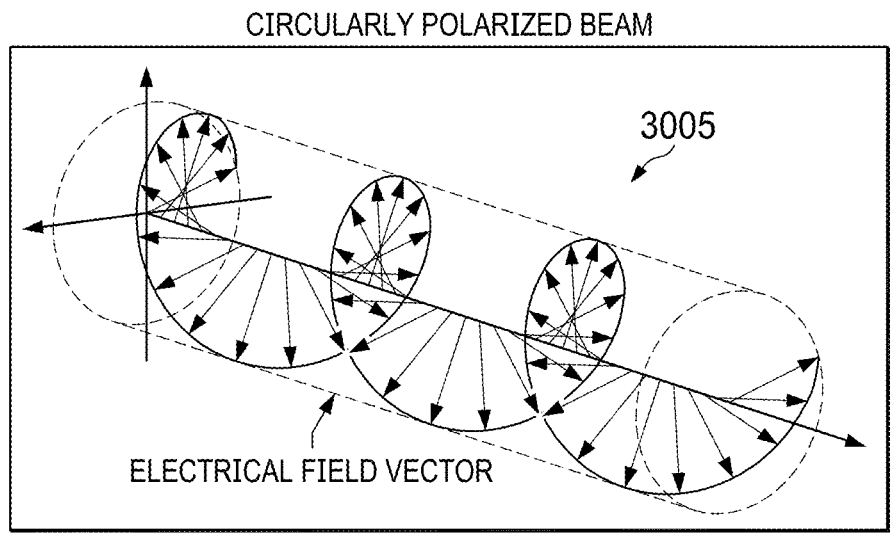
Figure 30D:
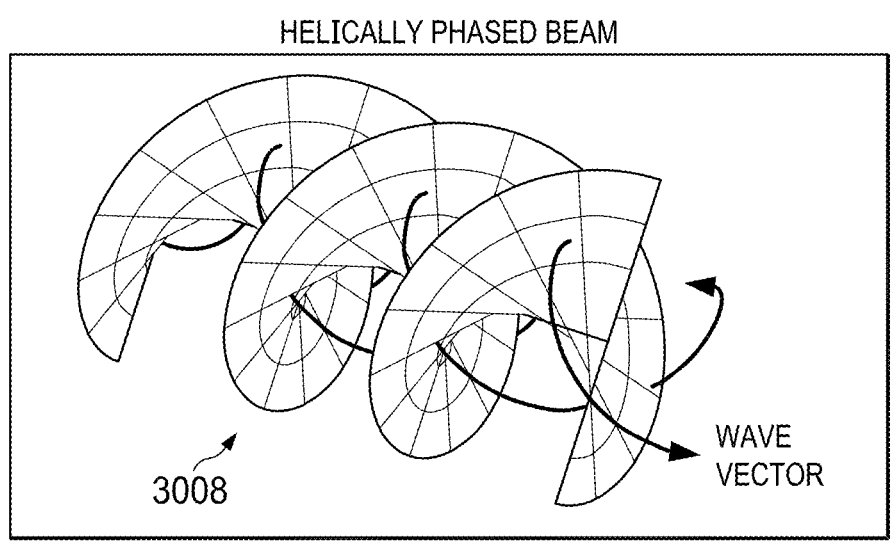

It is well-known that the concept of linear momentum is usually associated with objects moving in a straight line. The object could also carry angular momentum if it has a rotational motion, such as spinning (i.e., spin angular momentum (SAM) 3002), or orbiting around an axis 3006 (i.e., OAM 3004), as shown in FIGS. 30A and 30B, respectively. A light beam may also have rotational motion as it propagates. In paraxial approximation, a light beam carries SAM 3002 if the electrical field rotates along the beam axis 3006 (i.e., circularly polarized light 3005), and carries OAM 3004 if the wave vector spirals around the beam axis 3006, leading to a helical phase front 3008, as shown in FIGS. 30C and 30D. In its analytical expression, this helical phase front 3008 is usually related to a phase term of $\exp(i\ell\theta)$ in the transverse plane, where $\theta$ refers to the angular coordinate, and $\ell$ is an integer indicating the number of intertwined helices (i.e., the number of $2\pi$ phase shifts along the circle around the beam axis). $\ell$ could be a positive, negative integer or zero, corresponding to clockwise, counterclockwise phase helices or a Gaussian beam with no helix, respectively.

Two important concepts relating to OAM include:
1) OAM and polarization: As mentioned above, an OAM beam is manifested as a beam with a helical phase front and therefore a twisting wavevector, while polarization states can only be connected to SAM 3002. A light beam carries SAM 3002 of $\pm h/2\pi$ (h is Plank's constant) per photon if it is left or right circularly polarized and carries no SAM 3002 if it is linearly polarized. Although the SAM 3002 and OAM 3004 of light can be coupled to each other under certain scenarios, they can be clearly distinguished for a paraxial light beam. Therefore, with the paraxial assumption, OAM 3004 and polarization can be considered as two independent properties of light.

2) OAM beam and Laguerre-Gaussian (LG) beam: In general, an OAM-carrying beam could refer to any helically phased light beam, irrespective of its radial distribution (although sometimes OAM could also be carried by a non-helically phased beam). LG beam is a special subset among all OAM-carrying beams, due to that the analytical expression of LG beams are eigen-solutions of paraxial form of the wave equation in cylindrical coordinates. For an LG beam, both azimuthal and radial wavefront distributions are well defined, and are indicated by two index numbers, $\ell$ and p, of which $\ell$ has the same meaning as that of a general OAM beam, and p refers to the radial nodes in the intensity distribution. Mathematical expressions of LG beams form an orthogonal and complete basis in the spatial domain. In contrast, a general OAM beam actually comprises a group of LG beams (each with the same $\ell$ index but a different p index) due to the absence of radial definition. The term of "OAM beam" refers to all helically phased beams and is used to distinguish from LG beams.

Using the orbital angular momentum state of the transmitted energy signals, physical information can be embedded within the radiation transmitted by the signals. The Maxwell-Heaviside equations can be represented as:

$$\nabla \cdot E = \frac{\rho}{\varepsilon_0}$$

$$\nabla \times E = -\frac{\partial B}{\partial t}$$

$$\nabla \cdot B = 0$$

$$\nabla \times B = \varepsilon_0 \mu_0 \frac{\partial E}{\partial t} + \mu_0 j(t, x)$$

where $\nabla$ is the del operator, E is the electric field intensity and B is the magnetic flux density. Using these equations, one can derive 23 symmetries/conserved quantities from Maxwell's original equations. However, there are only ten well-known conserved quantities and only a few of these are commercially used. Historically if Maxwell's equations where kept in their original quaternion forms, it would have been easier to see the symmetries/conserved quantities, but when they were modified to their present vectorial form by Heaviside, it became more difficult to see such inherent symmetries in Maxwell's equations.

The conserved quantities and the electromagnetic field can be represented according to the conservation of system energy and the conservation of system linear momentum. Time symmetry, i.e. the conservation of system energy can be represented using Poynting's theorem according to the equations:

$$H = \sum_i m_i \gamma_i c^2 + \frac{\varepsilon_0}{2} \int d^3 x (|E|^2 + c^2 |B|^2) \text{ Hamiltonian (total energy)}$$

$$\frac{dU^{mech}}{dt} + \frac{dU^{em}}{dt} + \oint_{s'} d^2 x' \hat{n}' \cdot S = 0 \text{ conservation of energy}$$

The space symmetry, i.e., the conservation of system linear momentum representing the electromagnetic Doppler shift can be represented by the equations:

$$p = \sum_i m_i \gamma_i v_i + \varepsilon_0 \int d^3 x (E \times B) \text{ linear momentum}$$

$$\frac{dp^{mech}}{dt} + \frac{dp^{em}}{dt} + \oint_{s'} d^2 x' n' \cdot T = 0 \text{ conservation of linear momentum}$$

The conservation of system center of energy is represented by the equation:

$$R = \frac{1}{H} \Sigma_i (x_i - x_0) m_i \gamma_i c^2 + \frac{\varepsilon_0}{2H} \int d^3 x (x - x_0)(|E|^2 + c^2 |B|^2)$$

Similarly, the conservation of system angular momentum, which gives rise to the azimuthal Doppler shift is represented by the equation:

$$\frac{dJ^{mech}}{dt} + \frac{dJ^{em}}{dt} + \oint_{s'} d^2 x' n' \cdot M = 0 \text{ conservation of angular momentum}$$

For radiation beams in free space, the EM field angular momentum $J^{em}$ can be separated into two parts:

$$J^{em} = \varepsilon_0 \int_{V'} d^3 x' (E \times A) + \varepsilon_0 \int_{V'} d^3 x' E_i [(x' - x_0) \times \nabla] A_i$$

For each singular Fourier mode in real valued representation:

$$J^{em} = -i \frac{\varepsilon_0}{2\omega} \int_{V'} d^3 x' (E^* \times E) - i \frac{\varepsilon_0}{2\omega} \int_{V'} d^3 x' E_i [(x' - x_0) \times \nabla] E_i$$

The first part is the EM spin angular momentum $S^{em}$, its classical manifestation is wave polarization. And the second part is the EM orbital angular momentum $L^{em}$ its classical manifestation is wave helicity. In general, both EM linear momentum $P^{em}$, and EM angular momentum $J^{em} = L^{em} + S^{em}$ are radiated all the way to the far field.

By using Poynting theorem, the optical vorticity of the signals may be determined according to the optical velocity equation:

$$\frac{\partial U}{\partial t} + \nabla \cdot S = 0,$$

continuity equation
where S is the Poynting vector $$S = \frac{1}{4}(E \times H^* + E^* \times H),$$

and U is the energy density $$U = \frac{1}{4}(\varepsilon|E|^2 + \mu_0 |H|^2),$$

with E and H comprising the electric field and the magnetic field, respectively, and $\varepsilon$ and $\mu_0$ being the permittivity and the permeability of the medium, respectively. The optical vorticity V may then be determined by the curl of the optical velocity according to the equation:

$$V = \nabla \times v_{opt} = \nabla \times \left( \frac{E \times H^* + E^* \times H}{\varepsilon|E|^2 + \mu_0 |H|^2} \right)$$

The use of the OAM of light for the metrology of glucose, amyloid beta and other chiral materials has been demonstrated using the above-described configurations. OAM beams are observed to exhibit unique topological evolution upon interacting with chiral solutions within 3 cm optical path links. It should be realized that unique topological evolution may also be provided from non-chiral materials. Chiral solution, such as Amyloid-beta, glucose and others, have been observed to cause orbital angular momentum (OAM) beams to exhibit unique topological evolution when interacting therewith. OAM is not typically carried by naturally scattered photons which make use of the twisted beams more accurate when identifying the helicities of chiral molecules because OAM does not have ambient light scattering (noise) in its detection. Thus, the unique OAM signatures imparted by a material is not interfered with by ambient light scattering (noise) that does not carry OAM in naturally scattered photons making detection much more accurate. Given these unique topological features one can detect the amyloid-beta presence and concentration within a given sample based upon a specific signature in both amplitude and phase measurements. Molecular chirality signifies a structural handedness associated with variance under spatial inversion or a combination of inversion and rotation, equivalent to the usual criteria of a lack of any proper axes of rotation. Something is chiral when something cannot be made identical to its reflection. Chiral molecules that are not superimposable on their mirror image are known as Enantiomers. Traditionally, engages circularly polarized light, even in the case of optical rotation, interpretation of the phenomenon commonly requires the plane polarized state to be understood as a superposition of circular polarizations with opposite handedness. For circularly polarized light, the left and right forms designate the sign of intrinsic spin angular momentum, ±h and also the helicity of the locus described by the associated electromagnetic field vectors. For this reason its interactions with matter are enantiomerically specific.

The continuous symmetry measure (CSM) is used to evaluate the degree of symmetry of a molecule, or the chirality. This value ranges from 0 to 100. The higher the symmetry value of a molecule the more symmetry distorted the molecule and the more chiral the molecule. The measurement is based on the minimal distance between the chiral molecule and the nearest achiral molecule.

The continuous symmetry measure may be achieved according to the equation:

$$S(G) = 100 \times \min \frac{1}{Nd^2} \sum_{k=1}^{N} |Q_k - \hat{Q}_k|^2$$

$Q_k$: The original structure
$\hat{Q}_k$: The symmetry-operated structure
N: Number of vertices
d: Size normalization factor
*The scale is 0-1 (0-100):
The larger S(G) is, the higher is the deviation from G-symmetry SG as a continuous chirality measure may be determined according to:

$$S(G) = 100 \times \min \frac{1}{Nd^2} \sum_{k=1}^{N} |Q_k - \hat{Q}_k|^2$$

G: The achiral symmetry point group which minimizes S(G)
Achiral molecule: S(G)=0

An achiral molecule has a value of S(G)=0. The more chiral a molecule is the higher the value of S(G).

The considerable interest in orbital angular momentum has been enhanced through realization of the possibility to engineer optical vortices. Here, helicity is present in the wave-front surface of the electromagnetic fields and the associated angular momentum is termed "orbital". The radiation itself is commonly referred to as a 'twisted' or 'helical' beam. Mostly, optical vortices have been studied only in their interactions with achiral matter—the only apparent exception is some recent work on liquid crystals. It is timely and of interest to assess what new features, if any, can be expected if such beams are used to interrogate any system whose optical response is associated with enantiomerically specific molecules.

First the criteria for manifestations of chirality in optical interactions are constructed in generalized form. For simplicity, materials with a unique enantiomeric specificity are assumed—signifying a chirality that is intrinsic and common to all molecular components (or chromophores) involved in the optical response. Results for systems of this kind will also apply to single molecule studies. Longer range translation/rotation order can also produce chirality, as for example in twisted nematic crystals, but such mesoscopic chirality cannot directly engender enantiomerically specific interactions. The only exception is where optical waves probe two or more electronically distinct, dissymmetrically oriented but intrinsically achiral molecules or chromophores.

Chiroptical interactions can be distinguished by their electromagnetic origins: for molecular systems in their usual singlet electronic ground state, they involve the spatial variation of the electric and magnetic fields associated with the input of optical radiation. This variation over space can be understood to engage chirality either through its coupling with di-symmetrically placed, neighbouring chromophore groups (Kirkwood's two-group model, of limited application) or more generally through the coupling of its associated electric and magnetic fields with individual groups. As chirality signifies a local breaking of parity it permits an interference of electric and magnetic interactions. Even in the two-group case, the paired electric interactions of the system correspond to electric and magnetic interactions of the single entity which the two groups comprise. Thus, for convenience, the term 'chiral center' is used in the following to denote either chromophore or molecule.

With the advent of the laser, the Gaussian beam solution to the wave equation came into common engineering parlance, and its extension two higher order laser modes, Hermite Gaussian for Cartesian symmetry; Laguerre Gaussian for cylindrical symmetry, etc., entered laboratory optics operations. Higher order Laguerre Gaussian beam modes exhibit spiral, or helical phase fronts. Thus, the propagation vector, or the eikonal of the beam, and hence the beams momentum, includes in addition to a spin angular momentum, an orbital angular momentum, i.e. a wobble around the sea axis. This phenomenon is often referred to as vorticity. The expression for a Laguerre Gaussian beam is given in cylindrical coordinates:

$$u(r, \theta, z) = \sqrt{\frac{2p!}{1 + \delta_{0,m}\pi(m+p)!}} \frac{1}{w(z)}$$

$$\exp[j(2p + m + 1)(\psi(z) - \psi_0)] \left(\frac{\sqrt{2}r}{w(z)}\right) L_p^m\left(\frac{2r^2}{w(z)^2}\right) \exp\left[-jk\frac{r^2}{2q(z)} + im\theta\right]$$

Here, w (x) is the beam spot size, q(c) is the complex beam parameter comprising the evolution of the spherical wave front and the spot size. Integers p and m are the radial and azimuthal modes, respectively. The exp(imθ) term describes the spiral phase fronts.

Figure 31:
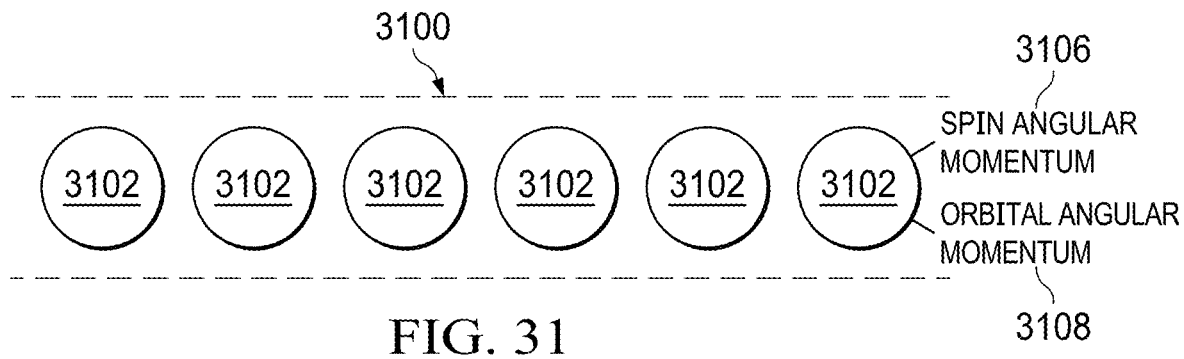

Referring now also to FIG. 31, there is illustrated one embodiment of a beam for use with the system. A light beam 3100 consists of a stream of photons 3102 within the light beam 3100. Each photon has an energy±ℏω and a linear momentum of ±ℏk which is directed along the light beam axis 3104 perpendicular to the wavefront. Independent of the frequency, each photon 3102 within the light beam has a spin angular momentum 3106 of ±ℏ aligned parallel or antiparallel to the direction of light beam propagation. Alignment of all of the photons 3102 spins gives rise to a circularly polarized light beam. In addition to the circular polarization, the light beams also may carry an orbital angular momentum 3108 which does not depend on the circular polarization and thus is not related to photon spin.

Figure 32:
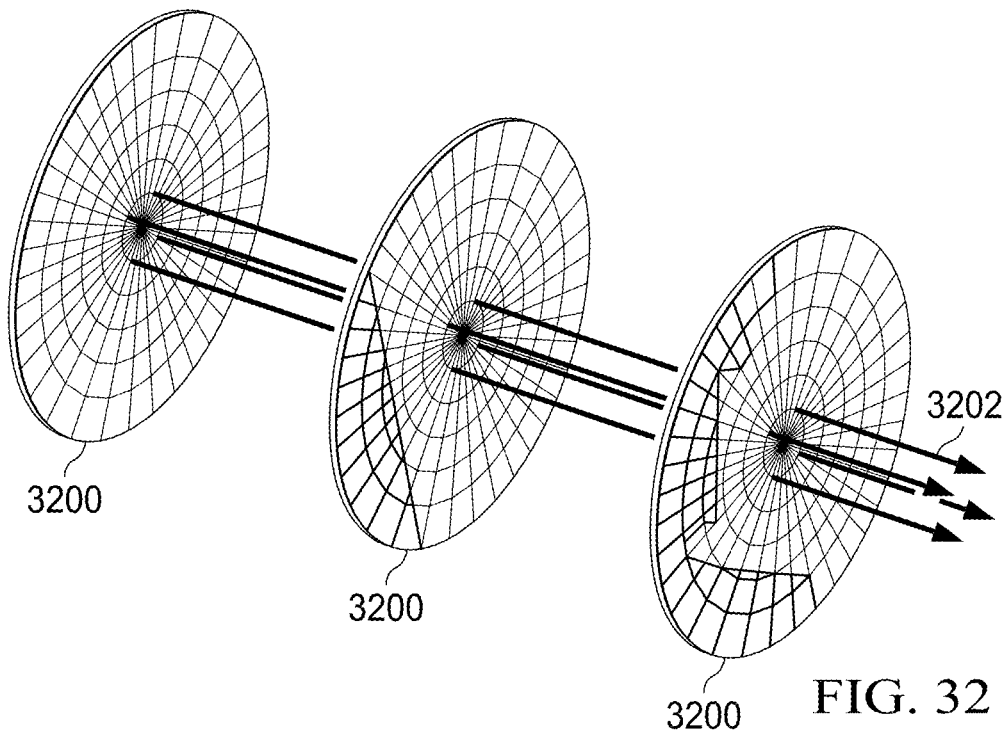

Lasers are widely used in optical experiments as the source of well-behaved light beams of a defined frequency. A laser may be used for providing the light beam 3100. The energy flux in any light beam 3100 is given by the Poynting vector which may be calculated from the vector product of the electric and magnetic fields within the light beam. In a vacuum or any isotropic material, the Poynting vector is parallel to the wave vector and perpendicular to the wavefront of the light beam. In a normal laser light, the wavefronts 3200 are parallel as illustrated in FIG. 32. The wave vector and linear momentum of the photons are directed along the axis in a z direction 3202. The field distributions of such light beams are paraxial solutions to Maxwell's wave equation but although these simple beams are the most common, other possibilities exist.

Figure 33:
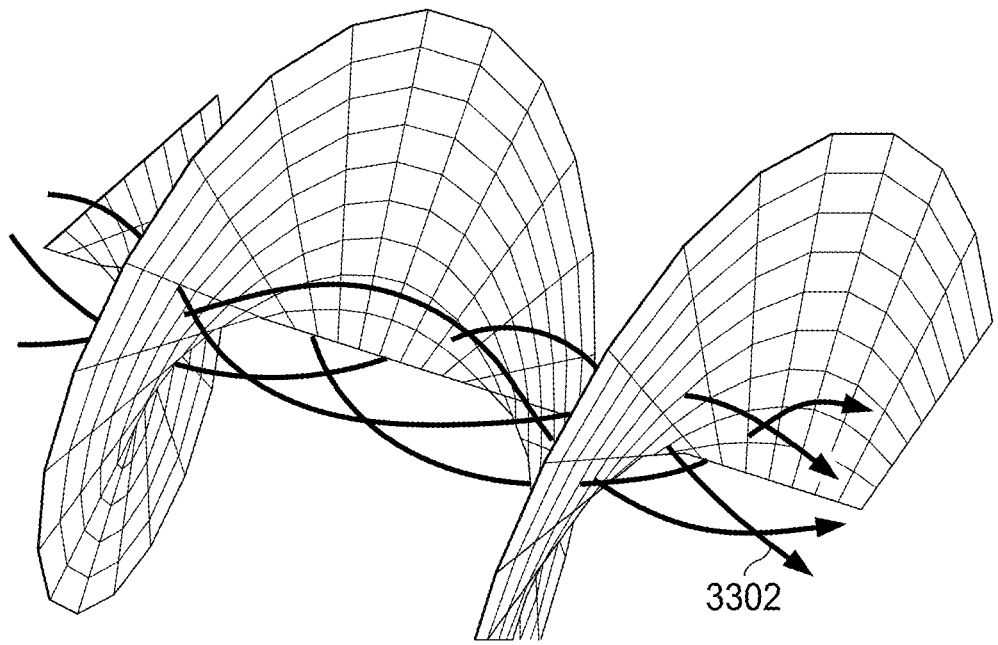

For example, beams that have l intertwined helical fronts are also solutions of the wave equation. The structure of these complicated beams is difficult to visualize, but their form is familiar from the l=3 fusilli pasta. Most importantly, the wavefront has a Poynting vector and a wave vector that spirals around the light beam axis direction of propagation as illustrated in FIG. 33 at 3302.

A Poynting vector has an azimuthal component on the wave front and a non-zero resultant when integrated over the beam cross-section. The spin angular momentum of circularly polarized light may be interpreted in a similar way. A beam with a circularly polarized planer wave front, even though it has no orbital angular momentum, has an azimuthal component of the Poynting vector proportional to the radial intensity gradient. This integrates over the cross-section of the light beam to a finite value. When the beam is linearly polarized, there is no azimuthal component to the Poynting vector and thus no spin angular momentum.

Thus, the momentum of each photon 3102 within the light beam 3100 has an azimuthal component. A detailed calculation of the momentum involves all of the electric fields and magnetic fields within the light beam, particularly those electric and magnetic fields in the direction of propagation of the beam. For points within the beam, the ratio between the azimuthal components and the z components of the momentum is found to be l/kr. (where l=the helicity or orbital angular momentum; k=wave number $2\pi/\lambda$; r=the radius vector.) The linear momentum of each photon 3102 within the light beam 3100 is given by $\hbar k$, so if we take the cross product of the azimuthal component within a radius vector, r, we obtain an orbital momentum for a photon 3102 of $l\hbar$. Note also that the azimuthal component of the wave vectors is l/r and independent of the wavelength.

Figure 34:
Figure 35:
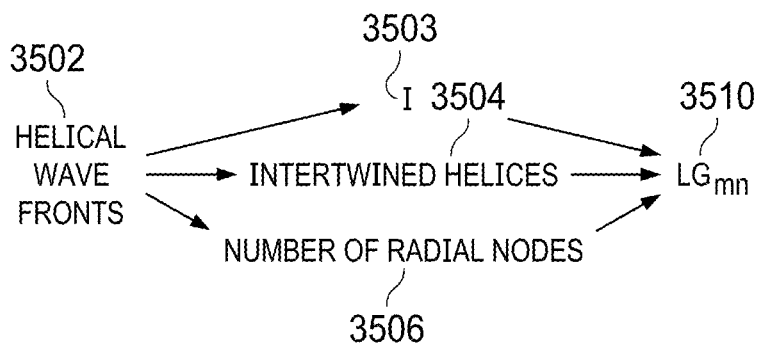

Referring now to FIGS. 34 and 35, there are illustrated plane wavefronts and helical wavefronts. Ordinarily, laser beams with plane wavefronts 3402 are characterized in terms of Hermite-Gaussian modes. These modes have a rectangular symmetry and are described by two mode indices m 3404 and n 3406. There are m nodes in the x direction and n nodes in the y direction. Together, the combined modes in the x and y direction are labeled HGmn 3408. In contrast, as shown in FIG. 35, beams with helical wavefronts 3502 are best characterized in terms of Laguerre-Gaussian modes which are described by indices I 3503, the number of intertwined helices 3504, and p, the number of radial nodes 3506. The Laguerre-Gaussian modes are labeled LGmn 14710. For l≠0, the phase singularity on a light beam 3100 results in 0 on axis intensity. When a light beam 300 with a helical wavefront is also circularly polarized, the angular momentum has orbital and spin components, and the total angular momentum of the light beam is ($l\pm\hbar$) per photon.

Using the orbital angular momentum state of the transmitted energy signals, physical information can be embedded within the electromagnetic radiation transmitted by the signals. The Maxwell-Heaviside equations can be represented as:

$$\nabla \cdot E = \frac{\rho}{\varepsilon_0}$$

$$\nabla \times E = -\frac{\partial B}{\partial t}$$

$$\nabla \cdot B = 0$$

$$\nabla \times B = \varepsilon_0 \mu_0 \frac{\partial E}{\partial t} + \mu_0 j(t, x)$$

where $\nabla$ is the del operator, E is the electric field intensity and B is the magnetic flux density. Using these equations, we can derive 23 symmetries/conserve quantities from Maxwell's original equations. However, there are only ten well-known conserve quantities and only a few of these are commercially used. Historically if Maxwell's equations where kept in their original quaternion forms, it would have been easier to see the symmetries/conserved quantities, but when they were modified to their present vectorial form by Heaviside, it became more difficult to see such inherent symmetries in Maxwell's equations.

The conserved quantities and the electromagnetic field can be represented according to the conservation of system energy and the conservation of system linear momentum. Time symmetry, i.e. the conservation of system energy can be represented using Poynting's theorem according to the equations:

$$H = \sum_i m_i \gamma_i c^2 + \frac{\varepsilon_0}{2} \int d^3 x (|E|^2 + c^2 |B|^2)$$

$$\frac{dU^{mech}}{dt} + \frac{dU^{em}}{dt} + \oint_{s'} d^2 x' \hat{n}' \cdot S = 0$$

The space symmetry, i.e., the conservation of system linear momentum representing the electromagnetic Doppler shift can be represented by the equations:

$$P = \sum_i m_i \gamma_i v_i + \varepsilon_0 \int d^3 x (E \times B)$$

$$\frac{dp^{mech}}{dt} + \frac{dp^{em}}{dt} + \oint_{s'} d^2 x' \hat{n}' \cdot T = 0$$

The conservation of system center of energy is represented by the equation:

$$R = \frac{1}{H} \sum_i (x_i - x_0) m_i \gamma_i c^2 + \frac{\varepsilon_0}{2H} \int d^3 x (x - x_0)(|E^2| + c^2 |B^2|)$$

Similarly, the conservation of system angular momentum, which gives rise to the azimuthal Doppler shift is represented by the equation:

$$\frac{dJ^{mech}}{dt} + \frac{dJ^{em}}{dt} + \oint_{s'} d^2 x' \hat{n}' \cdot M = 0$$

For radiation beams in free space, the EM field angular momentum Jem can be separated into two parts:

$$J^{em} = \varepsilon_0 \int_{V'} d^3x' (E \times A) + \varepsilon_0 \int_{V'} d^3x' E_i[(x' - x_0) \times \nabla] A_i$$

For each singular Fourier mode in real valued representation:

$$J^{em} = -i\frac{\varepsilon_0}{2\omega} \int_{V'} d^3x' (E^* \times E) - i\frac{\varepsilon_0}{2\omega} \int_{V'} d^3x' E_i^*[(x' - x_0) \times \nabla] E_i$$

The first part is the EM spin angular momentum Sem, its classical manifestation is wave polarization. And the second part is the EM orbital angular momentum Lem its classical manifestation is wave helicity. In general, both EM linear momentum Pem, and EM angular momentum Jem=Lem+Sem are radiated all the way to the far field.

By using Poynting theorem, the optical vorticity of the signals may be determined according to the optical velocity equation:

$$\frac{\partial U}{\partial t} + \nabla \cdot S = 0$$

where S is the Poynting vector $$S = \tfrac{1}{4}(E \times H^* + E^* \times H)$$

and U is the energy density $$U = \tfrac{1}{4}(\varepsilon |E|^2 + \mu_0 |H|^2)$$

with E and H comprising the electric field and the magnetic field, respectively, and $\varepsilon$ and $\mu_0$ being the permittivity and the permeability of the medium, respectively. The optical vorticity V may then be determined by the curl of the optical velocity according to the equation:

$$V = \nabla \times v_{opt} = \nabla \times \left( \frac{E \times H^* + E^* \times H}{\varepsilon |E|^2 + \mu_0 |H|^2} \right)$$

Figure 36:
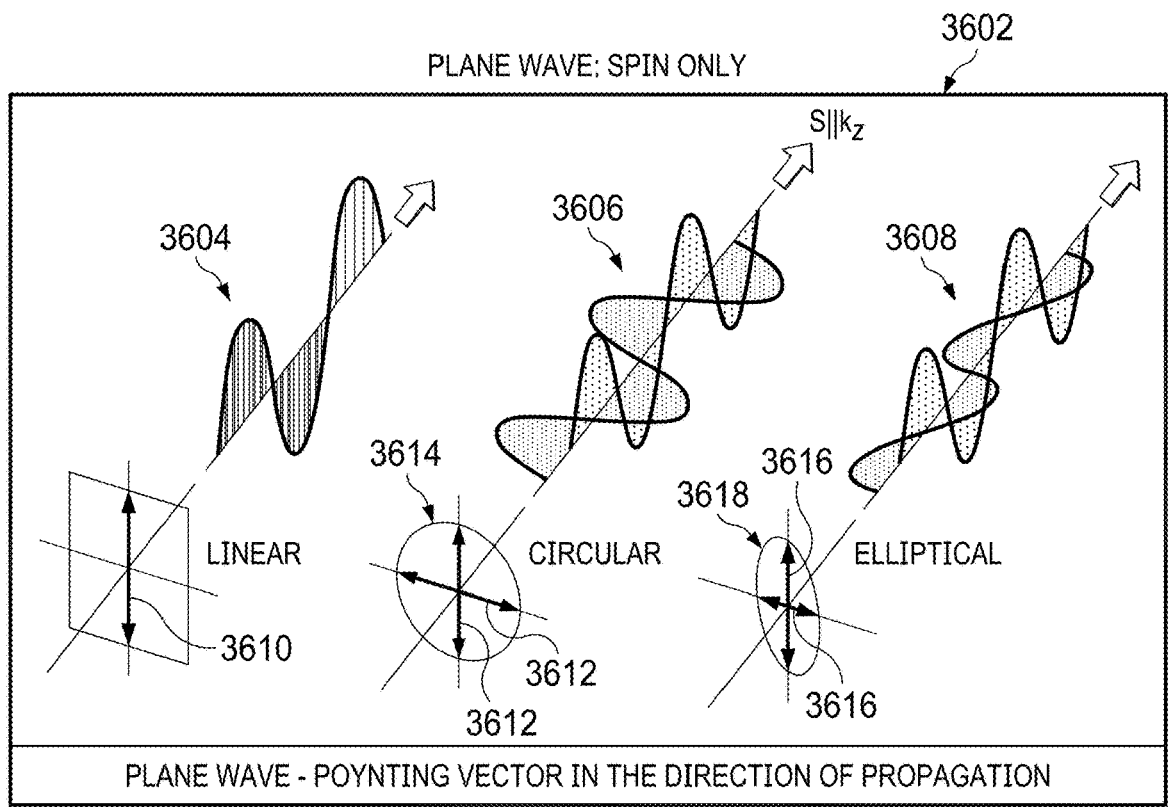
Figure 37:
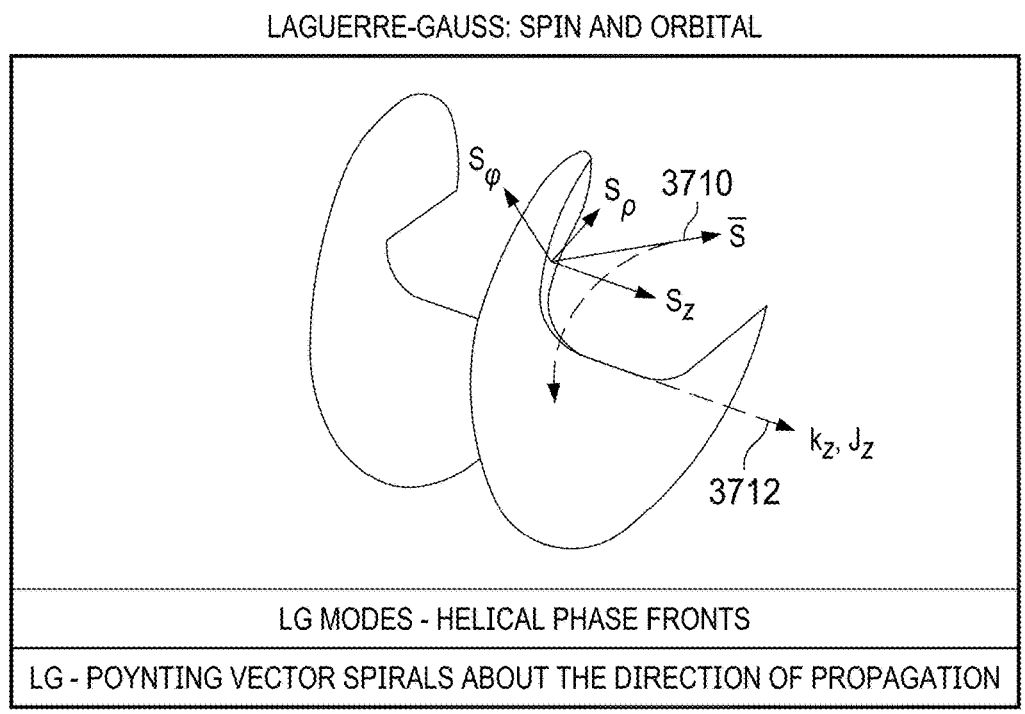

Referring now to FIGS. 36 and 37, there are illustrated the manner in which a signal and an associated Poynting vector of the signal vary in a plane wave situation (FIG. 36) where only the spin vector is altered, and in a situation wherein the spin and orbital vectors are altered in a manner to cause the Poynting vector to spiral about the direction of propagation (FIG. 37).

In the plane wave situation, illustrated in FIG. 36, when only the spin vector of the plane wave is altered, the transmitted signal may take on one of three configurations. When the spin vectors are in the same direction, a linear signal is provided as illustrated generally at 3604. It should be noted that while 3604 illustrates the spin vectors being altered only in the x direction to provide a linear signal, the spin vectors can also be altered in the y direction to provide a linear signal that appears similar to that illustrated at 3604 but in a perpendicular orientation to the signal illustrated at 3604. In linear polarization such as that illustrated at 3604, the vectors for the signal are in the same direction and have a same magnitude.

Within a circular polarization as illustrated at 3606, the signal vectors 3612 are 90 degrees to each other but have the same magnitude. This causes the signal to propagate as illustrated at 3606 and provide the circular polarization 3614 illustrated in FIG. 36. Within an elliptical polarization 3608, the signal vectors 3616 are also 90 degrees to each other but have differing magnitudes. This provides the elliptical polarizations 3618 illustrated for the signal propagation 408. For the plane waves illustrated in FIG. 36, the Poynting vector is maintained in a constant direction for the various signal configurations illustrated therein.

The situation in FIG. 37 illustrates when a unique orbital angular momentum is applied to a signal or beam. When this occurs, Poynting vector S 3710 will spiral around the general direction of propagation 3712 of the signal. The Poynting vector 3710 has three axial components $S\varphi$, $Sp$ and $Sz$ which vary causing the vector to spiral about the direction of propagation 3712 of the signal. The changing values of the various vectors comprising the Poynting vector 3710 may cause the spiral of the Poynting vector to be varied in order to enable signals to be transmitted on a same wavelength or frequency as will be more fully described herein. Additionally, the values of the orbital angular momentum indicated by the Poynting vector 3710 may be measured to determine the presence of particular materials and the concentrations associated with particular materials being processed by a scanning mechanism.

Figure 38A:
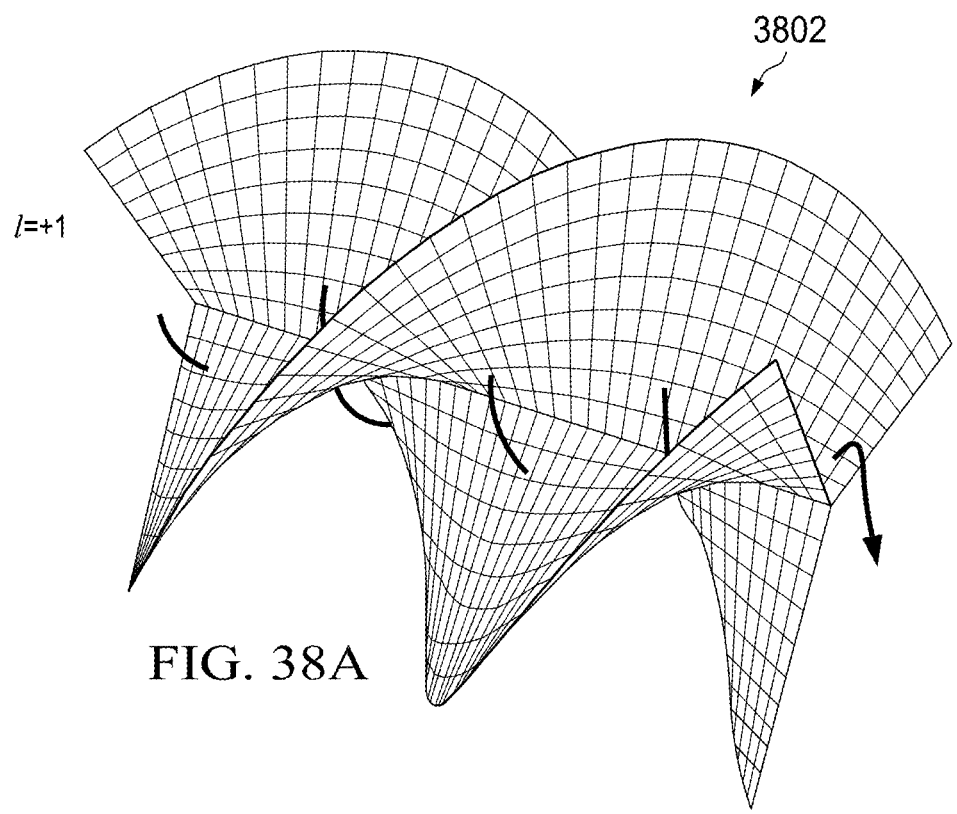
Figure 38B:
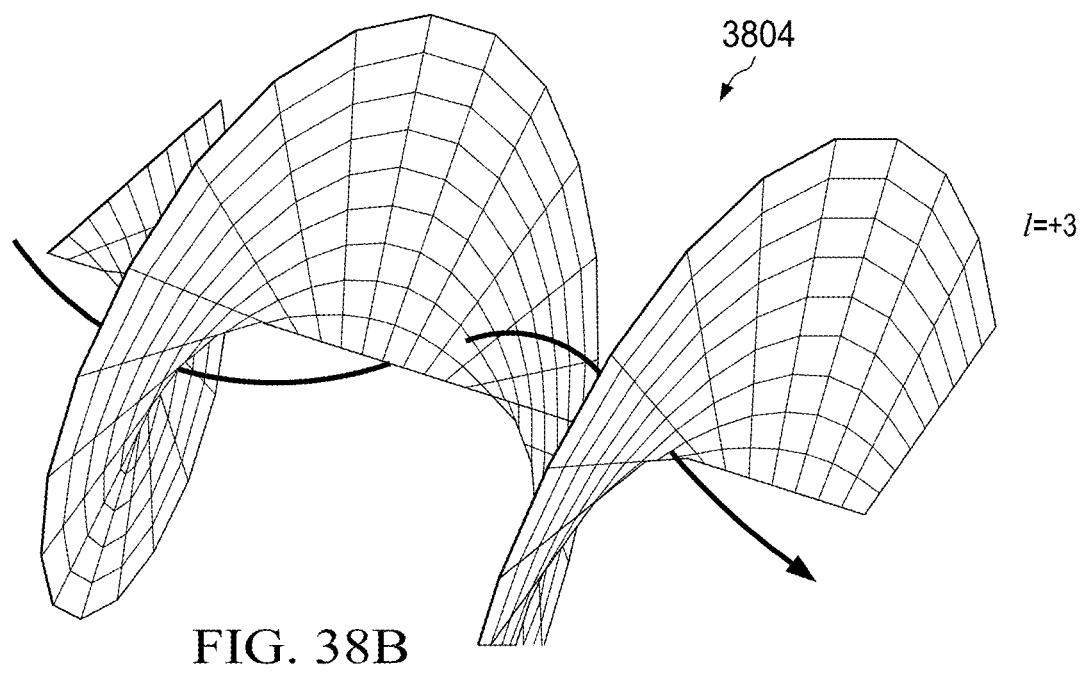
Figure 38C:
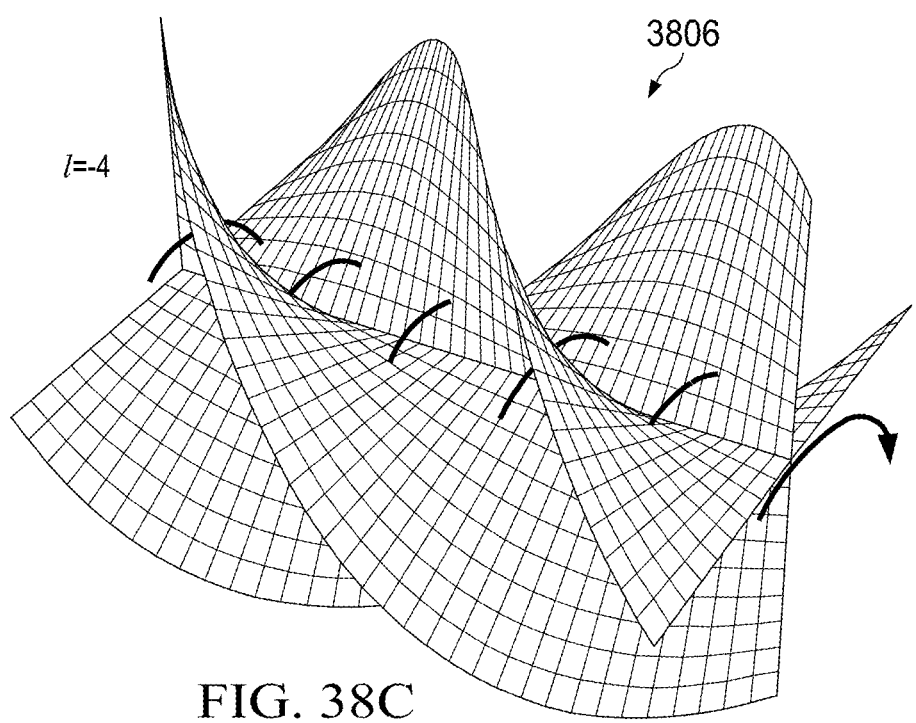

FIGS. 38A-38C illustrate the differences in signals having a different helicity (i.e., orbital angular momentum applied thereto). The differing helicities would be indicative of differing materials and concentration of materials within a sample that a beam was being passed through. By determining the particular orbital angular momentum signature associated with a signal, the particular material and concentration amounts of the material could be determined. Each of the spiralling Poynting vectors associated with a signal 3802, 3804 and 3806 provides a different-shaped signal. Signal 3802 has an orbital angular momentum of +1, signal 3804 has an orbital angular momentum of +3 and signal 3806 has an orbital angular momentum of −4. Each signal has a distinct orbital angular momentum and associated Poynting vector enabling the signal to be indicative of a particular material and concentration of material that is associated with the detected orbital angular momentum. This allows determinations of materials and concentrations of various types of materials to be determined from a signal since the orbital angular momentums are separately detectable and provide a unique indication of the particular material and the concentration of the particular material that has affected the orbital angular momentum of the signal transmitted through the sample material.

Figure 39A:
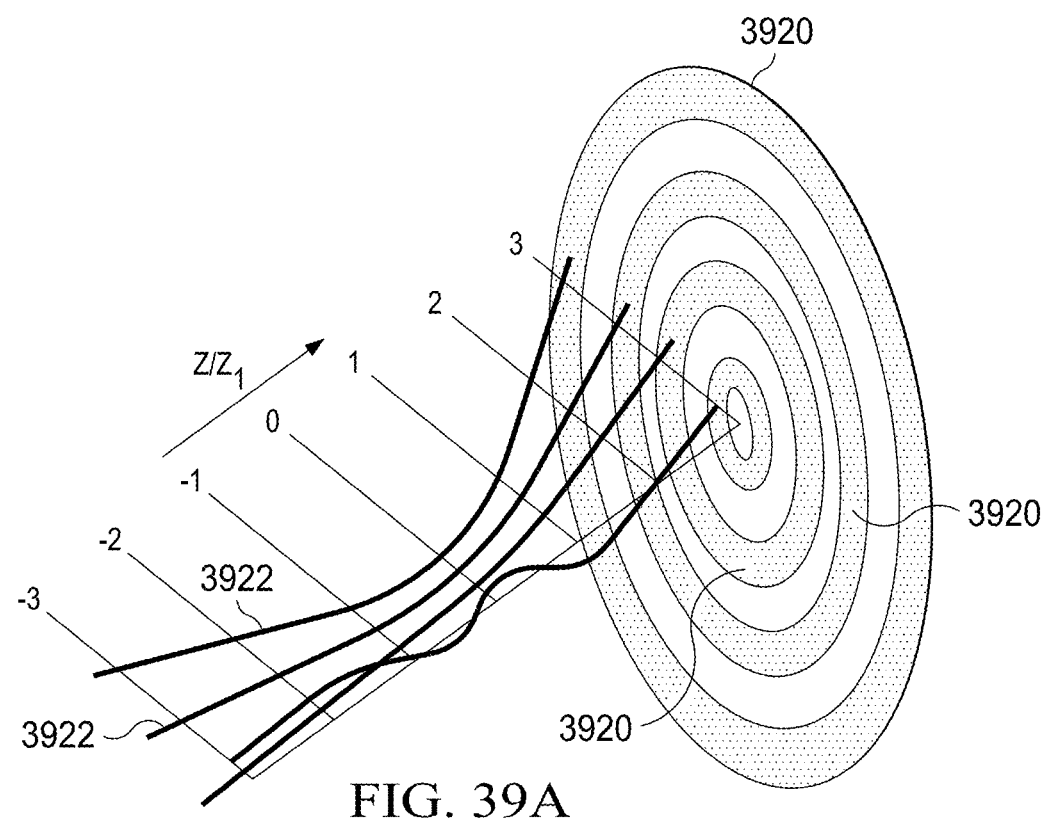

FIG. 39A illustrates the propagation of Poynting vectors for various Eigen modes. Each of the rings 3920 represents a different Eigen mode or twist representing a different orbital angular momentum. Each of the different orbital angular momentums is associated with particular material and a particular concentration of the particular material. Detection of orbital angular momentums provides an indication of the presence of an associated material and a concentration of the material that is being detected by the apparatus. Each of the rings 3920 represents a different material and/or concentration of a selected material that is being monitored. Each of the Eigen modes has a Poynting vector 3922 for generating the rings indicating different materials and material concentrations.

Topological charge may be multiplexed to the frequency for either linear or circular polarization. In case of linear polarizations, topological charge would be multiplexed on vertical and horizontal polarization. In case of circular polarization, topological charge would multiplex on left hand and right-hand circular polarizations. The topological charge is another name for the helicity index "l" or the amount of twist or OAM applied to the signal. The helicity index may be positive or negative.

Figure 39B:
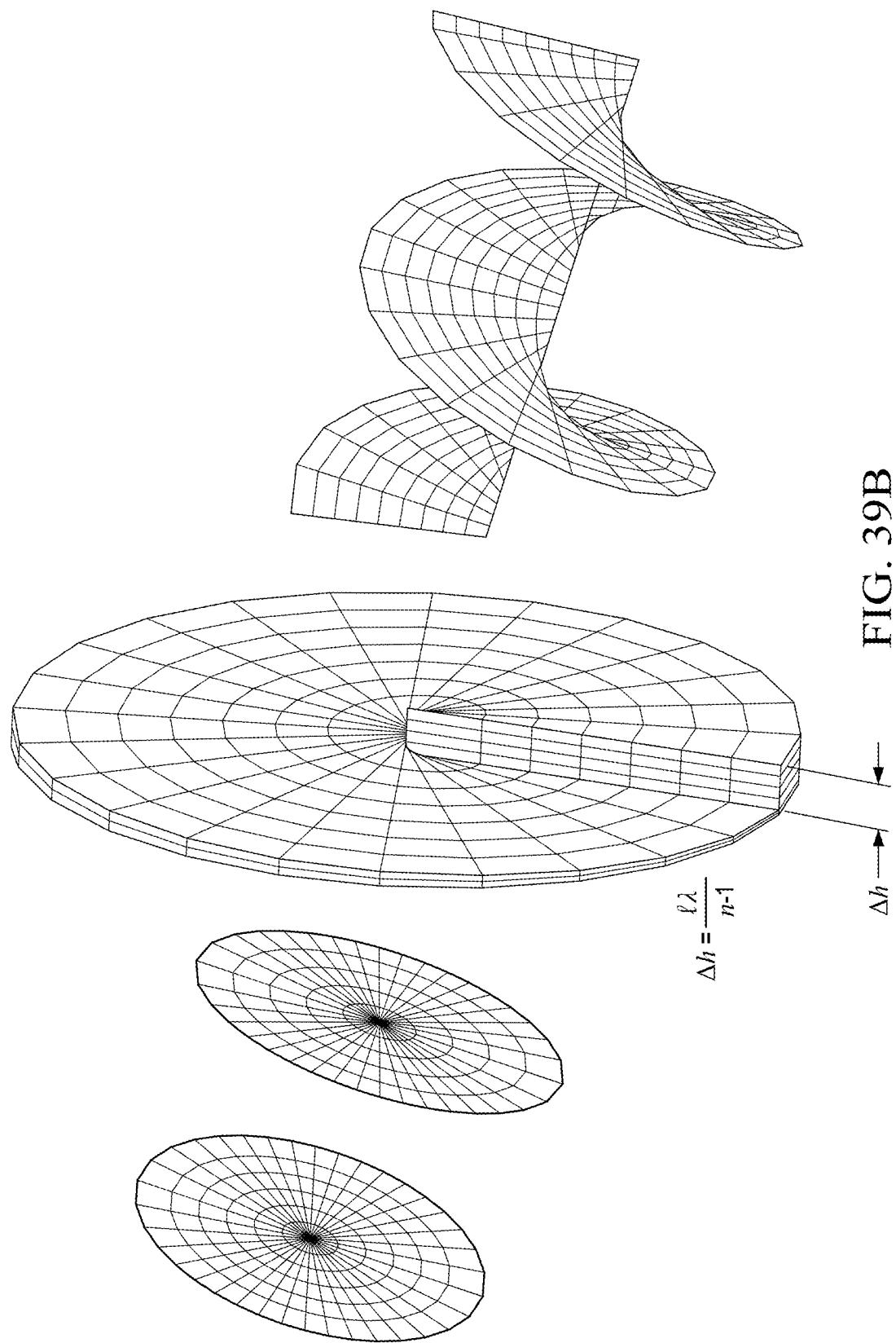

The topological charges 1 s can be created using Spiral Phase Plates (SPPs) as shown in FIG. 39B using a proper material with specific index of refraction and ability to machine shop or phase mask, holograms created of new materials. Spiral Phase plates can transform a RF plane wave (l=0) to a twisted wave of a specific helicity (i.e. l=+1).

Figure 40:
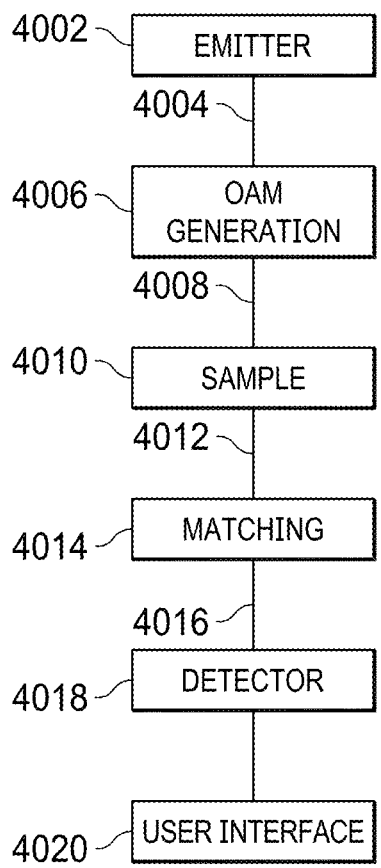

Referring now to FIG. 40, there is illustrated a block diagram of the apparatus for providing detection of the presence of a material and concentration measurements of various materials responsive to the orbital angular momentum detected by the apparatus in accordance with the principles described herein above. An emitter 4002 transmits wave energy 4004 that comprises a series of plane waves. The emitter 4002 may provide a series of plane waves such as those describes previously with respect to FIG. 32. The orbital angular momentum generation circuitry 4006 generates a series of waves having an orbital angular momentum applied to the waves 4008 in a known manner. The orbital angular momentum generation circuitry 4006 may utilize holograms or some other type of orbital angular momentum generation process as will be more fully described herein below. The OAM generation circuitry 4006 may be generated by transmitting plane waves through a spatial light modulator (SLM), an amplitude mask or a phase mask. The orbital angular momentum twisted waves 4008 are applied to a sample material 4010 under test. The sample material 4010 contains a material, and the presence and concentration of the material is determined via a detection apparatus in accordance with the process described herein. The sample material 4010 may be located in a container or at its naturally occurring location in nature such as an individual's body.

A series of output waves 4012 from the sample material 4010 exit the sample and have a particular orbital angular momentum imparted thereto as a result of the material and the concentration of the particular material under study within the sample material 4010. The output waves 4012 are applied to a matching module 4014 that includes a mapping aperture for amplifying a particular orbital angular momentum generated by the specific material under study. The matching module 4014 will amplify the orbital angular momentums associated with the particular material and concentration of material that is detected by the apparatus. The amplified OAM waves 4016 are provided to a detector 4018. The detector 4018 detects OAM waves relating to the material and the concentration of a material within the sample and provides this information to a user interface 4020. The detector 4018 may utilize a camera to detect distinct topological features from the beam passing through the sample. The user interface 4020 interprets the information and provides relevant material type and concentration indication to an individual or a recording device.

Figure 41:
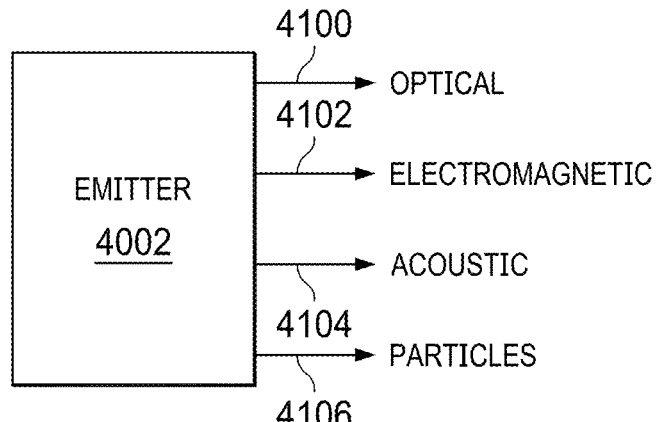

Referring now to FIG. 41, there is more particularly illustrated the emitter 4002. The emitter 4002 may emit a number of types of energy waves 4004 to the OAM generation module 4006. The emitter 4002 may emit optical waves 4100, electromagnetic waves 4102, acoustic waves 4104 or any other type of particle waves 4106. The emitted waves 4004 are plane waves such as those illustrated in FIG. 32 having no orbital angular momentum applied thereto and may come from a variety of types of emission devices and have information included therein. In one embodiment, the emission device may comprise a laser. Plane waves have wavefronts that are parallel to each other having no twist or helicity applied thereto, and the orbital angular momentum of the wave is equal to 0. The Poynting vector within a plane wave is completely in line with the direction of propagation of the wave.

Figure 42:
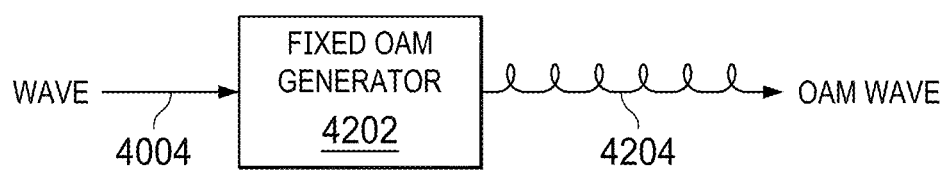

The OAM generation module 4006 processes the incoming plane wave 4004 and imparts a known orbital angular momentum onto the plane waves 4004 provided from the emitter 4002. The OAM generation module 4006 generates twisted or helical electromagnetic, optic, acoustic or other types of particle waves from the plane waves of the emitter 4002. A helical wave 4008 is not aligned with the direction of propagation of the wave but has a procession around direction of propagation as shown in FIG. 42. The OAM generation module 4006 may comprise in one embodiment a fixed orbital angular momentum generator 4202 as illustrated in FIG. 42. The fixed orbital angular momentum generator 4202 receives the plane waves 4004 from the emitter 4002 and generates an output wave 4204 having a fixed orbital angular momentum applied thereto.

Figure 43:
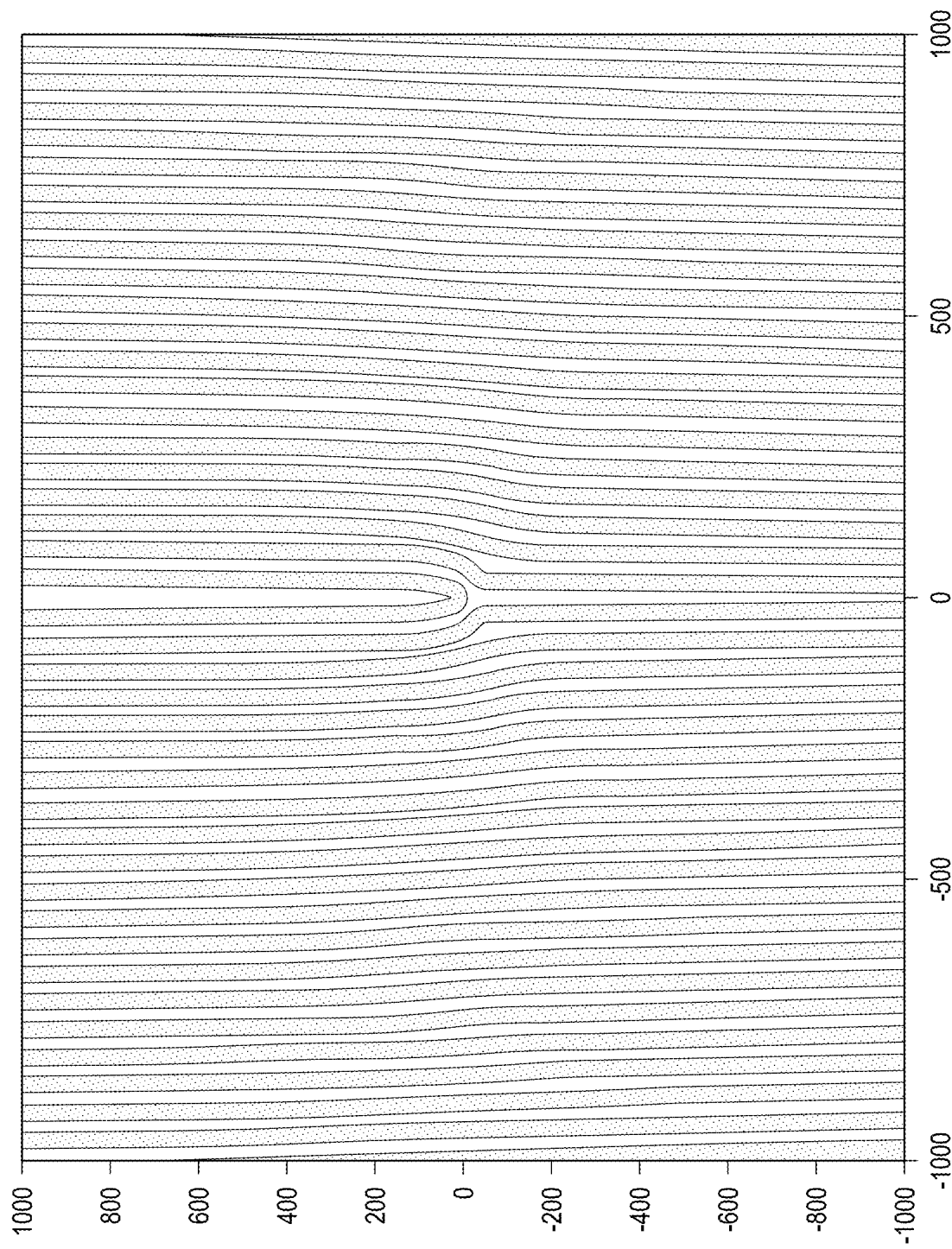

The fixed orbital angular momentum generator 4202 may in one embodiment comprise a holographic image for applying the fixed orbital angular momentum to the plane wave 4004 in order to generate the OAM twisted wave 4204. Various types of holographic images may be generated in order to create the desired orbital angular momentum twist to an optical signal that is being applied to the orbital angular momentum generator 4202. Various examples of these holographic images are illustrated in FIG. 43. In one embodiment, the conversion of the plane wave signals transmitted from the emitter 4002 by the orbital angular momentum generation circuitry 4006 may be achieved using holographic images.

Figure 44:
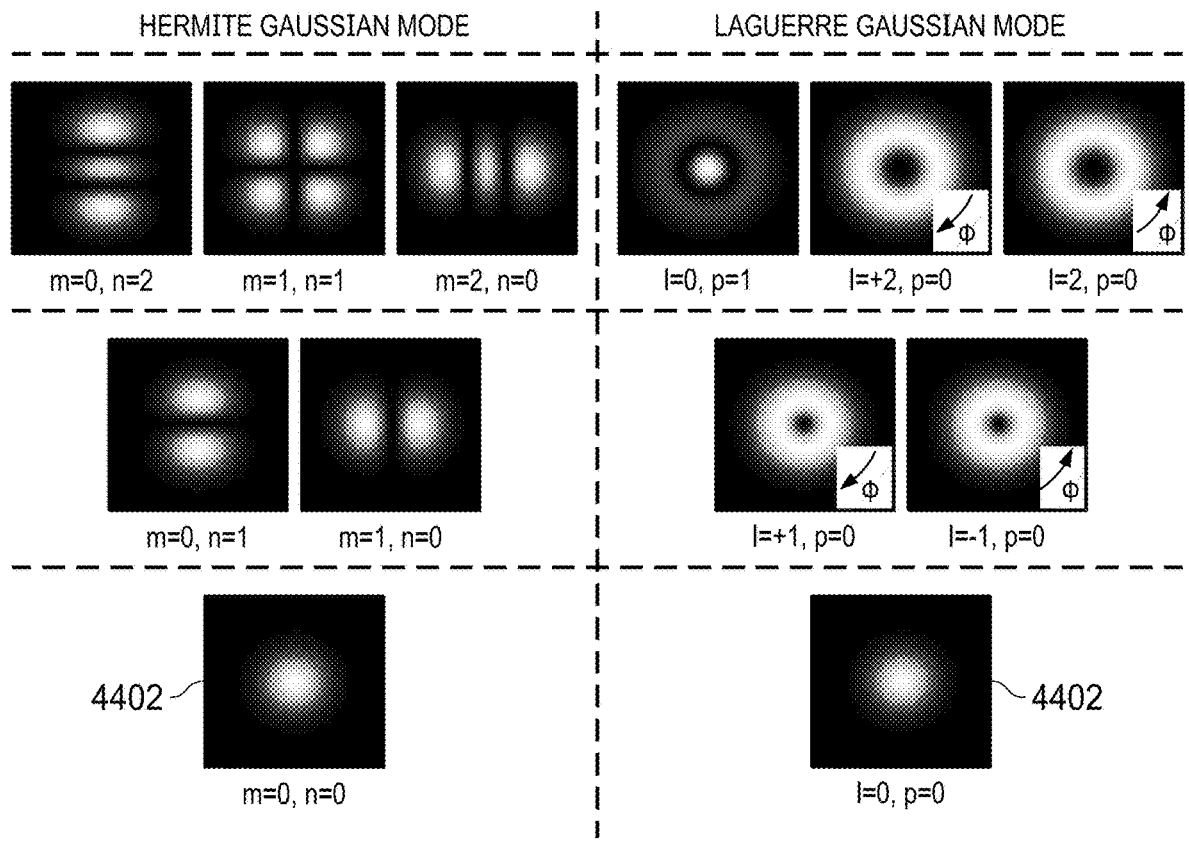

Most commercial lasers emit an HG00 (Hermite-Gaussian) mode 4402 (FIG. 44) with a planar wave front and a transverse intensity described by a Gaussian function. Although a number of different methods have been used to successfully transform an HG00 Hermite-Gaussian mode 4402 into a Laguerre-Gaussian mode 4404, the simplest to understand is the use of a hologram.

The cylindrical symmetric solution upl (r,φ,z) which describes Laguerre-Gaussian beams, is given by the equation:

$$u_{pl}(r, \phi, z) = \frac{C}{(1+z^2/z_R^2)^{1/2}} \left[\frac{r\sqrt{2}}{w(z)}\right]^l L_p^l \left[\frac{2r^2}{w^2(z)}\right]$$

$$\exp\left[\frac{-r^2}{w^2(z)}\right] \exp\left[\frac{-ikr^2z}{2(z^2+z_R^2)}\right] \exp(-il\phi) \times \exp\left[i(2p+l+1)\tan^{-1}\frac{z}{z_R}\right]$$

Where $z_R$ is the Rayleigh range, w(z) is the radius of the beam, $L_P$ is the Laguerre polynomial, C is a constant, and the beam waist is at z=0.

In its simplest form, a computer-generated hologram is produced from the calculated interference pattern that results when the desired beam intersects the beam of a conventional laser at a small angle. The calculated pattern is transferred to a high-resolution holographic film. When the developed hologram is placed in the original laser beam, a diffraction pattern results. The first order of which has a desired amplitude and phase distribution. This is one manner for implementing the OAM generation module 4006. An example of holographic images for use within a OAM generation module is illustrated with respect to FIG. 43.

There are various levels of sophistication in hologram design. Holograms that comprise only black and white areas with no grayscale are referred to as binary holograms. Within binary holograms, the relative intensities of the two interfering beams play no role and the transmission of the hologram is set to be zero for a calculated phase difference between zero and $\pi$, or unity for a phase difference between $\pi$ and $2\pi$. A limitation of binary holograms is that very little of the incident power ends up in the first order diffracted spot, although this can be partly overcome by blazing the grating. When mode purity is of particular importance, it is also possible to create more sophisticated holograms where the contrast of the pattern is varied as a function of radius such that the diffracted beam has the required radial profile.

A plane wave shining through the holographic images 1502 will have a predetermined orbital angular momentum shift applied thereto after passing through the holographic image 1502. OAM generator 4002 is fixed in the sense that a same image is used and applied to the beam being passed through the holographic image. Since the holographic image 1502 does not change, the same orbital angular momentum is always applied to the beam being passed through the holographic image 1502. While FIG. 43 illustrates an embodiment of a holographic image that might be utilized within the orbital angular momentum generator 4002, it will be realized that any type of holographic image 1502 may be utilized in order to achieve the desired orbital angular momentum within an beam being shined through the image 1502.

Figure 45:
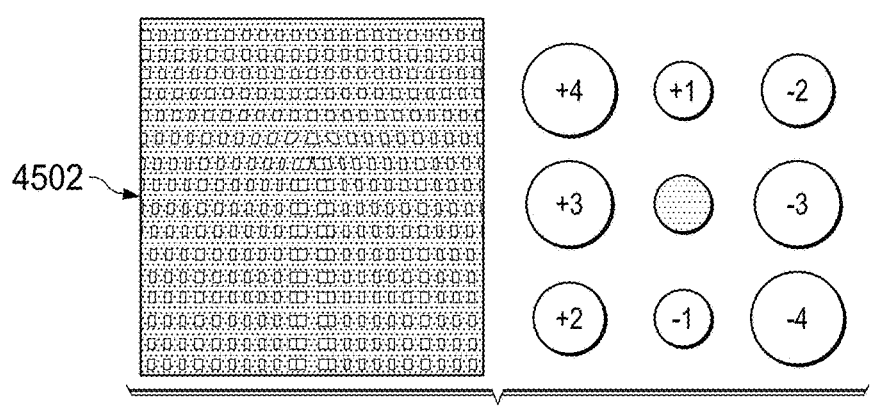

In another example of a holographic image illustrated in FIG. 45, there is illustrated a hologram that utilizes two separate holograms that are gridded together to produce a rich number of orbital angular momentum (l). The superimposed holograms of FIG. 45 have an orbital angular momentum of l=1 and l=3 which are superimposed upon each other to compose the composite vortex grid 4502. The holograms utilized may also be built in a manner that the two holograms are gridded together to produce a varied number of orbital angular momentums (l) not just on a line (l=+1, l=0, l=−1) but on a square which is able to identify the many variables more easily. Thus, in the example in FIG. 45, the orbital angular momentums along the top edge vary from +4 to +1 to −2 and on the bottom edge from +2 to −1 to −4. Similarly, along the left edge the orbital angular momentums vary from +4 to +3 to +2 and on the right edge from −2 to −3 to −4. Across the horizontal center of the hologram the orbital angular momentums provided vary from +3 to 0 to −3 and along the vertical axis vary from +1 to 0 to −1. Thus, depending upon the portion of the grid a beam may pass through, varying orbital angular momentum may be achieved.

Figure 46:
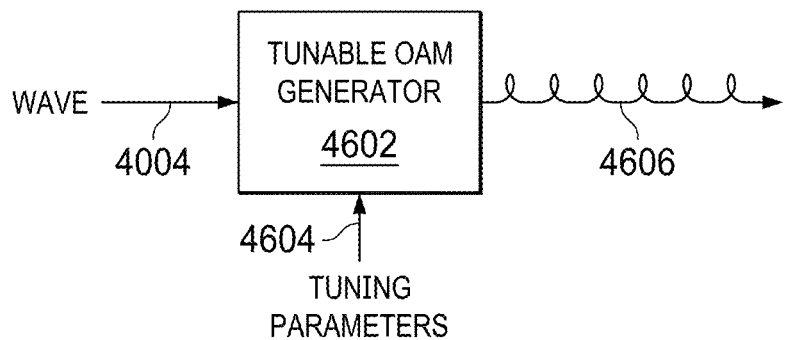

Referring now to FIG. 46, in addition to a fixed orbital angular momentum generator, the orbital angular momentum generation circuitry 4006 may also comprise a tunable orbital angular momentum generator circuitry 4602. The tunable orbital angular momentum generator 4602 receives the input plane wave 4004 but additionally receives one or more tuning parameters 4604. The tuning parameters 4604 tune the tunable OAM generator 4602 to apply a selected orbital angular momentum so that the tuned OAM wave 4606 that is output from the OAM generator 4602 has a selected orbital angular momentum value applied thereto. This can prove useful in inducing different resonances in different types of viruses.

This may be achieved in any number of fashions. In one embodiment, illustrated in FIGS. 46 and 26, the tunable orbital angular momentum generator 4602 may include multiple hologram images 2602 within the tunable OAM generator 4602. The tuning parameters 4604 enable selection of one of the holographic images 2602 in order to provide the desired OAM wave twisted output signal 4606 through a selector circuit 2604. Alternatively, the gridded holographic image such as that described in FIG. 45 may be utilized and the beam shined on a portion of the gridded image to provide the desired OAM output. The tunable OAM generator 4602 has the advantage of being controlled to apply a particular orbital angular momentum to the output orbital angular momentum wave 4606 depending upon the provided input parameter 4604. This enables the presence and concentrations of a variety of different materials to be monitored, or alternatively, for various different concentrations of the same material to be monitored or for different viruses to be attacked.

Figure 47:
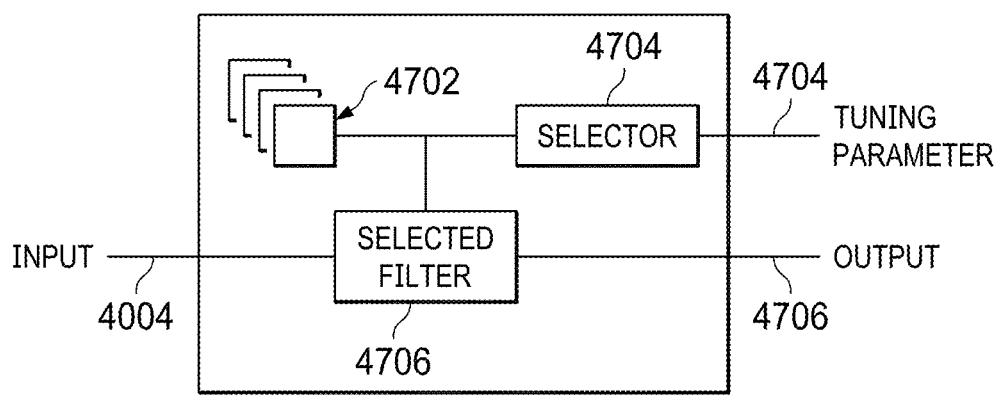

Referring now to FIG. 47, there is more particularly implemented a block diagram of a tunable orbital angular momentum generator 4602. The generator 4602 includes a plurality of holographic images 4702 for providing orbital angular momentums of various types to a provided light signal. These holographic images 4702 are selected responsive to a selector circuitry 4704 that is responsive to the input tuning parameters 4604. The selected filter 4706 comprises the holographic image that has been selected responsive to the selector controller 4704 and receives the input plane waves 4004 to provide the tuned orbital angular momentum wave output 4606. In this manner, signals having a desired orbital angular momentum may be output from the OAM generation circuitry 4006.

Figure 48:
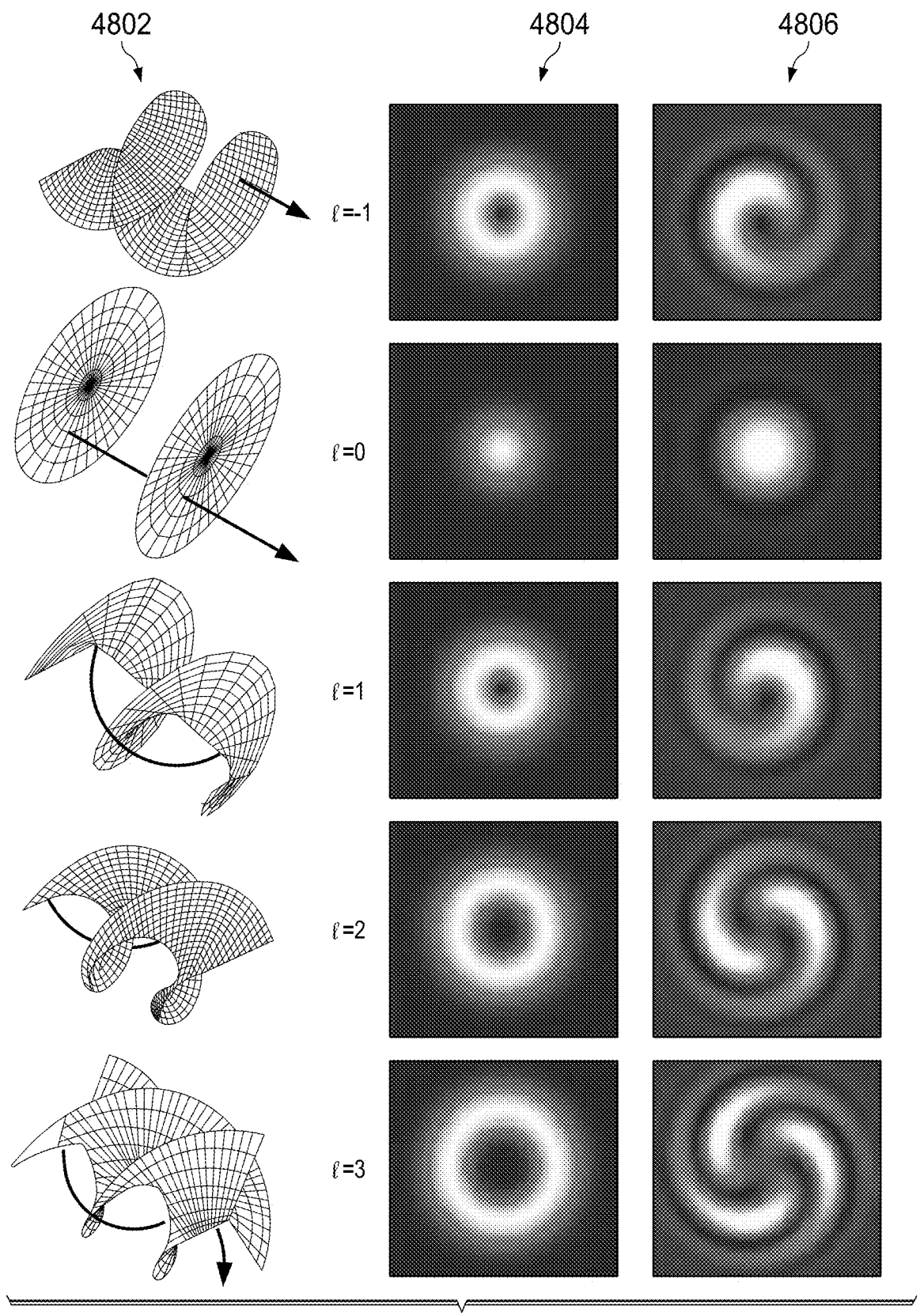

Referring now to FIG. 48, there is illustrated the manner in which the output of the OAM generator 4006 may vary a signal by applying different orbital angular momentums thereto. FIG. 48 illustrates helical phase fronts in which the Poynting vector is no longer parallel to the beam axis and thus has an orbital angular momentum applied thereto. In any fixed radius within the beam, the Poynting vector follows a spiral trajectory around the axis. Rows are labeled by l, the orbital angular momentum quantum number, $L=l\hbar$ is the beams orbital angular momentum per photon within the output signal. For each l, the left column 4802 is the light beam's instantaneous phase. The center column 4804 comprises the angular intensity profiles and the right column 4806 illustrates what occurs when such a beam interferes with a plane wave and produces a spiral intensity pattern. This is illustrated for orbital angular momentums of −1, 0, 1, 2 and 3 within the various rows of FIG. 48.

Figure 49:
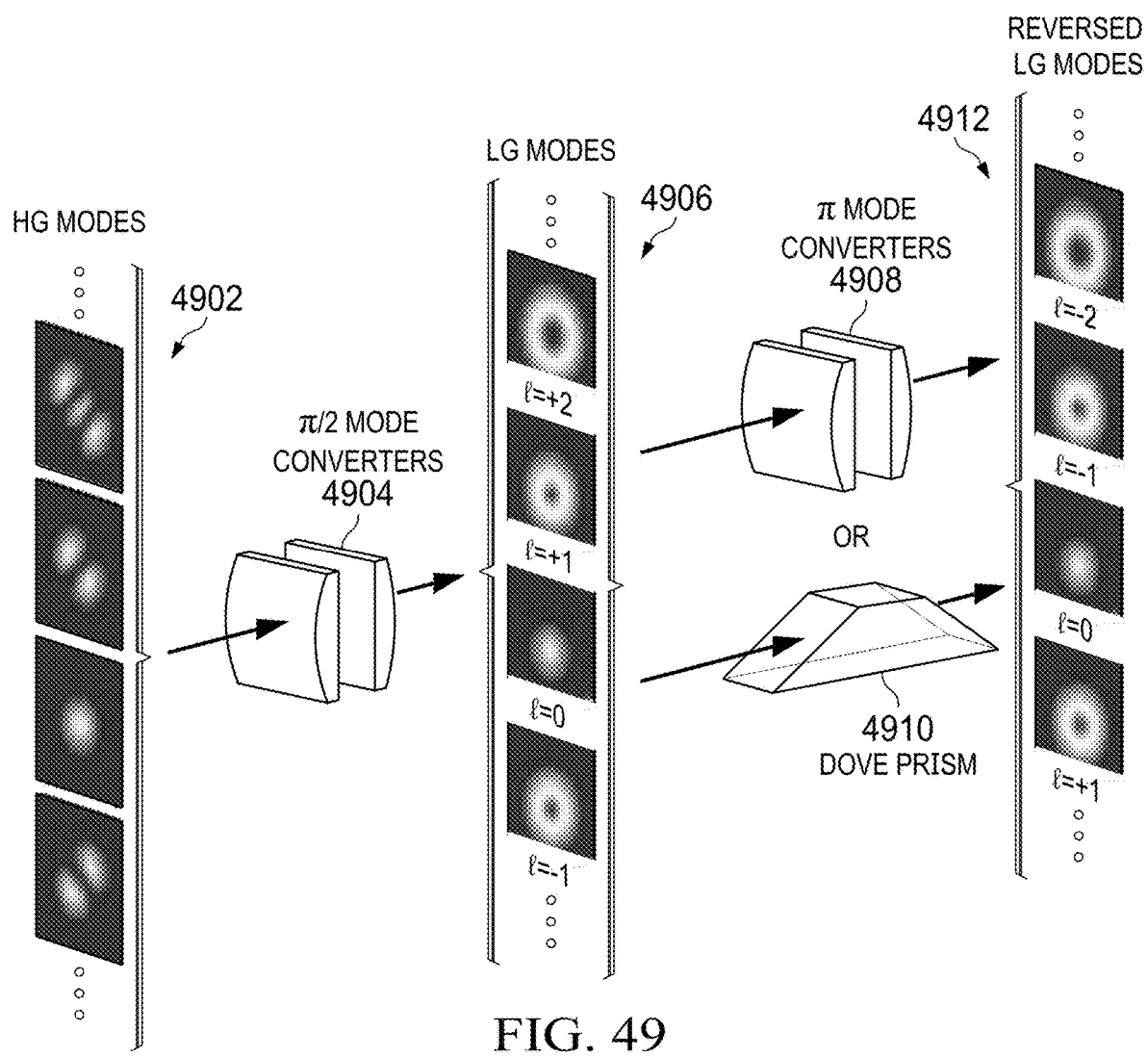

Referring now to FIG. 49, there is illustrated an alternative manner in which the OAM generator 4006 may convert a Hermite-Gaussian beam output from an emitter 4002 to a Laguerre-Gaussian beams having imparted therein an orbital angular momentum using mode converters 4904 and a Dove prism 4910. The Hermite-Gaussian mode plane waves 4902 are provided to a $\pi/2$ mode convertor 4904. The $\pi/2$ mode convertor 4904 produce beams in the Laguerre-Gaussian modes 4906. The Laguerre-Gaussian modes beams 4906 are applied to either a $\pi$ mode convertor 4908 or a dove prism 4910 that reverses the mode to create a reverse Laguerre-Gaussian mode signal 4912.

Figure 50:
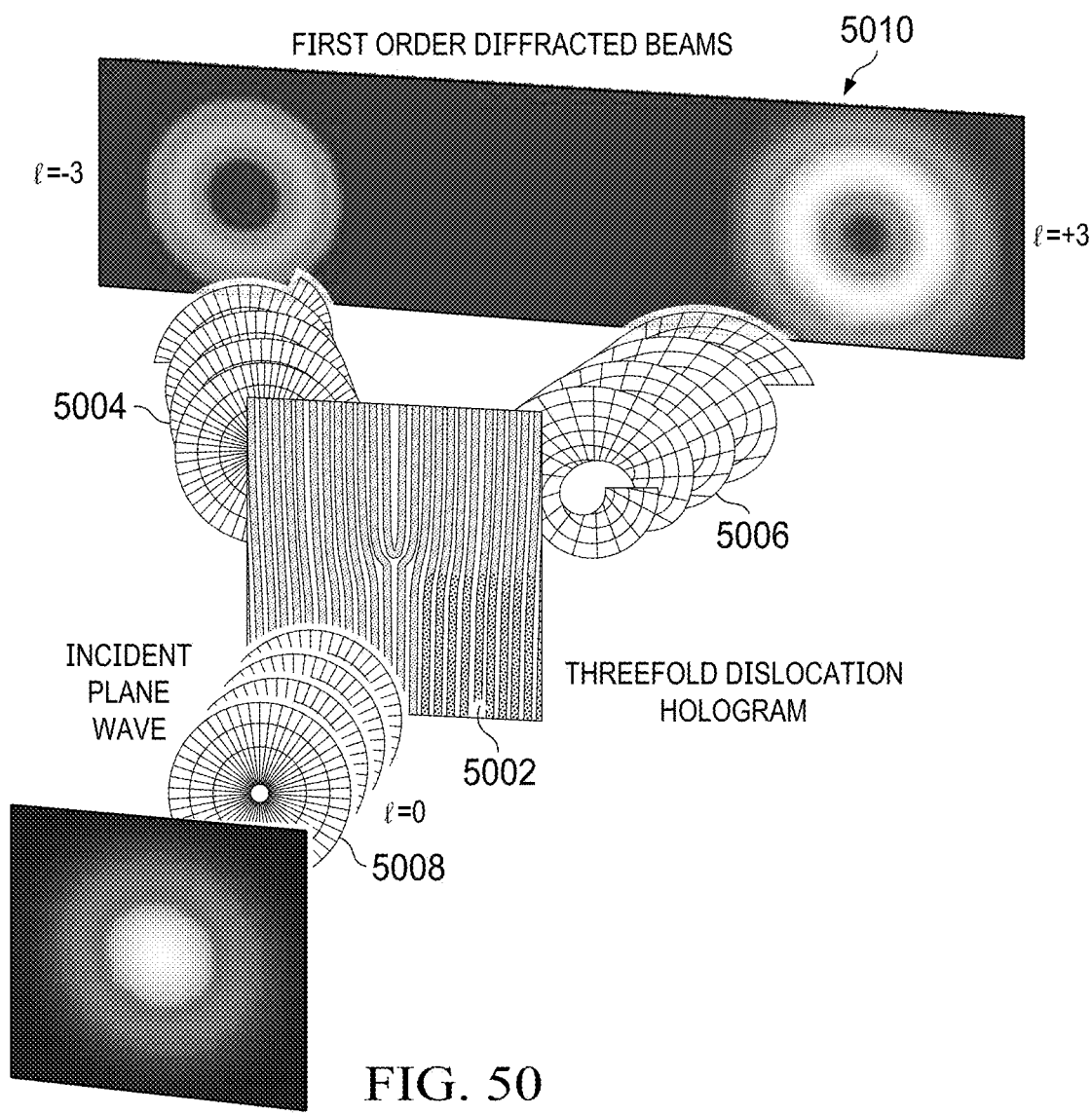

Referring now to FIG. 50, there is illustrated the manner in which holograms within the OAM generator 4006 generate a twisted light beam. A hologram 5002 can produce light beam 5004 and light beam 5006 having helical wave fronts and associated orbital angular momentum lh per photon. The appropriate hologram 5002 can be calculated or generated from the interference pattern between the desired beam form 5004, 5006 and a plane wave 5008. The resulting holographic pattern within the hologram 5002 resembles a diffraction grating but has a 1-pronged dislocation at the beam axis. When the hologram is illuminated with the plane wave 5008, the first-order diffracted beams 5004 and 5006 have the desired helical wave fronts to provide the desired first ordered diffracted beam display 5010.

Figure 51:
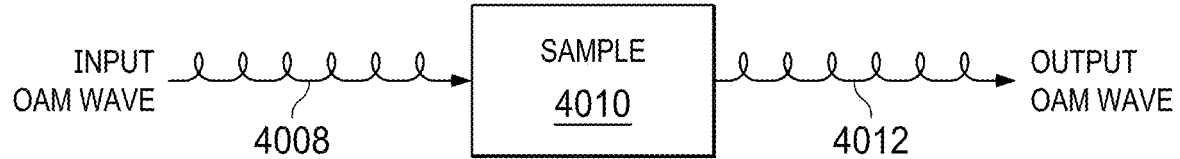

Referring now to FIG. 51, there is more particularly illustrated the manner in which the sample 4010 receives the input OAM twisted wave 4008 provided from the OAM generator 4006 and provides an output OAM wave 4012 having a particular OAM signature associated therewith that depends upon the material or the concentration of a particular monitored material within the sample 4010. The sample 4010 may comprise any sample that is under study and may be in a solid form, liquid form or gas form. The sample material 4010 that may be detected using the system described herein may comprise a variety of different materials. As stated previously, the material may comprise liquids such as blood, water, oil or chemicals. The various types of carbon bondings such as C—H, C—O, C—P, C—S or C—N may be provided for detection. The system may also detect various types of bondings between carbon atoms such as a single bond (methane or Isooctane), dual bond items (butadiene and benzene) or triple bond carbon items such as acetylene.

The sample 4010 may include detectable items such as organic compounds including carbohydrates, lipids (cylcerol and fatty acids), nucleic acids (C,H,O,N,P) (RNA and DNA) or various types of proteins such as polyour of amino $NH_2$ and carboxyl COOH or aminos such as tryptophan, tyrosine and phenylalanine. Various chains within the samples 4010 may also be detected such as monomers, isomers and polymers. Enzymes such as ATP and ADP within the samples may be detected. Substances produced or released by glands of the body may be in the sample and detected. These include items released by the exocrine glands via tube/ducts, endocrine glands released directly into blood samples or hormones. Various types of glands that may have their secretions detected within a sample 4010 include the hypothalamus, pineal and pituitary glands, the parathyroid and thyroid and thymus, the adrenal and pancreas glands of the torso and the hormones released by the ovaries or testes of a male or female.

The sample 4010 may also be used for detecting various types of biochemical markers within the blood and urine of an individual such as melanocytes and keratinocytes. The sample 4010 may include various parts of the body to detect defense substances therein. For example, with respect to the skin, the sample 4010 may be used to detect carotenoids, vitamins, enzymes, b-carotene and lycopene. With respect to the eye pigment, the melanin/eumelanin, dihydroxyindole or carboxylic may be detected. The system may also detect various types of materials within the body's biosynthetic pathways within the sample 4010 including hemoglobin, myoglobin, cytochromes, and porphyrin molecules such as protoporphyrin, coporphyrin, uroporphyrin and nematoporphyrin. The sample 4010 may also contain various bacterias to be detected such as propion bacterium, acnes. Also, various types of dental plaque bacteria may be detected such as porphyromonos gingivitis, *Prevotella intremedi* and *Prevotella nigrescens*. The sample 4010 may also be used for the detection of glucose in insulin within a blood sample 4010. The sample 4010 may also include amyloid-beta detection. Detection of amyloid-beta within the sample may then be used for determinations of early onset Alzheimer's. Higher levels of amyloid-beta may provide an indication of the early stages of Alzheimer's. The sample 4010 may comprise any material that is desired to be detected that provides a unique OAM twist to a signal passing through the sample.

Figure 52:
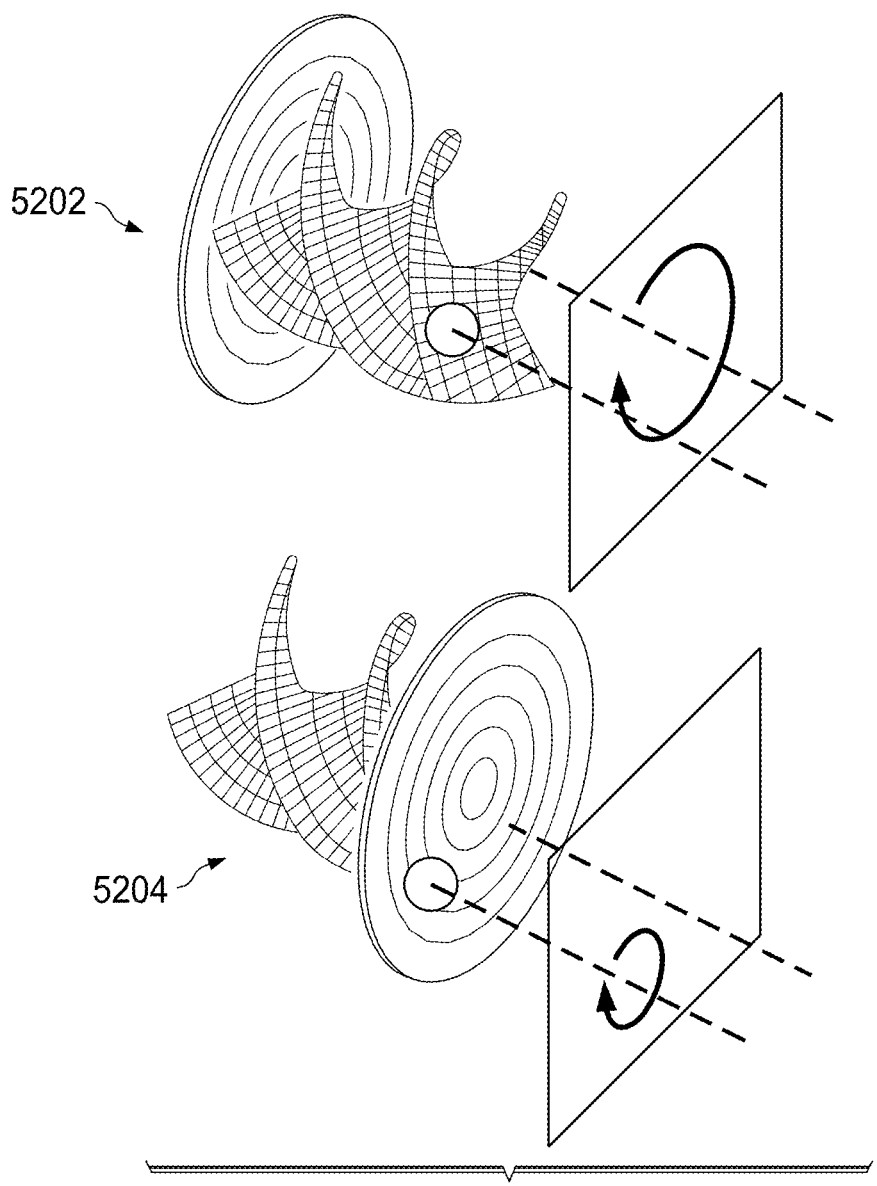

The orbital angular momentum within the beams provided within the sample 4010 may be transferred from light to matter molecules depending upon the rotation of the matter molecules. When a circularly polarized laser beam with a helical wave front traps a molecule in an angular ring of light around the beam axis, one can observe the transfer of both orbital and spin angular momentum. The trapping is a form of optical tweezing accomplished without mechanical constraints by the ring's intensity gradient. The orbital angular momentum transferred to the molecule makes it orbit around the beam axis as illustrated at 5202 of FIG. 52. The spin angular momentum sets the molecule spinning on its own axis as illustrated at 5204. This transference is also useful in inducing resonance within virus to destroy them.

The output OAM wave 4012 from the sample 4010 will have an orbital angular momentum associated therewith that is different from the orbital angular momentum provided on the input OAM wave 4008. The difference in the output OAM wave 4012 will depend upon the material contained within the sample 4010 and the concentration of these materials within the sample 4010. Differing materials of differing concentration will have unique orbital angular momentums associated therewith. Thus, by analyzing the particular orbital angular momentum signature associated with the output OAM wave 4012, determinations may be made as to the materials present within the sample 4010 and the concentration of these materials within the sample may also be determined.

Figure 53:
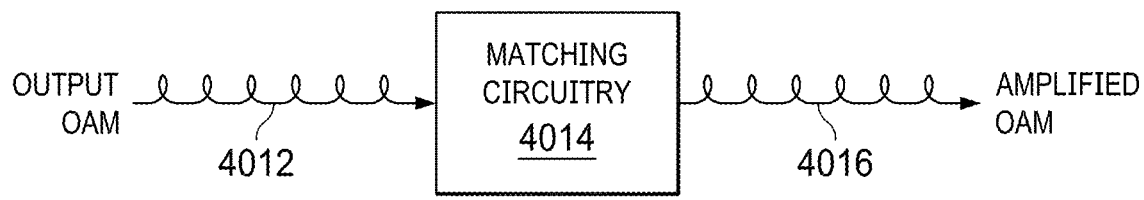

Referring now to FIG. 53, the matching module 4014 receives the output orbital angular momentum wave 4012 from the sample 4010 that has a particular signature associated therewith based upon the orbital angular momentum imparted to the waves passing through the sample 4010. The matching module 4014 amplifies the particular orbital angular momentum of interest in order to provide an amplified wave having the desired orbital angular momentum of interest 4016 amplified. The matching module 4014 may comprise a matching aperture that amplifies the detection orbital angular momentum associated with a specific material or characteristic that is under study. The matching module 4014 may in one embodiment comprise a holographic filter such as that described with respect to FIG. 43 in order to amplify the desired orbital angular momentum wave of interest. The matching module 4014 is established based upon a specific material of interest that is trying to be detected by the system. The matching module 4014 may comprise a fixed module using holograms as illustrated in FIG. 43 or a tunable module in a manner similar to that discussed with respect to the OAM generation module 4006. In this case, a number of different orbital angular momentums could be amplified by the matching module in order to detect differing materials or differing concentrations of materials within the sample 4010. Other examples of components for the matching module 4014 include the use of quantum dots, nanomaterials or metamaterials in order to amplify any desired orbital angular momentum values within a received wave form from the sample 4010.

Figure 54:
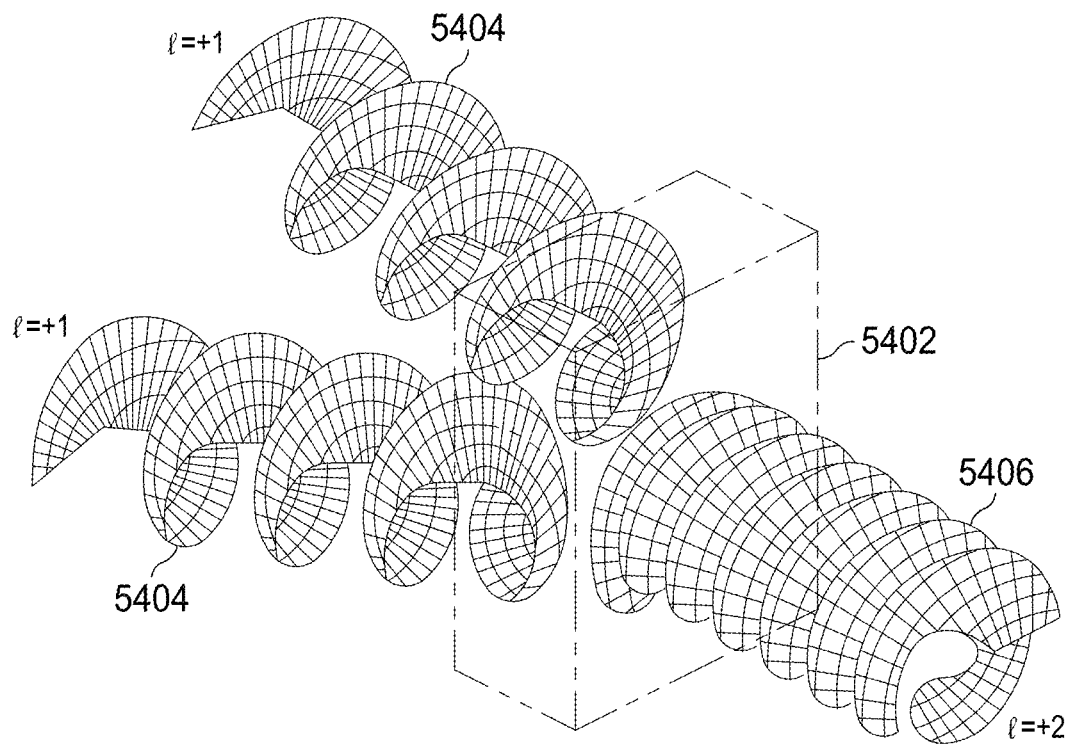

Referring now to FIG. 54, the matching module 4014 rather than using holographic images in order to amplify the desired orbital angular momentum signals may use non-linear crystals in order to generate higher orbital angular momentum light beams. Using a non-linear crystal 5402, a first harmonic orbital angular momentum beam 5404 may be applied to a non-linear crystal 5402. The non-linear crystal 5402 will create a second order harmonic signal 5406.

Figure 55:
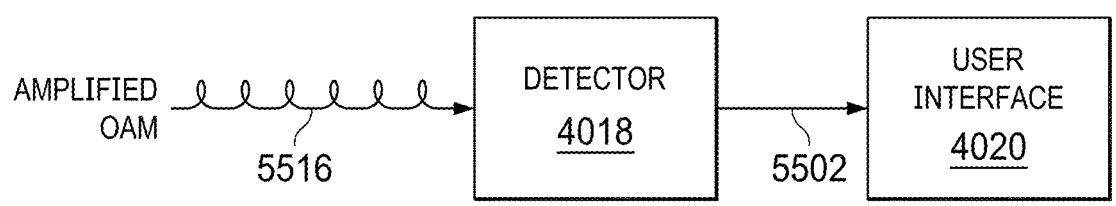

Referring now to FIG. 55, there is more particularly illustrated the detector 4018 to which the amplified orbital angular momentum wave 4016 from the matching circuit 4014 in order that the detector 4018 may extract desired OAM measurements 5502. The detector 4018 receives the amplified OAM waves 4016 and detects and measures observable changes within the orbital angular momentum of the emitted waves due to the presence of a particular material and the concentration of a particular material under study within the sample 4010. The detector 4018 is able to measure observable changes within the emitted amplified OAM wave 4016 from the state of the input OAM wave 4008 applied to the sample 4010. The extracted OAM measurements 5502 are applied to the user interface 4020. The detector 4018 includes an orbital angular momentum detector 4204 for determining a profile of orbital angular momentum states of the orbital angular momentum within the orbital angular momentum signal 4016 and a processor 4206 for determining the material within the sample responsive to the detected profile of the orbital angular momentum states of the orbital angular momentum. The manner in which the detector 4018 may detect differences within the orbital angular momentum is more particularly illustrates with respect to FIG. 56-58.

Figure 56:
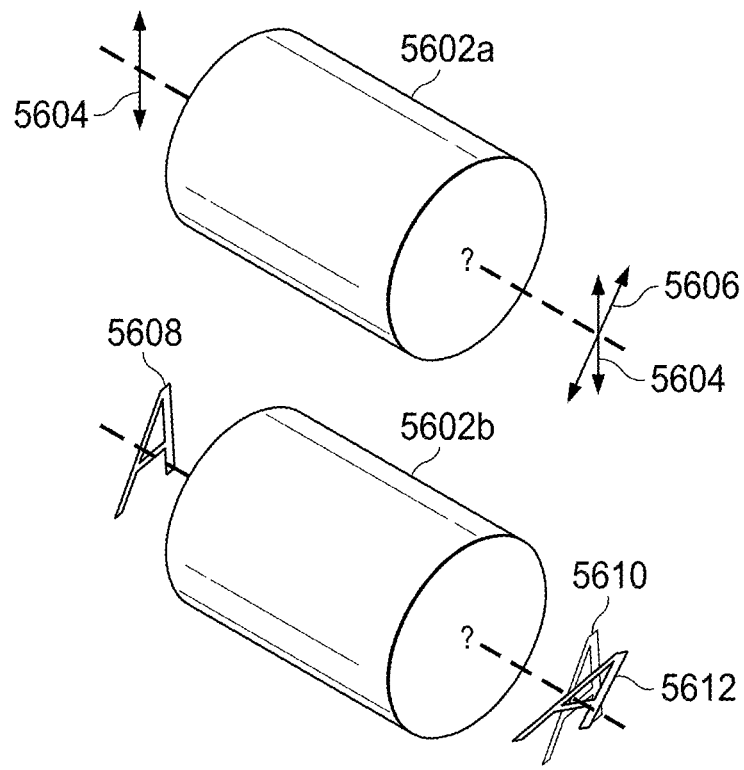

FIG. 56 illustrates the difference in impact between spin angular polarization and orbital angular polarization due to passing of a beam of light through a sample 5602. In sample 5602*a*, there is illustrated the manner in which spin angular polarization is altered responsive to a beam passing through the sample 5602*a*. The polarization of a wave having a particular spin angular momentum 5604 passing through the sample 5602*a* will rotate from a position 5604 to a new position 5606. The rotation occurs within the same plane of polarization. In a similar manner, as illustrated with respect to sample 5602*b*, an image appears as illustrated generally at 5608 before it passes through the sample 5602*b*. Upon passing the image through the sample 5602*b* the image will rotate from the position illustrated at 5610 to a rotated position illustrated at 5612. The amount of rotation is dependent upon the presence of the material being detected and the level of concentration of the material being detected within the sample 5602. Thus, as can be seen with respect to the sample 5602 of FIG. 56, both the spin angular polarization and the orbital angular momentum will change based upon the presence and concentration of materials within the sample 5602. By measuring the amount of rotation of the image caused by the change in orbital angular momentum, the presence and concentration of a particular material may be determined.

Figure 57:
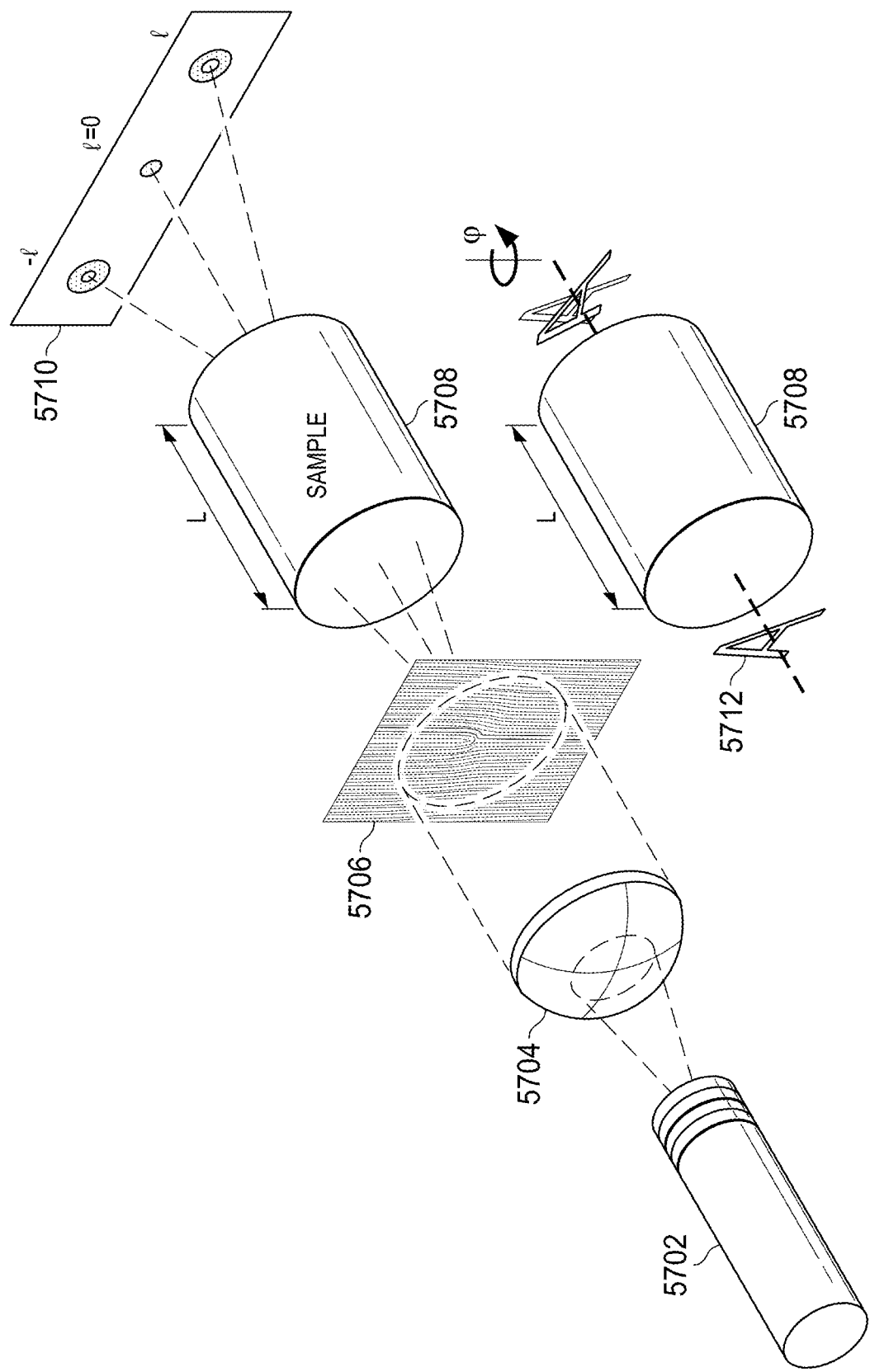

This overall process can be more particularly illustrated in FIG. 57. A light source 5702 shines a light beam through expanding optics 5704. The expanded light beam is applied through a metalab generated hologram 5706 that imparts an orbital angular momentum to the beam. The twisted beam from the hologram 5706 is shined through a sample 5708 having a particular length L. As mentioned previously, the sample 5708 may be located in a container or in its naturally occurring state. This causes the generation of a twisted beam on the output side of the sample 5708 to create a number of detectable waves having various orbital angular momentums 5710 associated therewith. The image 5712 associated with the light beam that is applied to sample 5708 will rotate at an angle φ depending upon the presence and concentration of the material within the sample 5708. The rotation φ of the image 5712 is different for each value orbital angular momentum −1 or +1. The change in rotation of the image Δφ may be described according to the equation:

$$\Delta\varphi = \varphi_l - \varphi_{-1} = f(l, L, C)$$

Where l is orbital angular momentum number, L is the path length of the sample and C is the concentration of the material being detected.

Thus, since the length of the sample L is known and the orbital angular momentum may be determined using the process described herein, these two pieces of information may be able to calculate a concentration of the material within the provided sample.

Figure 58:
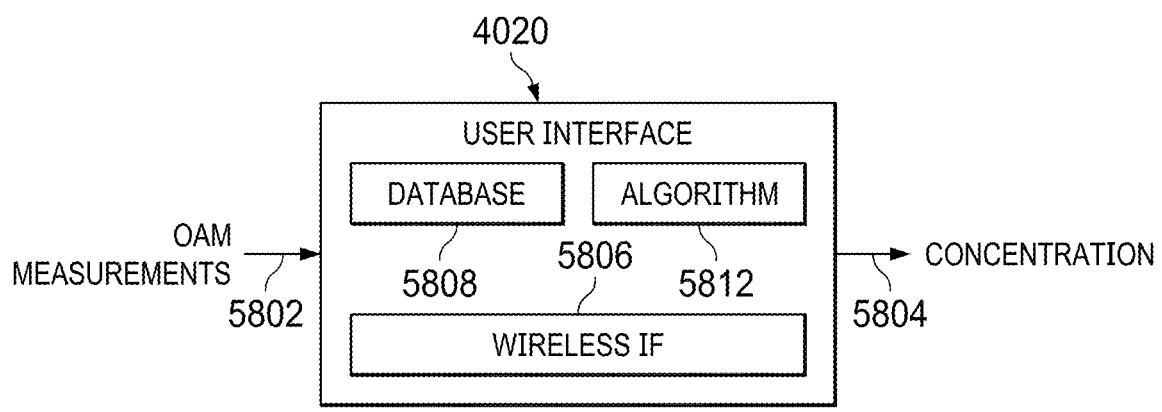

The above equation may be utilized within the user interface more particularly illustrated in FIG. 58. The user interface 4020 processes the OAM measurements 5802 using an internal algorithm 5802 that provides for the generation of material and/or concentration information 5804 that may be displayed in some type of user display. The algorithm would in one embodiment utilize that equation described herein above in order to determine the material and/or concentration based upon the length of a sample and the detected variation in orbital angular momentum. The process for calculating the material and/or concentration may be done in a laboratory setting where the information is transmitted wirelessly to the lab or the user interface can be associated with a wearable device connected to a meter or cell phone running an application on the cell phone connected via a local area network or wide area network to a personal or public cloud. The user interface 5820 of the device can either have a wired or wireless connection utilizing Bluetooth, ZigBee or other wireless protocols.

Figure 59:
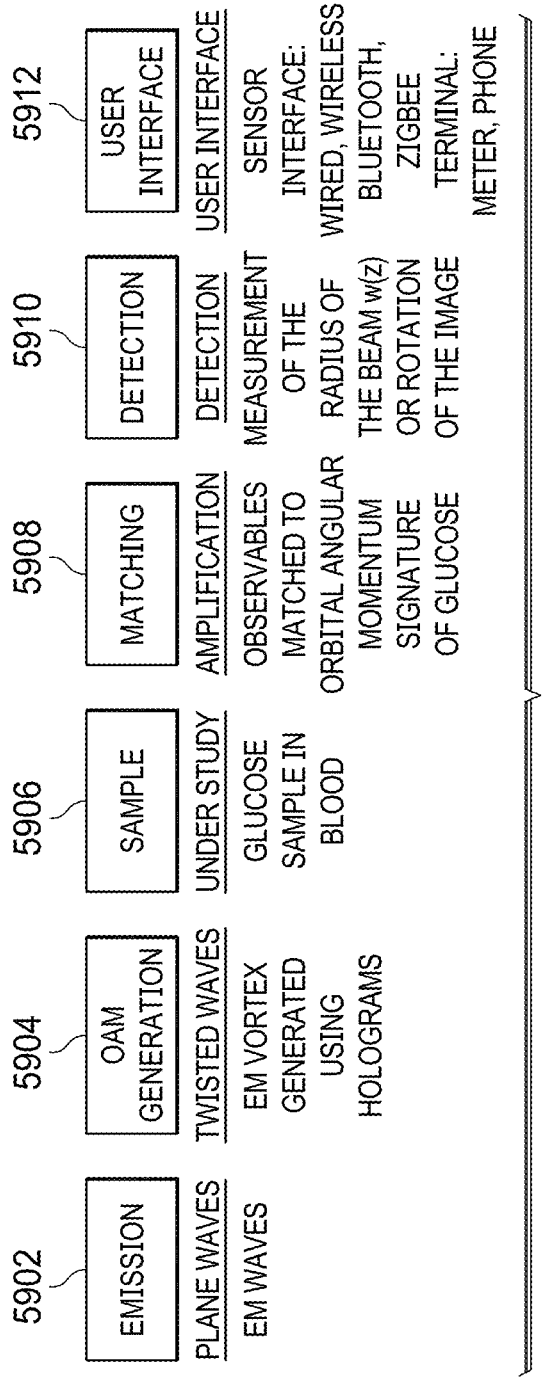

Referring now to FIG. 59, there is illustrated a particular example of a block diagram of a particular apparatus for measuring the presence a concentration of glucose using the orbital angular momentum of photons of a light beam shined through a glucose sample. While the present example is with respect to the detection of glucose, one skilled in the art would realize that the example would be applicable to the detection of the presence and concentration of any material. The process creates a second-order harmonic with helical light beam using a non-linear crystal such as that described with respect to FIG. 54. The emission module 5902 generates plane electromagnetic waves that are provided to an OAM generation module 5904. The OAM generation module 5904 generates light waves having an orbital angular momentum applied thereto using holograms to create a wave having an electromagnetic vortex. The OAM twisted waves are applied to the sample 5906 that is under study in order to detect the glucose and glucose concentration within a sample. A rotated signature exits the sample 5906 in the manner described previously with respect to FIGS. 56-57 and is provided to the matching module 5908. The matching module 5908 will amplify the orbital angular momentum such that the observed concentrations may be calculated from the orbital momentum of the signature of the glucose. These amplified signals are provided to detection module 5910 which measures the radius of the beam w(z) or the rotation of the image provided to the sample via the light beam. This detected information is provided to the user interface that includes a sensor interface wired or wireless Bluetooth or ZigBee connection to enable the provision of the material to a reading meter or a user phone for the display of concentration information with respect to the sample. In this manner concentrations of various types of material as describe herein may be determined utilizing the orbital angular momentum signatures of the samples under study and the detection of these materials or their concentrations within the sample determine as described.

Provided the orthogonality of Laguerre polynomials, Laguerre Gaussian beams exhibiting orbital angular momentum (OAM) have been determined as a basis for spatial division multiplexing (SDM) in communication applications using for example a mux-demux optical element design. OAM beams are also of interest in quantum informatics. OAM also enables the probing of solutions of chiral and non-chiral molecules.

Figure 60:
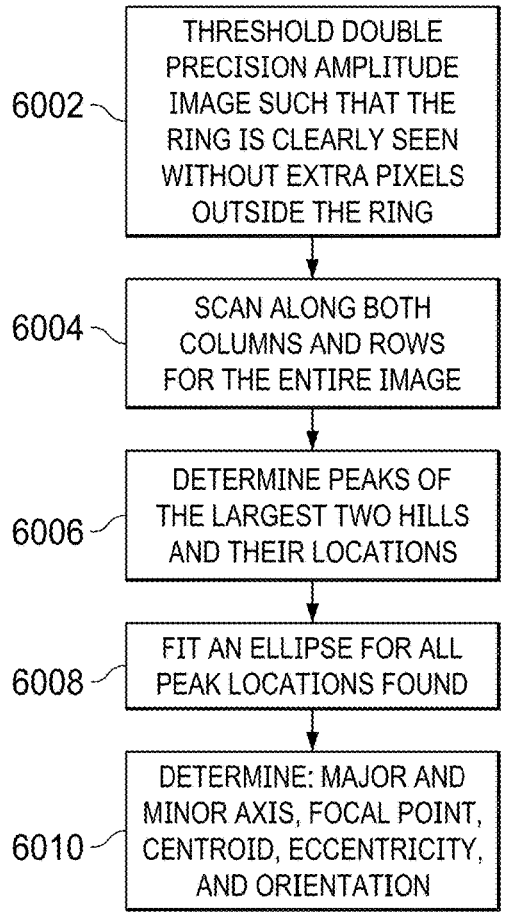

Referring now to FIG. 60, there is illustrated a flow diagram for analyzing intensity images taken by a camera. The intensity image has applied thereto threshold double precision amplitude to enable the ring to be clearly seen without extra pixels outside of the ring at step 6002. Next at step 6001, both columns and rows are scanned along for the entire image. The peaks of the two largest hills and their locations are determined at step 6006. An ellipse is fit at step 4008 for all peak locations found. Finally, at step 6010, a determination is made of the major and minor axis of the ellipse, the focal point of the ellipse, the centroid, eccentricity and orientation of the ellipse.

Figure 61:
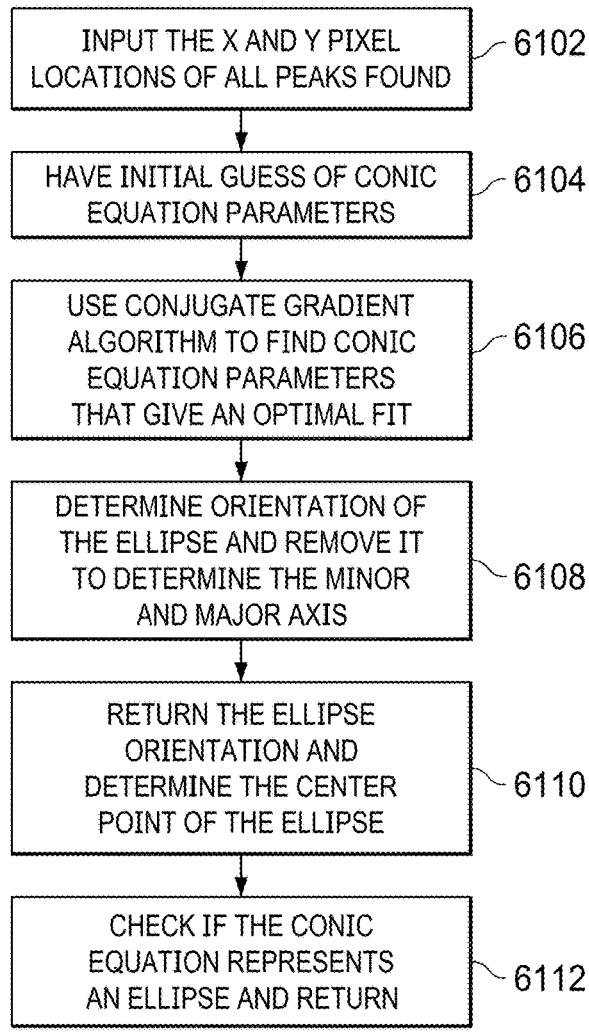

FIG. 61 illustrates an ellipse fitting algorithm flowchart. The X and Y pixel locations are input at step 6102 for all peaks that are found. An initial guess is provided at step 6104 for the conic equation parameters. The conic equation parameters comprise parameters A, B, C, D and E for the equation $Ax^2+By^2+Cx+Dy+E=0$. The conjugate gradient algorithm is used at step 6106 to find conic equation parameters that provide an optimal fit. An orientation of the ellipse is determined at step 6108 and moved to determine the major and minor axis. The determination of step 6108 is determined according to the equation $$\phi = \frac{1}{2}\tan^{-1}\frac{B}{C-A}$$

The ellipse orientation is returned at step 6110 to determine the central point of the ellipse. Finally, at step 6112, a determination is made if the conic equation represents an ellipse. For an ellipse parameters A and B will exist and have the same sign but will not be equal. Based upon this analysis it is been determined that lateral shift of up to 1 mm can cause significant changes in the measured eccentricity due to clipping of up to 0.2.

Fractional OAM Signals

Molecular spectroscopy using OAM twisted beams can leverage fractional OAM states as a molecular signature along with other intensity signatures (i.e. eccentricity, shift of center of mass and rotation of the elliptical intensity) as well as phase signatures (i.e. changes in the phase of the scattered beam) and specific formation of publicity distributed spectrum. The method of optical orientation of electronics been by circularly polarized photons has been heavily used to study spin angular momentum in solid state materials. The process relies on spin-orbit coupling to transfer angular momentum from the spin of protons to the spin of electrons and has been Incorporated into pump-probe Kerr and Faraday rotation experiments to study the dynamics of optically excited spends. By enabling the study is spin decoherence, transport and interactions, this strategy has played a role in the development of semiconductor spintronics.

The proposed spectroscopy technique focuses instead on localized orbital angular momentum (OAM) and solids. Specifically, one can distinguish between delocalized OAM associated with the envelope wave function which may be macroscopic in spatial extent, and local OAM associated with atomic sites, which typically is incorporated into the effect of spin and associated electronic states. The former type of angular momentum is a fundamental interest to orbital fleet coherent systems, for example, quantum Hall layers, superconductors and topological insulators. Techniques to study non-equilibrium delocalized OAM in these and other systems create opportunities to improve understanding of scattering and quantum coherence of chiral electronic states, with potential implications for materials discovery.

The interaction of light with glucose in beta amyloid and the spectroscopy applications of OAM with respect to these. Additionally, the generation of Rahman sideband carrying OAM, OAM using a pleasant Monica lens, the study of optically coherent OAM in excite ions using for wave mixing in the application of linearly polarized light to create a 2-D pleasant Monica analog to OAM light in patterned sin metallic film, and the possibility of OAM light producing spin polarized vote till electronics for efficient semiconductors may also find application in these techniques.

Figure 62:
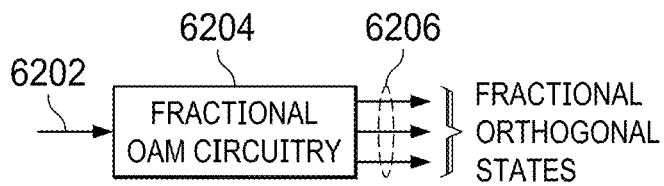

Referring now to FIG. 62, one manner for using nested fractional OAM states to alleviate the problems associated with integer OAM states and to enable the use of stable states of fractional OAM for similar purposes as those described herein above. In this case the input signals 6202 are provided to fractional OAM generation circuitry 6204. The fractional OAM generation circuitry 6204 generates output signals 6206 having fractional orthogonal states which may then be further applied or detected as discussed herein.

The orbital angular momentum of light beams is a consequence of their azimuthal phase structure. Light beams have a phase factor $\exp(im\varphi)$, where m is an integer and φp is the azimuthal angle, and carry orbital angular momentum (OAM) of $m\hbar$ per photon along the beam axis. These light beams can be generated in the laboratory by optical devices, such as spiral phase plates or holograms, which manipulate the phase of the beam. In cases where such a device generates a light beam with an integer value of m, the resulting phase structure has the form of |m| intertwined helices of equal phase. For integer values of m, the chosen height of the phase step generated by the optical device is equal to the mean value of the OAM in the resulting beam.

Recently, spiral phase steps with fractional step height as well as spatial holograms have been used to generate light beams with fractional OAM states. In these implementations, the generating optical device imposes a phase change of $\exp(iM\varphi)$ where M is not restricted to integer values. The phase structure of such beams shows a far more complex pattern. A series of optical vortices with alternating charge is created in a dark line across the direction of the phase discontinuity imprinted by the optical device. In order to obtain the mean value of the orbital angular momentum of these beams, one has to average over the vortex pattern. This mean value coincides with the phase step only for the integer and half integer values. There are certainly more connections between optics and quantum theory to represent beams with fractional OAM as quantum states.

The theoretical description of light modes with fractional OAM is based on the generating optical device. For integer OAM values, a theoretical description may exist which provides the way to treat the angle itself as quantum mechanical Hermitian operator. The description can provide the underlying theory for a secure quantum communication system and give form to the uncertainty relation for angle and angular momentum. The theory may be generalized for fractional values of M thereby creating a quantum mechanical description of fractional OAM. Such a rigorous formulation is of particular interest is the use of half integer spiral phase plates have been used to study high dimensional entanglement. Fractional OAM states are characterized not only by the height of the phase step, but also by the orientation of the phase dislocation α. For half odd integer values of M, M mod 1=½, states with the same M but a π difference in α are orthogonal. In light of recent applications of integer OAM in quantum key distribution in the conversion of spin to orbital angular momentum in an optical medium, a rigorous formulation is important for possible applications of fractional OAM to quantum communication.

The component of the OAM in the propagation direction $L_z$ and the azimuthal rotation angle form a pair of conjugate variables (just like time-frequency or space-momentum). Unlike linear position and momentum, which are both defined on an unbound and continuous state space, the state spaces for OAM and the rotation angle are different in nature. The OAM eigenstates form a discrete set of states with m taking on all integer values. Eigenstates of the angle operator are restricted to a $2\pi$ radian interval since it is physically impossible to distinguish between rotation angles differing by less than $2\pi$ radians. The properties of the angle operator are rigorously derived in an arbitrarily large, yet finite state space of 2L+1 dimensions. This space is spanned by the angular momentum states |m⟩ with m ranging from −L, −L+1, . . . , L. Accordingly, the $2\pi$ radian interval [θ0, θ0+2π) is spanned by 2L+1 orthogonal angle states |θn⟩ with θn=θ0+2πn/(2L+1). Here, $\theta_0$ determines the starting point of the interval and with it a particular angle operator $\varphi^\theta$. Only after physical results have been calculated within this state space is L allowed to tend to infinity, which recovers the result of an infinite but countable number of basis states for the OAM and a dense set of angle states within a $2\pi$ radian interval.

A quantum state with fractional OAM is denoted by |M⟩, where M=m+μ and m is the integer part and μ∈[0, 1) is the fractional part. The state |M⟩ is decomposed in angle states according to:

$$|M\rangle = (2L+1)^{-\frac{1}{2}} \sum_{n=0}^{2L} \exp(iM\theta_n)|\theta_n\rangle$$

$$|M\rangle = (2L+1)^{-\frac{1}{2}} \sum_{n=0}^{2L} \exp(im\theta_n)\exp(i\mu\theta_n)|\theta_n\rangle$$

It is important to note that α is bounded by 0≤α<2π, so that the orientation of the discontinuity is always understood as measured from $\theta_0$. With this construction the fractional state |Mℓ can be written as:

$$|M(\alpha)\rangle = (2L+1)^{-\frac{1}{2}}\exp(i\mu\alpha)\sum_{n=0}^{2L}\exp(iM\theta_n)\exp[i2\pi\mu f_\alpha(\theta_n)]|\theta_n\rangle$$

Figure 63:
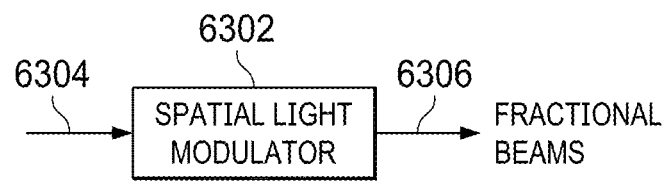

In integer-based OAM generation applications light beams may be generated using a spiral phase plate. However, light beams generated using a spiral phase plate with a non-integer phase step are unstable on propagation. However, one can generate light carrying fractional orbital angular momentum beams not with a phase step of a spiral phase plate but by a synthesis of Laguerre-Gaussian modes. This may be accomplished as illustrated in FIG. 63 using a spatial light modulator 6302. Input signals 6304 are provided to the spatial light modulator 6302 and used for the generation of fractional OAM beams 6306. The spatial light modulator 6302 synthesizes Laguerre Gaussian modes rather than using a phase step of a spiral phase plate. By limiting the number of Gouy phases in the superposition, one can produce a light beam from the SLM 6302 which is well characterized in terms of its propagation. The structural stability of these fractional OAM light beams from an SLM make them ideal for communications using fractional OAM states. Additionally, as will be described herein below, the beams would be useful for concentration measurements of various organic materials.

Figure 64:
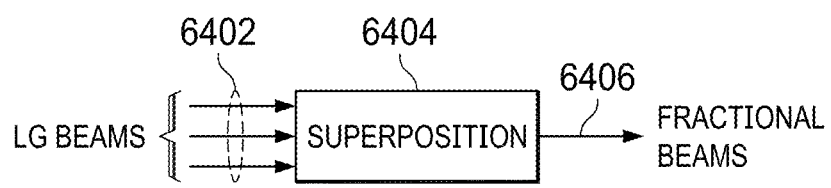
Figure 65:
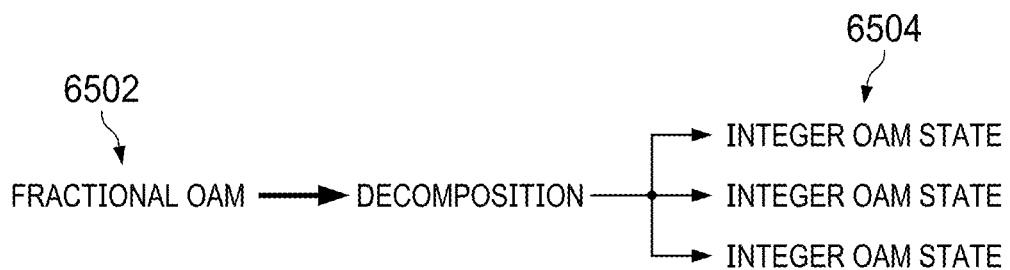

Using the spatial light modulator 6302, a light beam with fractional OAM may be produced as a generic superposition of light modes with different values of m. As illustrated in FIG. 64, various Laguerre-Gaussian beam modes 6402 may have a superposition process 6404 applied thereto by the spatial light modulator 6302 in order to generate the fractional beam outputs 6406. Using the correspondence between optics and quantum theory, OAM can be represented as a quantum state. This quantum state 6502 can be decomposed into a basis of integer OAM states 6504 as generally illustrated in FIG. 65. The decomposition only determines the OAM index m which in a superposition of LG beams leaves the index for the number of concentric rings unspecified. Therefore, one can make use of this flexibility to find a representation of a fractional OAM state in terms of superimposed LG beams with a minimal number of Gouy phases to increase propagation stability. One can produce these beams using the spatial light modulator 6302 and study their propagation and vortex structure. Light beams constructed in this manner are in excellent realization of non-integer OAM states and are more stable on propagation and light emerging from fractional faced steps of a spiral phase plate.

Figure 66:
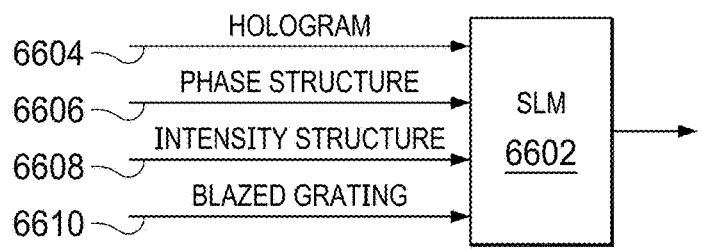

Referring now to FIG. 66, there is illustrated the manner in which an SLM may be programmed to provide fractional OAM beams. Rather than using multiple optical elements to generate each Laguerre Gaussian mode separately a single SLM 6602 may be programmed with a hologram 6604 that sets the phase structure 6606 and intensity structure 6608 for generating the superposition. A blazed grating 6610 is also included in the hologram 6604 to separate angularly the first fractional order. The formula for the resulting phase distribution of the hologram 6604 and rectilinear coordinates $\Phi(x,y)_{holo}$ is given by:

$$\Phi(x,y)_{holo}=[\Phi(x,y)_{beam}+\Phi(x,\Lambda)_{grating} \bmod 2\pi-\pi]\mathrm{sinc}^2 [(1-I(x,y)_{beam})\pi]+\pi$$

In this equation Φ(x,y) beam is the phase profile of the superposition at the beam waist for z=0 and Φ(x,Λ) grating is the phase profile of the blazed grating which depends on the period of the grating Λ. The two-phase distributions are added to modulo 2π and, after subtraction of π are multiplied by an intensity mask. In regions of low intensity, the intensity mask reduces the effect of the blazed grating 6610, which in turn leads to reduced intensity in the first diffraction order. The mapping between the phase depth and the desired intensity is not linear but rather given by the trigonometric sinc function.

Figure 67:
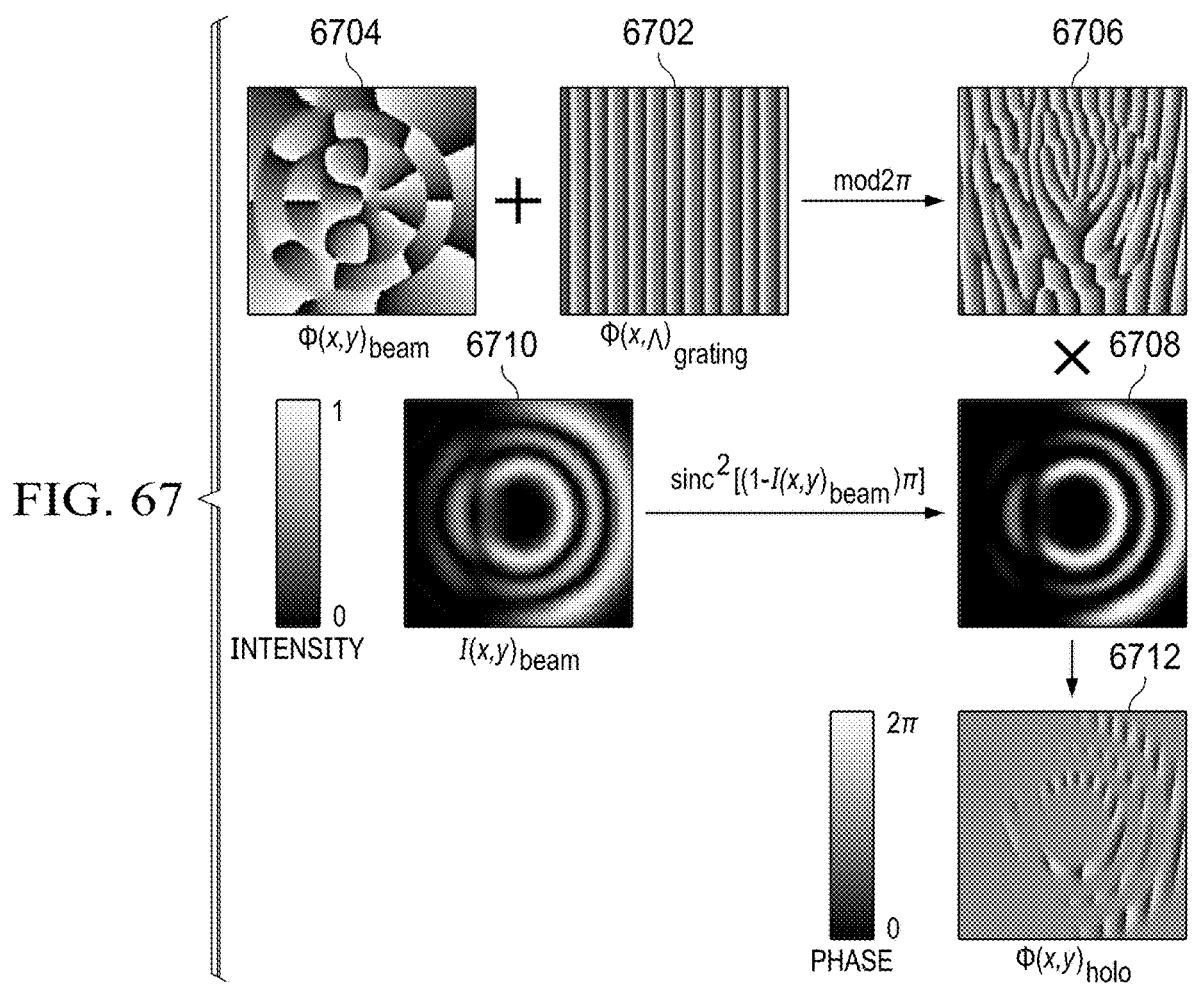
Figure 68:
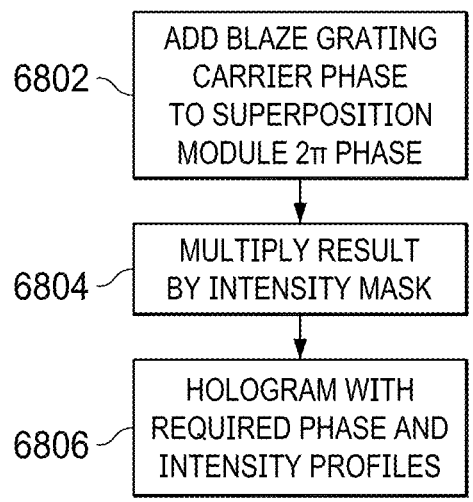

Referring now to FIG. 67 and FIG. 68, there are illustrated the steps necessary to generate a hologram for producing a non-integer OAM beam. Initially, at step 6802 a carrier phase representing a blazed grating 6702 is added to the phase 6704 of the superposition modulo 2π. This combined phase 6706 is multiplied at step 6804 by an intensity mask 6708 which takes account of the correct mapping between the phase depth and diffraction intensity 3010. The resulting hologram 6712 at step 6806 is a hologram containing the required phase and intensity profiles for the desired non-integer OAM beam.

Figure 69:
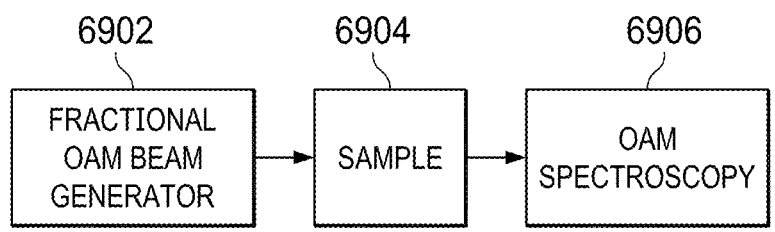

The use of fractional OAM beams may be used in a number of fashions. In one embodiment, as illustrated in FIG. 69, fractional OAM beams may be generated from a fractional OAM beam generator 6902. These fractional OAM beams are then shown through a sample 6904 in a manner similar to that discussed herein above. OAM spectroscopy detection circuitry 6906 may then be used to detect certain OAM fraction state profiles caused by the OAM beam shining through the sample 6904. Particular OAM fraction states will have a particular fractional OAM state characteristic caused by the sample 6904. This process would work in the same manner as that described herein above. Fractional OAM beams can also be used to generate different resonances in a virus such as Covid-19.

Figure 70:
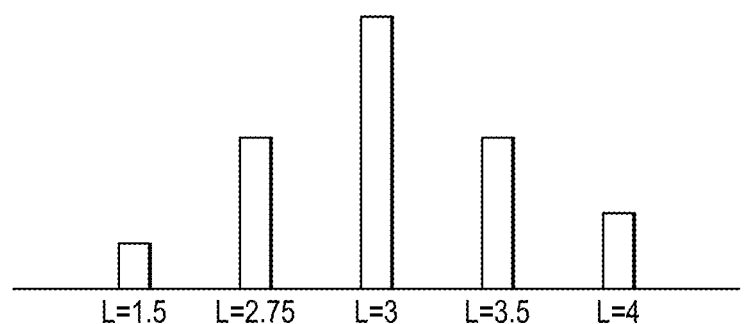

FIG. 70 illustrates one example of a OAM state profile that may be used to identify a particular material within a sample. In this case, the highest number of OAM states is illustrated at L=3. Additional state levels are also illustrated at L=1.5; L=2.75; L=3.5 and L=4. This particular OAM state profile would be uniquely associated with a particular material and could be used to identify the material within a sample when the profile was detected. The interaction of Laguerre Gaussian light beams with glucose and beta amyloid have been the initial spectroscopy application of OAM to sample types.

The transfer of OAM between the acoustic and photonic modes, the generation of Raman side bands carrying OAM, OAM using a plasmonic lens, the study of optically coherent OAM in excitons using four-wave mixing, the application of linearly polarized light to create a 2-D plasmonic analog to OAM light in a patterned thin metallic film and the possibility of OAM light producing spin polarized photoelectrons for efficient semiconductors are other potential spectroscopy applications.

Other means of generation and detection of OAM state profiles may also be utilized. For example, a pump-probe magneto-orbital approach may be used. In this embodiment Laguerre-Gaussian optical pump pulses impart orbital angular momentum to the electronic states of a material and subsequent dynamics are studied with femto second time resolution. The excitation uses vortex modes that distribute angular momentum over a macroscopic area determined by the spot size, and the optical probe studies the chiral imbalance of vortex modes reflected off of a sample. There will be transients that evolve on timescales distinctly different from population and spin relaxation but with large lifetimes.

Multi-Parameter Spectroscopy

The following discussions with respect to spectroscopy describe the detection and creation of vibrational modes, molecular vibrations, etc. with respect to various spectroscopic techniques. The creation and detection of these vibrational modes, molecular vibrations, etc. are also applicable to viruses to induce the molecular resonance therein to destroy and sterilize the viruses.

Figure 71:
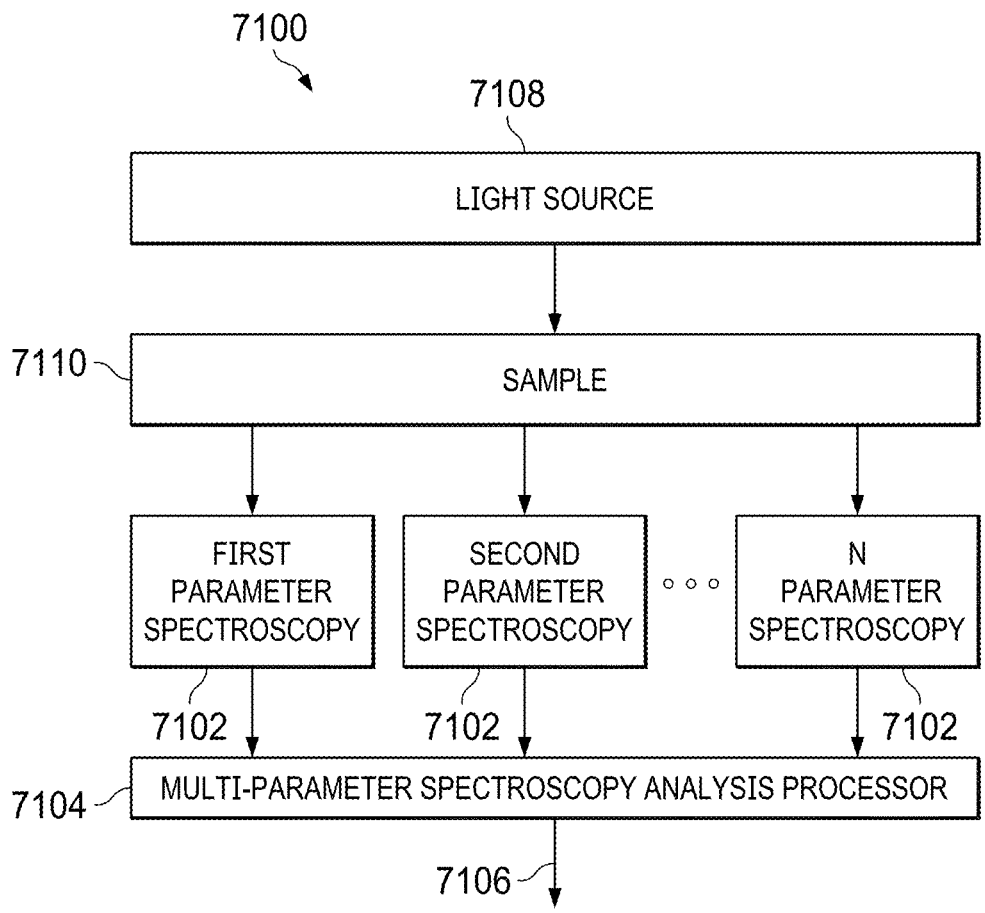

A further application of the OAM spectroscopy may be further refined by identifying items using a number of different types of spectroscopy to provide a more definitive analysis. Referring now to FIG. 71, there is generally illustrated a multi-parameter spectroscopy system 7100. A plurality of different spectroscopy parameters 7102 may be tracked and analyzed individually. The group of parameters is then analyzed together using multi-parameter spectroscopy analysis processor or system 7104 to determine and identify a sample with output 7106. The different spectroscopic techniques receive a light beam generated from a light source 7108, for example a laser, that has passed through a sample 7110 that a material or concentration of material therein that is being detected. While the light source of FIG. 71 illustrates a single laser and light beam, multiple light sources may provide multiple light beams, or a single source may be used to provide multiple light beams. In one example, development of a single optical spectroscopy system to fully characterize the physical and electronic properties of small samples in real time may be accomplished using the polarization, wavelength, and orbital angular momentum (OAM) of light. A polarized optical source is used to characterize the atomic and molecular structure of the sample. The wavelength of the source characterizes the atomic and molecular electronic properties of the sample including their degree of polarizability. OAM properties of the source are principally used to characterize the molecular chirality, but such new techniques are not limited to chiral molecules or samples and can be applied to non-chiral molecules or samples. These three spectroscopy dimensions combine to greatly improve the process of identifying the composition of materials. Integrated into a compact handheld spectrometer, 3D or multi-parameter spectroscopy empowers consumers with numerous applications including useful real time chemical and biological information. Combined with other pump-probe spectroscopy techniques, 3D/multi-parameter spectroscopy promises new possibilities in ultrafast, highly selective molecular spectroscopy. While the following description discusses a number of different spectroscopy techniques that may be implemented in multi-parameter spectroscopy system 7100, it should be realized that other spectroscopy techniques may be combined to provide the multi-spectroscopy analysis system of the present disclosure.

Optical Spectroscopy

Spectroscopy is the measurement of the interaction of light with various materials. The light may either be absorbed or emitted by the material. By analyzing the amount of light absorbed or emitted, a materials composition and quantity may be determined.

Some of the light's energy is absorbed by the material. Light of a given wavelength interacting with a material may be emitted at a different wavelength. This occurs in phenomena like fluorescence, luminescence, and phosphorescence. The effect of light on a material depends on the wavelength and intensity of the light as well as its physical interaction with the molecules and atoms of the material such as virus.

Figure 72:
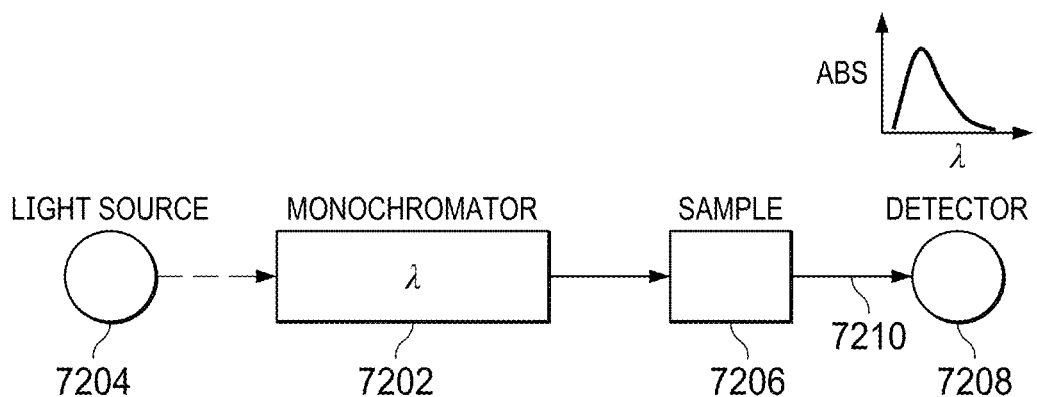

A schematic of a spectrometer which makes relative measurements in the optical spectral region of the electromagnetic spectrum uses light that is spectrally dispersed by a dispersing element is shown in FIG. 72. In particular, a device 7202, such as a monochromator, polychromator, or interferometer, selects a specific wavelength from a light source 7204. This single-wavelength light interacts with a sample 7206. A detector 7208 is used to measure the spectrum of light resulting from this interaction. A change in the absorbance or intensity of the resulting light 7210 is measured as the detector 7208 sweeps across a range of wavelengths. A range of different spectroscopic techniques, based on these fundamental measurements, have been developed such as those discussed in A. Hind, "Agilent 101: An Introduction to Optical Spectroscopy," 2011. (http://www.agilent.com/labs/features/2011_101_spectroscopy.html) which is incorporated herein by reference in its entirety. Here, attention is given to molecular spectroscopy techniques including infrared, Raman, terahertz, fluorescence, and orbital angular momentum spectroscopy.

Molecular Spectroscopy

Infrared Spectroscopy

Various types of molecular spectroscopy techniques may also be used in the multi-parameter spectroscopy system. These techniques include infrared spectroscopy and others.

Infrared frequencies occur between the visible and microwave regions of the electromagnetic spectrum. The frequency, ν, measured in Hertz (Hz), and wavelength, λ, typically measured in centimeters (cm) are inversely related according to the equations:

$$\nu = \frac{c}{\lambda} \text{ and } \lambda = \frac{c}{\nu}$$

where c is the speed of light ($3\times10^{10}$ cm/sec).

The energy of the light is related to λ and ν by $$E = h\nu = \frac{hc}{\lambda}$$

where h is Planck's constant ($h=6.6\times10^{-34}$ J·s).

The infrared (IR) spectrum is divided into three regions: the near-, mid-, and far-IR. The mid IR region includes wavelengths between $3\times10^{-4}$ and $3\times10^{-3}$ cm.

In the process of infrared spectroscopy, IR radiation is absorbed by organic molecules. Molecular vibrations occur when the infrared energy matches the energy of specific molecular vibration modes. At these frequencies, photons are absorbed by the material while photons at other frequencies are transmitted through the material.

The IR spectrum of different materials typically includes unique transmittance, T, peaks and absorbance troughs occurring at different frequencies such as the measured IR spectrum of water vapor.

The absorbance, A, is related to the transmittance by $$A=\log_{10}(1/T).$$

Each material exhibits a unique infrared spectral fingerprint, or signature, determined by its unique molecular vibration modes which permit identification of the material's composition by IR spectroscopy. In the case of water vapor (FIG. 62), for example, the water molecules absorb energy within two narrow infrared wavelengths bands that appear as absorbance troughs 6202.

Molecular Vibrations

Figure 73:
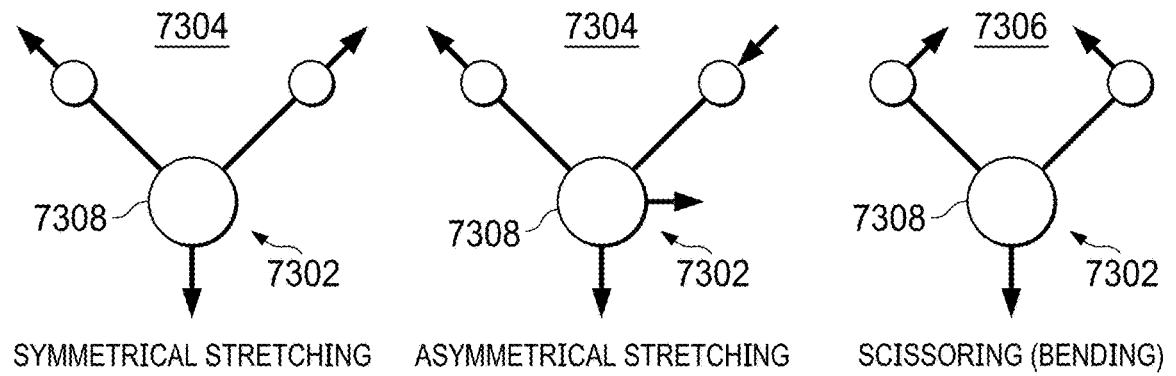
Figure 74:
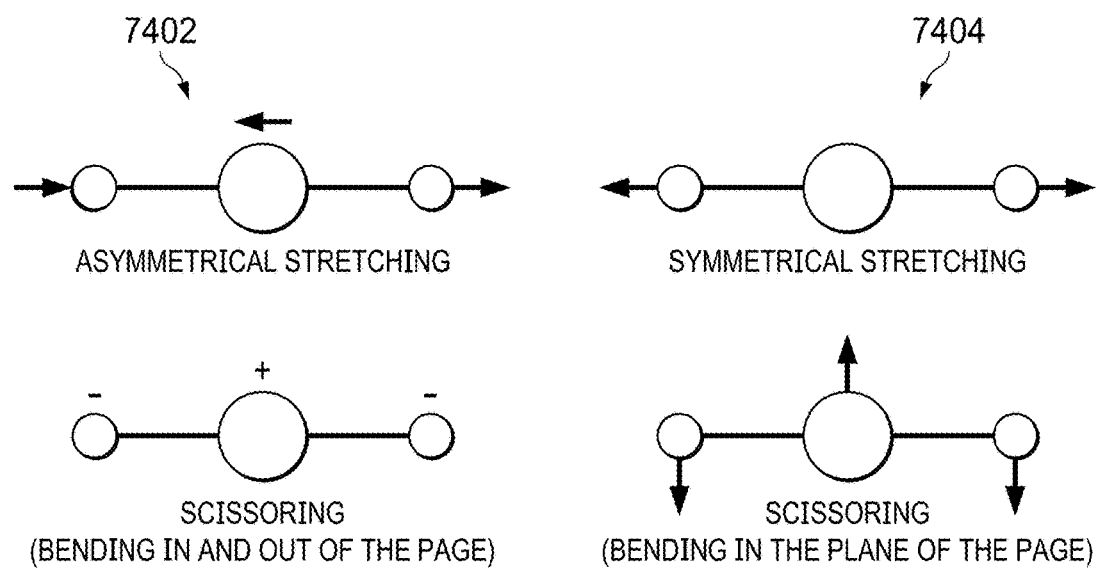

As described above one manner for inactivating viruses is by the inducement of molecular vibrations within the viruses using OAM and other techniques. Referring now to FIG. 73, water molecules exhibit two types of molecular vibrations: stretching and bending. A molecule 7302 consisting of n atoms 7308 has 3n degrees of freedom. In a nonlinear molecule like water, three of these degrees are rotational, three are translational, and the remaining correspond to fundamental vibrations. In a linear molecule 7302, two degrees are rotational and three are translational. The net number of fundamental vibrations for nonlinear and linear molecules is therefore, 3n−6 and 3n−5, respectively.

For water vapor, there are two strong absorbance troughs occurring at approximately 2.7 μm and 6.3 μm as a result of the two stretching vibrational modes 7304 of water vapor and its bending mode 7306, respectively. In particular, the symmetric and asymmetric stretching modes 7304 absorb at frequencies in very close proximity to each other (2.734 μm and 2.662 μm, respectively) and appear as a single, broader absorbance band between the troughs.

Carbon dioxide, $CO_2$, exhibits two scissoring and bending vibrations 5302, 5304 (FIG. 53) that are equivalent and therefore, have the same degenerate frequency. This degeneracy appears in the infrared spectrum at λ=15 μm. The symmetrical stretching vibrational mode 5304 of $CO_2$ is inactive in the infrared because it doesn't perturb its molecular dipole moment. However, the asymmetrical stretching vibration mode 5302 of $CO_2$ does perturb the molecule's dipole moment and causes an absorbance in $CO_2$ at 4.3 μm.

Both molecular stretching and bending vibration modes of molecules (FIGS. 73 and 74) can be predicted to useful theoretical approximation using simple classical mechanics models.

Stretching Vibrations

Similarly stretching vibrations may be used to induce vibrations within viruses to destroy them. The stretching frequency of a molecular bond may be approximated by Hooke's Law when treated as a simple classical harmonic oscillator consisting of two equal masses bound by a spring $$\nu = \frac{1}{2\pi}\sqrt{\frac{k}{m}}$$

where k is the force constant of the spring and m is the mass of an atom.

In the classical harmonic oscillator, the energy depends on the extent to which the spring is stretched or compressed, $$E=\tfrac{1}{2}kx^2=h\nu$$

where x is the displacement of the spring. The classical model of Hooke's Law, however, is inconsistent with the absorbance of energy by molecules as it would suggest that energy of any frequency is absorbed. In real molecules, vibrational motion is quantized and appropriately modeled by the quantum mechanical expression, $$E_n=(n+\tfrac{1}{2})h\nu$$

where n is the principal quantum number (n=0, 1, 2, 3 . . . ) characteristic of each permitted energy level.

The lowest energy level is $E_0=\tfrac{1}{2}h\nu$ followed by $E_1=3/2h\nu$. Only transitions to the next energy level are allowed according to the selection rule. Subsequently, molecules absorb photonic energy in integer increments of hv. For photon absorption energies of 2hv or 3hv, however, the resulting absorbance bands are called overtones of the infrared spectrum and are of lesser intensity than fundamental vibrational bands.

Energy of a harmonic oscillator as a function of the interatomic distance is shown in FIG. 75 with an energy minimum occurs at the normal bond length 7502 (equivalent to a relaxed classical mechanical spring). As the interatomic distance increases the quantized energy levels 7504 become more closely spaced and the energy reaches a maximum. The allowed transitions, hv become smaller in magnitude which gives lower overtone energies than would otherwise be predicted using the simply harmonic oscillator theory depicted in FIG. 76.

Though this mathematical framework represents a useful, if not simple, approximation, the vibrational activity between two atoms in a large molecule cannot be isolated from the vibrational behavior of other atoms in the molecule. Vibrations of two bonds within a molecule may be coupled in such a manner that one contracts or expands while the other contracts as in either asymmetrical or symmetrical stretching vibrations. When this occurs different absorbance frequency bands are observed instead of superimposed, or degenerate, bands as observed when two identical atoms in a bond vibrate with an identical force constant.

Infrared spectroscopy is used to identify material species by their unique vibrational and rotational optical signatures. A complementary spectroscopy technique, Raman spectroscopy is used to identify materials by their unique light-scattering signatures as discussed in the next section.

Raman Spectroscopy

Since Raman spectroscopy is a technique used to characterize a material by the amount of light it scatters. Raman spectroscopy complements infrared spectroscopy which instead measures the amount of light absorbed by a material. Raman and infrared spectroscopy may further be used in conjunctions with OAM and polarization spectroscopy to further improve analysis results. When light interacts with matter, changes in the dipole moment of its molecules yield infrared absorption bands while changes in their polarizability produce Raman bands. The sequence of observed energy bands arises from specific molecular vibrations which collectively produce a unique spectral signature indicative of each type of molecule. Certain vibrational modes occurring in Raman spectroscopy are forbidden in infrared spectroscopy while other vibrational modes may be observed using both techniques or a multi-parameter technique using OAM. When these latter modes are common to both techniques, their intensities differ significantly.

The most frequent interaction of photons with molecules results in Rayleigh scattering in which photons are elastically scattered as the result of excited electrons that decay to their original energy level. Consequently, Rayleigh scattered photons have the same energy as incident photons.

With the discovery of inelastic photonic scattering phenomena in 1928 by C. V. Raman and K. S. Krishnan, Raman spectroscopy was established as a practical chemical analysis method useful to characterize a wide variety of chemical species including solid, liquid, and gaseous samples. Solid crystal lattice vibrations are typically active in Raman spectroscopy and their spectra appear in polymeric and semiconductor samples. Gaseous samples exhibit rotational structures that may be characterized by vibrational transitions.

Approximately one percent of incident photons scatter inelastically and yield lower energy photons. Raman scattering results from changes in the vibrational, rotational, or electronic energy of a molecule. The vibrational energy of the scattering molecule is equivalent to the difference between incident and Raman scattered photons. When an incident photon interacts with the electric dipole of a molecule, this form of vibronic spectroscopy is often classically viewed as a perturbation of the molecule's electric field. Quantum mechanically, however, the scattering event is described as an excitation to a virtual energy state lower in energy than a real electronic transition with nearly coincident decay and change in vibrational energy. Such spectroscopy can work in conjunction with incident photons that carry OAM. In Raman spectroscopy, incident photons excite electrons to a different final energy level than its original energy level (FIG. 77).

Since the intensity of Raman scattering is low, heat produced by the dissipation of vibrational energy does not yield an appreciable rise in material temperature. Such Raman spectroscopy can work in conjunction with incident photons that carry OAM. At room temperature, the population of vibrationally excited states is small. Stokes-shifted scattering events shown in FIG. 77 are typically observed in Raman spectroscopy since at room temperature the excited vibrational states are low, and the electron originates in the ground state. The inelastic Raman scattered photon 7702 has lower energy than the incident photon 7704 as the electron decays to an energy level 7706 higher than the original ground state 7708. Anti-Stokes shifted scattering events 7710 result from a small fraction of molecules originally in vibrationally excited states (FIG. 77) which leave them in the ground state 7712 and results in Raman scattered photons with higher energy. At room temperature, anti-Stokes shifted Raman spectra are always weaker than Stokes-shifted spectrum since the Stokes and anti-Stokes spectra contain the same frequency information. Most Raman spectroscopy focuses exclusively on Stokes-shifted scattering phenomena for this reason.

The force constant by which the vibrational mode energy may be modeled is affected by molecular structure including atomic mass, molecular species, bond order, and the geometric arrangement of molecules. However, Raman scattering occurs when the polarizability of molecules may be affected.

The polarizability, $\alpha$, of a molecule appears as a proportionality constant between the electric field and the induced dipole moment, $$P = \alpha E.$$

The induced dipole scatters a photon at the frequency of the incident photon (Rayleigh scattering). Molecular vibration, however, may change the polarizability and give rise to inelastic Raman scattering of photons. Changes in polarizability may be expressed by $$\frac{\partial \alpha}{\partial Q} \neq 0$$

where Q is in a direction normal to the vibration, and is considered a selection rule for Raman-active vibrations.

Raman-active vibrations are non-existent in the infrared for molecules having a center of symmetry while the existence of a perturbed symmetry center (e.g. permanent dipole moment) indicates the absence of infrared-active vibrations.

The intensity of a Raman band is proportional to the square of the spatial change of polarizability, or the induced dipole moment, $$I_{Raman} \propto \left(\frac{\partial \alpha}{\partial Q}\right)^2.$$

Hence, incident photons that slightly induce a dipole moment will yield a Raman band with a very small intensity. Stronger Raman scattering systems are those with higher values of $\alpha$ such as molecules having double carbon bonds which exhibit more broadly distributed electrons susceptible to polarization. Subsequently, the range of chemical concentrations measurable by Raman spectroscopy is considerably wide given that the scattering intensity is directly proportional to concentration.

Raman spectroscopy exhibits several advantages over other spectroscopy techniques. Raman bands exhibit good signal-to-noise ratios owing to its detection of fundamental vibrational modes. Hence, the Raman signature of measured samples is typically more pronounced and definitive.

Raman spectroscopy is more useful for analyzing aqueous solutions than infrared spectroscopy since the Raman spectrum of water is weak and unobtrusive while the infrared spectrum of water is very strong and more complex. In organic and inorganic chemistries, the existence of covalent bonds yields a unique Raman signature. A Raman spectroscopy setup only requires an appropriate laser source incident on a material and a detector to collect scattered photons which minimizes the need for elaborate sample preparation. Raman spectroscopy is non-destructive as the material is merely illuminated with a laser. Because the Raman effect is weak, the efficiency and optimization of a Raman spectroscopy instrument is critically important to providing measurements of the slightest molecular concentrations within the shortest possible time.

Spontaneous Raman Spectroscopy

The intensity of spontaneous Raman scattering is linearly dependent on the incident intensity of light but of several orders of magnitude less intense. Treating the light-matter interaction quantum mechanically, the total Hamiltonian may be expressed in terms of the energy associated with the vibrational modes of the molecule, $H_v$, the light, $H_\gamma$, and their interaction, $H_{v\gamma}$, $$H = H_v + H_\gamma + H_{v\gamma}.$$

In this framework $$H_v = \frac{1}{2m}(p^2 + \omega_0^2 q^2)$$

with vibrational frequency $\omega_0$ and the normal mode amplitude q which may be expressed in terms of creation and annihilation operators of the molecular vibrations, $$q = \sqrt{\frac{2\pi\hbar}{8\pi^2\mu\omega_0}}\,[b^\dagger + b]$$

with the electric dipole moment μ. This leaves $$H_v = \hbar\omega_0(b^\dagger b + \tfrac{1}{2}).$$

Using creation and annihilation operators for light, $a^\dagger$ and a, field quantization is obtained, $$E_\lambda = \sqrt{\frac{2\pi h\nu_L}{\varepsilon V_{int}}}\sum_{k_\lambda} e_{k_\lambda} i[\alpha k_\lambda^\dagger - \alpha k_\lambda]$$

where $e_{k_\lambda}$ is the field polarization unit vector field and $V_{int}$ the interaction volume. The Hamiltonian for the light is then $$H_\gamma = \sum_{k_\lambda}\hbar\omega_{k_\lambda}\bigl(a_{k_\lambda}^\dagger a_{k_\lambda} + 1/2\bigr).$$

Using the first order perturbation of the electric dipole approximation the interaction Hamiltonian may be obtained in terms of the molecule's polarizability, α, $$H_{int} = E \cdot \alpha \cdot E$$

$$= E \cdot \alpha_0 \cdot E + \left(\frac{\partial\alpha}{\partial q}\right)_0 E \cdot q \cdot E + \cdots$$

within the local coordinate system, q. The first term characterizes Rayleigh scattering. The remaining first order Raman scattering term is needed to characterize spontaneous Raman scattering including the coherent laser field, $E_L$, in addition to the Stokes and anti-Stokes fields, $E_S$ and $E_{AS}$, respectively. Substituting q and $E_\gamma$ into this expression yields $$H_{int} = H_{\gamma S} + H_{\gamma AS} \sim$$

$$\left(\frac{\partial\alpha}{\partial q}\right)_0 \sum_{k_S k_L} \sqrt{\frac{(2\omega_L\omega_S)}{\omega_0}}\,(e_{k_L}\cdot e_{k_S})(a_{k_S}^\dagger b^\dagger a_{k_L} + a_{k_S} b a_{k_L}^\dagger)\delta(k_L - k_S - k_v) +$$

$$\left(\frac{\partial\alpha}{\partial q}\right)_0 \sum_{k_{AS} k_L} \sqrt{\frac{(2\omega_L\omega_{AS})}{\omega_0}}\,(e_{k_L}\cdot e_{k_{AS}})$$

$$(a_{k_S}^\dagger b a_{k_L} + a_{k_{AS}} b^\dagger a_{k_L}^\dagger)\delta(k_L - k_{AS} + k_v)$$

where $H_{\gamma S}$ and $H_{\gamma AS}$ are the interaction Hamiltonians of the Stokes and anti-Stokes branches, respectively.

The steady state transition rate between the initial, $|i\rangle$, and final, $|f\rangle$ states is given according to Fermi's golden rule, $$W_{i\to f} = \frac{2\pi}{\hbar}|\langle f|H_{int}|i\rangle|^2 \rho(\hbar\omega_f).$$

In the simple harmonic oscillator picture, the eigenstates, $|n_v\rangle$ with excitation quanta $n_v$ are acted upon by creation and annihilation operators to yield the Stokes and anti-Stokes transition rates $$W_{n_v \to n_v+1}, \text{ and } W_{n_v \to n_v-1} \sim n_v.$$

Hence, it is easy to determine $n_v$ from the Raman signal intensity given a linear dependence.

Raman intensities from each vibrational level are used to identify unique vibrational molecular modes and characterize the material's composition.

The integrated anti-Stokes intensity of a Raman mode is proportional to the average vibrational quantum number of the mode, $\langle n_v \rangle$, $$I_{AS} = A\left(\frac{E_R}{h\nu_R}\right) = A\langle n_v\rangle$$

where A is the Raman cross section. Normalizing $I_{AS}$ with respect to the room temperature Stokes signal of the same mode in addition to using the Boltzmann distribution, $$\langle n_v\rangle_0 = \frac{E_R^0}{h\nu_R} = \frac{1}{e^{\frac{h\nu_R}{kT_0}} - 1}$$

where $E_R^0$ is the room temperature ($T_0$) energy of the Raman mode. Generally, $h\nu_R \gg kT_0$, so $\langle n_v\rangle_0 = 0$, and the normalized anti-Stokes signal is approximately $\langle n_v\rangle$, $$I_{norm} \equiv \frac{I_{AS}}{I_R^0} = \frac{A\langle n_v \rangle}{A(1+\langle n_v \rangle_0)} \approx \langle n_v \rangle.$$

By comparing the normalized scattering intensities associated with different vibrational moved, the distribution of energy over different molecular modes after infrared excitation may be obtained.

Stimulated Raman Spectroscopy

Stimulated Raman intensity is nonlinearly dependent on the incident intensity of photons but of similar magnitude. Inelastic scattering of a photon with an optical phonon originating from a finite response time of the third order nonlinear polarization of a material is characteristic of Raman scattering. Monochromatic light propagating in an optical material yields spontaneous Raman scattering in which some photons are transitioned to new frequencies. The polarization of scattered photons may be parallel or orthogonal if the pump beam is linearly polarized. Stimulated Raman scattering occurs when the scattering intensity of photons at shifted frequencies is enhanced by existing photons already present at these shifted frequencies. Consequently, in stimulated Raman scattering, a coincident photon at a downshifted frequency receives a gain which may be exploited in Raman amplifiers, for example, or usefully employed in molecular spectroscopy.

Raman amplification became a mature technology with the availability of sufficiently high-power pump lasers.

Within a classical electromagnetic framework, the stimulated Raman scattered signal intensity increases proportionally with the pump and signal intensities $$\frac{dI_s}{dz} = g_R I_P I_S$$

and the Raman-gain coefficient, $g_R$, which is related to the spontaneous Raman scattering cross section. Hence, the probability of Raman scattering is directly related to the photon density in the pump wave and the Raman cross section.

The Stokes and pump waves must overlap spatially and temporally to generate stimulated emission. Since, the Raman process involves vibrational modes of molecules within a material; its intensity spectrum determines the material composition. In amorphous materials, for example, the vibrational energy levels tend to merge, and form bands and the pump frequency may differ from the Stokes frequency over a wide range. In crystalline materials, however, the intensity peaks tend to be well-separated as they have narrow bandwidths.

The coupled wave equations for forward Raman scattering include $$\frac{dI_S}{dz} = g_R I_P I_S - \alpha_S I_S$$

for Stokes intensities with $\alpha_S$ the Stokes attenuation coefficient, and $$\frac{dI_P}{dz} = -\frac{\omega_P}{\omega_S} g_R I_P I_S - \alpha_P I_P$$

for pump wave intensities where $\omega_P$ and $\omega_S$ are pump and Stokes frequencies, respectively. For backward scattering, $dI_S/dz \rightarrow -dI_S/dz$. In the absence of loss, these expressions reduce to $$\frac{d}{dz}\left(\frac{I_S}{\omega_S} + \frac{I_P}{\omega_P}\right) = 0$$

which embodies the conservation of photon number in Stokes and pump waves during stimulated Raman scattering processes.

Stimulated scattering intensity increases when the stimulated gain exceeds the linear loss which is the source of the threshold power which must be overcome to initiate stimulated Raman scattering. In a material system in which forward and backward scattering occurs, a beat frequency drives molecular oscillations responsible for increasing the scattered wave amplitude. In turn, the increasing wave amplitude enhances the molecular oscillations as part of a positive feedback loop that results in the stimulated Raman scattering effect. For forward scattering processes, the pump depletion term is removed, $$\frac{dI_P}{dz} = -\alpha_p I_P.$$

Solving this equation yields $I_P(z) = I_0 e^{-\alpha_P z}$ giving the stimulated Stokes scattering intensity $$I_S(L) = I_S(0) e^{g_R I_0 L_{eff} - \alpha_P L}$$

where the effective optical path length is given by $$L_{eff} = \frac{1 - e^{-\alpha_P L}}{\alpha_P}.$$

Stimulated Raman scattering intensifies from scattering events occurring throughout the optical path length in the material, making it a useful molecular spectroscopy technology.

Resonance Raman Spectroscopy

The Raman effect in classical Raman spectroscopy depends only on the frequency of incident light with scattered intensity dependence on $v_0^4$ as discussed earlier. If the vibrational mode of a molecular absorption transition precisely matches the energy of incident light, the observed scattered intensity may be as intense as $\sim v_0^6$. This resonance Raman effect permits highly sensitive spectroscopic discrimination of a molecular species within a complex material medium such as chromophores within proteins embedded in a biological membrane.

In resonance Raman spectroscopy, only a small fraction of molecular vibrational modes are enhanced. In the simplest scenario, only one electronic state may be resonant. In this case, the resonant Raman signal is the result of nuclear motion resulting from distortions of the molecule while transitioning between the ground state and the excited state in which resonance is induced by incident light.

The functional component of most biological chromophores consists of atoms conjugated with the particular electronic transition to which resonance Raman spectroscopy is selectively sensitive. The frequency of measured resonance Raman bands yields information about the vibrational structure of the electronic states involved in the transition used for inducing the resonance. The scattering intensities provide information about the nature of mode coupling with the electronic transition.

Raman Effect in Vortex Light

A molecule in vibronic state m subjected to a plane-polarized incident light of frequency $v_0$ and intensity $I_0$ is perturbed into a new vibronic state n. This interaction causes the frequency of light to shift by $v_{mn}=v_m-v_n$ and scatter with a frequency $v_0+v_{mn}$ through a solid angle $4\pi$. The scattering intensity during the transition from m to n is given by $$I_{mn} = \frac{2^6\pi^4}{3c^3}(v_0 + v_{mn})^4 |\mathcal{E}_{mn}|^2$$

in which the amplitude $\mathcal{E}\_mn$ of the electric field is given by $$\mathcal{E}_{mn} = \frac{1}{h}\sum_r \left(\frac{M_m(M_{mr}\mathcal{U})}{v_{rm}-v_0} + \frac{M_{mr}(M_m\mathcal{U})}{v_{rn}+v_0}\right)$$

where, m, r and n are quantum numbers of the initial, intermediate and final energy states $E_m$, $E_r$, $E_n$, respectively.

Between the amplitude $\mathcal{U}$ of the electric field strength $$\mathcal{E} = \mathcal{U}e^{-2\pi i v_0 t} + \mathcal{U}^* e^{2\pi i v_0 t}$$

and its amplitude $\mathcal{E}_{mn}$ associated with the shifted scattered radiation induced torque, $$M_{mn} = \mathcal{E}_{mn}e^{-2\pi i(v_0+v_{mn})t} + \mathcal{E}_{mn}^* e^{2\pi i(v_0+v_{mn})t}$$

is a tensor relation that may be expressed in terms of scattering tensor $A_{mn}=(\alpha_{\rho\sigma})_{mn}$ the form:

$$\mathcal{E}_{mn} = A_{mn}\mathcal{U}$$

or in component representation, $$(\mathcal{E}_\rho)_{mn} = \sum_\sigma (\alpha_{\rho\sigma})_{mn}\mathcal{U}_\sigma$$

while the scattering tensor $A_{mn}$ may be expressed as $$A_{mn} = \frac{1}{h}\sum_r \left(\frac{M_m M_{mr}}{v_{rm}-v_o} + \frac{M_{mr}M_m}{v_{rn}+v_0}\right),$$

Since $\mathcal{E}_{mn}$ written in terms dyadic components of the tensor $A_{mn}$ includes $M_{rn}M_{mr}$, each path matrix element of the polarizability tensor, $\alpha$, for a transition from m to n, may be written in terms of intermediate vibronic states $$(\alpha_{\rho\sigma})_{mn} = \frac{1}{2\pi\hbar}\sum_r \left(\frac{(M_\rho)_m(M_\sigma)_{mr}}{v_{rm}-v_0} + \frac{(M_\rho)_{mr}(M_\sigma)_m}{v_{rn}+v_0}\right),$$

Where $(M_\rho)_{mn}$ is the transition matrix between vibrational levels m and n in the presence of the radiation operator $\hat{m}_\rho$, $$(M_\rho)_{mn} = \Psi_r^* \hat{m}_\rho \Psi_m d\tau$$

Herein, $(M_\ell)_{rn}(M_o)_{mr}$ are ordinary products of scalar vector components $(M_\ell)_{rn}$ and $(M_o)_{mr}$ of a unit vector $a_o$. In the three mutually perpendicular directions spatially fixed $\ell$, $\sigma=1, 2, 3$ as follows:

$$|\mathcal{E}_{mn}|^2 = \sum_\rho (\mathcal{E}_\ell)_{mn}^2 = \sum_\rho \left|\sum_\sigma (\alpha_{\rho\sigma})_{mn}\mathcal{U}_\sigma\right|^2 = A^2\sum_\rho \left|\sum_\sigma (\alpha_{\rho\sigma})_{mn}a_\sigma\right|^2$$

With an incident intensity, $I_0=(c/2\pi)A^2$, then, $$I_{mn} = \frac{2^6\pi^4 A^2}{3c^3}(v_0 + v_{mn})^4 \sum_\rho \left|\sum_\sigma (\alpha_{\rho\sigma})_{mn}a_\sigma\right|^2 =$$

$$\frac{2^7\pi^5}{3c^3}I_0(v_0 + v_{mn})^4 \sum_\rho \left|\sum_\sigma (\alpha_{\rho\sigma})_{mn}a_\sigma\right|^2.$$

The total scattering intensity is therefore dependent on the state of polarization of the exciting light. By averaging over all positions of a, or averaging over all modes of the scattering molecule at a fixed incident wave direction and polarization, $$\overline{\left|\sum_\sigma (\alpha_{\rho\sigma})_{mn}a_\sigma\right|^2} = \frac{1}{3}\sum_\sigma |(\alpha_{\rho\sigma})|^2.$$

Finally, for an electron transition from m→n per molecule an average total intensity of the scattered radiation is obtained $$I_{mn} = \frac{2^7\pi^5}{3^2 c^4}I_0(v_0 + v_{mn})^4 \sum_{\rho,\sigma} |(\alpha_{\rho\sigma})_{mn}|^2$$

in which $\rho=x, y, z$ and $\sigma=x', y', z'$ are independently the fixed coordinate systems of the molecule for incident and scattered photons, respectively.

Selection Rules for Raman Effect Using Vortex Light

Of interest to studies of the Raman effect using vortex light is a particular set of solutions of Maxwell's equations in a paraxial approximation. Laguerre-Gaussian functions may mathematically characterize a beam of vortex light in terms of generalized Laguerre polynomials, $L_p^{\ell\hbar}(x)$ with a Gaussian envelope. In the Lorentz-gauge, the vector potential of a Laguerre-Gaussian beam is:

$$A_{\ell,p} = A_0(\alpha\hat{e}_x + \beta\hat{e}_y)\sqrt{\frac{2p!}{\pi(|\ell|+p)!}}\frac{w_0}{w(z)}L_{LP}^{|\ell|}\left(\frac{2\rho^2}{w^2(z)}\right)\left(\frac{\sqrt{2}\rho}{w(z)}\right)^{|\ell|}e^{i\ell\phi-i\omega t+ikz}$$

in a $(\rho, \phi, z)$ coordinate system in which $w(z)$ is the beam waist (radius) at which the radial field amplitude goes to 1/e. For simplicity, only $p=0$ is typically chosen. In the dipole approximation, the term, $e^{ikz}$ is negligible, so the radiation operator of a Laguerre-Gaussian beam may be expressed as $$\hat{m}_\rho = \left[ A_0(\alpha \hat{e}_x + \beta \hat{e}_y) \sqrt{\frac{1}{\pi!|\ell|!}} \frac{w_0}{w(z)} L_0^{i\hbar}\left(\frac{2\rho^2}{w^2(z)}\right)\left(\frac{\sqrt{2}\rho}{w(z)}\right)^{i\hbar} e^{i\ell\phi - i\omega t} \right] \cdot p + c \cdot c$$

Here, $e^{i\omega t}$ is associated with photon emission and $e^{-i\omega t}$ is associated with photon absorption.

The following generalized framework for developing a set of selection rules to measure unique OAM Raman signatures of different materials applies to the intensity profiles associated with both stimulated and spontaneous Raman spectroscopy.

The relationship among irreducible representations of the phonon, the incident photon, and the scattering photon, $\Gamma_\alpha$, $\Gamma_\rho$, and $\Gamma_\sigma$, required to ensure non-vanishing matrix elements of $A_{\nu\rho}$ is $$\Gamma_\alpha \otimes \Gamma_\rho \otimes \Gamma_\sigma \ni \Gamma_1$$

such that $h_{e,s}^\alpha$, $(M_\rho)_{g,e}$, and $(M_\sigma)_{g,s}$ are non-zero. Introducing, the Raman tensor $P_{\alpha\beta\gamma\delta}(\Gamma_j^\sigma)$ having index $\Gamma_j^\sigma$ to denote the jth branch of the σth phonon to replace the single index α, we similarly replace the incident photon index, ρ, with (α, β) and the scattered photon index, σ with (γ, δ).

As the interaction of light with matter in Raman scattering processes leaves the orbital angular momentum of photons unperturbed the incident and scattered photons may be expressed in the following respective forms, $$(\rho \cdot \epsilon_I)\rho^\ell e^{i\ell\phi} \text{ and } (\rho \cdot \epsilon_S)\rho^\ell e^{i\ell\phi}.$$

Then $P_{\alpha\beta\gamma\delta}(\Gamma_j^\sigma)$ may be determined by the Clebsch-Gordan coefficients for all three representations $$P_{z,\epsilon_S,\epsilon_F}(\Gamma_j^\sigma) = (\rho \cdot \epsilon_S)\rho^\ell e^{-i\ell\phi} \otimes (\rho \cdot \epsilon_I)\rho^\ell e^{i\ell\phi} \otimes \phi_\sigma^j$$

For crystalline materials, the special case of forward scattering reduces 3×3 Raman tensors to 2×2. In this case, the Raman tensors for $\ell \geq 2$ excitations all have the same form. So from symmetry considerations, the $\ell$-dependence vanishes for $\ell \geq 2$. Since the constants a, b, c, d, and e depend on $\ell$ and the symmetry of the crystal, non-zero OAM yields a $\Gamma_2$ phonon for $\ell \geq 2$ photon excitation and decouples the two Raman tensors for the $\Gamma_3$ phonon for $\ell \geq 1$ photon excitation.

OAM Raman spectroscopy exhibits the capacity to characterize the atomic and molecular composition of a crystalline material. More complicated selection rules are needed to fully obtain an OAM Raman signature of chiral materials which present their own unique atomic and molecular symmetry properties.

In the highly symmetric case of crystalline materials, for example, the approach is rather straightforward. Given a periodic lattice potential, electrons in crystal solids may be expressed as Bloch waves $$\psi_{n,k}(r) = e^{ik \cdot r} u_{nk}(r)$$

such that the electron transition moment connecting the ground state, $\psi_{g,k}$, to the excited state, $\psi_{e,k}$, may be written $$M_{g,e} = \sum_k \int \psi_{e,k}^*(r)[A_0(\rho^\ell e^{i\ell\phi}) \cdot p] \psi_{g,k}(r) dr.$$

The first order Taylor expansion with $\ell = 0$ is then $$(\hat{M}_\rho)_{g,e} = (\hat{M}_\rho)_{g,e}^0 + \sum_{\alpha,S} \frac{h_{es}^\alpha Q_\alpha}{\Delta E_{e,S}} (\hat{M}_\rho)_{g,e}^0.$$

Since $h_{e,s}^\alpha$, $Q_a$, and $\Delta E_{es}$ depend only on the properties of the crystal and not $\ell$, only M affects scattering intensities when using vortex light. Subsequently, the electronic wavefunction and e are left as relative values of $M(\ell \neq 0)$ with respect to $M(\ell = 0)$ for the Raman effect with vortex light interactions with crystal solids.

Raman scattering intensity enhancements may be identified by selecting appropriate values of $\ell$ such as in the case of zinc blende crystals, for example, in which a maximum was reported for $\ell = 30$ based on symmetry considerations using the approach presented above. In practice, focusing a laser producing vortex light has little impact on the intensity enhancement of M given its similarity to focusing light in an ordinary Raman scattering measurement.

Polarized Raman Spectroscopy

Given that the polarizability of molecules varies spatially with respect to the distribution of molecules in a sample, a plane-polarized Raman source may be used to characterize the atomic structure of crystals and molecular structure of polymeric films, crystals, and liquid crystals.

Figure 78:
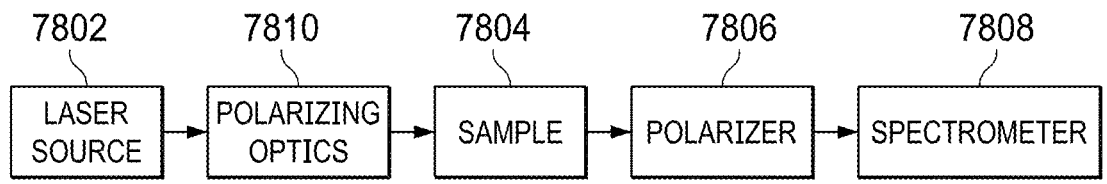

Referring now to FIG. 78, polarized Raman techniques involve a polarizer 7806 between the sample 7804 and the spectrometer 7808 oriented either parallel (∥) or perpendicular (⊥) to the polarization state of the laser source 7802. As well, polarizing optics 7810 may be inserted between the laser 7802 and sample 7804 to select an appropriate state of polarization incident on the sample.

The symmetry properties of bond vibrations in a molecule are characterized by polarized Raman spectroscopy by evaluating the depolarization, ρ, of particular intensity peaks, $$\rho = \frac{I_\perp}{I_\parallel}$$

where $I_\perp$ and $I_\parallel$ are the Raman spectral band intensities with polarizations perpendicular and parallel, respectively, to the state of polarization of the laser source 7802.

Figure 79:
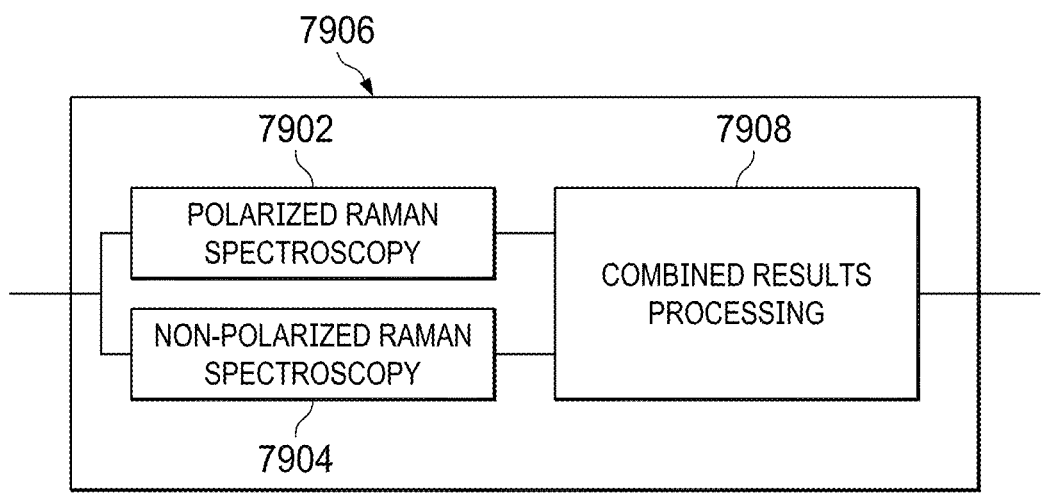

As shown in FIG. 79, information gained by polarized Raman spectroscopy 7902 can be used to supplement atomic and molecular information gained by non-polarized Raman spectroscopy 7904. A single integrated spectroscopy unit 7906 exploiting both polarized and non-polarized Raman effects using combined results processing 7908 that improves overall quality and amount of information gained by spectroscopically processing data from a sample using multiple types of spectroscopic analysis.

Raman Spectroscopy with Optical Vortices

The typical Raman source is a Gaussian laser operating in its fundamental mode with an electric field $$E(x, y, z) = \hat{e} E_0 \exp\left(-\frac{x^2 + y^2}{w^2}\right) \exp[-i(kz - \omega t)]$$

traveling in the z-direction, where ê is the polarization vector. Light produced by such a source has either linear or circular polarization which are limited to the transverse (x, y) plane with no electric field component in the z-direction. The induced dipole moments of interest then are only $P_x$ and $P_y$.

A longitudinal mode along the z-direction incident on a molecule scatters light that completes the picture of the molecule's polarizability to include $P_z$. An electric field having a z-component is a radially polarized beam with a polarization vector $$\hat{e} = x\hat{x} + y\hat{y} = \hat{r}.$$

Figure 80:
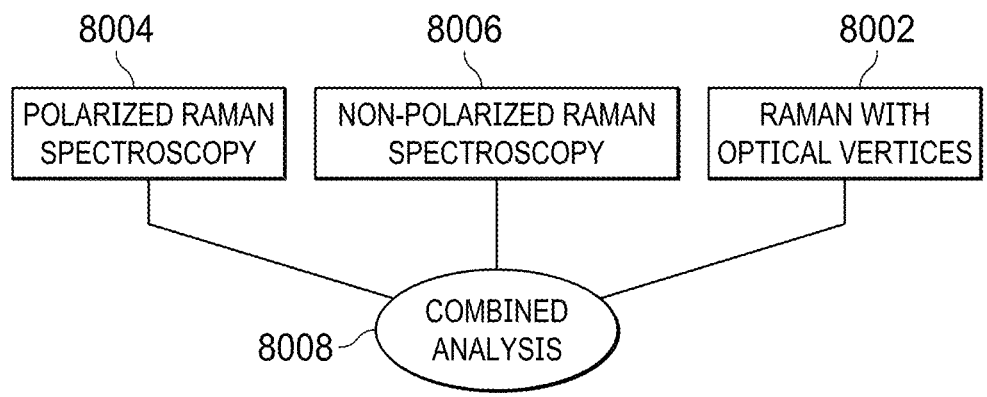

Several methods exist to generate radially polarized fields having longitudinal components when tightly focused. In Raman spectroscopy, the induced dipole moment, $P_z$, is the result of $E_z$ which may increase the strength of vibrational modes in addition to generating new vibrational modes previously unobserved with conventional Raman spectroscopy. As shown in FIG. 80, information gained by Raman beams endowed with optical vortices 8002 adds a third degree of spectroscopic capability when coupled with polarized 8004 and non-polarized 8006 Raman spectroscopy in a combined analysis 8008. Such Raman spectroscopy can also work in conjunction with incident photons that carry OAM.

THz Spectroscopy

Terahertz spectroscopy is conducted in the far-infrared frequency range of the electromagnetic spectrum and is therefore useful for identifying far-infrared vibrational modes in molecules. THz spectroscopy can provide a higher signal-to-noise ratio and wider dynamic range than far-infrared spectroscopy due the use of bright light sources and sensitive detectors. This provides for selective detection of weak inter- and intra-molecular vibrational modes commonly occurring in biological and chemical processes which are not active in IR-spectroscopy. THz spectroscopy may also be used in conjunction with incident photons that carry OAM. Terahertz waves pass through media that are opaque in the visible and near-IR spectra and are strongly absorbed by aqueous environments.

THz spectroscopy was historically hindered by a lack of appropriately high-powered light sources. However, access to practical THz spectroscopy in the far-infrared range was permitted by the generation of THz rays based on picosecond and femtosecond laser pulses. Today, THz sources include either short pulse mode (e.g. photoconductive antennas, optical rectifiers) or continuous wave (CW) mode having a wide range of available output power (nanowatts to 10 watts).

Several different types of THz sources are used today to interrogate biological, chemical and solid-state processes. Sources in the 1-3.5 THz range are frequently used in biology and medicine, for example, to investigate conformational molecular changes. THz spectroscopy is used today as frequently as Raman spectroscopy.

Terahertz Time-Domain Spectroscopy

Terahertz time-domain spectroscopy (THz-TDS) is one of the most widely used THz techniques which includes coherent emission of single-cycle THz pulses such as provided by a femtosecond laser. The detection of these pulses occurs at a repetition rate of about 100 MHz.

Two dimensional THz absorption properties of samples are characterized by a THz imaging technique. This technique was demonstrated in systems designed for THz-TDS based on picosecond pulses as well as systems utilizing continuous-wave (CW) sources such as a THz-wave parametric oscillator, quantum cascade laser, or optically pumped terahertz laser. THz spectroscopy can be used in conjunction with incident photons that carry OAM.

THz pulse imaging provides broad image frequency information between 0.1-5 THz while THz CW imaging may be performed in real-time, is frequency-sensitive, and has a higher dynamic range due to significantly higher spectral power density. In both pulse and CW THz imaging the characteristics of the light source (coherency, power, and stability) are important. A THz spectrometer may mechanically scan a sample in two dimensions, but the time of each scan scales with sample size. Real time THz imaging is often conducted with an array of THz wave detectors composed of electro-optic crystals or a pyroelectric camera. Such THz spectroscopy can be used in conjunction with incident photons that carry OAM.

THz imaging suffers from poor resolution as estimated in terms of its diffraction limit which is less than a millimeter and from low transmission through an aperture resulting in low sensitivity. To exceed the diffraction limitation near-field microscopy is used to achieve sub-wavelength resolution, though low transmission remains an issue.

Fluorescence Spectroscopy

Figure 81:
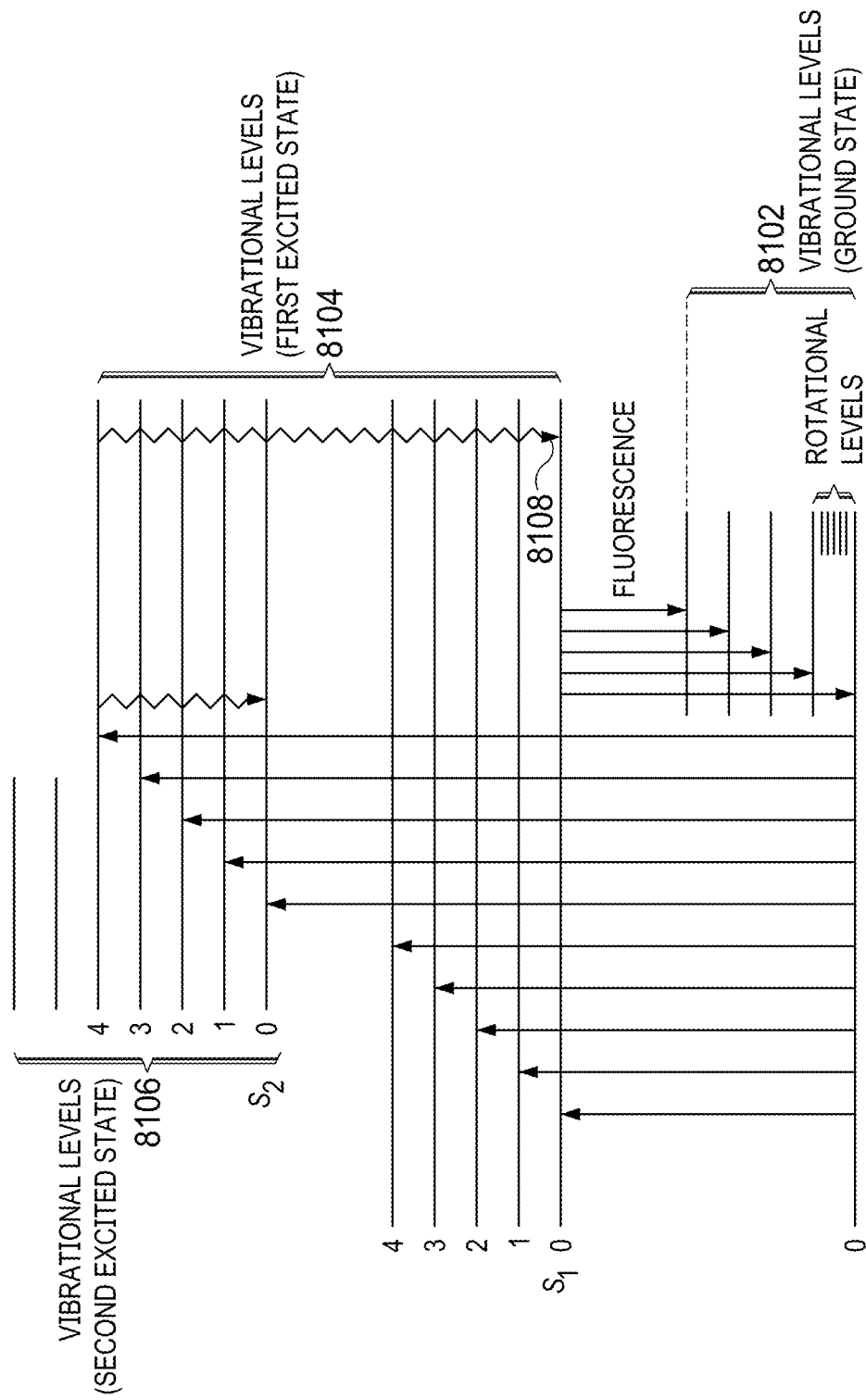

Perturbed by incident light, electrons in molecules at room temperature are excited from the lowest vibrational energy level 8102 of the electronic ground state to either the first ($S_1$) 8104 or second ($S_2$) 8106 vibrational state (FIG. 81) and may occupy any one of several vibrational sub-levels. Each vibrational sub-level has many neighboring rotational energy levels in such close proximity that inter-sub-level energy transitions are almost indistinguishable. Consequently, most molecular compounds have broad absorption spectra with the exception of those having negligible rotational characteristics such as planar and aromatic compounds.

In fluorescence spectroscopy, molecules absorb energy from incident photons, obtain a higher vibrational energy sub-level of an excited state ($S_1$ or $S_2$), then lose their excess vibrational energy through collisions and return to the lowest vibrational sub-level of the excited state. Most molecules occupying an electronic state above $S_2$, experience internal conversion and decay by collision through the lowest vibrational energy sub-level of the upper state to a higher vibrational sub-level of a lower excited state having the same energy. The electrons continue to lose energy until they occupy the lowest vibrational energy sub-level of $S_1$ 8108. The decay of the molecule into any vibrational energy sub-level of the ground state causes the emission of fluorescent photons.

If the absorption and emission process differ from this sequence, the quantum efficiency is less than unity. The "0-0" transition from the lowest vibrational ground state sub-level to the lowest vibrational $S_1$ sub-level 8108 is common to both the absorption and emission phenomena while all other absorption transitions occur only with more energy than any transition in the fluorescence emission. The emission spectrum subsequently overlaps the absorption spectrum at the incident photon frequency corresponding to this "0-0" transition while the rest of the emission spectrum will have less energy and equivalently occurs at a lower frequency. The "0-0" transition in the absorption and emission spectra rarely coincide exactly given a small loss of energy due to interaction of the molecule with surrounding solvent molecules.

Hence, distributions of vibrational sub-levels in $S_1$ and $S_2$ are very similar since incident photon energy doesn't significantly affect the shape of the molecule. Energy differences between bands in the emission spectrum will be similar to those in the absorption spectrum and frequently, the emission spectrum will be approximately a mirror image of the absorption spectrum. The shape of the emission spectrum is always the same despite an incident photon frequency shift from that of the incident radiation since the emission of fluorescent photons always occurs from the lowest vibrational energy sub-level of $S_2$. If the incident radiation intensity yielding excitation remains constant as the frequency shifts, the emission spectrum is considered a corrected excitation spectrum.

The quantum efficiency of most complex molecules is independent of the frequency of incident photons and the emission is directly correlated to the molecular extinction coefficient of the compound. In other words, the corrected excitation spectrum of a substance will be the same as its absorption spectrum. The intensity of fluorescence emission is directly proportional to the incident radiation intensity.

Fluorescence spectroscopy results in emission and excitation spectra. In emission fluoroscopy, the exciting radiation is held at a fixed wavelength and the emitted fluorescent intensity is measured as a function of emission wavelength. In excitation fluoroscopy, the emission wavelength is held fixed and the fluorescence intensity is measured as a function of the excitation wavelength. This type of fluorescence spectroscopy may also be used in conjunction with incident photons that carry OAM. Performing both emission and excitation spectra together yields a spectral map of the material under interrogation. Materials of interest may contain many fluorophores, and different excitation wavelengths are required to interrogate different molecules.

Fluorescence spectrometers analyze the spectral distribution of the light emitted from a sample (the fluorescence emission spectrum) by means of either a continuously variable interference filter or a monochromator. Monochromators used in more sophisticated spectrometers select the exciting radiation and analyze the sample emission spectra. Such instruments are also capable of measuring the variation of emission intensity with exciting wavelength (the fluorescence excitation spectrum).

One advantage of fluorescence spectroscopy compared to equivalent absorption techniques is that the sample may be contained in simple test tubes rather than precision cuvettes without appreciable loss in precision because of the geometrical configuration of simple fluorimeters in which only the small central region of the cuvette is interrogated by the detector. Hence, the overall size of the cuvette is less important.

Sensitivity of fluorescence spectroscopy depends largely on the properties of the measured sample and is typically measured in parts per billion or trillion for most materials. This remarkable degree of sensitivity permits reliable detection of very small sample sizes of fluorescent materials (e.g. chlorophyll and aromatic hydrocarbons).

Fluorescence spectroscopy is exceptionally specific and less prone to interference because few materials absorb or emit light (fluoresce) and rarely emit at the same frequency as compounds in the target material.

Fluorescence measurements scale directly with sample concentration over a broad frequency range and can be performed over a range of concentrations of up to about one six orders of magnitude without sample dilution or alteration of the sample cell. Additionally, the sensitivity and specificity of fluoroscopy reduces or eliminates the need for costly and time-consuming sample preparation procedures, thus expediting the analysis. Overall, fluoroscopy represents a low-cost material identification technique owing to its high sensitivity (small sample size requirement).

Pump-Probe Spectroscopy

Pump-probe spectroscopy is used to study ultrafast phenomena in which a pump beam pulse perturbs atomic and molecular constituents of a sample and a probe beam pulse is used to interrogate the perturbed sample after an adjustable period of time. This optical technique is a type of transient spectroscopy in which the electronic and structural properties of short-lived transient states of photochemically or photophysically relevant molecules may be investigated. The resulting excited state is examined by monitoring properties related to the probe beam including its reflectivity, absorption, luminescence, and Raman scattering characteristics. Electronic and structural changes occurring within femto- to pico-second timeframes may be studied using this technique.

Generally, pump-induced states represent higher energy forms of the molecule. These higher energy molecular forms differ from their lowest ground state energy states including a redistribution of electrons and/or nuclei.

Within a basic pump probe configuration, a pulse train generated by a laser is split into a pump pulse and a probe pulse using a beam splitter. The pump pulse interacts with the atoms and molecules in a sample. The probe pulse is used to probe the resulting changes within the sample after a short period of time between the pulse train and the probe pulse train. By changing the delay time between pulse trains with an optical delay line, a spectrum of absorption, reflectivity, Raman scattering, and luminescence of the probe beam may be acquired after the sample to study the changes made by the pump pulse train at detector. It is possible to obtain information concerning the decay of the pump-induced excitation by monitoring the probe train as a function of the relative time delay. The probe train is typically averaged over many pulses and doesn't require a fast photodetector. The temporal resolution of measurements in pump-probe spectroscopy is limited only by the pulse durations of each train. In general, the uncertainty in timing must be smaller than the timescale of the structural or electronic process induced by the pump train.

In two-color pump-probe spectroscopy, the pump and probe beams have different wavelengths produced by two synchronized sources. While this technique provides additional capabilities in ultrafast spectroscopy, it's essential to ensure precise source synchronization with a very low relative timing jitter.

In comparison with spontaneous Raman scattering intensities, the scattered intensities provided by a pump-probe Raman spectroscopy technique may be tremendously enhanced with different pump and probe frequencies, $\Omega$ and $\omega$. The frequency of the pump beam is changed, while the frequency of the probe beam is fixed. The pump beam is used to induce Raman emission, while the probe beam serves to reveal Raman modes. Both the pump and the probe beam traverse a Raman-active medium in collinearity. When the difference between the pump and probe frequencies coincide with a Raman vibrational mode frequency, $v$, of the medium, the weak spontaneous Raman light is amplified by several orders of magnitude ($10$-$10^4$) due to the pump photon flux. Gain is achieved.

The pump beam is essentially engineered to provide a variety of perturbative excitations within a wide range of samples. Pump-probe spectroscopy is therefore applicable to use within the context of other spectroscopy techniques including the use of a pump beam endowed with orbital angular momentum as discussed in the next section.

Orbital Angular Momentum (OAM) Spectroscopy

Chiral optics conventionally involved circularly polarized light in which a plane polarized state is understood as a superposition of circular polarizations with opposite handedness. The right- and left-handedness of circularly polarized light indicates its spin angular momentum (SAM), ±h in addition to the polarization one can use the helicity of the associated electromagnetic field vectors. Its interaction with matter is enantiomerically specific. The combined techniques would have specific signatures for different materials.

As described more fully herein above, optical vortices occurring in beams of light introduce helicity in the wavefront surface of the electromagnetic fields and the associated angular momentum is considered "orbital". Orbital angular momentum (OAM) of photonic radiation is frequently called a "twisted" or "helical" property of the beam. Most studies of OAM-endowed light interactions with matter involve achiral molecules.

Delocalized OAM within solid materials associated with the envelope wavefunction in a Bloch framework, which may be spatially macroscopic in extent, may be distinguished from local OAM associated with atoms. The latter is associated with the Landé g-factor of electronic states and part of the effective spin while the former is of interest to orbitally coherent systems (e.g. quantum Hall layers, superconductors, and topological insulators). Development of these techniques represents opportunities to improve our understanding of scattering and quantum coherence of chiral electronic states, with potential implications for materials discovery and quantum information. To this end, theoretical frameworks describing the OAM-matter interaction, such as with dielectric materials are useful.

OAM-endowed beams of light have been used to induce such delocalized OAM-states in solids using a time-resolved pump-probe scheme using LG beams in which the OAM-sensitive dichroism of bulk n-doped ($3 \times 10^{16}$ cm$^{-3}$ Si) and undoped GaAs (held in a cryostat at 5K) is exploited. Using this method, "whirlpools" of electrons were induced and measured with a time-delayed probe beam whose OAM components were detected in a balanced photodiode bridge. The study demonstrates that time-resolved OAM decay rates (picoseconds to nanoseconds) are doping dependent, differed from spin and population lifetimes, and longer than anticipated as described in M. A. Noyan and J. M. Kikkawa, "Time-resolved orbital angular momentum spectroscopy," Appl. Phys. Lett. 107 032406 (2015), which is incorporated herein by reference in its entirety.

A simple pump-probe OAM spectroscopy instrument in which the OAM pump beam is an $\ell = \pm 1$ Laguerre-Gaussian beam cycled between $\ell = +1$ and $\ell = -1$ at some frequency, $\nu_\ell$. The pump beam perturbs target molecules in the sample while a direct probe beam is used to interrogate the resulting perturbation. The sample may be a crystalline solid, amorphous solid, liquid, biological, or inorganic.

The interaction of light exhibiting OAM, an azimuthal photonic flow of momentum, with chiral molecules is the subject of several recent theoretical and experimental reports. On one hand, the strength of the interaction has been conjectured as negligible, while on the other hand, not only does such an interaction exist, it may be stronger than the interactions occurring in conventional polarimetry experiments in which the direction of linearly polarized light incident on a solution is rotated by some angle characteristic of the solution itself. A few limited experimental studies have suggested that the former theoretical body of work is correct—that such an interaction is negligible.

Nonetheless, a variety of light-matter interactions involving OAM-endowed optical beams indicate a broad range of possibilities in spectroscopy including OAM transfer between acoustic and photonic modes, OAM-endowed Raman sideband generation, and the manipulation of colloidal particles manipulation with optical OAM "tweezers".

OAM Spectroscopy of Chiral Molecules

Recent experiments using Laguerre-Gaussian (LG) beams of varying integer azimuthal order, $\ell$, traveling through a short optical path length of various concentrations of glucose, support the theoretical body of work suggesting the existence of measureable OAM light-matter interactions. These experiments suggest that not only does the interaction exist, but it appears to be stronger than with polarimetry since perturbations of the OAM beam occur within a very short optical path length (1-3 cm) than commonly required in conventional polarimetry studies (>10 cm) to obtain a measurable perturbation of the linear state of polarization.

The Gaussian beam solution to the wave equation and its extension to higher order laser modes, including Hermite-Gaussian (HG) and commonly studied in optics labs. Of particular interest, LG modes exhibit spiral, or helical, phase fronts. In addition to spin angular momentum, the propagation vector includes an orbital angular momentum (OAM) component often referred to as vorticity.

A spatial light modulator (SLM) is frequently used to realize holograms that modulate the phase front of a Gaussian beam and has renewed interest in engineered beams for a variety of purposes.

The expression for the electric field of an LG beam in cylindrical coordinates is $$u(r, \theta, z) = \left[\frac{2p!}{1 + \delta_{\sigma,m}\pi(\ell + p)!}\right]^{\frac{1}{2}} \exp\{j(2p + \ell + 1)[\psi(z) - \psi_0]\} \cdot \frac{\sqrt{2}\,r}{w^2(z)} L_p^\ell\left(\frac{2r^2}{w^2(z)}\right) \exp\left[-jk\frac{r^2}{2q(z)} + i\ell\theta\right]$$

with w(z) the beam spot size, q(z) a complex beam parameter comprising evolution of the spherical wavefront and spot size, and integers p and $\ell$ index the radial and azimuthal modes, respectively. The exp(i$\ell$ $\theta$) term describes spiral phase fronts. A collimated beam is reflected off the SLM appropriately encoded by a phase retarding forked grating, or hologram, like the one shown in FIG. 43. The generating equation for the forked hologram may be written as a Fourier series, $$T(r, \varphi) = \sum_{m=-\infty}^{\infty} t_m \exp\left[-im\left(\frac{2\pi}{D}r\cos\varphi - \ell\varphi\right)\right],$$

where r and $\varphi$ are coordinates, $\ell$ is the order of vorticity, and D is the rectilinear grating period far from the forked pole. Weights, t_m, of the Fourier components may be written in terms of integer-order Bessel functions, $$t_m = (-i)^m J_m(k\beta) \exp(ik\alpha).$$

where k$\alpha$ and k$\beta$ bias and modulate the grating phase, respectively. Only a few terms are needed to generate OAM beams, such as $-1 \leq m \leq 1$, $$T(r, \varphi) = \frac{1}{2} - \frac{1}{2}\sin\left(\frac{2\pi}{D}r\cos\varphi\varphi - \ell\varphi\right).$$

Molecular Chirality

The chirality of a molecule is a geometric property of its "handedness" characterized by a variety of spatial rotation, inversion, and reflection operations. Conventionally, the degree of chirality of molecules was starkly limited to a molecule being either "chiral" or "achiral" in addition to being "left-handed" or "right-handed". However, this binary scale of chirality doesn't lend well to detailed spectroscopic studies of millions of molecular systems that may be studied. In its place, a continuous scale of 0 through 100 has been implemented for the past two decades called the Continuous Chirality Measure (CCM). Essentially, this continuous measure of chirality involves the Continuous Symmetry Measure (CSM) function, $$S'(G) = \frac{1}{n}\sum_{i=1}^{n}\|P_i - \hat{P}_i\|^2$$

where G is a particular symmetry group, $P_i$ are the points of the original configuration, $\hat{P}_i$ are the corresponding points in the nearest G-symmetric configuration, and n is the total number of configuration points.

The objective is to identify a point set, $P_i$, having a desired G-symmetry such that the total normalized displacement from the original point set $P_i$ is a minimum. The range of symmetry, $0 \leq S'(G) \leq 1$, may be expanded such that $S=100S'$. The advantages of CCM over other chiral measure schemes include its ease of application to a wide variety of chiral structures including distorted tetrahedra, helicenes, fullerenes, frozen rotamers, knots, and chiral reaction coordinates, as well as being a measured without reference to an ideal shape. Unique chirality values are made with reference to nearest symmetry groups ($\sigma$ or $S_{2n}$), thus allowing for direct comparison with a wide variety of geometric.

Yet, since the new technique described above discusses the use of Stimulated Raman or Resonant Raman spectroscopy with vector beams (i.e., beams with "twistedness" plus polarization), the technique can equally be applied to both chiral and non-chiral molecules.

Raman with Orbital Angular Momentum

Figure 82:
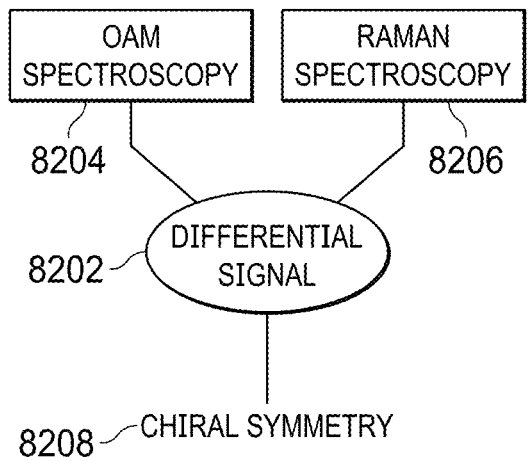
FIG. 82 illustrates a combination of OAM spectroscopy with Ramen spectroscopy for the generation of differential signals.

The effect of orbital angular momentum on the Raman scattering spectra of glucose has been investigated. Changes have been observed in the Raman spectra, in particular at 2950 $cm^{-1}$ with L=2 (helical beam) as compared to L=0 (Gaussian beam). The innovation is that if the sugar molecules possess some types of chiral symmetry 8208 than there may be a differential signal 8202 (FIG. 82) using OAM 8204 and Raman 8206 spectroscopy. The Raman spectra of glucose, sucrose and fructose have already been collected for the three laser wavelengths 488, 514.5 and 632.8 nm from argon-ion and helium neon laser sources, the signals have been tabulated and the agreement of each vibration is justified with the other two laser lines. No resonances were observed as would be expected since there is no direct electronic absorption with these energies. The Raman spectra, however, are sensitive to local and global symmetries of the molecule at any wavelength. Differential Raman signals will give fundamental information about the interaction of a chiral electromagnetic field with the sugar molecules, as well as potentially lead to a selected symmetry resonance for low level glucose detection in the blood.

The system used for these measurements is a confocal microscope attached to a 75 cm single stage spectrometer using a grating blazed at 500 nm and 1200 lines/mm groove density. The microscope objective used was 10× magnification. To generate the OAM beam with angular momentum value L=2, a Q plate was incorporated into the system.

Figure 83:
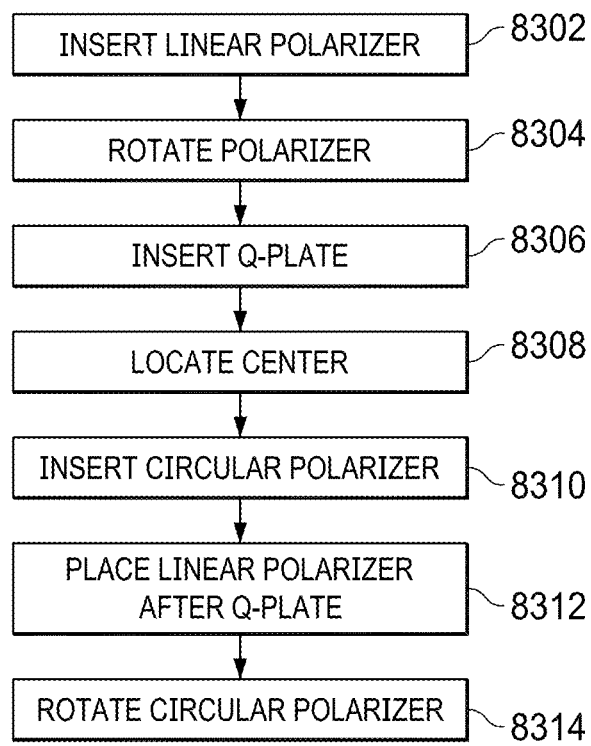
FIG. 83 illustrates a flow diagram of an alignment procedure

Referring now to FIG. 83 there is illustrated the alignment procedure. A linear polarizer is inserted at step 8302 into the beam path and rotated at step 8304 until maximum transmission intensity is achieved. A Q-plate is inserted at step 8306 into the beam path and locates at step 8308 the center that produces the OAM beam (by observation of the donut). The circular polarizer is inserted at step 8310 before the Q-Plate. The linear polarizer is placed at step 8312 after the Q-plate to observe the 4 lobed structure. Finally, the circular polarizer is rotated at step 8314 until the output from final linear polarizer shows donut for all angles of final linear polarization. This procedure is iterative also adjusting applied voltage to Q-plate (appx 4 Volts) and the square wave driving frequency (appx 2 KHz). The measurements are taken without the final linear polarizer.

The resulting spectra with L=2 along with a spectra with L=0 (no elements in the beam path) both normalized to the maximum value which for both cases is the Raman signal near 2800 $cm^{-1}$. From these measurements it does show that there are differential intensities between the two different excitations. At 400 and 550 $cm^{-1}$ there is almost a 50 percent increase in scattering intensity while the L=2 spectrum shows a few additional shoulders of each of these lines. Most pronounced is the intensity ratio of the doublet around 2950 $cm^{-1}$.

The Raman system used for these measurements is alignment restricted. The incorporation of the additional waveplates causes slight walk-off which leads to significant collection intensity drop in the confocal system. Presumably, normalization would eliminate any alignment intensity issues, however signal to noise suffers and longer integrations are required. Long integration times are not always possible or feasible.

These measurements need to be repeated for glucose and also done for fructose. Also needed to be checked is the response to pure circular polarization without OAM. We should be able to access the alignment and optimize for the Q-plate operation. Also, to do is use L=1 value and L=20 values of OAM. With promising results, we will use a quarter waveplate for 488 nm as this laser produces the best spectra in the shortest acquisition times on the system.

Although the higher energy Raman signals are not unique to glucose as they represent generic carbon and carbon hydrogen bonds present in many organic systems, it may prove to be unique to chiral systems. Additionally, the lower energy modes that are more unique to glucose may show better differentiation with OAM once the system is better optimized for Q-plates.

Raman Detection of Glycated Protein

Hb and Hb-A1c a proteins by Raman spectroscopy using OAM may also be investigated. Mammalian blood is considered as connective tissue because of its cellular composition and due to its embryonic origin and also due to the origin and presence of colloidal proteins in its plasma. Red Blood cells and Plasma proteins are the major constituents of blood. These connective tissue components are targets for metabolic stress under disease conditions and result in the chemical alterations. All the blood components are subjected to excessive metabolic stress under hyperglycemic states. Blood acts a primary transporter of nutrients, gases and wastes. Blood plasma acts as a primary carrier for glucose to the tissues. Normal pre-prandial plasma glucose levels are 80 mg/dl to 130 mg/dl and normal postprandial plasma glucose is <180 mg/dl. The Renal Threshold for Glucose (RTG) is the physiologic maximum of plasma glucose beyond which kidneys fail to reabsorb the glucose and get excreted in urine. This is a condition called glycosuria. Glycosuria is the key characteristic of Diabetes mellitus (DM). High plasma glucose in DM will cause increased levels of Glycosylated Hemoglobin also known as HbA1c. Under normal physiological conditions HbA1c levels are <7%, this also expressed as eAG which should be below 154 mg/dl in Normo-glycemic condition.

Glycation of Plasma Proteins in DM

Glycation is defined as the non-enzymatic random non-specific covalent linking of glucose or other hexose sugar moieties to the proteins. Under normal blood glucose levels in healthy individuals will have levels <7% Glycated Hemoglobin (HbA1c) in the blood, however under hyperglycemic conditions like DM, its levels will increase. Higher blood glucose levels can induce glycation of other major proteins of blood plasma like albumin.

Advantages of Measurement of Glycated Proteins in DM:

Measurements of blood glucose levels only provide the information about the glycemic status of a subject at a given moment, i.e. a diabetic person with uncontrolled blood sugar levels for several months may yield normal blood glucose level if he/she gets the test under fasting state or with low carbohydrate intake on a given day. However, the measurement of Glycated hemoglobin (HbA1c) levels in blood yield the information about average blood sugar levels in patient for past 2 to 3 months. Therefore, it has become a standard clinical practice since past decade to measure Glycated Hemoglobin in patients with DM with the development sensitive and reliable laboratory analyses. We propose the use of Raman spectroscopic studies on Diabetic blood and its components for the detection of specific Raman fingerprints that may result from non-enzymatic glycosylation of key blood proteins Hemoglobin, plasma albumin and others in its native and altered physical states. The process of glycation in proteins induces the chemical alterations, structural modifications, conformational changes. Any or all of these can result in special Raman spectral changes which can used as a clinical marker.

Measurements were carried out with a small benchtop OceanOptics Raman system with 532 nm excitation.

Raman Spectroscopy of Tryptophan:

The Hemoglobin (tetramer) has 6 residues of Tryptophan therefore Hemoglobin is a fluorescent protein. Tryptophan can undergo glycation and result in conformational changes in Hemoglobin. The tryptophan changes can be identified by using Raman studies (Masako Na-Gai et al. Biochemistry, 2012, 51 (30), pp 59325941) which is incorporated herein by reference. In order to understand the glycation induced Raman spectral changes in Tryptophan residues Raman spectra is obtained from analytical grade amorphous Tryptophan using 532 nm OceanOptics Raman.

Raman Spectra of Proteins:

Solid amorphous powders of albumin and Glycated albumin samples were subjected to Raman measurements using a OceanOptic 532 nm Raman system and the confocal Raman system using 488, 514.5 and 632.8 nm. No Raman signal was observed from these samples, and therefore we need to retest in solution at a physiologic pH of 7.4.

The next steps are:

1. NIR Raman: Blood and its components have intense fluorescence in visible range so NIR Raman may help reduce fluorescence and get good Raman signals from target protein molecules.

2. OceanOptics 532 nm Raman: This can be used detect some of Glycation derivatives in blood. This needs normal and diabetic blood either from human subjects or animal models. And also Reference spectra of synthetic glycation products can be obtained by using this system, which can later be compared with the Raman signal from blood samples.

3. In Vivo Animal model: For future experiments to be successful for in vivo blood glucose and diabetes testing, the Raman measurements need to be carried out in a rat diabetes animal model.

OAM with Raman for Food Freshness, Spoilage, and Organic Detection

Another aspect that will be investigated is food safety concerns due to spoilage of meats, produce, diary, and grains and determination if labeled food is organic using Raman and OAM. Public and individual concern led to both governmental regulation and commercial requirements of quality, stability, and safety of food storage periods. Moreover, food deterioration resulting in food spoilage leads to not only health issues but also economic loss to food manufacturing and related industries. Thus, minimizing food spoilage, determining food freshness, or maximizing shelf life of food is desired.

Moreover, in 2000, the U.S. Department of Agriculture ("USDA") established guidelines and national standards for the term "organic." For example, organic food, as defined by USDA guidelines, means that food must be produced without sewer-sludge fertilizers, synthetic fertilizers and pesticides, genetic engineering, growth hormones, irradiation, and antibiotics.

The traditional physical characteristics of food spoilage, such as unpleasant smells, unpleasant tastes, color changes, texture changes, and mold growth, manifest well after biochemical processes have occurred that impair food quality or safety. As a result, they are not adequate indicators of determining acceptable criteria to use for food freshness, preservation, and spoilage.

Thus, research to date includes the identification of so-called "biomarkers" of food spoilage. This research includes identification of the biochemical mechanisms that produce certain chemical by-products that are associated with the physical characteristics of food spoilage. These mechanisms can be physical (e.g., temperature, pH, light, mechanical damage); chemical (e.g., enzymatic reaction, non-enzymatic reaction, rancidity, chemical interaction); microorganism-based (e.g., bacteria, viruses, yeasts, molds); or other (e.g., insects, rodents, animals, birds).

One aspect of the investigation is to use OAM and Raman techniques to identify these so-called biomarkers and their associated concentrations to better determine shelf life of basic food categories. Additionally, another aspect of the invention is to investigate the chemicals used that would fail to qualify foodstuffs as "organic." For example, the Table 1 below shows several researched biochemical processes and chemical by-products associated with food spoilage mechanisms associated with common food groups:

| Biochemical Process | Mechanism | Food Category/Spoilage Action | Resulting Biomarker |
| --- | --- | --- | --- |
| Oxidation | Light | Reversion Flavor of Soybean | 2-pentyl furan |
| Oxidation | Light | Sunlight flavor in milk | dimethyl disulfide, 2-butanone, ethanol, diacetyl, n-butanol |

-continued

| Biochemical Process | Mechanism | Food Category/ Spoilage Action | Resulting Biomarker |
|---|---|---|---|
| Oxidation | Light | Loss of Riboflavin, Vitamins D, E, and C | vitamin D-5,6 ep25 oxide |
| Oxidation | Light | Greening of Potato | alpha-solanine, alpha-chaconine |
| Oxidation | Decay | meat and diary (fats, oils, lipids) | aldehydes |
| Enzymatic | Decay | Chicken/Meat | dimethylsulfide, dimethyl disulfide, dimethyl trisulfide, dimethyl tetrasulfide, hydrogen sulfide, ethanol, 3-methyl-1-butanol, acetic acid, propanioc acid, methanethiol, free fatty acids (FFAs) |
| Enzymatic: Decarboxylation of free amino acids (natural fermentation or via contimation of microorganisms) | Decay | Fruits, Vegatables, Meat, Fish, Poultry | biogenic amines (tyraimine, putrescine, cadaverine, histamine) |
| Enzymatic | Decay | Vegatables vitamin (loss of C) | ascrbic acid, oxidase |
| Enzymatic | Decay | Milk, oils (hydrolytic rancidity) | lipase, glycerol, free fatty acids (FFAs), 3-(E)-hexenal, 2-(E)-hexenal |
| Enzymatic | Decay | Vegatables (loss of vitamin A) | lipoxygenase |
| Enzymatic | Decay | Fruits (loss of pectic substances, i.e., softing) | petic enzymes |
| Enzymatic | Decay | Fruits (browning) | peroxidases (polyphenol oxidase, o-diphenol, monophenol, o-quinone) |
| Enzymatic | Decay | Fruits, Vegatables (browning, sour flavor, vitamin loss) | melanin |
| Enzymatic | Decay | Eggs, Crab, Lobster, Flour (reduction of shelf life, overtenderization, reduction in gluten network formation) | proteases |
| Enzymatic | Decay | Meats, Fish | thiaminase |
| Microbial | Bacteria | Carbohydrates (fermentation) | alcoholic (ethanol, CO2); homofermentative lactic acid (lactic acid); heterofermentative lactic acid (lactic acid, acetic aci, ethanol, CO2); propionic acid fermentation (propionic acid, aetic acid, CO2); butyric acid fermentation (butyric acid, acetic acid, CO2, H2); mixed acid fermentation (lactic acid, acetic acid, CO2, H2, ethanol); 2,3-butanediol fermentation (CO2, ethanol, 2,3-butanediol, formic acid) |
| Microbial | Bacteria | Degradation of N-Compounds | (H2S, methyl mercaptns, indole, cadaverine, putrescine, histamine) |

| Biochemical Process | Mechanism | Food Category/Spoilage Action | Resulting Biomarker |
|---|---|---|---|
| Microbial | bacteria | Fish (odor) | trimethylamine |
| Microbial | Bacteria | Lipids | aldehyde, ketones |
| Microbial | Bacteria | Pectin Degradation | polygalcturonic acid, galacturonic acid, methanol |
| Fishy Odor | Decay | Meat, Egg, Fish | trimethylamine |
| Garlic odor | Decay | Wine, Fish, Meat, Milk | dimethyl trisulfide |
| Onion odor | Decay | Wine, Fish, Meat, Milk | dimethyl disulfide |
| Cabbage odor | Decay | Wine, Fish, Meat, Milk | dimethyl sulfide |
| Fruity odor | Decay | Milk, Fish, Wine | esters |
| Potato odor | Decay | Meat, Egg, Fish | 2-methoxy-3-isopropylprazine |
| Alcoholic odor | Decay | Fruit juices, Mayonnaise | ethanol |
| Musty odor | Decay | Bread, Wine | tricholoranisole |
| Cheesy odor | Decay | Meat | diacetyl, acetoin |
| Medicinal odor | Decay | Juice, Wine | 2-methoxy phenol |
| Souring | Decay | Wine, Beer, Dairy | acetic acid, lactic acid, citric acid |
| Slime | Decay | Meat, Juices, Wine | polysaccharide |
| Curdling | Decay | Milk | lactic acid |
| Holes | Decay | Hard cheese | carbon dioxide |

A person skilled in the art would be well aware of various other mechanisms and biochemical indicators evidencing food spoilage of common foodstuffs, including other reactions or volatile or non-volatile organic compound (VOC) by-products associated with food spoilage. Likewise, a person skilled in the art would be well aware of the chemicals and additives that do not qualify food as organic, whether investigating grains, diary, produce, or meats.

Traditional spectroscopy techniques are not adequate to identify in real-time or adequate concentration these bio-markers in any meaningful manner to determine shelf life of the food sample or organic nature of the food in question. The present investigation and invention will employ Raman and OAM techniques described above to classify, identify, and quantify the various bio-markers in the table above and the common chemicals that do not qualify food as organic as defined in federal regulations.

Such techniques are equally applicable whether the bio-marker or chemical is a chiral or non-chiral molecule. Such data can then be correlated to concentration of degradation of the sampled food group to determine minimum and maximum concentrations acceptable to food freshness, spoilage, organic quality, and safety.

Ince-Gaussian Spectroscopy

Another type of spectroscopic technique that may be combined with one or more other spectroscopic techniques is Ince-Gaussian Spectroscopy. Ince Gaussian (IG) beams are the solutions of paraxial beams in an elliptical coordinate system. IG beams are the third calls of orthogonal Eigen states and can probe the chirality structures of samples. Since IG modes have a preferred symmetry (long axis versus short axis) this enables it to probe chirality better than Laguerre Gaussian or Hermite Gaussian modes. This enables the propagation of more IG modes than Laguerre Gaussian modes or Hermite Gaussian modes. Thus, IG modes can be used as a program signal for spectroscopy in the same manner that Laguerre Gaussian modes or Hermite Gaussian modes are used. This enables the detection of types of materials and concentration of materials using an IG mode probe signal.

The wave equation can be represented as a Helmholtz equation in Cartesian coordinates as follows $$(\nabla^2 + k^2) E(x,y,z) = 0$$

$E(x, y, z)$ is complex field amplitude which can be expressed in terms of its slowly varying envelope and fast varying part in z-direction.

$$E(x,y,z) = \psi(x,y,z) e^{jkz}$$

A Paraxial Wave approximation may be determined by substituting our assumption in the Helmholtz Equation.

$$(\nabla^2 + k^2)\psi \cdot e^{jkz} = 0$$

$$\frac{\delta^2 \psi}{\delta x^2} + \frac{\delta^2 \psi}{\delta y^2} + \frac{\delta^2 \psi}{\delta z^2} - j2k\frac{\delta \psi}{\delta z} = 0$$

We then make our slowly varying envelope approximation $$\left|\frac{\delta^2 \psi}{\delta z^2}\right| \ll \left|\frac{\delta^2 \psi}{\delta x^2}\right|, \left|\frac{\delta^2 \psi}{\delta y^2}\right|, 2k\left|\frac{\delta \psi}{\delta z}\right|$$

$$\nabla_t^2 \psi + j2k\frac{\delta \psi}{\delta z} = 0$$

Which comprises a Paraxial wave equation.

The elliptical-cylindrical coordinate system may be defined:

$$x = a\cosh\xi\cos\eta$$

$$y = a\sinh\xi\sin\eta$$

$$\xi \in (0, \infty), \eta \in (0, 2\pi)$$

$$a = f(z) \text{ where } f(z) = \frac{f_0 w(z)}{w_0}$$

Curves of constant value of $\xi$ trace confocal ellipses.

$$\frac{x^2}{a^2\cosh^2\xi} + \frac{y^2}{a^2\sinh^2\xi} = 1 \text{ (Ellipse)}$$

Figure 84:
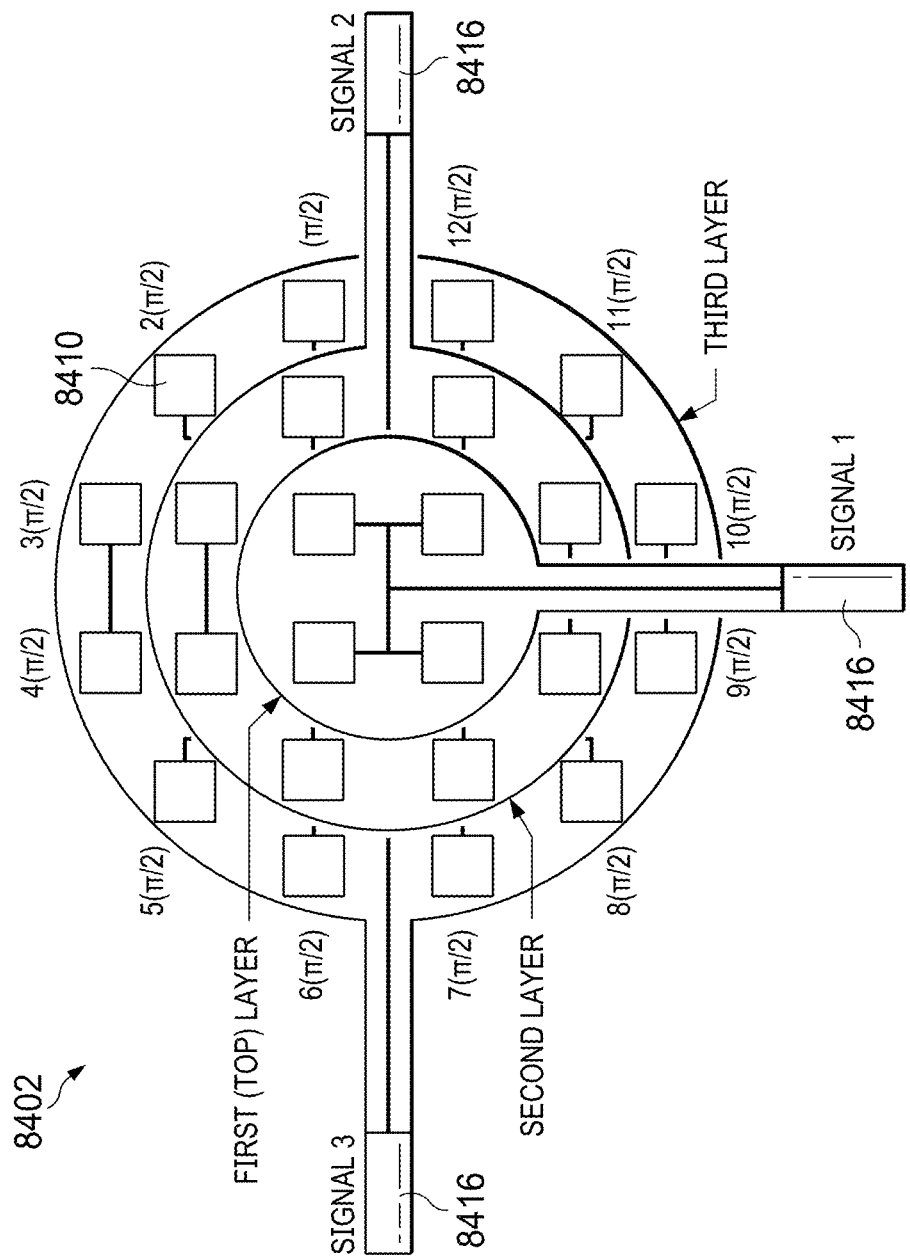
FIG. 84 illustrates a top view of a multilayer patch antenna array.

A constant value of η give confocal hyperbolas as shown in FIG. 84.

$$\frac{x^2}{a^2\cos^2\eta} - \frac{y^2}{a^2\sin^2\eta} = 1 \text{ (hyperbola)}$$

An elliptical-cylindrical coordinate system may then be defined in the following manner $$\nabla_t^2 = \frac{1}{h_\xi^2}\frac{\delta^2}{\delta\xi^2} + \frac{1}{h_\eta^2}\frac{\delta^2}{\delta\eta^2}$$

Where $h_\xi$, $h_\eta$ are scale factors $$h_\xi = \sqrt{\left(\frac{\delta x}{\delta\xi}\right)^2 + \left(\frac{\delta y}{\delta\xi}\right)^2}$$

$$h_\eta = \sqrt{\left(\frac{\delta x}{\delta\eta}\right)^2 + \left(\frac{\delta y}{\delta\eta}\right)^2}$$

$$h_\xi = h_\eta = a\sqrt{\sinh^2\xi + \sin^2\eta}$$

$$\nabla_t^2 = \frac{1}{a^2\sinh^2\xi\sin^2\eta}\left(\frac{\delta^2}{\delta\xi^2} + \frac{\delta^2}{\delta\eta^2}\right)$$

The solution to the paraxial wave equations may then be made in elliptical coordinates. Paraxial Wave Equation in Elliptic Cylindrical co-ordinates are defined as $$\frac{1}{a^2(\sinh^2\xi\sin^2\eta)}\left(\frac{\delta^2\psi}{\delta\xi^2} + \frac{\delta^2\psi}{\delta\eta^2}\right) - j2k\frac{\delta\psi}{\delta z} = 0$$

Assuming separable solution as modulated version of fundamental Gaussian beam.

$$IG(\vec{r}) = E(\xi)N(\eta)\exp(jZ(z))\psi_{GB}(\vec{r})$$

Where $$\psi_{GB}(\vec{r}) = \frac{w_0}{w(z)}\exp\left[-\frac{r^2}{w^2(z)} + j\frac{kr^2}{2R(z)} - j\psi_{GS}(z)\right]$$

E, N & Z are real functions. They have the same wave-fronts as $\psi_{GB}$ but different intensity distribution.

Separated differential equations are defined as $$\frac{d^2E}{d\xi^2} - \epsilon\sinh 2\xi\frac{dE}{d\xi} - (a - p\epsilon\cosh 2\xi)E = 0$$

$$\frac{d^2N}{d\eta^2} - \epsilon\sin 2\eta\frac{dN}{d\eta} - (a - p\epsilon\cos 2\eta) = 0$$

$$-\left(\frac{z^2 + z_r^2}{z_r}\right)\frac{dZ}{dz} = p$$

Where a and p are separation constants $$\epsilon = \frac{f_0 w_0}{w(z)}$$

The even solutions for the Ince-Gaussian equations are $$IG_{pm}^e(\vec{r}, \epsilon) = \frac{Cw_0}{w(z)}C_p^m(j\xi, \epsilon)C_p^m(\eta, \epsilon)\exp\left(-\frac{r^2}{w^2(z)}\right) \times \exp j\left(kz + \frac{kr^2}{2R(z)} - (p+1)\psi_{GS}(z)\right)$$

The odd solutions for the Ince-Gaussian equations are $$IG_{pm}^o(\vec{r}, \epsilon) = \frac{sw_0}{w(z)}S_p^m(j\xi, \epsilon)S_p^m(\eta, \epsilon)\exp\left(-\frac{r^2}{w^2(z)}\right) \times \exp j\left(kz + \frac{kr^2}{2R(z)} - (p+1)\psi_{GS}(z)\right)$$

Thus, as previously discussed, by combining two or more different types of spectroscopy techniques, various types of different parameters may be monitored and used for determining types and concentrations of sample materials. The use of multiple types of spectroscopic parameter analysis enables for more accurate and detailed analysis of sample types and concentrations. Thus, any number of spectroscopic techniques such as optical spectroscopy, infrared spectroscopy, Ramen spectroscopy, spontaneous Ramen spectroscopy, simulated Ramen spectroscopy, resonance Ramen spectroscopy, polarized Ramen spectroscopy, Ramen spectroscopy with optical vortices, THz spectroscopy, terahertz time domain spectroscopy, fluorescence spectroscopy, pump probe spectroscopy, OAM spectroscopy, or Ince Gaussian spectroscopy may be used in any number of various combinations in order to provide better detection of sample types in concentrations. It should be realized that the types of spectroscopy discussed herein are not limiting in any combination of spectroscopic techniques may be utilized in the analysis of sample materials.

Using the orbital angular momentum state of the transmitted energy signals, physical information can be embedded within the electromagnetic radiation transmitted by the signals. The Maxwell-Heaviside equations can be represented as:

$$\nabla E = \frac{\rho}{\epsilon_0}$$

$$\nabla \times E = -\frac{\partial B}{\partial t}$$

$$\nabla \cdot B = 0$$

$$\nabla \times B = \epsilon_0\mu_0\frac{\partial E}{\partial t} + \mu_0 j(t, x)$$

the where ∇ is the del operator, E is the electric field intensity and B is the magnetic flux density. Using these equations, we can derive 23 symmetries/conserve quantities from Maxwell's original equations. However, there are only ten well-known conserve quantities and only a few of these are commercially used. Historically if Maxwell's equations where kept in their original quaternion forms, it would have been easier to see the symmetries/conserved quantities, but when they were modified to their present vectorial form by Heaviside, it became more difficult to see such inherent symmetries in Maxwell's equations.

The conserved quantities and the electromagnetic field can be represented according to the conservation of system energy and the conservation of system linear momentum. Time symmetry, i.e. the conservation of system energy can be represented using Poynting's theorem according to the equations:

$$H = \sum_i m_i \gamma_i c^2 + \frac{\varepsilon_0}{2} \int d^3 x (|E|^2 + c^2 |B|^2)$$

$$\frac{dU^{mech}}{dt} + \frac{dU^{em}}{dt} + \oint_{s'} d^2 x' \hat{n}' \cdot S = 0$$

The space symmetry, i.e., the conservation of system linear momentum representing the electromagnetic Doppler shift can be represented by the equations:

$$P = \sum_i m_i \gamma_i v_i + \varepsilon_0 \int d^3 x (E \times B)$$

$$\frac{dp^{mech}}{dt} + \frac{dp^{em}}{dt} + \oint_{s'} d^2 x' n^f \cdot T = 0$$

The conservation of system center of energy is represented by the equation:

$$R = \frac{1}{H} \sum_i (x_i - x_0) m_i \gamma_i c^2 + \frac{\varepsilon_0}{2H} \int d^3 x (x - x_0)(|E^2| + c^2|B^2|)$$

Similarly, the conservation of system angular momentum, which gives rise to the azimuthal Doppler shift is represented by the equation:

$$\frac{dJ^{mech}}{dt} + \frac{dJ^{em}}{dt} + \oint_{s'} d^2 x' n' \cdot M = 0$$

For radiation beams in free space, the EM field angular momentum $J^{em}$ can be separated into two parts:

$$J^{em} = \varepsilon_0 \int_{V'} d^3 x' (E \times A) + \varepsilon_0 \int_{V'} d^3 x' E_i [(x' - x_0) \times \nabla] A_i$$

For each singular Fourier mode in real valued representation:

$$J^{em} = -i \frac{\varepsilon_0}{2\omega} \int_{V'} d^3 x' (E^* \times E) - i \frac{\varepsilon_0}{2\omega} \int_{V'} d^3 x' E_i [(x' - x_0) \times \nabla] E_i$$

The first part is the EM spin angular momentum $S^{em}$, its classical manifestation is wave polarization. And the second part is the EM orbital angular momentum $L^{em}$ (or other orthogonal function) its classical manifestation is wave helicity. In general, both EM linear momentum $P^{em}$, and EM angular momentum $J^{em} = L^{em} + S^{em}$ are radiated all the way to the far field.

By using Poynting theorem, the optical vorticity of the signals may be determined according to the optical velocity equation:

$$\frac{\partial U}{\partial t} + \nabla \cdot S = 0,$$

where S is the Poynting vector
$S = \frac{1}{4}(E \times H^* + E^* \times H),$ and U is the energy density
$U = \frac{1}{4}(\varepsilon |E|^2 + \mu_0 |H|^2),$ with E and H comprising the electric field and the magnetic field, respectively, and $\varepsilon$ and $\mu_0$ being the permittivity and the permeability of the medium, respectively. The optical vorticity V may then be determined by the curl of the optical velocity according to the equation:

$$V = \nabla \times v_{opt} = \nabla \times \left( \frac{E \times H^* + E^* \times H}{\varepsilon |E|^2 + \mu_0 |H|^2} \right)$$

The creation and detection of one embodiment using orbital angular momentum signals comprises one embodiment. However, any orthogonal function can be used, including Jacobi functions, Gegenbauer functions, Legendre functions, Chebyshev functions, Laguerre functions, Gaussian functions, ect.

These techniques are more fully described in U.S. Pat. No. 9,662,019, entitled Orbital Angular Momentum and Fluorescence-Based Microendoscope Spectroscopy for Cancer Diagnosis, filed on Apr. 8, 2015, which is incorporated herein by reference.

One manner for applying the resonance signal from the device to the surface or area to be sanitized involves the use of patch antenna arrays in the microwave band and within the photonic bands using DLP technologies or spiral phase plates. The patch antenna arrays could be those discussed in corresponding U.S. Pat. No. 10,608,768, entitled Patch Antenna Array for Transmission of Hermite-Gaussian and Laguerre Gaussian Beams, filed on Jul. 17, 2018, which is incorporated herein by reference.

With respect to the patch antenna arrays, FIGS. 84 and 85 illustrates a multilayer patch antenna array 8402. The multilayer patch antenna array 8402 includes a first antenna layer 8404 for transmitting a first ordered beam, a second antenna layer 8406 for transmitting a second ordered beam and a third layer 8408 for transmitting a third ordered beam. Each of the layers 8404, 8406 and 8408 are stacked on a same center. While the present embodiment is illustrated with respect to a multilayer patch antenna array 8402 including only three layers, it should be realized that either more or less layers may be implemented in a similar fashion as described herein. On the surface of each of the layers 8404, 8406 and 8408 are placed patch antennas 8410. Each of the patch antennas are placed such that they are not obscured by the above layer. The layers 8404, 8406 and 8408 are separated from each other by layer separator members 8412 that provide spacing between each of the layers 8404, 8406 and 8408. The configuration of the layers of the patch antenna may be in rectangular, circular or elliptical configurations to generate Hermite-Gaussian, Laguerre-Gaussian or Ince-Gaussian beams.

The patch antennas 8410 used within the multilayer patch antenna array 8402 are made from FR408 (flame retardant 408) laminate that is manufactured by Isola Global, of Chandler Ariz. and has a relative permittivity of approximately 3.75. The antenna has an overall height of 125 μm. The metal of the antenna is copper having a thickness of approximately 12 μm. The patch antenna is designed to have an operating frequency of 73 GHz and a free space wavelength of 4.1 mm. The dimensions of the input 50 Ohm line of the antenna is 280 μm while the input dimensions of the 100 Ohm line are 66 μm.

Each of the patch antennas 8410 are configured to transmit signals at a predetermined phase that is different from the phase of each of the other patch antenna 8410 on a same layer. Thus, as further illustrated in FIG. 86, there are four patch antenna elements 8410 included on a layer 8404. Each of the antenna elements 8404 have a separate phase associated there with as indicated in FIG. 86. These phases include π/2, 2(π/2), 3(π/2) and 4(π/2). Similarly, as illustrated in FIG. 4 layer 8406 includes eight different patch antenna elements 8410 including the phases π/2, 2(π/2), 3(π/2), 4(π/2), 5(π/2), 6(π/2), 7(π/2) and 8(π/2) as indicated. Finally, referring back to FIG. 84, there are included 12 patch antenna elements 8410 on layer 8408. Each of these patch antenna elements 8410 have a phase assigned thereto in the manner indicated in FIG. 84. These phases include π/2, 2(π/2), 3(π/2), 4(π/2), 5(π/2), 6(π/2), 7(π/2), 8(π/2), 9(π/2), 10(π/2), 11(π/2) and 12(π/2).

Each of the antenna layers 8404, 8406 and 8408 are connected to a coaxial end-launch connector 8416 to feed each layer of the multilayer patch antenna array 8402. Each of the connectors 8416 are connected to receive a separate signal that allows the transmission of a separate ordered antenna beam in a manner similar to that illustrated in FIG. 85. The emitted beams are multiplexed together by the multilayered patch antenna array 8402. The orthogonal wavefronts transmitted from each layer of the multilayered patch antenna array 8402 in a spatial manner to increase capacity as each wavefront will act as an independent Eigen channel. The signals are multiplexed onto a single frequency and propagate without interference or crosstalk between the multiplexed signals. While the illustration with respect to FIG. 85 illustrates the transmission of OAM beams at OAM 1, OAM 2 and OAM 3 ordered levels.

It should be understood that other types of Hermite Gaussian and Laguerre Gaussian beams can be transmitted using the multilayer patch antenna array 8402 illustrated. Hermite-Gaussian polynomials and Laguerre-Gaussian polynomials are examples of classical orthogonal polynomial sequences, which are the Eigenstates of a quantum harmonic oscillator. However, it should be understood that other signals may also be used, for example orthogonal polynomials or functions such as Jacobi polynomials, Gegenbauer polynomials, Legendre polynomials and Chebyshev polynomials. Legendre functions, Bessel functions, prolate spheroidal functions and Ince-Gaussian functions may also be used. Q-functions are another class of functions that can be employed as a basis for orthogonal functions.

The feeding network 8418 illustrated on each of the layers 8404, 8406, 8408 uses delay lines of differing lengths in order to establish the phase of each patch antenna element 8410. By configuring the phases as illustrated in FIG. 87 the OAM beams of different orders are generated and multiplexed together.

Figure 88:
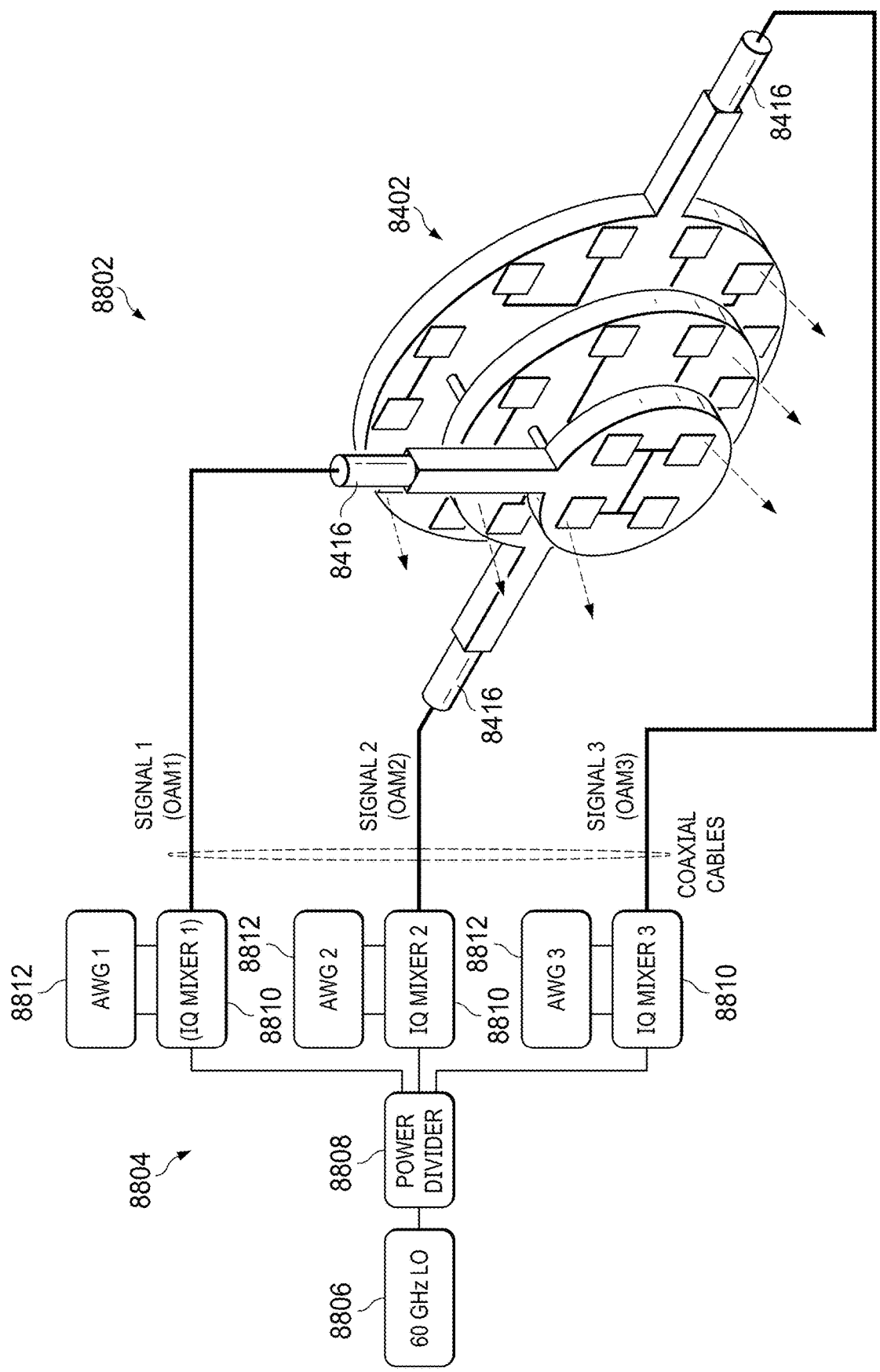
FIG. 88 illustrates a transmitter for use with a multilayer patch antenna array.

Referring now to FIG. 88, there is illustrated a transmitter 8802 for generating a multiplexed beam for transmission toward a virus. As discussed previously, the multilayered patch antenna array 8402 includes a connector 8416 associated with each layer 8404, 8406, 8408 of the multilayer patch antenna array 8402. Each of these connectors 8416 are connected with signal generation circuitry 8804. The signal generation circuitry 8804 includes, in one embodiment, a 60 GHz local oscillator 8806 for generating a 60 GHz carrier signal. The signal generation circuit 8804 may also work with other frequencies, such as 84/80 GHz. The 60 GHz signal is output from the local oscillator 8806 to a power divider circuit 8808 which separates the 60 GHz signal into three separate transmission signals. Each of these separated transmission signals are provided to an IQ mixer 8810 that are each connected to one of the layer input connectors 8416. The IQ mixer circuits 8810 are connected to an associated additive white gaussian noise circuit 8812 for inserting a noise element into the generated transmission signal. The AWG circuit 8812 may also generate SuperQAM signals for insertion into the transmission signals. The IQ mixer 8810 generates signals in a manner such as that described in U.S. patent application Ser. No. 14/323,082, filed on Jul. 3, 2014, now U.S. Pat. No. 9,331,875, issued on May 3, 2016, entitled SYSTEM AND METHOD FOR COMMUNICATION USING ORBITAL ANGULAR MOMENTUM WITH MULTIPLE LAYER OVERLAY MODULATION, which is incorporated herein by reference in its entirety.

Using the transmitter 8802 illustrated in FIG. 88. A multiplexed beam (Hermite Gaussian, Laguerre Gaussian, etc.) can be generated. The multilayered patch antenna array 8402 will generate a multiplexed beam for transmission. In the present example, there are multiplex OAM beam that has twists for various order OAM signals in a manner similar to that disclosed in U.S. patent application Ser. No. 14/323, 082, which is incorporated herein by reference. An associated receiver detector would detect the various OAM rings wherein each of the rings is associated with a separate OAM processed signal.

When signals are transmitted in free space (vacuum), the signals are transmitted as plane waves. They may be represented as described herein below. Free space comprises a nonconducting medium (σ=0) and thus J=σE=0.

From experimental results Ampere's law and Faraday's law are represented as:

$$\vec{B} = \mu \vec{H}$$

$$\nabla \times H = \frac{\partial D}{\partial t} + J \text{ Ampere's}$$

$$\vec{D} = \epsilon \vec{E}$$

-continued $$\vec{J} = \sigma \vec{E}$$

$$\nabla \times E = \frac{-\partial B}{\partial t} \text{ Faraday's}$$

If there is propagation in the z direction and therefore E and H are in the xy plane.

Without the loss of any generality E may be oriented in the x-direction and H may be oriented in the y-direction thus providing propogation in the z-direction. From Ampere's-Maxwell equation, the following equations are provided:

$$\nabla \times H = \frac{\partial D}{\partial t}$$

$$\nabla \times H = \begin{vmatrix} \hat{x} & \hat{y} & \hat{z} \\ \frac{\partial}{\partial x} & \frac{\partial}{\partial y} & \frac{\partial}{\partial z} \\ H_x & H_y & H_z \end{vmatrix}$$

$$\left(\frac{\partial Hz}{\partial y} - \frac{\partial Hy}{\partial z}\right)\hat{x} + \left(\frac{\partial Hz}{\partial z} - \frac{\partial Hz}{\partial z}\right)\hat{y} + \left(\frac{\partial Hy}{\partial x} - \frac{\partial Hx}{\partial y}\right)\hat{z} = \frac{\partial}{\partial t}\epsilon E$$

Next, the vectorial wave equations may be represented as:

$$\nabla \times H = \frac{\partial D}{\partial t} + J$$

$$\nabla \times H = \epsilon \frac{\partial E}{\partial t}$$

$$\nabla \times E = \frac{-\partial B}{\partial t}$$

$$\nabla \times E = -\mu \frac{\partial H}{\partial t}$$

$$\nabla \times B = 0$$

$$\nabla \times E = S$$

$$\nabla \times \nabla \times H = \nabla(\nabla H) - \nabla^2 H = -\nabla^2 H$$

$$\nabla \times \nabla \times E = \nabla(\nabla E) - \nabla^2 E = -\nabla^2 E$$

$$\nabla \times (\nabla \times H) = \nabla \times \left(\epsilon \frac{\partial E}{\partial t}\right) = \epsilon \frac{\partial}{\partial t}(\nabla \times E) = -\epsilon\mu \frac{\partial}{\partial t}\left(\frac{\partial}{\partial t}H\right)$$

$$\nabla^2 H = +\epsilon\mu \frac{\partial^2}{\partial t^2} H$$

$$\nabla^2 H - \epsilon\mu \frac{\partial^2}{\partial t^2} H = 0$$

$$\nabla \times (\nabla \times E) =$$

$$\nabla \times \left(-\mu \frac{\partial}{\partial t}H\right) = -\mu \frac{\partial}{\partial t}(\nabla \times H) = -\mu \frac{\partial}{\partial t}\left(\epsilon \frac{\partial E}{\partial t}\right) + \nabla^2 E = +\mu\epsilon \frac{\partial^2}{\partial t^2}E$$

$$\nabla^2 E - \mu\epsilon \frac{\partial^2}{\partial t^2} E = 0$$

Therefore, in general:

$$\vec{\nabla}\vec{E} + \vec{K}^2 \vec{E} = 0 \; E(\vec{r},t)$$

$$\vec{E}(r,t) = \vec{E}(\vec{r})e^{-jwt}e^{jkz} \text{ Propagating in z-direction}$$

Therefore:

$$\left(\frac{\partial^2}{\partial x^2} + \frac{\partial^2}{\partial y^2} + \frac{\partial^2}{\partial z^2}\right)\vec{E}(\vec{r})e^{-jwt}e^{jkz} + \frac{W^2}{y^2}\vec{E}(\vec{r})e^{-jwt}e^{jkz} = 0$$

In free space $$w = \frac{1}{\sqrt{\mu\epsilon}} = \to c = \frac{1}{\sqrt{\mu\epsilon o}}$$

$$k^2 = \frac{w^2}{c^2}$$

Now:

$$\frac{\partial}{\partial z}\vec{E}(\vec{r})e^{jkz} = e^{jkz}\left[\frac{\partial \vec{E}(\vec{r})}{\partial z} + jk\vec{E}(\vec{r})\right]$$

$$\frac{\partial}{\partial z^2}\vec{E}(\vec{r})e^{jkz} = e^{jkz}\left[\frac{\partial \vec{E}(\vec{r})}{\partial z} + jk\vec{E}(\vec{r})\right] + e^{jkz}\left[\frac{\partial^2 \vec{E}(\vec{r})}{\partial z^2} + jk\frac{\partial \vec{E}(\vec{r})}{\partial z}\right] =$$

$$e^{jkz}\left[jk\frac{\partial \vec{E}}{\partial z} - k^2\vec{E}(\vec{r})\right] + e^{jkz}\left[\frac{\partial^2 \vec{E}}{\partial z^2} + jk\frac{\partial \vec{E}}{\partial z}\right]$$

Because $$\left|2k\frac{\partial E}{\partial z}\right| \gg \left|\frac{\partial^2 E(r)}{\partial z^2}\right|$$

Paraxial assumption $$\frac{\partial^2 \vec{E}(\vec{r})e^{jkz}}{\partial z^2} = e^{jkz}\left[2jk\frac{\partial^2 \vec{E}(\vec{r})}{\partial z} - k^2\vec{E}(\vec{r})\right]$$

Then:

$$\left(\frac{\partial^2}{\partial x^2} + \frac{\partial^2}{\partial y^2} + 2jk\frac{\partial^2}{\partial z}\right)E(x, y, z) = 0$$

Which may be represented in cylindrical coordinates as:

$$\frac{\partial^2}{\partial x^2} + \frac{\partial^2}{\partial y^2} = \frac{1}{q}\frac{\partial}{\partial q}\left(q\frac{\partial}{\partial q}\right) + \frac{1}{q^2}\frac{\partial^2}{\partial \Phi^2}$$

This provides a paraxial wave equation in cylindrical coordinates:

$$\frac{1}{q}\frac{\partial}{\partial q}\left(q\frac{\partial}{\partial q}\right)E(q, \Phi, z) + \frac{1}{q^2}\frac{\partial^2}{\partial \Phi^2}E(q, \Phi, z) + 2jk\frac{\partial E}{\partial z}(q, \Phi, z) = o$$

$$P(z), q(z)$$

Then:

$$E_0 \sim e^{-j\left[P+\frac{k}{2q}(x^2+y^2)\right]}$$

In general, $E_o$ can rotate on the xy-plane and the wave still propagates in the z-direction.

$$\frac{\partial q}{\partial z} = 1$$
$$\frac{\partial P}{\partial z} = -\frac{j}{q}$$

q~Curvature of the phase front near the optical axis.

$$q_2 = q_1 + z$$

where $q_2$ is the output plane and $q_1$ is the input plane. $\infty\infty$ $$\frac{1}{q} = \frac{1}{R} - j\frac{\lambda}{\pi W^2}$$

where $$\frac{1}{R}$$

is the curvature of the wavefront intersecting the z-axis.

Thus, for a complete plane wave $R=\infty$, the equation becomes:

$$\frac{1}{q} = \frac{1}{R \to \infty} - j\frac{\lambda}{\pi W^2}$$
$$q_0 = \frac{\pi W^2}{-j\lambda} = \frac{j\pi W^2}{\lambda}$$

where $W_o$ is the beam waist.

$$q = q_0 + z = \frac{j\pi W_0^2}{\lambda} + z$$
$$w(z) = w_0\sqrt{1+\left(\frac{z}{z_r}\right)^2}$$
$$W^2(z) = W_0^2\left[1+\left(\frac{\lambda z}{\pi W_0^2}\right)^2\right]$$
$$R(z) = z\left[1+\left(\frac{\pi W_0^2}{\lambda z}\right)^2\right]$$

$$R(z) = z\left[1+\left(\frac{z^R}{z}\right)^2\right]$$
$$\Phi(z) = \tan^{-1}\left(\frac{z}{z_R}\right)$$
$$\theta = \frac{\lambda}{\pi w_0}$$
$$z = z_R$$
$$w(z) = \sqrt{2}\,w_0$$

The Rayleigh length is.

$$z_R = \frac{\pi n}{\lambda_0}$$

where n is the index of refraction.

$$w_0^2 = \frac{w^2}{1+\left(\frac{\pi w^2}{\lambda R}\right)^2}$$
$$z = \frac{R}{1+\left(\frac{\lambda R}{\pi w^2}\right)^2}$$

The complex phase shift is represented by:

$$jP(z) - \mathrm{Ln}\left[1-j\left(\frac{\lambda z}{\pi w_0^2}\right)\right] = \mathrm{Ln}\sqrt{1+\left(\frac{\lambda z}{\pi w_0^2}\right)^2} - j\tan^{-1}\frac{\lambda z}{\pi w_0^2}$$

The real part of P(z) represents a phase shift difference between the Gaussian beam and an ideal plane wave. Thus, the fundamental mode is provided:

$$E_0(x,y,z) = E_0(r,z)\frac{w_0}{w}e^{-j(jz-\phi)}e^{-r^2\left(\frac{1}{w^2}+\frac{jk}{2R}\right)}$$

where:

$$\phi = \tan^{-1}\frac{\lambda z}{\pi w_0^2}$$

Higher order modes may also provide other solutions. The solution of rectangular equation:

$$\left(\frac{\partial^2}{\partial x^2}+\frac{\partial^2}{\partial y^2}+2jk\frac{\partial}{\partial z}\right)E(x,y,z) = 0$$

Can be determined in rectangular coordinates to be:

$$E(x,y,z) = \sum_{mn}C_{nm}E_0\frac{w_0}{w(z)}H_m\left[\frac{\sqrt{2}\,x}{w(z)}\right]H_n\left[\frac{\sqrt{2}\,y}{w(z)}\right]e^{\frac{-(x^2+y^2)}{w(z)^2}}e^{-j(m+n+1)\tan^{-1}\frac{z}{z_0}}e^{j\frac{k(x^2+y^2)}{2R(z)}}$$

$$z_0 = \frac{kw_0^2}{2}$$

-continued $$w(z) = w_0\sqrt{1 + \frac{z^2}{z_0^2}}$$

$C_{60} \Rightarrow TEM_{OD}$ $$R(z) = z + \frac{z_0^2}{z} = \frac{z_0^2}{z}\left(1 + \frac{z^2}{z_0^2}\right) = \frac{z_0^2}{zw_0^2}w^2(z) = \frac{kz_0}{2z}w^2(z)$$

The solution of cylindrical coordinates of equation:

$$\frac{1}{\rho}\frac{\partial}{\partial\rho}\left(\rho\frac{\partial}{\partial\rho}\right)E(\rho,\phi,z) + \frac{1}{\rho^2}\frac{\partial^{\wedge}2E(\rho,\phi,z)}{\delta\phi^2} + 2jk\frac{\partial E(\rho,\phi,z)}{\delta z} = 0$$

Can be determined in cylindrical coordinates to be:

$E(\rho, \phi, z) =$ $$\sum_{\ell\rho} C_{\ell\rho}E_0 \frac{w_0}{w(z)}\left(\frac{\sqrt{2}\rho}{w(z)}\right)^{\ell} L_{\ell}^{\rho}\left(\frac{\sqrt{2}\rho}{w(z)}\right) e^{-\frac{\rho^2}{w^2(t)}} e^{-j(2\rho+\ell+1)\tan^{-1}\frac{z}{z_0}} e^{j\ell\phi} e^{j\frac{k\rho^2}{2R(z)}}$$

The equation $$L_{\ell}^{\rho}\left(\frac{\sqrt{2}\rho}{w(z)}\right)$$

may also be shown as $$L_{\ell}^{\rho}\left[\frac{2\rho^2}{w^2(t)}\right].$$

The lowest mode is the most important mode and in fact this transverse mode is identical for both rectangular and cylindrical coordinates.

$\varphi(\ell, P; z) = (2P + \ell + 1)\tan^{-1}\frac{z}{z_0}$ $TEM_{00}^{rect} = TEM_{00}^{Cyl}$ $C_{00} = 1 \quad H_0 = 1 \quad L_0^0 = 1$ then $$TEM_{00} \Longrightarrow E(\rho, z) \sim E_0 \frac{w_0}{w(z)} e^{-\frac{\rho^2}{w^2(t)}} e^{-j\tan^{-1}\frac{Z}{Z_0}} e^{jk\frac{\rho^2}{2R(z)}}$$

Figure 89:
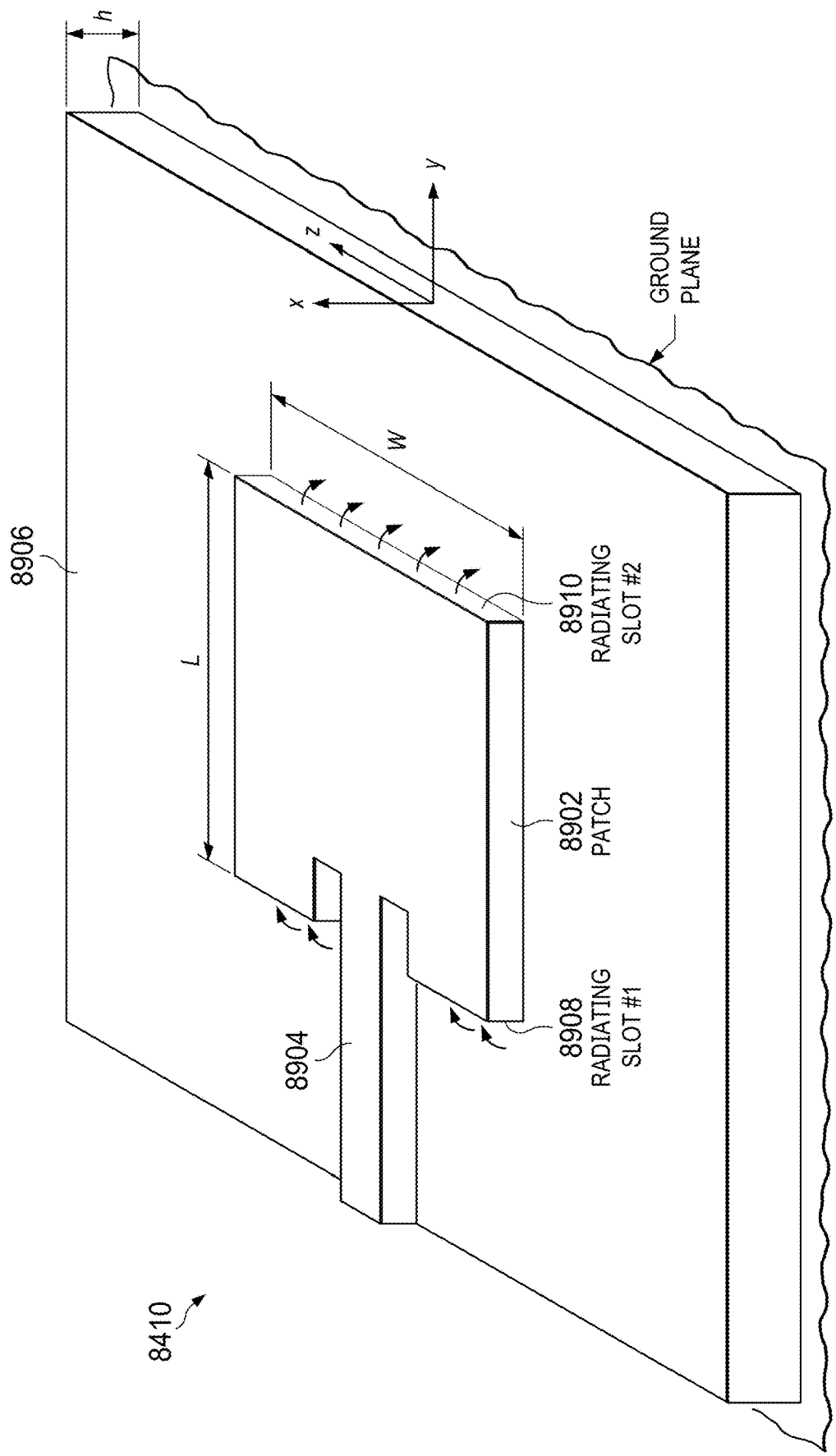
FIG. 89 illustrates a microstrip patch antenna.
Figure 90:
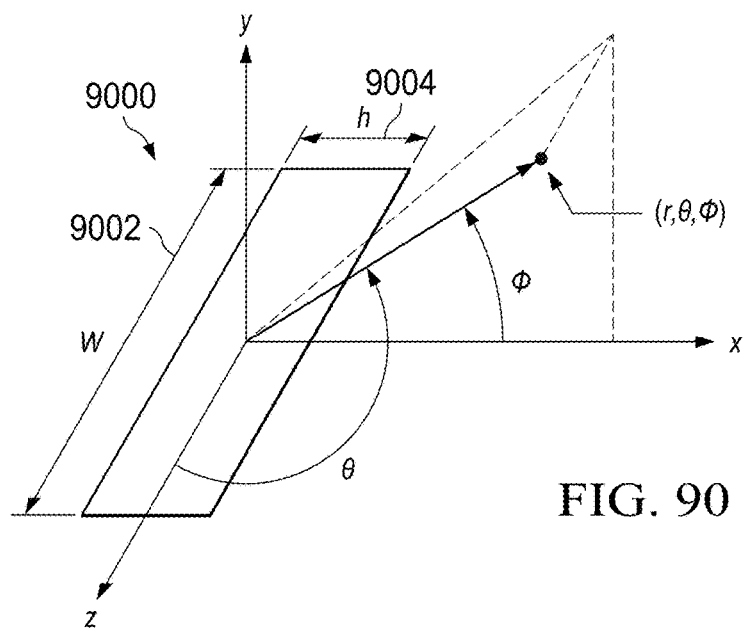
FIG. 90 illustrates a coordinate system for an aperture of a microstrip patch antenna.

Referring now more particularly to FIG. 89, there is illustrated a patch antenna element 8410. Multiple ones of these patch antenna elements 8410 our located upon the multilayer patch antenna array 8402 as discussed hereinabove. The antenna element 8410 includes a patch 8902 having a length L and a width W. The patch 8902 is fed from an input transmission line 8904 that is connected with the feed network 8404 (FIG. 84) and is resting upon a substrate 8906 having a height h. The microstrip patch antenna includes a first radiating slot 8908 along a first edge of the patch 8902 and a second radiating slot 8910 along a second edge of the patch 8902. The electronic field at the aperture of each slot can be decomposed into X and Y components as illustrated in FIG. 9. The Y components are out of phase and cancel out because of the half wavelength transmission line 8904. The radiating fields can be determined by treating the antenna as an aperture 9000 as shown in FIG. 90 having a width W 9002 and a height h 9004.

The transmission line model can be further analyzed in the following manner. $G_r$ is the slot conductance and $B_r$ is the slot susceptance. They may be determined according to the equations:

$$G_r = \begin{cases} \dfrac{W^2}{90\lambda_0^2} & \text{for } W < \lambda_0 \\ \dfrac{W}{120\lambda_0} & \text{for } W > \lambda_0 \end{cases}$$

$$B_r = \frac{2\pi\Delta\ell\sqrt{\varepsilon_{\mathit{eff}}}}{\lambda_0 Z_0}$$

The input admittance of the patch antenna 8410 can be approximated as:

$$Y_{in} = Y_{slot} + Y_0 \frac{Y_{slot} + jY_0\tan(\beta(L+2\Delta\ell))}{Y_0 + jY_{slot}\tan(\beta(L+2\Delta\ell))}$$

where Δl is the end effect of the microstrip.

The rectangular patch antenna 8410 will resonate when the imaginary part of the input admittance goes to zero.

The end effect may be calculated according to the equation:

$$\Delta\ell = 0.412h\left(\frac{\varepsilon_{\mathit{eff}} + 0.3}{\varepsilon_{\mathit{eff}} - 0.258}\right)\frac{(W/h) + 0.264}{(W/h) + 0.8}$$

$$L + 2\Delta\ell = \frac{\lambda_g}{2} = \frac{\lambda_0}{2\sqrt{\varepsilon_{\mathit{eff}}}}$$

$$\varepsilon_{\mathit{eff}} = \frac{\varepsilon_r + 1}{2} + \frac{\varepsilon_r - 1}{2}\left(1 + \frac{10h}{W}\right) - 0.5$$

The resonant frequency of the patch antenna 8410 is given by:

$$f_r = \frac{C}{2\sqrt{\varepsilon_{\mathit{eff}}}\,(L + 2\Delta\ell)}$$

Typically the width W of the aperture is given by:

$$W = \frac{C}{2f_r}\left(\frac{\varepsilon_r + 1}{2}\right)^{-1/2}$$

The multilayered patch antenna array 8402 may transmit both Hermite Gaussian beams using the processing discussed with respect to U.S. patent application Ser. No. 14/323,082 or Laguerre Gaussian beams. When transmitting Laguerre Gaussian beams information may be transmitted in a number of fashions. A spiral phase plate and beam splitter approach may be used, a dual OAM mode antenna approach may be used, or the patched antenna described herein may be utilized. These implementations would be beneficial in both fronthaul and backhaul applications.

In order to transmit several OAM modes of order l and amplitude $a_l^{OAM}$, the antenna elements must be fed by an input signal according to the equation:

$$a_n^{feed} \frac{1}{\sqrt{N}} \sum_{l=0}^{N-1} a_l^{OAM} e^{-j2\pi \frac{ln}{N}}, \; n \in \{0, \ldots, N-1\},$$

Note that the number of elements in the multilayer patch antenna array 8402 limits the number of possible OAM modes due to sampling. Due to aliasing, modes of order greater than N/2 are actually modes of negative orders.

$$b_{l'}^{OAM} = \frac{1}{\sqrt{N}} \sum_{p=0}^{N-1} b_p^{feed} e^{j2\pi \frac{pl'}{N}}, \; p \in \{0, \ldots, N-1\},$$

$$h_{pn} = \beta e^{-jkr_{np}} \frac{\lambda}{4\pi r_{np}},$$

$$r_{pn} = \sqrt{D^2 + R_t^2 + R_r^2 - 2R_t R_r \cos(\theta_{np})},$$

$$\theta_{pn} = 2\pi\left(\frac{n-P}{N}\right),$$

$$\beta = \sqrt{g_t g_r}$$

Single Mode Link Budget $$H_{tot} = U^H H U$$

$$b^{OAM} = H_{tot} a^{OAM}$$

$$\frac{P_r}{P_t}(l) = \left|\frac{b_l^{OAM}}{a_l^{OAM}}\right|^2 = \left|\sum_{p=0}^{N-1}\sum_{n=0}^{N-1} \frac{\beta}{N} e^{-jl\theta_{np}} e^{-jkr_{np}} \frac{\lambda}{4\pi r_{np}}\right|^2$$

Asymptotic Formulation

The object is to determine an asymptotic formulation of the Link budget at large distances, i.e. when D→+(∞), we seek the leading term for each value of l Link budget –l are the same.

The link budget is asymptotically given by:

$$\frac{P_r}{P_t}(|l|) = \left|\frac{\lambda \beta}{4\pi |l|!}\left(\frac{kR_t R_r}{2}\right)^{|l|} \frac{1}{D^{|l|+1}}\right|^2$$

From the Fraunhofer distance 2 $(2\max(R_t, R_r))^2/\lambda = 200\lambda$, the link budget asymptotically tends to straight lines of slope $-20 \; (|l|+1)$ dB per decade, which is consistent with an attenuation in $1/D^{2|l|+2}$.

Asymptotic Expressions with Gains and Free Space Losses

Gains and free space losses may be determined by:

$$\frac{P_r}{P_t}(|l|) = \frac{Ng_t}{|l|!}\left(\frac{4\pi(\pi R_t^2)}{\lambda^2}\right)^{|l|} \frac{Ng_r}{|l|!}\left(\frac{4\pi(\pi R_r^2)}{\lambda^2}\right)^{|l|}\left(\frac{\lambda}{4\pi D}\right)^{2|l|+2}$$

$$L_{FS_{eq}}(l) = \left(\frac{4\pi D}{\lambda}\right)^{2|l|+2}$$

$$G_{eq}(l) = \frac{Ng}{|l|!}\left(\frac{4\pi(\pi R^2)}{\lambda^2}\right)^{|l|}$$

For a fixed value of |l|, each equivalent gain increases $R^{2|l|}$ So that the link budget improves by a factor of $R^{4|l|}$. On the contrary, for a fixed value of R, when |l| increases, the link budget decreases since asymptotically the effect of D is greater than those of $R_t$ and $R_r$.

Figure 91:
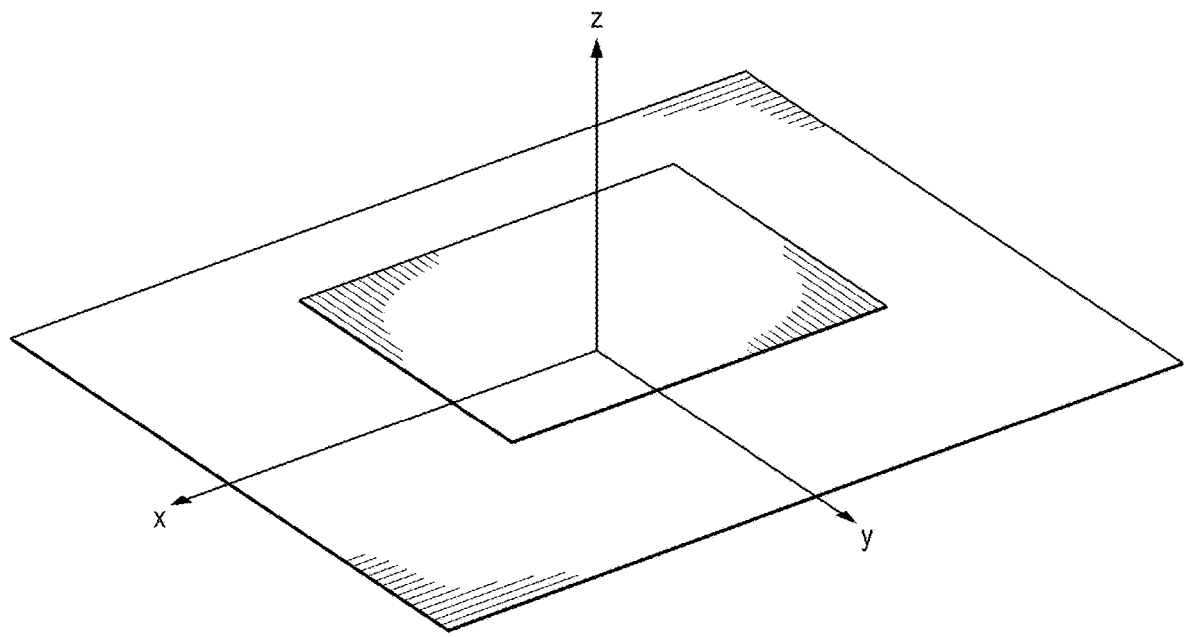
FIG. 91 illustrates a 3-D model of a single rectangular patch antenna.
Figure 92:
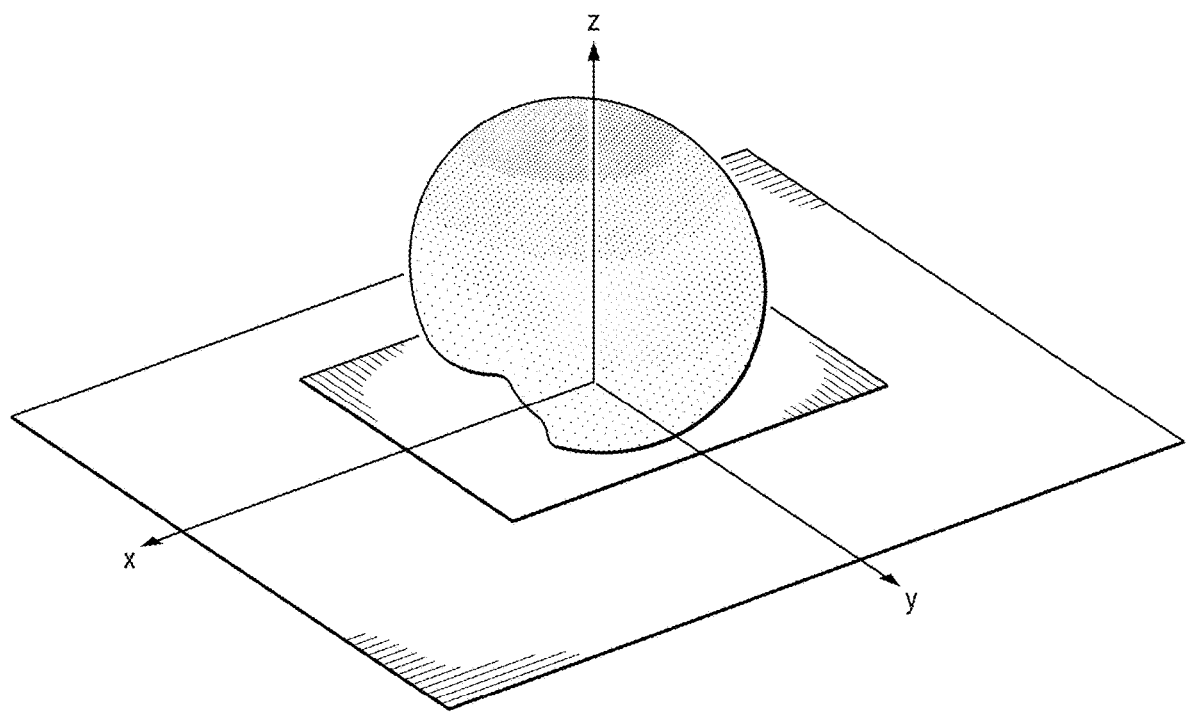
FIG. 92 illustrates the radiation pattern of the patch antenna.

Referring now to FIG. 91, there is illustrated a 3-D model of a single rectangular patch antenna designed for 2.42 GHz and only one linear polarization. The radiation pattern for this antenna is illustrated in FIG. 92.

Based on our hypothesis, the vibrational modes of COVID-19 virus can be explored due to the dipolar mode of acoustic vibrations inside the virus which can be resonantly excited by microwaves of the same frequency. This is due to energy transfer from microwaves to acoustic vibrations (photon to phonon). The overall efficiency of this transfer is also related to the mechanical properties of the surrounding environment which influences the quality factor of the oscillation of the virus.

The virus inactivation threshold needs to be able to be measured. The inactivation thresholds of simpler to use viruses that are close to the geometry, size, and composition of COVID1-9 can be studied. If this is a problem, bacteria can instead be used. The response of the sample to dipolar-mode-resonance and off-resonance microwave frequencies as well as with different microwave powers can be more fully explored. One technique involves using *Staph aureus* or *Pseudomonas aeruginosa* suspended in culture medium. However, the experimental procedures involve first testing with the culture medium alone and then repeat the experiments with the bacteria in the medium so signal processing can be performed to separate any possible contributions from the culture medium.

To identify the mechanical vibrations, microwave resonance spectral measurements on the viruses must be performed. To do that, viruses are prepared where they are cultured, isolated, purified, and then preserved in phosphate buffer saline liquids at PH of 7.4 at room temperature. In each measurement, one microliter solution is taken by a micropipette and uniformly dropped on a coplanar waveguide apparatus. The guided microwaves should be incident on the virus-containing solution. The reflection $S_{11}$ and transmission $S_{21}$ parameters are recorded simultaneously using a high bandwidth network analyzer (one that can measure from few tens of MHz to tens of GHz). The microwave attenuation spectra can be evaluated by $|S_{11}|^2 + |S_{21}|^2$. The attenuation spectrum of the buffer liquids needs to be measured with the same volume on the same device so the attenuation spectra of the buffer solutions can be compared with and without viruses, and deduce the microwave attenuation spectra of the viruses and identify the dominant resonance and spurious resonances of the specific virus.

Higher inactivation of viruses at the dipolar resonant frequency can be achieved. The microwave power density threshold for a sample (COVID-19) needs to be below the IEEE safety standards for microwaves. Real-time experiments for reverse transcription polymerase chain reaction (RT-PCR) can confirm that the main inactivation mechanism is entirely based on physically fracturing the viruses and the RNA genome is not impacted by the microwave radiation.

In the IEEE Microwave Safety Standard, the spatial averaged value of the power density in air in open public space shall not exceed the equivalent power density of $100(f_{GHz}/3)^{1/5}$ W/m$^2$ at frequencies between 3 and 96 GHz. This corresponds to 115 W/m$^2$ at 6 GHz, 122 W/m$^2$ at 8 GHz, and 127 W/m$^2$ at 10 GHz for averaged values of the power densities in air. Assuming all the microwave power in air transmitted into a sample, and by taking the dielectric constant of water 71.92 (6 GHz), 67.4 (8 GHz), and 63.04 (10 GHz) for calculation, this safety standard then corresponds to the average electric field magnitude of 101 V/m (6 GHz), 106 V/m (8 GHz), 110 V/m (10 GHz) inside the water-based specimens. The required threshold electric field magnitudes at the resonant frequency that rupture the viruses must be within the IEEE Microwave Safety Standard (106 V/m), indicating high energy transfer efficiency, even if the quality factor may be low. The reason for assuming water dielectric constant is that the active airborne viruses are always transported inside tiny water droplets.

The structure of the coplanar waveguide by the microfluidic channel with a sensing zone to measure the microwave absorption spectrum of sample must be analyzed. This microwave microfluidic channel can provide a wide microwave bandwidth (i.e. 40 GHz). The power absorption ratio by the virus at the resonant frequency and the Q are measured by measuring the full width at half maximum of the power spectral density. Given the density of viruses or bacteria in the solution, an absorption cross section of the virus at the resonant frequency can be determined. The threshold electric field magnitude to fracture the virus as a function of microwave frequency can then be estimated.

To discover the resonances, the residual infectivity of the virus after radiating microwave of different frequency ranges are measured. In this case, the samples need be placed below a horn antenna. Microwave anechoic chamber or material can be used to decrease the reflection of the microwave. However, to check the inactivation ratio, the radiated viruses need be analyzed by other biological methods as well to measure the residual infectivity of viruses.

The field intensity threshold for inactivating the virus ranges between $E_1$ to $E_2$ V/m, which corresponds to power density $Pd_1$ to $Pd_2$ W/m$^2$, for microwaves between $f_1$ to $f_2$ GHz. Given the aperture size of the horn antenna used, the required threshold power input ranges from $P_1$ to $P_2$ Watt for $f_1$ to $f_2$ GHz microwaves can be calculated. Fixed microwave power (higher than all the threshold power input) are first applied into the horn antenna for studying the frequency response given the transmission coefficient of the horn antenna. If the peak inactivation happens at dipolar mode and at resonance the measured titer count would be zero, indicating 100% inactivation ratio, which means that the remaining active viral/bacterial concentration would be smaller than the system sensitivity of XX pfu/mL (specify later our sample). The result would indicate at least a few-order of magnitudes attenuation on the virus titer when the microwave frequency is tuned to the dipolar mode resonant frequency with the electric field intensity few times higher than the threshold.

The microwave absorption spectrum measurement need be performed by combining the coplanar waveguide circuit with a microfluidic channel. The gap between the signal electrode and the ground electrode of the waveguide need be recorded. To decrease microwave loss on the electrodes, gold layer electrodes may be used. On the surface of electrodes, a thermal isolator layer may be used (silicon dioxide on the sensing zone by PECVD to lower the temperature rise of fluids due to microwave dielectric heating). A network analyzer is used as the source to measure the absorption spectrum of viruses from $f_1$ GHz to $f_2$ GHz. The spectrum of the solution without viruses is measured first as a reference and then solution with viruses for comparison. By removing the solution background (signal processing or post processing), the microwave absorption spectrum of viruses can be measured.

For microwave radiation, a network analyzer or an YIG oscillator may be used. The microwave signal is amplified by a power amplifier and radiate it from the horn antenna. To prevent damage on oscillator and amplifier due to back reflection, an isolator and a directional coupler are added and everything is kept under a flow hood. The antenna should be directed normally incident on acrylic cuvettes at a short distance (i.e. 5 cm below the exit of horn antenna). To prevent reflection from the metal hood surface, the cuvette can be put in a plastic dish supported by a broad band pyramidal absorber like the ones used in anechoic chambers. For each measurement, the sample under radiation should be inside the cuvettes with 15 minutes at different microwave frequencies or at different microwave powers. After radiation, a buffer is used to wash and collect the viruses or bacteria and then the radiated solutions are used for biological study of inactivated viruses or bacteria.

A structured vector beams using patch antennas to provide the resonant frequencies. These patch antennas radiate at frequencies as determined above but may be discovered by another source if needed.

Antenna Equations

The antenna signal propagation for inducing the resonance within a virus (such as COVID-19), bacterial or other organism can be modeled in the following manner. The virus can be modeled as:

$$m_*\ddot{x}(t)+m_*\gamma\dot{x}(t)+m_*\omega_0^2 x(t)=qE(t) \quad \text{Virus Model:}$$

where $m_*$=effective mass

Assuming $E(t)=E_0 e^{-i\omega t}$ define harmonic oscillations as:

$$x(t) = X_0 e^{-i\omega t} \sim X_0 \cos\omega t$$

$$\dot{x}(t) = -i\omega X_0 e^{-i\omega t} = -i\omega x$$

$$\ddot{x}(t) = (-i\omega)^2 X_0 e^{-i\omega t} = -\omega^2 X_0 e^{-i\omega t} = -\omega^2 x$$

$$-m_*\omega^2 X_0 e^{-i\omega t} - im_*\gamma\omega X_0 e^{i\omega t} + m_*\omega_0^2 X_0 e^{-i\omega t} = qE_0 e^{-i\omega t}$$

$$X_0 = \frac{\frac{qE_0}{m_*}}{\omega_0^2 - \omega^2 - i\gamma\omega}$$

$$-m_*\omega^2 x - im_*\gamma\omega x + m_*\omega^2 x = 0$$

$$-m_*\omega^2 + i\omega\gamma m_* + m\omega_0^2 = 0$$

$$\omega = \frac{-i\gamma m_* \pm \sqrt{-\gamma^2 m_*^2 + 4km_*}}{-2m_*}$$

-continued $$\omega = \frac{i\gamma m_* \pm \sqrt{-\gamma^2 m_*^2 + 4km_*}}{2m_*}$$

The Decay rate=imaginary part of $\omega$ $$\frac{\gamma m_*}{2m_*} = \frac{\omega_0}{2Q}$$

Damping $$\gamma = \frac{\omega_0}{Q}$$

$$k = m_* \omega_0^2 \quad \omega_0 = \sqrt{\frac{k}{m_*}}$$

$$|X_0| = \frac{\frac{qE_0}{m_*}}{\sqrt{(\omega_0^2 - \omega^2)^2 + (-\gamma\omega)^2}} = \frac{\frac{qE_0}{m_*}}{\sqrt{(\omega_0^2 - \omega^2) + \gamma^2\omega^2}}$$

$$|X_0| = \frac{\frac{qE_0}{m_*}}{\sqrt{(\omega_0^2 - \omega^2)^2 + \left(\frac{\omega\omega_0}{Q}\right)^2}}$$

$$\gamma = \frac{\omega_0}{Q} \quad Q = \frac{\omega_0}{\gamma}$$

$$\angle X_0 \to \tan\phi = \frac{\omega\omega_0}{Q(\omega_0^2 - \omega^2)} \quad \phi = \tan^{-1}\frac{\omega\omega_0}{Q(\omega_0^2 - \omega^2)}$$

$$x(t) = |X_0|\cos(\omega t + \phi)$$

The absorption model for determining the absorption of radiating signals from an antenna may be determined in the following manner. The Absorption Model is defined by:

$$\epsilon_r\epsilon_0 + \frac{i\sigma}{\omega} = \epsilon$$

$$\delta = \frac{1}{\omega}\left[\frac{\mu\epsilon}{2}\left(\sqrt{1 + \left(\frac{\sigma}{\omega\epsilon}\right)^2} - 1\right)\right]^{\frac{1}{2}}$$

$f = 1$ GHz  $\delta = 3.4$ cm
$f = 10$ GHz  $\delta = 0.27$ cm

The Specific absorption rate (SAR) is defined by:

$$SAR = \frac{d}{dt}\left[\frac{dW}{dm}\right] = \frac{d}{dt}\left[\frac{dW}{pdv}\right]$$

Energy absorption is defined by:
W=energy $$SAR = \frac{\sigma|E|^2}{\rho}$$

The Poynting vector $\vec{P}$ is power density of EM Power flow/unit area. The radiated power crossing a surface $\vec{ds}$ is for an Isotropic case:

$$dW_{tx} = \vec{P} \cdot \vec{ds} \to w = \oiint \vec{P} \cdot \vec{ds} = \oiint P_r ds = P_r \oiint_{\theta=0\ \phi=0}^{\pi\ 2\pi} r^2\sin\theta d\theta d\phi$$

Radial Part of the Poynting Vector or Power Density $P_r = \frac{W_{tx}}{4\pi r^2} \frac{W}{m^2}$ Radiation intensity $U \to$ power per unit *solid* angle $\frac{W}{4\pi}$ For isotropic $U=U_0$ $$U_0 = r^2 P_r = \frac{W}{4\pi}$$

The directivity of various types of antennas can then be defined by:

Directivity of antenna $D = \frac{\text{maximum radiated intensity}}{\text{intensity radiated by isotropic}} = \frac{U_{max}}{U_0}$ Directivity of isotropic antenna $D_0 = \frac{\text{maximum radiated intensity}}{\text{intensity radiated by isotropic}} = \frac{U_{max}}{U_0}$ Directivity of a hemispherical antenna $D_h = \frac{2U_o}{U_o} = 2$ Therefore $D$ is also $D = \frac{\text{maximum radiated intensity}}{\text{average radiated intensity}}$ $$D = \frac{U_{max}}{\frac{W}{4\pi}} = \frac{4\pi U_{max}}{W} = \frac{4\pi}{B} \quad B = \frac{W}{U_{max}}\text{beam area}$$

$$D = \frac{U_{max}}{r^2 P_r} = \frac{4\pi}{B} \quad B = \frac{W}{U_{max}} = \frac{\oiint P_r ds}{U_{max}} = \frac{\oiint \frac{U}{r^2}ds}{U_{max}} = \frac{\oiint U d\Omega}{U_{max}}$$

The Total power W within a conical region is:

$$W = \int_0^{2\pi}\int_0^\theta U_{max}\sin\theta' d\theta' d\phi = 2\pi(1-\cos\theta)U_{max}$$

Therefore $$D = \frac{4\pi}{2\pi(1-\cos\theta)} = \frac{W}{U_{max}}$$

For hemisphere $\theta = \frac{\pi}{2} D_{hemi} = 2$
For a complete sphere $\theta = \pi D_{sphere} = 1$ isotropic
Approximate beam area $= B = \Delta\theta\Delta\phi \quad \Delta\theta, \Delta\phi$ are half–beam widths The Gain of an antenna can be determined according to:

$$G = \eta D$$

Therefore power density is determined according to:

$$P_r = \frac{G_t W_t}{4\pi r^2}$$

$$W_t = \frac{(4\pi r^2) P_r}{G_t}$$

For a uni-directional cosine power source:

$$U = U_{max} \cos\theta$$

$$W = \int_0^{2\pi}\int_0^{\frac{\pi}{2}} U_{max} \cos\theta \sin\theta \, d\theta \, d\phi = \pi U_{max}$$

$$D = \frac{4\pi}{2\pi(1-\cos\theta)} = \frac{4\pi}{2\pi(1-\cos 60°)} = \frac{4\pi}{\pi} = 4 \quad \theta = 60°$$

$$D = \frac{4\pi}{2\pi(1-\cos\theta)} = \frac{4\pi}{2\pi(1-\cos 90°)} = \frac{2\pi}{\pi} = 2 \quad \theta = 90°$$

According to IEEE safety standards:

$$P_r^{IEEE} = 100\left(\frac{f_{GHz}}{3}\right)^{\frac{1}{5}} \, W/m^2$$

With 50% antenna efficiency $\eta = \frac{1}{2}$ $$G = \eta D \approx \frac{D}{2}$$

$$P_r = \frac{\left(\frac{D}{2}\right) W_t}{4\pi r^2} \quad \frac{W}{m^2}$$

To be lower than IEEE safety standard $P_r^{IEEE}$ by 10%:

$$P_{r_c} = (90\%) 100 \left(\frac{f}{3}\right)^{\frac{1}{5}}$$

$$\frac{\left(\frac{D}{2}\right) W_t}{4\pi r^2} = 90\left(\frac{f_{GHz}}{3}\right)^{\frac{1}{5}}$$

$$W_t = 90\left(\frac{f_{GHz}}{3}\right)^{\frac{1}{5}} \frac{4\pi r^2}{\frac{D}{2}} \quad \text{Watts}$$

For $D = 2 \quad \theta = 90°$ $$W_t^{\frac{\pi}{2}} = 90\left(\frac{f_{GHz}}{3}\right)^{\frac{1}{5}} 4\pi r^2$$

For $D = 4 \quad \theta = 60°$ $$W_t^{\frac{\pi}{3}} = 90\left(\frac{f_{GHz}}{3}\right)^{\frac{1}{5}} 2\pi r^2$$

In general:

$$W_t = \frac{4\pi r^2 P_r}{G_t} = \frac{4\pi r^2 P_r}{\eta D} =$$

For $U = U_{max} \cos\theta$ cosine power source $$D = \frac{2}{1-\cos\theta}$$

$$W_t^\theta = \frac{4\pi r^2 P_r}{\eta\left(\frac{2}{1-\cos\theta}\right)} = \frac{4\pi r^2 (1-\cos\theta) P_r}{2\eta}$$

$$W_t^\theta = \frac{2\pi r^2}{\eta}(1-\cos\theta) P_r$$

$$W_t^\theta = \frac{2\pi r^2}{\eta}(1-\cos\theta)\left[90\left(\frac{f_{GHz}}{3}\right)^{\frac{1}{5}}\right]$$

Microwave Resonance

Figure 93:
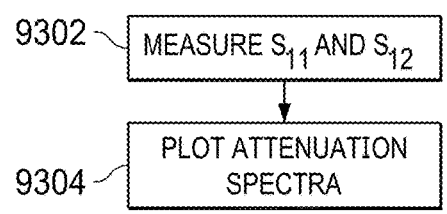
FIG. 93 illustrates microwave resonance absorption measurements.
Figure 94:
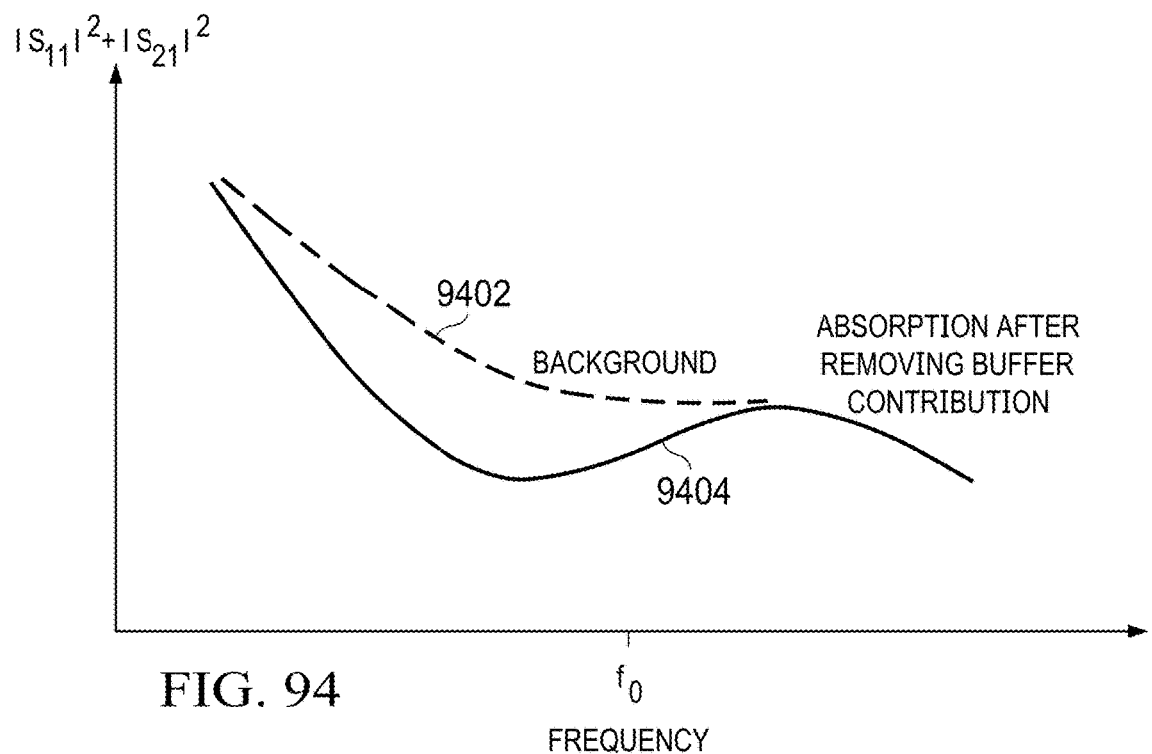
FIG. 94 illustrates attenuation spectra and background attenuation spectra.
Figure 95:
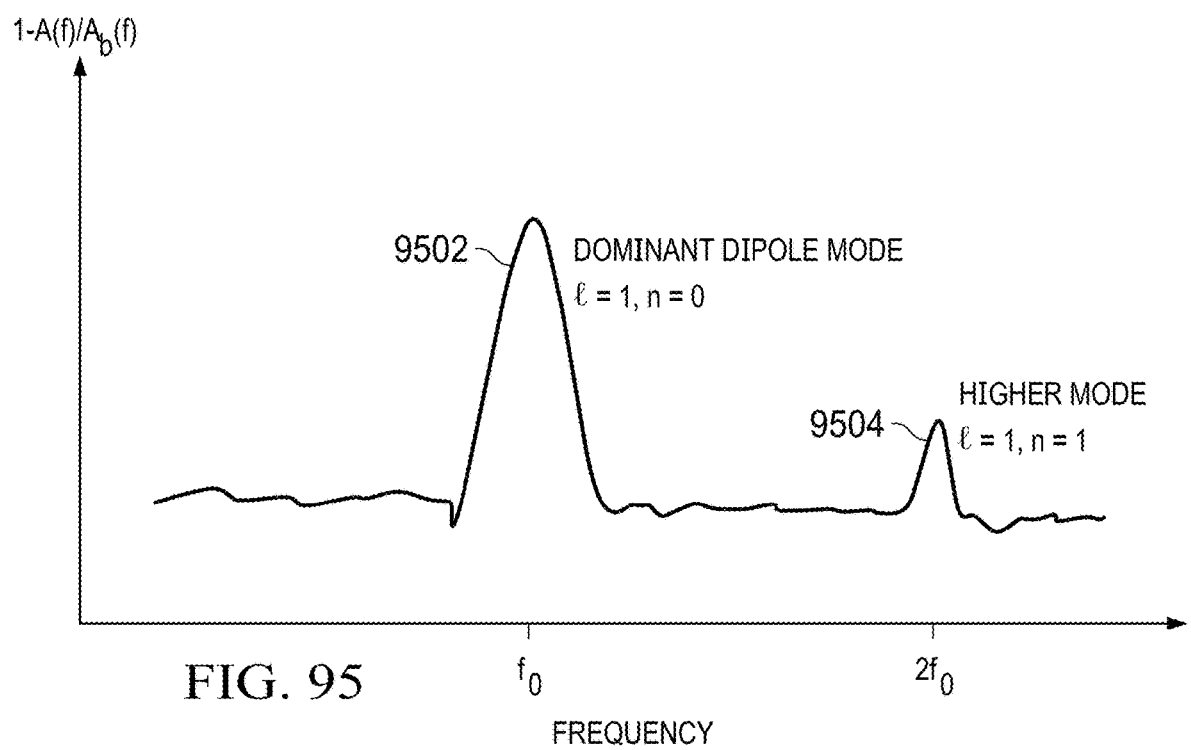
FIG. 95 illustrates a plot of resonance frequency.

There has been a lot of work done on the influenza virus and the measurements of parameters done on the influenza virus can be used to estimate some of the parameters for Covid-19. In general, microwave resonance absorption measurements are performed to identify the mechanical resonance of the virus/bacteria as shown in FIG. 93. Initially, the reflection $S_{11}$ and transmission $S_{12}$ parameters must be measured simultaneously with a large bandwidth network analyzer at step 9302. The attenuation spectra is plotted at step 9304 as a function of frequency (GHz) attenuation due to absorption, reflection and transmission. This is more particularly illustrated in FIG. 94. As shown in FIG. 95, the background attenuation spectra is shown generally at 9402. The overall background attenuation is shown generally at 9404.

Various absorption related terms are defined in the following manner:

$$\text{Normalized insertion loss} = 1 - \frac{A(f)}{A_b(f)}$$

$A(f)$ = Absorption spectra $A_b(f)$ = non-resonant background absorption

This can be plotted as displayed in FIG. 95.

The resonance frequency can be defined as:

$\omega_0 = 2\pi f_0$ resonance frequency $$Q = \frac{f_0}{\Delta f} = \frac{\omega_0}{\Delta \omega}$$

The plot with respect to the resonance frequency is shown in FIG. 95. The dominate dipole mode 9502 occurs at frequency $f_o$ and the higher mode 9504 occurs at frequency $2f_o$ As described herein above, the equation for the Electric field necessary to rupture the capsid of the virus/bacteria is defined by:

$$E = \frac{c_2}{c_1} P_{stress}^{avg} \frac{\pi r^2}{q\omega_0^2}\left[\sqrt{(\omega_0^2 - \omega^2)^2 + \left(\frac{\omega\omega_0}{Q}\right)^2}\right]$$

where $\omega=2\pi f$ is the microwave radiation frequency
$\omega_0$=the resonance frequency of the virus/bacteria
r=radius of the virus/bacteria
q=charge of the virus/bacteria
$P_{stress}^{avg}$=average stress to rupture the virus/bacteria
$c_1$=constant 1 $P_{stress}^{max}=c_1*P_{stress}^{avg}$
$c_2$=constant 2 $c_2$=% shell region of equatorial plane
From microwave resonance absorption measurements, $\omega_0$ and Q are available.
r=known
For influenza H3N2, the following values have been determined:

$$c_1 = 2, c_2 = 0.58, P_{stress}^{avg} = 0.141 \times 10^6 \frac{N}{m^2}, q = 1.16 \times 10^7 e$$

Shell area=$A_s$
Total equatorial area=$A_T$
Core area=$A_c$ $$A_t = \pi r_0^2$$

$$A_c = \pi r_i^2$$

$$A_s = \pi(r_0^2 - r_i^2)$$

$$\frac{A_s}{A_t} = \frac{\pi(r_0^2 - r_i^2)}{\pi r_0^2} = \frac{r_0^2 - r_i^2}{r_0^2} = 1 - \frac{r_i^2}{r_0^2} = 1 - \left(\frac{r_i}{r_0}\right)^2 = c_2$$

$$1 - c_2 = \left(\frac{r_i}{r_0}\right)^2$$

$$\frac{r_i}{r_0} = \sqrt{1 - c_2}$$

$$r_i = \sqrt{1 - c_2}\, r_0$$

$$E|_{\omega=\omega_0} = \frac{\beta}{\alpha} P \frac{\pi r^2}{qQ}$$

The Charge q can be estimated from absorption measurements. From absorption cross section $\sigma_{abs}$:

$$\sigma_{abs} = -\frac{1}{N*L}\ln(1-\alpha) = 2.5 \times 10^{-13} \text{ m}^2$$

In influenza measurements $N=7.5\times 10^{14}$ 1/m³

$L=1.25\times 10^{-3}$ m $\alpha=21\%=0.21$

However, theoretical absorption cross-section of virus/bacteria at resonant frequency is:

$$\sigma_{abs} = \frac{Qq^2}{\omega_0 m_* c\sqrt{\epsilon_r}\,\epsilon_0}$$

$\epsilon_r$ = permitivity of phosphate buffer saline $$q^2 = \frac{\sigma_{abs}\omega_0 m_* c\sqrt{\epsilon_r}\,\epsilon_0}{Q} = 1.16 \times 10^7 e$$

for influenza $H3N2$

The reduced or effective mass m, must then be found. For influenza H3N2 most of the mass is concentrated in shell of the virus.

$m_{virus}$=161 MDa=161×10⁶ Da $m_{shell}$=90% of $m_{virus}$ $m_{core}$=10% of $m_{virus}$ The virus shell has lipid, neuraminidase (NA), hemagglutinin (HA) and M-Proteins. The virus core has RNA, RNP (ribonucleoproteins). Because of the spring-mass model of the core and shell the reduced mass $m_*$ is found from:

$$\frac{1}{m_*} = \frac{1}{m_s} + \frac{1}{m_c} = \frac{m_s + m_c}{m_s m_c} = \frac{m_{virus}}{m_s m_c}$$

$$m_* = \frac{m_s m_c}{m_{virus}} = \frac{(0.90)m_v(0.10)m_v}{m_v}$$

$m_* = 0.09 m_v = 14.5 \times 10^6$ Da

1 Da = $1.66054 \times 10^{-21}$ kg

The information needed to calculate the magnitude of electric field E except $P_{stress}^{avg}$ that is needed to rupture the capsid of the virus/bacteria and ensure it is below the IEEE safety standard is now available based upon this data. The German paper by Sai Li & Frederic Eghiaian, "Bending & Puncturing the Influenza lipid Envelope" Biophys J., Feb. 2, 2011; 100(3): 637-645, which is incorporated herein by reference in its entirety, covers the exact Atomic Force Microscopy (AFM) measurements to show that:

$P_{stress}^{avg}$=0.141×10⁶ N/m²

The minimum of the Electric field can be determined according to:

Let $x = \frac{\omega}{\omega_0}$ $$\frac{dE}{dx} = \frac{2Q^2 x^3 - 2Q^2 x - x}{Q^2 \sqrt{\left(\frac{1}{Q^2} - 2\right)x^2 + x^4 + 1}}$$

$$\frac{dE}{d\omega} = \frac{1}{\omega_0}\frac{dE}{dx} = \left[\frac{1}{\omega_0} \frac{2Q^2\left(\frac{\omega}{\omega_0}\right)^3 - 2Q^2\left(\frac{\omega}{\omega_0}\right) + \frac{\omega}{\omega_0}}{Q^2\sqrt{\left(\frac{1}{Q^2} - 2\right)\left(\frac{\omega}{\omega_0}\right)^2 + \left(\frac{\omega}{\omega_0}\right)^4 + 1}}\right] C_1$$

$$\frac{dE}{d\omega} = \frac{\beta}{\alpha} P_{stress}^{avg} \frac{\pi r^2}{q}\left[\frac{1}{\omega_0}\frac{2Q^2\left(\frac{\omega}{\omega_0}\right)^3 + \left(\frac{\omega}{\omega_0}\right)[1 - 2Q^2]}{Q^2\sqrt{\left(\frac{1}{Q^2} - 2\right)\left(\frac{\omega}{\omega_0}\right)^2 + \left(\frac{\omega}{\omega_0}\right)^4 + 1}}\right]$$

$$\frac{dE}{d\omega} = 0$$

$$2Q^2\left(\frac{\omega}{\omega_0}\right)^3 + \frac{\omega}{\omega_0}[1 - 2Q^2] = 0$$

$$2Q^2\left(\frac{\omega}{\omega_0}\right)^2 + [1 - 2Q^2] = 0$$

$$2Q^2\left(\frac{\omega}{\omega_0}\right)^2 = 2Q^2 - 1$$

$$\left(\frac{\omega}{\omega_0}\right) = \sqrt{\frac{2Q^2-1}{2Q^2}}$$

$$\omega = \sqrt{\frac{2Q^2-1}{2Q^2}}\,\omega_0$$

Figure 96:
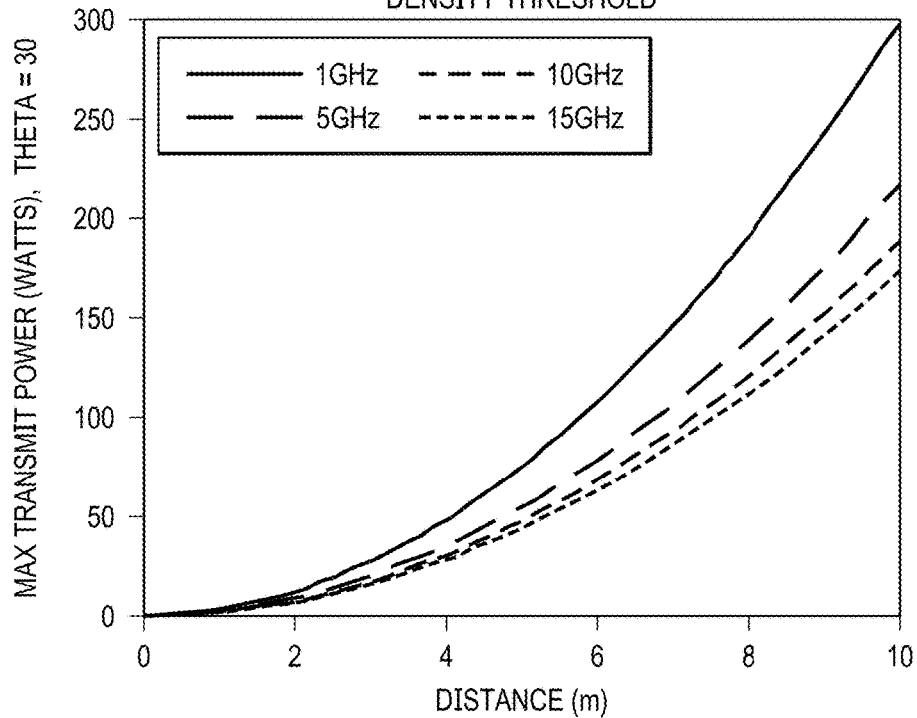
FIG. 96 illustrates maximum transmit power to achieve IEEE safety power density thresholds for a first theta.
Figure 97:
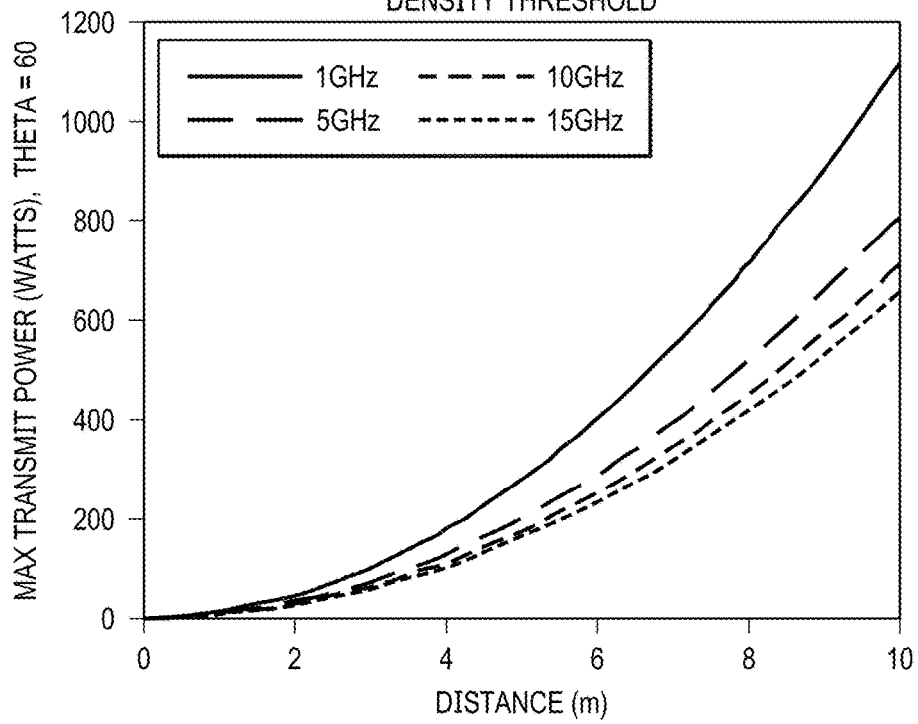
FIG. 97 illustrates maximum transmit power to achieve IEEE safety power density thresholds for a second theta.
Figure 98:
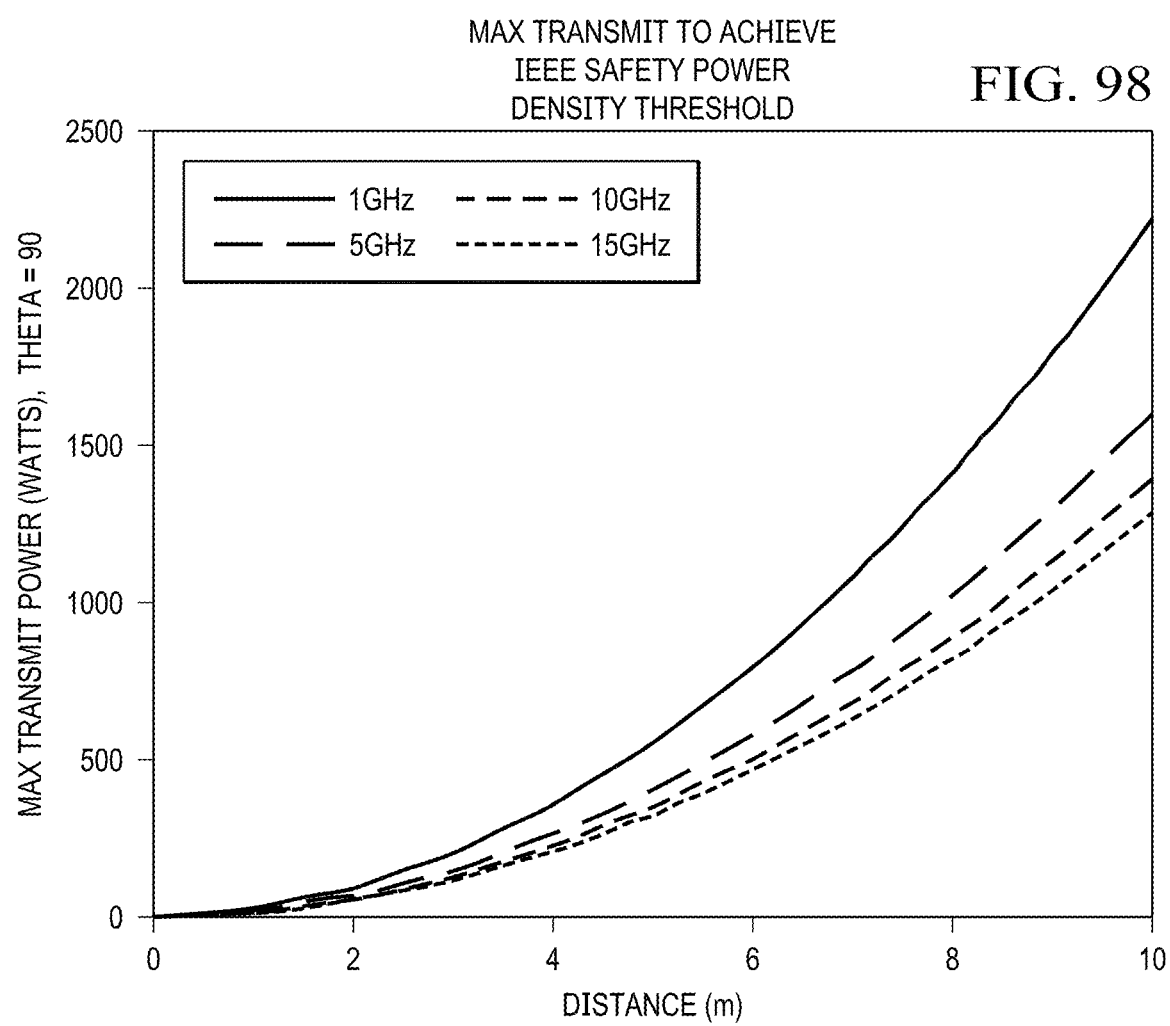
FIG. 98 illustrates maximum transmit power to achieve IEEE safety power density thresholds for a third theta.

FIGS. 96-100 illustrates power density matlab plots for the above antenna equations. FIG. 96 illustrates the maximum transmit power required to achieve the IEEE safety power density threshold for 1 GHz, 5 GHz, 10 GHz and 15 GHz for theta=30. FIG. 97 illustrates the maximum transmit power required to achieve the IEEE safety power density threshold for 1 GHz, 5 GHz, 10 GHz and 15 GHz for theta=60. FIG. 98 illustrates the maximum transmit power required to achieve the IEEE safety power density threshold for 1 GHz, 5 GHz, 10 GHz and 15 GHz for theta=90.

Figure 99A:
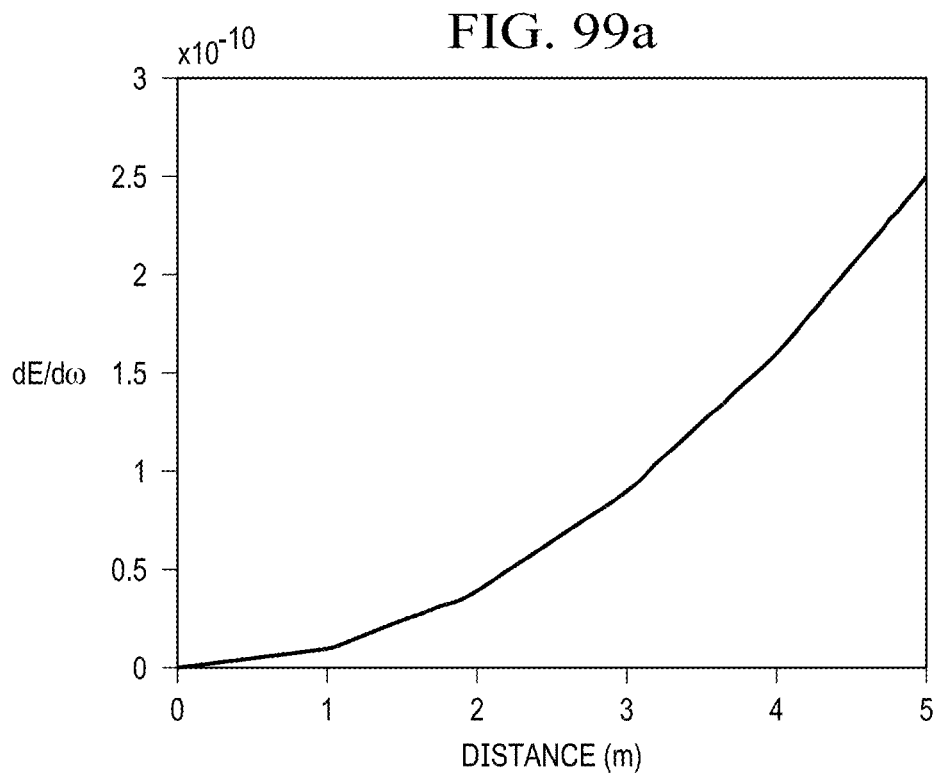
Figure 99B:
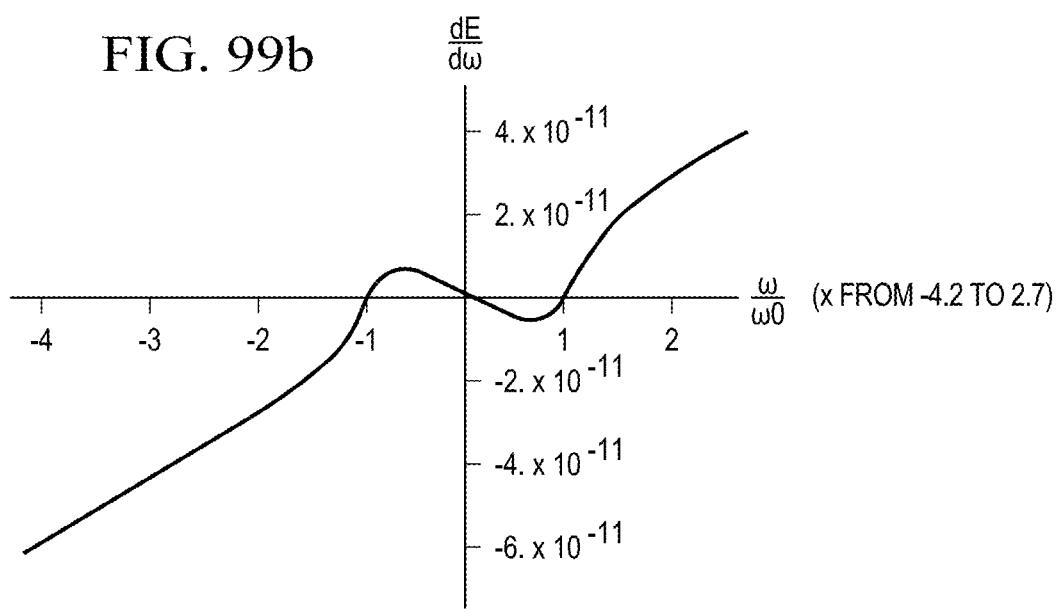

As described above the equation for the incident electric field (E) at the resonance frequency of the virus or bacteria. To calculate the minimum field necessary to rupture a capsid, the derivative of the minimum of the electric field verses angular frequency over distance (dE/dw) is taken and set to zero to calculate the minimum filed needed at the radiator antenna. FIGS. 99a and 99b illustrate a plot of dE/dw versus distance. FIG. 100 illustrates a plot of the minimum of the electric field (Emin) needed at the radiator antenna as a function of distance. The Emin needed at the antenna is larger as you go away from the antenna to achieve rupturing of the capsid.

FIG. 101 illustrates various manners for implementing an antenna for transmitting the signals as described herein through an antenna 9602 plugging into an electrical socket, an antenna 9604 mounted on a ceiling, an antenna 9606 screwing into a light socket or an antenna 9608 within a flashlight. The antennas which each include the structures described herein and provide a manner for radiating a virus, bacteria or other biological entity with a signal for inducing resonance therein as described above.

The determination of the frequency to rupture the capsid virus may be determined in one manner according to the following. The frequency of vibration of the virus or other biological material is a function of Youngs modulus of elasticity, density and Poisson ratio as well as the radius and as a unitless parameter from shell model of vibration in spherical coordinates. Starting from 3D Hooke's law, the stress and strain on the virus or biological material may be determined according to the normal stress and tangential stress as shown below:

Normal Stress $$\sigma_x = 2\mu\epsilon_{xx} + \lambda(\epsilon_{xx}+\epsilon_{yy}+\epsilon_{zz})$$

Tangential stress $$\tau_{xy} = \mu\epsilon_{xy}$$

Where $\mu$ and $\lambda$ are Lame's coefficients $$\mu = \frac{E}{2(1+v)} = G \text{ shear modules}$$

$$\lambda = \frac{Ev}{(1+v)(1-2v)}$$

Where E is modulus of Elasticity and v is Poisson coefficient then the motion of elastic body is described by Navier's equation.

$$\mu\nabla^2\vec{u} + (\lambda+\mu)\nabla(\nabla\cdot\vec{u}) + \rho\vec{f} = \rho\frac{\delta^2\vec{u}}{\delta t^2}$$

$u = u(\vec{x}, t)$ displacement
f body forces
$\rho$ density
$\lambda, \mu$ Lame's constants $$\vec{f} = \nabla f + \nabla \times F$$

f=scalar potential F=vector potential
Also $$\vec{u} = \nabla\Phi + \nabla\times\vec{\Psi} \quad \Phi\text{=scalar potential } \vec{\Psi}\text{=vector potential}$$

Then $$\nabla\left(c_1^2\nabla^2\Phi + f - \frac{\partial^2\Phi}{\partial t^2}\right) + \nabla\times\left(c_2^2\nabla^2\Psi + \vec{F} - \frac{\partial^2\Psi}{\partial t^2}\right) = 0$$

Where longitudinal wave velocity $$c_1 = \sqrt{\frac{\lambda+2\mu}{\rho}}$$

$$c_2 = \sqrt{\frac{\mu}{\rho}}$$

shear wave velocity
The Navier's equation is satisfied if:

$$c_1^2\nabla^2\Phi + f - \frac{\partial^2\Phi}{\partial t^2} = 0$$

And $$c_2^2\nabla^2\Psi + F - \frac{\partial^2\Psi}{\partial t^2} = 0$$

In spherical coordinates:

$$\Psi = r\Psi\hat{r} + \ell\,\nabla\times(r\chi\,\vec{r})$$

$\Psi, \chi$ scalar $\ell$ =length factor
Therefore, with body forces neglected:

$$c_1^2\nabla^2\Phi = \ddot{\Phi}$$

$$c_2^2\nabla^2\Psi = \ddot{\Psi}$$

$$c_2^2\nabla^2\chi = \ddot{\chi}$$

Then displacement components are:

$$u_r = \frac{\partial\Phi}{\partial r} + \ell\left[\frac{\partial^2(r\chi)}{\partial r^2} - r\nabla^2\chi\right]$$

$$u_\theta = \frac{1}{r}\frac{\partial\Phi}{\partial\theta} + \frac{1}{\sin\theta}\frac{\partial\Psi}{\partial\phi} + \frac{1}{r}\frac{\partial^2(r\chi)}{\partial\theta\partial r}$$

$$u_\phi = \frac{1}{r\sin\theta}\frac{\partial\Phi}{\partial\phi} - \frac{\partial\Psi}{\partial\phi}\frac{1}{r\sin\theta}\frac{\partial^2(r\chi)}{\partial\phi\partial r}$$

Therefore stress $$\sigma_{rr} = \lambda \nabla^2 \phi + 2\mu \frac{\partial^2 \Phi}{\partial r^2} + 2\mu \ell \frac{\partial}{\partial r}\left[\frac{\partial^2 (r\chi)}{\partial r^2} - r\nabla^2 \chi\right]$$

Similarly, we can find:

$$\sigma_{\theta\theta}, \sigma_{\phi\phi}, \sigma_{r\theta}, \sigma_{r\phi}, \sigma_{\theta\phi}$$

Using separation of variables, the Helmholtz equation can be solved in spherical coordinates (r, θ, φ) with:

Bessel equation for r
Legendre equation for θ
Simple $2^{nd}$ order equation for φ
Helmholtz equation $$\nabla^2 f - \frac{1}{c^2}\frac{\partial^2 f}{\partial t^2} = 0$$

Expanding the Laplacian in spherical coordinates provides:

$$\frac{1}{r^2}\frac{\partial}{\partial r}\left(r^2\frac{\partial f}{\partial r}\right) + \frac{1}{r^2\sin\theta}\frac{\partial}{\partial \theta}\left(\sin\theta\frac{\partial f}{\partial \theta}\right) + \frac{1}{r^2\sin^2\theta}\frac{\partial^2 f}{\partial \phi^2} - \frac{1}{c^2}\frac{\partial^2 f}{\partial t^2} = 0$$

Where $$f(r,\theta,\phi,t) = F_1(r)F_2(\theta)F_3(\phi)e^{-i\omega t}$$

Therefore equation $$r^2\frac{d^2 F_1}{dr^2} + 2r\frac{dF_1}{dr} + (k^2 r^2 - P^2)F_1 = 0 \quad \theta \text{ equation}$$

$$\frac{1}{\sin\theta}\frac{d}{d\theta}\left(\sin\theta \frac{dF_2}{d\theta}\right) + \left(P^2 - \frac{q^2}{\sin^2\theta}\right)F_2 = 0$$

$$\frac{d^2 F_3}{d\phi^2} + q^2 F_3 = 0 \quad \phi \text{ equation}$$

Where $$k = \frac{\omega}{c}$$

and $P^2$, $q^2$ are separation constants $$P^2 = v(v+1)$$
$$\mu = \cos\theta$$
$$F_1 = \frac{R(r)}{\sqrt{kr}}$$

Then the $$r^2\frac{d^2 R}{dr^2} + 2r\frac{dR}{dr} + \left(k^2 r^2 - \left(v + \frac{1}{2}\right)^2\right)R = 0 \text{ Bessel equation} \quad r \text{ equation}$$

$$(1-\mu^2)\frac{d^2 F_2}{d\mu^2} - 2\mu \frac{dF_2}{d\mu} + \left[v(v+1) - \frac{m^2}{1-\mu^2}\right]F_2 = \quad \theta \text{ equation}$$

0 Legendre equation

Therefore, the final solution is:

$$f(r, \theta, \phi, t) =$$

$$e^{-i\omega t}\frac{1}{\sqrt{kr}}\left[AJ_{n+\frac{1}{2}}(kr) + BY_{n+\frac{1}{2}}(kr)\right]\left[cP_n^m(\mu) + DQ_n^m(\mu)\right]\left[Ee^{im\phi} + Fe^{-im\phi}\right]$$

Where
$P_n^m(\mu)$, $Q_n^m(\mu)$ associated Legendre functions $J_{n+\frac{1}{2}}(kr)$ is Bessel function of first kind $Y_{n+\frac{1}{2}}(kr)$ is Bessel function of second kind $Q_n^m$ is singular at $\mu = \pm 1$ so we exclude it
Now the potentials are:

$$\Phi = Z_n^{(i)}(\alpha r)P_n^m(\cos\theta)e^{i(m\phi-\omega t)}$$

$$\Psi = Z_n^{(i)}(\beta r)P_n^m(\cos\theta)e^{i(m\phi-\omega t)}$$

$$\chi = Z_n^{(i)}(\beta r)P_n^m(\cos\theta)e^{i(m\phi-\omega t)}$$

where $$\alpha = \frac{\omega}{c_1}$$

$$\beta = \frac{\omega}{c_2}$$

$$Z_n^{(1)} = j_n(kr) = \sqrt{\frac{\pi}{2kr}}J_{n+\frac{1}{2}}(kr) \quad Z_n^{(2)} = y_n(kr) = \sqrt{\frac{\pi}{2kr}}Y_{n+\frac{1}{2}}(kr)$$

The values of $\mu_r$, $\mu_\theta$, $\mu_\phi$ may then be found as functions of the spherical Bessel functions. The values of $\sigma_{rr}$, $\sigma_{\theta\theta}$, $\sigma_{\phi\phi}$, $\sigma_{r\theta}$, $\sigma_{r\phi}$, $\sigma_{\theta\phi}$ can also be found as functions of $\Phi$, $\Psi$, $\chi$. The modal characteristic equations can then now be derived.

There are two cases for a vibrating sphere. These include 1) an Axi-symmetric case (symmetry axis θ=0) no φ component a, and 2) Traction-free boundary conditions.
With respect to the Axi-symmetric case:
Symmetry axis θ=0

$$u_\phi = 0$$

$$\frac{\partial}{\partial \phi} = 0$$

$$q = 0$$

$$F_3 = \text{constant}$$

$$m = 0$$

$$P_n^m(\mu) \to P_n(\mu)$$

Therefore $$\Phi = Z_n^{(i)}(\alpha r)P_n(\cos\theta)e^{-i\omega t} \quad u_r = \frac{\partial \Phi}{\partial r} + \ell\left[\frac{\partial^2 (rx)}{\partial r^2} - r\nabla^2 \chi\right]$$

$$\Psi = Z_n^{(i)}(\beta r)e^{-i\omega t} \quad u_\theta = \frac{1}{r}\frac{\partial \Phi}{\partial \theta} + \frac{1}{r}\frac{\partial^2 (r\chi)}{\partial \phi \partial r}$$

$$\chi = Z_n^{(i)}(\beta r)P_n(\cos\theta)e^{-i\omega t} \quad u_\phi = 0$$

The values of $\sigma_{rr}$, $\sigma_{\theta\theta}$, $\sigma_{\phi\phi}$, $\sigma_{r\theta}$ are can also be found and $\sigma_{r\phi}=0$ $\sigma_{\theta\phi}=0$ Substituting $\Phi$, $\Psi$, $\chi$ into stress components referenced above enables the finding of stresses in terms of Bessel and Legendre polynomials Traction Boundary Conditions Boundary conditions of inner & outer surfaces of sphere become $\sigma_{rr}=\sigma_{r\phi}=\sigma_{r\theta}=0$ at $r=r_i$ $\sigma_{rr}=\sigma_{r\phi}=\sigma_{r\theta}=0$ at $r=r_0$ New stress equations can be constructed satisfying the above boundary conditions. Therefore, modal characteristic equation becomes:

$$\Delta_n = \begin{vmatrix} T_{11}^{(1)}(\alpha r_i) & T_{11}^{(2)}(\alpha r_i) \\ T_{11}^{(1)}(\alpha r_0) & T_{11}^{(2)}(\alpha r_0) \end{vmatrix} = 0 \text{ for } n = 0$$

Where $$T_{11}^{(i)}(\alpha r) = (n^2 - n - \tfrac{1}{2}\beta^2 r^2)Z_n^{(i)}(\alpha r) + 2\alpha r Z_{n+1}^{(i)}(\alpha r)$$

Kirchhoff-Love Shell theory

Assuming that:

$h \ll a$ $h$=shell thickness $a$=radius of midsurface $u_r \ll h$ $u_\theta \ll h$ displacement$\ll$thickness $u_\phi \ll h$ $\sigma_{rr} \approx 0$ negligible Therefore Displacement vector: $u_r=U_r$: displacement of middle surface $$u_\theta = \left(1 + \frac{x}{a}\right)u_\theta - \frac{x}{a}\frac{\partial u_r}{\partial \theta}$$

Where $x=r-a$ $U_r$ and $U_\theta$ are functions of $\theta$ only

Then kinetic energy $$T = \frac{1}{2}\rho_s \int_0^{2\pi}\int_0^{\pi}\int_{-\frac{h}{2}}^{\frac{h}{2}} (\dot{u}_r^2 + \dot{u}_\theta^2)(a+x)^2 \sin\theta \, dx\, d\theta\, d\phi$$

Neglecting x in comparison to midsurface radius a $$T = \frac{1}{2}\rho_s \int_0^{2\pi}\int_0^{\pi}\int_{-\frac{h}{2}}^{\frac{h}{2}} (\dot{u}_r^2 + \dot{u}_\theta^2)a^2 \sin\theta \, dx\, d\theta\, d\phi$$

Neglecting rotatory inertia provides $$T = \pi\rho_s h a^2 \int_0^{2\pi} (\dot{U}_r^2 + \dot{U}_\theta^2)\sin\theta \, d\theta$$

And therefore, the strain components become $$\epsilon_{\theta\theta} = \frac{1}{a+x}\left(\frac{\partial u_\theta}{\partial \theta} + u_r\right)$$

$$\epsilon_{\phi\phi} = \frac{1}{a+x}(\cot\theta u_\theta + u_r)$$

Therefore $$\epsilon_{\theta\theta} = \frac{1}{a+x}\left(\frac{\partial U_\theta}{\partial \theta} + U_r\right) + \frac{x}{a(a+x)}\left(\frac{\partial U_\theta}{\partial \theta} - \frac{\partial^2 U_r}{\partial \theta^2}\right)$$

$$\epsilon_{\phi\phi} = \frac{1}{a+x}(\cot\theta U_\theta + U_r) + \frac{x}{a(a+x)}\cot\theta\left(u_\theta - \frac{\partial U_r}{\partial \theta}\right)$$

Following the same approach for strain potential energy the final equations of motions are determined as:

$$L_{\theta\theta}U_\theta + L_{\theta r}U_r + \Omega^2 U_\theta = 0$$

$$L_{r\theta}U_\theta + L_{rr}U_r + \Omega^2 U_r = 0$$

Where L is an operator in terms of $$\nabla_n^2 = \frac{d}{d\eta}(1+\eta^2)\frac{d}{d\eta}$$

$\eta = \cos\theta$ $\Omega = \dfrac{\omega a}{c_p}$ dimensionless frequency of shell Where $c_p$ = phase velocity of compressional waves $$c_p = \sqrt{\frac{E}{\rho(1-\nu^2)}}$$

So $$\omega = \frac{\Omega}{a}c_p$$

$$f = \frac{\Omega}{2\pi a}c_p$$

$$f = \frac{\Omega}{2\pi a}\sqrt{\frac{E}{\rho(1-v^2)}}$$

frequency of vibration of a spherical shell

Free Vibration
We can represent $$U_r(\eta) = \sum_{n=0}^{\infty} U_{rn} P_n(\eta) e^{-i\omega t}$$

$$U_\theta(\eta) = \sum_{n=0}^{\infty} U_{\theta n}\sqrt{(1-\eta^2)}\,(dP_n/d\eta) e^{-i\omega t}$$

And therefore $$[\Omega_2-(1+\beta^2)(v+\lambda_n-1)]u_{\theta n}-[\beta^2(v+\lambda_n-1)+(1+v)]u_{rn}=0-$$
$$\lambda_n[\beta^2(v+\lambda_n-1)+(1+v)]u_{\theta n}+[\Omega^2-2(1+v)-\beta^2\lambda_n(v+\lambda_n-1)]u_{rn}=0$$

For the above to have a non-trivial solution the following must be satisfied:

$$\Omega^4-[1+3v+\lambda_n-\beta^2(1-v-\lambda_n^2-v\lambda_n)]\beta^2+(\lambda_n-2)(1-v^2)+\beta^2$$
$$[\lambda_n^3-4\lambda_n^2+\lambda_n(5-v^2)-2(1-v^2)]=0$$

Where $$\lambda_n = n(n+1)$$

$$\beta = \frac{h^2}{12a^2}$$

Or $$[\Omega^2-\Omega_n^{(1)^2}][\Omega^2-\Omega_n^{(2)^2}]=0$$

$\Omega_n^{(1)}$ lower natural frequencies
$\Omega_n^{(2)}$ higher natural frequencies From the modal characteristic equation of 3D shell theory:

$$\Delta_n = \begin{vmatrix} T_{11}^{(1)}(\alpha r_i) & T_{11}^{(2)}(\alpha r_i) \\ T_{11}^{(1)}(\alpha r_0) & T_{11}^{(2)}(\alpha r_0) \end{vmatrix} = 0 \text{ for } n=0$$

Therefore $$T_{11}^{(1)}(\alpha r_i)T_{11}^{(2)}(\alpha r_0)-T_{11}^{(2)}(\alpha r_i)T_{11}^{(1)}(\alpha r_0)=0$$

Where $$T_{11}^{(i)}(\alpha r)=(n^2-n-\tfrac{1}{2}\beta^2 r^2)Z_n^{(i)}(\alpha r)+2\alpha r Z_{n+1}^{(i)}(\alpha r)$$

Where $$Z_n^{(1)} = j_n(kr) = \sqrt{\frac{\pi}{2kr}}\,J_{n+\frac{1}{2}}(kr)$$

$$Z_n^{(2)} = y_n(kr) = \sqrt{\frac{\pi}{2kr}}\,J_{n+\frac{1}{2}}(kr)$$

$$\alpha = \frac{\omega}{c_1}$$

$$\beta = \frac{\omega}{c_2}$$

$$\Omega^1 = \frac{\omega}{c_1} a$$

$$T_{11}^{(1)}(\alpha r_i) = \left(n^2-n-\frac{1}{2}\beta^2 r_i^2\right)j_n(kr_i)+2\alpha r_i j_{n+1}(\alpha r_i)$$

$$T_{11}^{(2)}(\alpha r_i) = \left(n^2-n-\frac{1}{2}\beta^2 r_i^2\right)y_n(kr_i)+2\alpha r_i y_{n+1}(\alpha r_i)$$

$$T_{11}^{(1)}(\alpha r_0) = \left(n^2-n-\frac{1}{2}\beta^2 r_0^2\right)j_n(kr_0)+2\alpha r_0 j_{n+1}(\alpha r_0)$$

$$T_{11}^{(2)}(\alpha r_0) = \left(n^2-n-\frac{1}{2}\beta^2 r_0^2\right)y_n(kr_0)+2\alpha r_0 y_{n+1}(\alpha r_0)$$

It will be appreciated by those skilled in the art having the benefit of this disclosure that this a miniaturized device to sterilize from COVID-19 and other viruses and bacteria provides a an improved manner for sanitizing areas and clearing them of viruses and other biological materials. It should be understood that the drawings and detailed description herein are to be regarded in an illustrative rather than a restrictive manner and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

What is claimed is:

1. A system for sterilizing viruses, comprising:
beam generation circuitry for generating a Hermite-Gaussian beam having radiating energy therein at a predetermined frequency for generating mechanical longitudinal eigen vibrations to a thin shell capsid of a virus to destroy the virus and a predetermined cartesian Hermite-Gaussian intensity for imparting transverse shear forces to an icosahedral lattice structure of the virus to destroy the icosahedral lattice structure of the virus;
a controller for controlling the beam generation circuitry to generate the Hermite-Gaussian beam at the predetermined frequency for generating the mechanical longitudinal eigen vibrations to the thin shell capsid of the virus to destroy the virus and the predetermined cartesian Hermite-Gaussian intensity for imparting the transverse shear forces to an icosahedral lattice structure of the virus to destroy the icosahedral lattice structure of the virus, wherein the predetermined frequency equals a resonance frequency of the virus having the thin shell capsid and the Hermite-Gaussian beam is ordered as a structured Hermite-Gaussian beam with the predetermined cartesian Hermite-Gaussian intensity of a specific order to destroy the icosahedral lattice structure of the virus, further wherein the predetermined frequency is determined responsive to a plurality of parameters from an influenza virus;
wherein the predetermined frequency induces a mechanical resonance vibration at the resonance frequency of the virus for destroying a capsid of the virus;
wherein the Hermite-Gaussian beam at the predetermined frequency and the predetermined cartesian Hermite-Gaussian intensity induces mechanical longitudinal eigen-vibrations at the resonance frequency of the virus having the thin shell capsid within the virus having the thin shell capsid for destroying the virus having the thin shell capsid and imparts the transverse shear forces to the icosahedral lattice structure of the virus; and radiating circuitry for projecting a radiating wave on a predetermined location to destroy the virus having the thin shell capsid at the predetermined location.

2. The system of claim 1, wherein the virus comprises a Covid-19 virus.

3. The system of claim 1, wherein the controller further determines a minimum magnitude of an electric field necessary to induce the mechanical resonance vibration in the virus.

4. The system of claim 1, wherein the radiating circuitry comprises an antenna incorporated into a device from the group consisting of a handheld flashlight, a light fixture, an electrical socket fixture and a ceiling mounted fixture.

5. The system of claim 1, wherein the beam generation circuitry generates a maximum transmit power required that does not exceed a predetermined power density threshold.

6. The system of claim 1, wherein the beam generation circuitry further generates a microwave beam and further, wherein the microwave beam generates an inactivation threshold within the virus responsive to microwave energy within the microwave beam.

7. The system of claim 1, wherein the controller causes generation of the radiating wave that has a structured vector beam for imparting stresses and torsion to the virus to rupture the capsid of the virus.

8. A system for sterilizing viruses, comprising:
beam generation circuitry for generating a Hermite-Gaussian beam having radiating energy therein at a predetermined frequency for generating mechanical longitudinal eigen vibrations to a thin shell capsid of a Covid-19 virus to destroy the Covid-19 virus;

a controller for controlling the beam generation circuitry to generate the Hermite-Gaussian beam at the predetermined frequency for generating the mechanical longitudinal eigen vibrations to the thin shell capsid of the Covid-19 virus to destroy the Covid-19 virus, wherein the predetermined frequency equals a resonance frequency of the Covid-19 virus, further wherein the predetermined frequency is determined responsive to a plurality of parameters from an influenza virus;

wherein the predetermined frequency induces a mechanical resonance vibration at the resonance frequency of the Covid-19 virus for destroying the thin shell capsid of the Covid-19 virus;

wherein the Hermite-Gaussian beam at the predetermined frequency induces mechanical longitudinal eigen-vibrations at the resonance frequency of the virus having the thin shell capsid within the virus having the thin shell capsid for destroying the virus having the thin shell capsid and imparts transverse shear forces to icosahedral lattice structure of the virus; and radiating circuitry for projecting a radiating wave on a predetermined location to destroy the Covid-19 virus at the predetermined location.

9. The system of claim 8, wherein the controller further determines a minimum magnitude of an electric field necessary to induce the mechanical resonance vibration in the Covid-19 virus.

10. The system of claim 9, wherein the controller causes the beam generation circuitry to generate the radiating wave having the minimum magnitude of the electric field.

11. The system of claim 8, wherein the radiating circuitry comprises an antenna incorporated into a device from the group consisting of a handheld flashlight, a light fixture, an electrical socket fixture and a ceiling mounted fixture.

12. The system of claim 8, wherein the beam generation circuitry generates a maximum transmit power required that does not exceed a predetermined power density threshold.

13. The system of claim 8, wherein the beam generation circuitry further generates a microwave beam and further wherein the microwave beam generates an inactivation threshold within the Covid-19 virus responsive to microwave energy within the microwave beam.

14. The system of claim 8, wherein the controller causes generation of the radiating wave that has a structured vector beam for imparting stresses and torsion to the Covid-19 virus to rupture the thin shell capsid of the Covid-19 virus.

\* \* \* \* \*